(12) United States Patent
Kakumanu et al.

(10) Patent No.: US 12,090,140 B2
(45) Date of Patent: *Sep. 17, 2024

(54) NON-SEDATING DEXMEDETOMIDINE TREATMENT REGIMENS

(71) Applicant: BioXcel Therapeutics, Inc., New Haven, CT (US)

(72) Inventors: Vasukumar Kakumanu, New Haven, CT (US); David Christian Hanley, New Haven, CT (US); Frank Yocca, New Haven, CT (US); Chetan Dalpatbhai Lathia, New Haven, CT (US); Lavanya Rajachandran, New Haven, CT (US); Robert Risinger, New Haven, CT (US)

(73) Assignee: BioXcel Therapeutics, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/526,686

(22) Filed: Dec. 1, 2023

(65) Prior Publication Data

US 2024/0252471 A1    Aug. 1, 2024

Related U.S. Application Data

(63) Continuation of application No. 18/189,073, filed on Mar. 23, 2023, now Pat. No. 11,998,528, and a continuation of application No. 18/153,870, filed on Jan. 12, 2023, now Pat. No. 11,806,334.

(51) Int. Cl.
| | | |
|---|---|---|
| *A01N 37/00* | (2006.01) | |
| *A01N 25/00* | (2006.01) | |
| *A01N 37/12* | (2006.01) | |
| *A01N 37/44* | (2006.01) | |
| *A61K 9/00* | (2006.01) | |
| *A61K 31/215* | (2006.01) | |
| *A61K 31/24* | (2006.01) | |
| *A61K 31/4174* | (2006.01) | |
| *A61K 47/38* | (2006.01) | |
| *A61P 25/18* | (2006.01) | |
| *A61P 25/20* | (2006.01) | |

(52) U.S. Cl.
CPC .......... *A61K 31/4174* (2013.01); *A61K 9/006* (2013.01); *A61K 47/38* (2013.01); *A61P 25/18* (2018.01); *A61P 25/20* (2018.01)

(58) Field of Classification Search
CPC ...... A61K 31/4174; A61K 9/006; A61K 9/06; A61K 9/08; A61K 9/12; A61P 25/28
See application file for complete search history.

(56) References Cited

U.S. PATENT DOCUMENTS

| 4,670,455 A | 6/1987 | Virtanen et al. |
|---|---|---|
| 4,839,170 A | 6/1989 | Sarnoff et al. |
| 5,395,907 A | 3/1995 | Zajaczkowski |
| 5,508,367 A | 4/1996 | Zajaczkowski |
| 5,565,268 A | 10/1996 | Zajaczkowski |
| 5,605,911 A | 2/1997 | Olney et al. |
| 5,700,873 A | 12/1997 | Zajaczkowski et al. |
| 5,712,301 A | 1/1998 | Jaatinen et al. |
| 5,726,250 A | 3/1998 | Zajaczkowski |
| 5,731,387 A | 3/1998 | Zajaczkowski |
| 5,951,999 A | 9/1999 | Therriault et al. |
| 6,174,546 B1 | 1/2001 | Therriault et al. |
| 6,200,604 B1 | 3/2001 | Pather et al. |
| 6,221,392 B1 | 4/2001 | Khankari et al. |
| 6,239,228 B1 | 5/2001 | Zajaczkowski |
| 6,716,867 B1 | 4/2004 | Aantaa et al. |
| 6,753,782 B2 | 6/2004 | Power |
| 7,001,609 B1 | 2/2006 | Matson et al. |
| 7,357,891 B2 | 4/2008 | Yang et al. |
| 7,425,292 B2 | 9/2008 | Yang et al. |
| 7,470,397 B2 | 12/2008 | Meathrel et al. |
| 7,579,019 B2 | 8/2009 | Tapolsky et al. |
| 7,630,758 B2 | 12/2009 | Lapinlampi et al. |
| 7,666,337 B2 | 2/2010 | Yang et al. |
| 7,727,466 B2 | 6/2010 | Meathrel et al. |
| 7,897,080 B2 | 3/2011 | Yang et al. |
| 7,972,618 B2 | 7/2011 | Fuisz et al. |
| 8,241,661 B1 | 8/2012 | Fuisz et al. |
| 8,242,158 B1 | 8/2012 | Roychowdhury et al. |
| 8,282,954 B2 | 10/2012 | Bogue et al. |

(Continued)

FOREIGN PATENT DOCUMENTS

| AU | 2007201370 B2 | 9/2009 |
|---|---|---|
| AU | 2009238370 B2 | 7/2011 |

(Continued)

OTHER PUBLICATIONS

Cognitive Vitalilty.org. (Dexmedetomidine Mar. 19, 2019).*
Aantaa, et al., "Intramuscular dexmedetomidine, a novel alpha2-adrenoceptor agonist, as premedication for minor gynaecological surgery." Acta Anaesthesiol Scand 35(4): 283-288 (1991).
Abdelaziz, et al., "Effect of intranasal dexmedetomidine or intranasal midazolam on prevention of emergence agitation in pediatric strabismus surgery: A randomized controlled study." Egyptian Journal of Anaesthesia 32: 285-291 (2016).
Abdel-Ghaffar et al., "Oral trans-mucosal dexmedetomidine for controlling of emergence agitation in children undergoing tonsillectomy: a randomized controlled trial," Rev Bras Anestesiol 69(5):469-476 (2019).

(Continued)

*Primary Examiner* — Layla Soroush
(74) *Attorney, Agent, or Firm* — Sterne, Kessler, Goldstein & Fox P.L.L.C.

(57) ABSTRACT

Disclosed herein are methods of administering relatively high doses of dexmedetomidine or a pharmaceutically acceptable salt thereof to a human subject, without also inducing significant sedation. The disclosed methods are particularly suitable for the treatment of agitation, especially when associated with neurodegenerative and/or neuropsychiatric diseases such as schizophrenia, bipolar illness such as bipolar disorder or mania, dementia, depression, or delirium.

6 Claims, 35 Drawing Sheets

(56) References Cited

U.S. PATENT DOCUMENTS

| | | |
|---|---|---|
| 8,324,260 B1 | 12/2012 | Garcia Da Rocha et al. |
| 8,338,470 B1 | 12/2012 | Roychowdhury et al. |
| 8,364,221 B2 | 1/2013 | Mannheimer et al. |
| 8,414,922 B2 | 4/2013 | Bryson et al. |
| 8,436,033 B1 | 5/2013 | Roychowdhury et al. |
| 8,455,527 B1 | 6/2013 | Roychowdhury et al. |
| 8,568,777 B2 | 10/2013 | Fuisz |
| 8,617,589 B2 | 12/2013 | Fuisz et al. |
| 8,648,106 B2 | 2/2014 | Roychowdhury et al. |
| 8,663,687 B2 | 3/2014 | Myers et al. |
| 8,663,696 B2 | 3/2014 | Myers et al. |
| 8,685,437 B2 | 4/2014 | Yang et al. |
| 8,846,074 B2 | 9/2014 | Bryson et al. |
| 8,882,684 B2 | 11/2014 | Halperin et al. |
| 8,882,703 B2 | 11/2014 | Hickle |
| 8,900,498 B2 | 12/2014 | Yang et al. |
| 8,936,825 B2 | 1/2015 | Myers et al. |
| 9,073,294 B2 | 7/2015 | Kumar et al. |
| 9,248,146 B2 | 2/2016 | Barnhart et al. |
| 9,283,219 B2 | 3/2016 | Bryson et al. |
| 9,303,918 B2 | 4/2016 | Li |
| 9,320,712 B2 | 4/2016 | Roychowdhury et al. |
| 9,346,601 B2 | 5/2016 | Bogue et al. |
| 9,427,412 B2 | 8/2016 | Bryson et al. |
| 9,441,142 B2 | 9/2016 | Malik et al. |
| 9,545,376 B2 | 1/2017 | Musho et al. |
| 9,561,191 B2 | 2/2017 | Myers et al. |
| 9,572,773 B2 | 2/2017 | Dormady et al. |
| 9,585,961 B2 | 3/2017 | Barnhart et al. |
| 9,616,049 B2 | 4/2017 | Roychowdhury et al. |
| 9,649,296 B1 | 5/2017 | Pizza |
| 9,662,297 B2 | 5/2017 | Musho et al. |
| 9,662,301 B2 | 5/2017 | Musho et al. |
| 9,717,796 B1 | 8/2017 | Pizza |
| 9,795,559 B2 | 10/2017 | Henwood et al. |
| 9,814,674 B2 | 11/2017 | Musho et al. |
| 9,855,221 B2 | 1/2018 | Myers et al. |
| 9,901,650 B2 | 2/2018 | Nedergaard et al. |
| 9,931,305 B2 | 4/2018 | Yang et al. |
| 9,937,122 B2 | 4/2018 | Zhu et al. |
| 9,937,123 B2 | 4/2018 | Barnhart et al. |
| 9,993,428 B2 | 6/2018 | Gerard et al. |
| 10,130,684 B2 | 11/2018 | Rubin et al. |
| 10,130,766 B1 | 11/2018 | Bibian et al. |
| 10,137,245 B2 | 11/2018 | Melker et al. |
| 10,285,953 B2 | 5/2019 | Bryson et al. |
| 10,314,503 B2 | 6/2019 | Prerau et al. |
| 10,383,574 B2 | 8/2019 | Purdon et al. |
| 10,602,978 B2 | 3/2020 | Purdon et al. |
| 10,792,246 B2 | 10/2020 | Kakumanu et al. |
| 11,116,723 B2 | 9/2021 | Temtsin-Krayz |
| 2002/0037977 A1 | 3/2002 | Feldstein et al. |
| 2003/0096012 A1 | 5/2003 | Besse et al. |
| 2003/0124191 A1 | 7/2003 | Besse et al. |
| 2003/0145854 A1 | 8/2003 | Hickle |
| 2003/0158242 A1 | 8/2003 | Kugelmann |
| 2004/0138312 A1 | 7/2004 | Wheeler et al. |
| 2005/0037055 A1 | 2/2005 | Yang et al. |
| 2005/0118217 A1 | 6/2005 | Barnhart et al. |
| 2005/0222270 A1 | 10/2005 | Olney et al. |
| 2006/0058590 A1 | 3/2006 | Shaw et al. |
| 2006/0058700 A1 | 3/2006 | Marro et al. |
| 2006/0069086 A1 | 3/2006 | Michalow |
| 2007/0281003 A1 | 12/2007 | Fuisz et al. |
| 2008/0026040 A1 | 1/2008 | Farr et al. |
| 2008/0124381 A1 | 5/2008 | Barnhart et al. |
| 2008/0280947 A1 | 11/2008 | Blondino et al. |
| 2008/0299005 A1 | 12/2008 | Meathrel et al. |
| 2008/0306980 A1 | 12/2008 | Brunner et al. |
| 2009/0076156 A1 | 3/2009 | Husain et al. |
| 2009/0099480 A1 | 4/2009 | Salgo et al. |
| 2009/0142850 A1 | 6/2009 | Meathrel et al. |
| 2009/0275853 A1 | 11/2009 | Sarkela |
| 2010/0130566 A1 | 5/2010 | Purpura et al. |
| 2010/0196286 A1 | 8/2010 | Armer et al. |
| 2011/0021588 A1 | 1/2011 | Henwood et al. |
| 2011/0066004 A1 | 3/2011 | Sullivan et al. |
| 2011/0245633 A1 | 10/2011 | Goldberg et al. |
| 2011/0290694 A1 | 12/2011 | Fuisz et al. |
| 2012/0076921 A1 | 3/2012 | Myers et al. |
| 2012/0100278 A1 | 4/2012 | Nowak et al. |
| 2012/0195955 A1 | 8/2012 | Bryson et al. |
| 2012/0309804 A1 | 12/2012 | Horn |
| 2012/0325209 A1 | 12/2012 | Quintin |
| 2012/0328688 A1 | 12/2012 | Fuisz et al. |
| 2013/0072532 A1 | 3/2013 | Henwood et al. |
| 2013/0095156 A1 | 4/2013 | Barnhart et al. |
| 2013/0096172 A1 | 4/2013 | Garcia Da Rocha et al. |
| 2013/0116215 A1 | 5/2013 | Coma et al. |
| 2013/0178465 A1 | 7/2013 | Henwood et al. |
| 2013/0225626 A1 | 8/2013 | Bryson et al. |
| 2014/0010873 A1 | 1/2014 | Tygesen et al. |
| 2014/0163080 A1 | 6/2014 | Horn |
| 2014/0203480 A1 | 7/2014 | Musho et al. |
| 2014/0261990 A1 | 9/2014 | Dadey et al. |
| 2014/0287181 A1 | 9/2014 | Malik et al. |
| 2014/0316217 A1 | 10/2014 | Purdon et al. |
| 2014/0323898 A1 | 10/2014 | Purdon et al. |
| 2014/0377329 A1 | 12/2014 | Bryson et al. |
| 2015/0098980 A1 | 4/2015 | Pongpeerapat et al. |
| 2015/0098981 A1 | 4/2015 | Pongpeerapat et al. |
| 2015/0098982 A1 | 4/2015 | Pongpeerapat et al. |
| 2015/0098983 A1 | 4/2015 | Pongpeerapat et al. |
| 2015/0098997 A1 | 4/2015 | Pongpeerapat et al. |
| 2015/0141772 A1 | 5/2015 | LeBOEUF et al. |
| 2015/0250957 A1 | 9/2015 | Albalat |
| 2015/0258067 A1 | 9/2015 | Kokkonen et al. |
| 2016/0000945 A1 | 1/2016 | Nedergaard et al. |
| 2016/0113885 A1 | 4/2016 | Myers et al. |
| 2016/0151299 A1 | 6/2016 | Bryson et al. |
| 2016/0310441 A1 | 10/2016 | Yamazaki et al. |
| 2016/0324446 A1 | 11/2016 | Prerau et al. |
| 2016/0338972 A1 | 11/2016 | Bryson et al. |
| 2016/0374588 A1 | 12/2016 | Shariff et al. |
| 2017/0087084 A1 | 3/2017 | Musho et al. |
| 2017/0087097 A1 | 3/2017 | Musho et al. |
| 2017/0128358 A1 | 5/2017 | Barnhart et al. |
| 2017/0128421 A1 | 5/2017 | Sura et al. |
| 2017/0165235 A1 | 6/2017 | Roychowdhury et al. |
| 2017/0231556 A1 | 8/2017 | Purdon et al. |
| 2017/0239221 A1 | 8/2017 | Harsh et al. |
| 2017/0246108 A1 | 8/2017 | Musho et al. |
| 2017/0252294 A1 | 9/2017 | Musho et al. |
| 2017/0273611 A1 | 9/2017 | Purdon et al. |
| 2017/0274174 A1 | 9/2017 | Purdon et al. |
| 2017/0296482 A1 | 10/2017 | Myers et al. |
| 2018/0055764 A1 | 3/2018 | Henwood et al. |
| 2018/0065767 A1 | 3/2018 | Bogue et al. |
| 2018/0098937 A1 | 4/2018 | Horn |
| 2018/0110897 A1 | 4/2018 | Bush et al. |
| 2018/0147201 A1 | 5/2018 | Toledano |
| 2018/0177797 A1 | 6/2018 | Berdahl et al. |
| 2018/0360736 A1 | 12/2018 | Obeid et al. |
| 2019/0209022 A1 | 7/2019 | Sobol et al. |
| 2019/0216345 A1 | 7/2019 | Scheib |
| 2019/0216389 A1 | 7/2019 | Scheib |
| 2019/0365715 A1 | 12/2019 | Nandabalan et al. |
| 2019/0374158 A1 | 12/2019 | Brown et al. |
| 2020/0000708 A1 | 1/2020 | Barnhart et al. |
| 2020/0000717 A1 | 1/2020 | Kakumanu et al. |
| 2020/0069650 A1 | 3/2020 | Korpivaara et al. |
| 2020/0093800 A1 | 3/2020 | Pongpeerapat et al. |
| 2020/0168340 A1 | 5/2020 | Park et al. |
| 2020/0345635 A1 | 11/2020 | Kakumanu et al. |
| 2021/0077388 A1 | 3/2021 | Kakumanu et al. |
| 2021/0267944 A1 | 9/2021 | Yocca et al. |
| 2022/0031663 A1 | 2/2022 | Nandabalan et al. |
| 2022/0110864 A1 | 4/2022 | Kakumanu et al. |
| 2022/0142918 A1 | 5/2022 | Kakumanu et al. |

(56) References Cited

U.S. PATENT DOCUMENTS

| | | | |
|---|---|---|---|
| 2022/0160629 A1 | 5/2022 | Kakumanu et al. | |
| 2022/0202373 A1 | 6/2022 | Yocca et al. | |

FOREIGN PATENT DOCUMENTS

| | | | |
|---|---|---|---|
| AU | 2014227693 B2 | 6/2018 | |
| CA | 2324967 A1 | 5/2002 | |
| CN | 101496801 A | 8/2009 | |
| CN | 102657635 A | 9/2012 | |
| CN | 104784174 A | 7/2015 | |
| CN | 105287519 A | 2/2016 | |
| CN | 106539778 A | 3/2017 | |
| CN | 106727443 A | 5/2017 | |
| CN | 106727524 A | 5/2017 | |
| CN | 107137399 A | 9/2017 | |
| CN | 107412204 A | 12/2017 | |
| CN | 107693485 A | 2/2018 | |
| CN | 109620802 A | 4/2019 | |
| CN | 110893186 A | 3/2020 | |
| CN | 111481506 A | 8/2020 | |
| CN | 112138250 A | 12/2020 | |
| EP | 0681601 B1 | 2/1999 | |
| EP | 1549305 B1 | 4/2009 | |
| EP | 1695094 B1 | 6/2013 | |
| EP | 3326612 A1 | 5/2018 | |
| JP | 2009526829 A | 7/2009 | |
| KR | 101859486 B1 | 6/2018 | |
| KR | 20190109310 A | 9/2019 | |
| RU | 2635532 C1 | 11/2017 | |
| WO | WO-9514746 A2 | 6/1995 | |
| WO | WO-9837111 A1 | 8/1998 | |
| WO | WO-2004032913 A1 | 4/2004 | |
| WO | WO-2005032519 A1 | 4/2005 | |
| WO | WO-2005039499 A2 | 5/2005 | |
| WO | WO-2006090371 A2 | 8/2006 | |
| WO | WO-2008079721 A1 | 7/2008 | |
| WO | WO-2008091588 A1 | 7/2008 | |
| WO | WO-2009048606 A1 | 4/2009 | |
| WO | WO-2009076165 A1 | 6/2009 | |
| WO | WO-2010132882 A2 | 11/2010 | |
| WO | WO-2012009144 A2 | 1/2012 | |
| WO | WO-2012075373 A2 | 6/2012 | |
| WO | WO-2012083269 A1 | 6/2012 | |
| WO | WO-2012177326 A1 | 12/2012 | |
| WO | WO-2013090278 A2 | 6/2013 | |
| WO | WO-2013103378 A1 | 7/2013 | |
| WO | WO-2013130577 A2 | 9/2013 | |
| WO | WO-2013173317 A1 | 11/2013 | |
| WO | WO-2014130777 A1 | 8/2014 | |
| WO | WO-2014153489 A1 | 9/2014 | |
| WO | WO-2014176444 A1 | 10/2014 | |
| WO | WO-2013090278 A3 | 12/2014 | |
| WO | WO-2015054058 A1 | 4/2015 | |
| WO | WO-2015054059 A2 | 4/2015 | |
| WO | WO-2015054061 A1 | 4/2015 | |
| WO | WO-2015054063 A1 | 4/2015 | |
| WO | WO-2016061413 A1 | 4/2016 | |
| WO | WO-2016061554 A1 | 4/2016 | |
| WO | WO-2016075365 A1 | 5/2016 | |
| WO | WO-2016089997 A1 | 6/2016 | |
| WO | WO-2017117627 A1 | 7/2017 | |
| WO | WO-2018072015 A1 | 4/2018 | |
| WO | WO-2018086498 A1 | 5/2018 | |
| WO | WO-2018109272 A1 | 6/2018 | |
| WO | WO-2018116202 A1 | 6/2018 | |
| WO | WO-2018126182 A1 | 7/2018 | |
| WO | WO-2019036253 A1 | 2/2019 | |
| WO | WO-2019070929 A1 | 4/2019 | |
| WO | WO-2019158810 A1 | 8/2019 | |
| WO | WO-2020006073 A1 | 1/2020 | |
| WO | WO-2020006092 A1 | 1/2020 | |
| WO | WO-2020006119 A1 | 1/2020 | |
| WO | WO-2020259440 A1 | 12/2020 | |
| WO | WO-2021016112 A2 | 1/2021 | |
| WO | WO-2021055595 A1 | 3/2021 | |

OTHER PUBLICATIONS

Abdelmageed, et al., "Intramuscular dexmedetomidine for prevention of shivering after general anesthesia in patients undergoing arthroscopic anterior cruciate ligament reconstruction." Ain-Shams Journal of Anesthesiology 7(2):156-162 (2014).
Adami, et al., "Combinations of dexmedetomidine and alfaxalone with butorphanol in cats: application of an innovative stepwise optimization method to identify optimal clinical doses for intramuscular anaesthesia." J Feline Med Surg. 18(10):846-853 (2016).
Ahmad, et al., "Effects of Midazolam or Midazolam-Fentanyl on Sedation and Analgesia Produced by Intramuscular Dexmedetomidine in Dogs." Asian Journal of Animal Sciences 5(5):302-316 (2011).
Aho, et al., "Intramuscularly administered dexmedetomidine attenuates hemodynamic and stress hormone responses to gynecologic laparoscopy." Anesth Analg 75(6):932-939 (1992).
Aich, et al., "A Comparison of Intranasal Dexmedetomidine and Intranasal Midazolam for Premedication in Children Undergoing Elective Surgeries." International Journal of Science and Research (IJSR) 5(7):1730-1737 (2016).
Akin, et al., "Dexmedetomidine vs midazolam for premedication of pediatric patients undergoing anesthesia." Pediatric Anesthesia 22 (9): 871-876 (2012).
Albertson et al., "Is It Prime Time for Alpha2-Adrenocepter Agonists in the Treatment of Withdrawal Syndromes?," J. Med. Toxicol 10:369-381 (2014).
Ali and Abdellatif, "Prevention of sevoflurane related emergence agitation in children undergoing adenotonsillectomy: A comparison of dexmedetomidine and propofol." Saudi J Anaesth. 7(3): 296-300, 7 pages (2013).
Ambi, et al., "Intranasal dexmedetomidine for paediatric sedation for diagnostic magnetic resonance imaging studies." Indian J Anaesth 56(6): 587-588 (2012).
Ansah, et al., "Comparison of three doses of dexmedetomidine with medetomidine in cats following intramuscular administration." Veterinary Pharmacology and Therapeutics 21(5):380-387 (1998).
Antonino and Junior, "Effectiveness of Intramuscular Dexmedetomidine and Methadone in Combination to Intratesticular Lidocaine for Orquiectomy in Dogs—Preliminary Study." Investigao vol. 16, No. 7. Abstract, 2 pages (2017).
Anttila, et al., "Bioavailability of dexmedetomidine after extravascular doses in healthy subjects." British Journal of Clinical Pharmacology 56(6): 691-693 (2003).
Anusua, et al., "Efficacy of Dexmedetomidine in Reducing Emergence Agitation After Sevoflurane Anaesthesia in Indian Paediatric Population." International Journal of Scientific Research 4(7): ISSN No. 2277-8179, pp. 458-461 (2015).
Anzctr Clinical Trial Id: ACTRN12616001522404, Does ketamine improve the quality of sedation of intranasal dexmedetomidine premedication in children. Fujian Provincial Hospital, Date Registered Nov. 4, 2016, Date Last Updated Jan. 29, 2018, https://www.anzctr.org.au/Trial/Registration/TrialReview.aspx?id=369976, downloaded May 6, 2018, 5 pages.
Aravindhanthan et al., "Sub lingual spray: a new technology oriented formulation with multiple benefits," International Journal of Research in Pharmaceutical Sciences 10(4):2875-2885 (2019).
Assad, et al., "Comparative study between prophylactic single dose of fentanyl and dexmedetomidine in the management of agitation after sevoflurane anesthesia in children." Egyptian Journal of Anaesthesia 27(1):31-37 (2011).
Aungst, et al., "Comparison of nasal, rectal, buccal, sublingual and intramuscular insulin efficacy and the effects of a bile salt absorption promoter." Journal of Pharmacology and Experimental Therapeutics 244(1):23-27 (1988).
Ayeko and Mohamed, "Prevention and treatment of sevoflurane emergence agitation and delirium in children with dexmedetomidine." Saudi J Anaesth 8(4):570-571 (2014).
Baddigam et al., "Dexmedetomidine in the Treatment of Withdrawal Syndromes in Cardiothoracic Surgery Patients," J. Intensive Care Med., 20(2):118-123 (2005).
Bajwa et al., "Dexmedetomidine: An Adjuvant Making Large Inroads into Clinical Practice," Annals of Medical and Health Sciences Research, 3(4):475-483 (Oct.-Dec. 2013).
Bakri, et al., "Comparison of dexmedetomidine or ondansetron with

(56) References Cited

OTHER PUBLICATIONS haloperidol for treatment of postoperative delirium in trauma patients admitted to intensive care unit: randomized controlled trial." Anaesth Pain & Intensive Care 19(2):118-123 (2015).
Barends et al., "Intranasal dexmedetomidine in elderly subjects with or without beta blockade: a randomised double-blind single-ascending-dose cohort study," British Journal of Anaesthesia 124(4):411-419 (2020).
Bartlett et al., "Understanding the Oral Mucosal Absorption and Resulting Clinical Pharmacokinetics of Asenapine," AAPS Pharm Sci Tech 13(4):1110-1115 (Dec. 2012).
Behrle, et al., "Intranasal Dexmedetomidine as a Sedative for Pediatric Procedural Sedation." J Pediatr Pharmacol Ther (2017); 22 (1): 4-8.
Belgrade et al., "Dexmedetomidine Infusion for the Management of Opioid-Induced Hyperalgesia," Pain Medicine, 2010; 11 :1819-1826.
Belkin et al., "Alpha-2 receptor agonists for the treatment of posttraumatic stress disorder," Drugs in Context 2015; 4: 212286, 5 pages.
Bergese et al., "A Phase lllb, Randomized, Double-blind, Placebo-controlled, Multicenter Study Evaluating the Safety and Efficacy of Dexmedetomidine for Sedation During Awake Fiberoptic Intubation," American Journal of Therapeutics (2010) 17, 586-595.
Bhardwaj, et al., "Abstract PR227: Comparison of Nasal Dexmedetomidine with Oral Midazolam for Premedication in Children Effect on Psychomotor Recovery." Anesthesia & Analgesia (2016); 123 (3S_Suppl): p. 288.
Bhat, et al., "Comparison of intranasal dexmedetomidine and dexmedetomidine-ketamine for premedication in pediatrics patients: A randomized double-blind study." Anesth Essays Res. (2016); 10 (2): 349-355.
Bienvenu et al., "Treatment of four psychiatric emergencies in the intensive care unit," Critical Care Medicine (2012) 40(9):2662-2670.
Biermann, et al., "Sedative, cardiovascular, haematologic and biochemical effects of four different drug combinations administered intramuscularly in cats." Veterinary Anaesthesia and Analgesia (2012); 39 (2): 137-150.
BioXcel Therapeutics, Inc., "BioXcel Therapeutics Announces BXCL501 Program Initiative for Prevention and Treatment of Acute Agitation using Wearable Digital Devices," Sep. 18, 2019, 3 pages, retrieved from: https://www.globenewswire.com/en/news-release/2019/09/18/1917334/0/en/BioXcel-Therapeutics-Announces-BXCL501-Program-Initiative-for-Prevention-and-Treatment-of-Acute-Agitation-using-Wearable-Digital-Devices.html.
BioXcel Therapeutics, Inc., "BioXcel Therapeutics Announces First Patient Enrolled in Phase 1b/2 Study of BXCL501 for Acute Treatment of Agitation Associated with Dementia," Jan. 7, 2020, 3 pages, retrieved from https://www.globenewswire.com/news-release/2020/01/07/1967125/0/en/BioXcel-Therapeutics-Announces-First-Patient-Enrolled-in-Phase-1b-2-Study-of-BXCLS01-for-Acute-Treatment-of-Agitation-Associated-with-Dementia.html.
BioXcel Therapeutics, Inc., "BioXcel Therapeutics, Inc. (BTAI) CEO Vimal Mehta on Q2 2018 Results—Earnings Call Transcript," Seeking Alpha, Aug. 12, 2018, 13 pages, retrieved from: https://seekingalpha.com/article/4198129-bioxcel-therapeutics-inc-btai-ceo-vimal-mehta-q2-2018-results-earnings-call-transcript?part=single.
BioXcel Therapeutics, Inc., "BioXcel Therapeutics Provides Update on the Clinical Advancement of BXCL501 for the Acute Treatment of Agitation," Globe Newswire, Oct. 30, 2018, 2 pages, retrieved from: https://www.globenewswire.com/news-release/2018/10/30/1638858/0/en/BioXcel-Therapeutics-Provides-Update-on-the-Clinical-Advan cement-of-BXC LSD 1-for-the-Acute-Treatment-of-Agitation.html.
BioXcel Therapeutics, Inc., "BioXcel Therapeutics Reports Positive Results from Study in Agitated Schizophrenia Patients Supporting BXCL501 Clinical Development," Globe Newswire, Nov. 14, 2018, 3 pages, retrieved from: https://www.globenewswire.com/news-release/2018/11/14/1651151/0/en/BioXcel-Therapeutics-Reports-Positive-Results-from-Study-in-Agitated-Schizophrenia-Patients-Supporting-BXCLS01-Clinical-Development.html.
BioXcel Therapeutics, Inc., "BioXcel Therapeutics Reports Second Quarter 2018 Financial Results and Provides Business Update," Globe Newswire, Aug. 8, 2018, 3 pages, retrieved from: https://ir.bioxceltherapeutics.com/press-releases/detail/49/bioxcel-therapeutics-reports-second-quarter-2018-financial.
BioXcel Therapeutics, Inc., "BioXcel Therapeutics Reports Third Quarter 2018 Quarterly Results and Provides Business Update," Globe Newswire, Nov. 9, 2018, 3 pages, retrieved from: https://ir.bioxceltherapeutics.com/press-releases/detail/61/bioxcel-therapeutics-reports-third-quarter-2018-quarterly.
BioXcel Therapeutics, Inc., "BioXcel Therapeutics to Host Second Quarter 2018 Financial Results and Business Update," Globe Newswire, Aug. 2, 2018, 2 pages, retrieved from: https://ir.bioxceltherapeutics.com/press-releases/detail/47/bioxcel- therapeutics-to-host-second-quarter-2018-financial.
BioXcel Therapeutics, Inc., "Next Wave of Medicines Utilizing Al," Jun. 2020, 30 pages, retrieved from https://dlio3yog0oux5.cloudfront.neU_ec77451d0911d660fb193909a0alba0e/bioxceltherapeutics/db/445/3421/pdf/BioXcel+Therapeutics+Presentation_June+11.pdf.
BioXcel Therapeutics, Inc., United States Securities and Exchange Commission, Form 10-K, Annual Report Pursuant to Section 13 or 15(d) of the Securities Exchange Act of 1934, For the year ended Dec. 31, 2019, 135 pages.
Bonanno, et al., "Effectiveness of preoperative intranasal dexmedetomidine compared with oral midazolam for the prevention of emergence delirium in pediatric patients undergoing general anesthesia: a systematic review protocol." JBI Database of Systematic Reviews and Implementation Reports: 2016; 14 (8): 70-79.
Bond, et al., "Dexmedetomidine Nasal Sedation Produces More Oculocardiac Reflex During Strabismus Surgery." Journal of Pediatric Ophthalmology and Strabismus (2016);53(5):318.
Boriosi et al., "Safety and Efficacy of Buccal Dexmedetomidine for MRI Sedation in School-Aged Children," Hospital Pediatrics, May 2019, vol. 9, Issue 5, pp. 348-354.
Boyer, Jeanne, "Calming patient agitation with dexmedetomidine." Nursing Critical Care (2010); 5 (1): 30-34.
Bryson E.O., et al., "Treatment-Resistant Postictal Agitation After Electroconvulsive Therapy (ECT) Controlled with Dexmedetomidine," The Journal of ECT, 2013, 29(2):e18.
Candiotti et al., "Monitored Anesthesia Care with Dexmedetomidine: A Prospective, Randomized, Double-Blind, Multicenter Trial," Anesth Analg 2010;110(1):47-56.
Canfran, et al., "Comparison of sedation scores and propofol induction doses in dogs after intramuscular administration of dexmedetomidine alone or in combination with methadone, midazolam, or methadone plus midazolam." The Veterinary Journal (2016);210:56-60.
Carrasco et al., "Dexmedetomidine for the Treatment of Hyperactive Delirium Refractory to Haloperidol in Nonintubated ICU Patients: A Nonrandomized Controlled Trial," Critical Care Medicine, 2016, 44:1295-1306, 12 pages.
Carter, et al., "Onset and quality of sedation after intramuscular administration of dexmedetomidine and hydromorphone in various muscle groups in dogs." Journal of the American Veterinary Medical Association (2013); 243(11): 1569-1572.
Center for Drug Evaluation and Research, Application No. 21-038, Medical Review(s), Drug Name: Precedex (dexmedetomidine HCl injection), Dec. 18, 1998, 183 pages.
Center for Drug Evaluation and Research, Application No. 21-038, Pharmacology Review(s), Drug Name: Precedex (dexmedetomidine HCl injection), Dec. 18, 1998, 184 pages.
Changlu et al., "Determination of Effective Dosage in Intranasal Dexmedetomidine Sedation for MRI Scanning with Modified Dixon's Up-and-Down Method in Children," China Pharmaceuticals, (2015), 24(22), 22-24, with English abstract.
Chao and Zhong, "Effects of preoperative intranasal Dexmedetomidine for the bispectral index and median effective concentration of Sevoflurane in children with abdominal surgery by inhalation anesthesia of Sevoflurane." China Medical Herald Magazine (2017); 14 (34): 66-69, 73 (with English Abstract).

(56) References Cited

OTHER PUBLICATIONS

Chen et al., "Dexmedetomidine alleviated isoflurane-induced neurotoxicity in aged rats," Int J Clin Exp Med 2018;11(4):3686-3692.
Chen, et al., "Effect of dexmedetomidine on emergence agitation after oral and maxillofacial surgery." Shanghai Journal of Stomatology (2013); 22(6): 698-701 [with English AbstracUSummary].
Chen et al., "Protective role of dexmedetomidine in unmethylated CpG-induced inflammation responses in BV2 microglia cells," Folia Neuropathol 2016; 54 (4): 382-391.
Cheon and Tkachenko, "Use of dexmedetomidine for prevention of post-operative agitation in a 14 year-old male with Angelman's Syndrome." University of Chicago, Chicago, IL (2014); 1 page.
Cheung, et al., "Analgesic and sedative effects of intranasal dexmedetomidine in third molar surgery under local anaesthesia." British Journal of Anaesthesia (2011); 107 (3): 430-437.
Cheung, et al., "Evaluation of the Analgesic Efficacy of Local Dexmedetomidine Application," Clin J Pain, Jun. 2011, vol. 27, No. 5, pp. 337-382.
Cheung, et al., "Intranasal dexmedetomidine in combination with patientcontrolled sedation during upper gastrointestinal endoscopy: a randomised trial." Acta Anestheologica Scandinavica (2015); 59 (2): 215-223.
Chokroverty, S., "Overview of sleep & sleep disorders," Indian J Med Res 131, Feb. 2010, pp. 126-140.
Chowdhury et al., "General intensive care for patients with traumatic brain injury: An update," Saudi Journal of Anaesthesia, 2014, vol. 8, Issue 2, pp. 256-263.
Christiansen, et al., "Sedation of red porgy (*Pagrus pagrus*) and black sea bass (*Centropristis striata*) using ketamine (K), dexmedetomidine (D) and midazolam (M) delivered via intramuscular injection." Journal of Zoo and Aquarium Research (2014); 2 (3): 62-68.
Cimen, et al., "Comparison of buccal and nasal dexmedetomidine premedication for pediatric patients." Paediatr Anaesth. (2013); 23(2): 134-138.
Citalopram/opiate alkaloids Serotonin syndrome, treated with dexmedetomidine: case report, Reactions Weekly, Nov. 2015, vol. 1579, Issue 1, p. 117.
Clinical Trial Registration No. ChiCTR-IOR-17012415, "Effect of nasal dexmedetomidine on the prevention of emergence agitation in children undergoing day surgery with desoflurane anesthesia." Guangzhou Women and Children Medical Center, Date of Registration: Aug. 18, 2017, Estimated Trial End Date: Mar. 31, 2018, http://www.chictr.org.cn/showprojen.aspx?proj=21174, downloaded May 5, 2018, 3 pages.
ClinicalTrials.gov Identifier: NCT00417664, Is Dexmedetomidine Associated With a Lower Incidence of Postoperative Delirium When Compared to Propofol or Midazolam in Cardiac Surgery Patients, First Posted—Jan. 4, 2007, Last Update Posted—Jan. 4, 2007, retrieved from https://clinicaltrials.gov/ct2/show/NCT00417664, 5 pages.
ClinicalTrials.gov Identifier: NCT02836431, Pharmacokinetic Study of Dexmedetomidine After Intra-nasal Dosing in Children, First Posted—Jul. 19, 2016, Last Update Posted—Jul. 30, 2018, retrieved from https://clinicaltrials.gov/ct2/show/NCT02836431, 8 pages.
ClinicalTrials.gov Identifier: NCT02955732, Pharmacological Characteristics of Intranasally Given Dexmedetomidine in Paediatric Patients (PINDEX), First Posted Nov. 4, 2016, Last Update Posted—Sep. 12, 2018, retrieved from https://clinicaltrials.gov/ct2/show/NCT02955732, 6 pages.
ClinicalTrials.gov Identifier: NCT03668951, Pharmacokinetic Study of Dexmedetomidine After Intra-Nasal and Buccal Dosing in Children (DexPK), First Posted—Sep. 13, 2018, Last Update Posted—May 18, 2021, retrieved from https://clinicaltrials.gov/ct2/show/study/NCT03668951, 7 pages.
ClinicalTrials.gov Identifier: NCT00095251, MENDS Study: Trial in Ventilated ICU Patients Comparing an Alpha2 Agonist Versus a Gamma Aminobutyric Acid (GABA)-Agonist to Determine Delirium Rates, Efficacy of Sedation, Analgesia and Discharge Cognitive Status, First Posted—Nov. 2, 2004, Last Update Posted—Sep. 11, 2018, retrieved from https://clinicaltrials.gov/ct2/show/NCT00095251, 8 pages.
ClinicalTrials.gov Identifier: NCT00351299, Randomized Controlled Trial of Dexmedetomidine for the Treatment of Intensive Care Unit (ICU) Delirium, Jul. 12, 2006, Last Update Posted—Jun. 9, 2017, retrieved from https://clinicaltrials.gov/ct2/show/NCT00351299, 15 pages.
ClinicalTrials.gov Identifier: NCT00455143, Cognitive Protection—Dexmedetomidine and Cognitive Reserve, First Posted—Apr. 3, 2007, Last Update Posted—Jul. 17, 2019, retrieved from https://clinicaltrials.gov/ct2/show/NCT00455143, 20 pages.
ClinicalTrials.gov Identifier: NCT00460473, A Research Study to Evaluate the Effectiveness of Dexmedetomidine in Preventing Delirium After Hip Fracture Repair Surgery, First Posted—Apr. 16, 2007, Last Update Posted—Jul. 24, 2015, retrieved from https://clinicaltrials.gov/ct2/show/NCT00460473, 7 pages.
ClinicalTrials.gov Identifier: NCT00464763, A Research Study to Evaluate the Effectiveness of Dexmedetomidine in Preventing Delirium After Heart Surgery, First Posted—Apr. 24, 2007, Last Update Posted—Mar. 21, 2017, retrieved fromhttps://clinicaltrials.gov/ct2/show/NCT00460473, 7 pages.
ClinicalTrials.gov Identifier: NCT00468052, Decrease Emergence Agitation and Provide Pain Relief for Children Undergoing Tonsillectomy & Adenoidectomy, First Posted—May 1, 2007, Last Update Posted—Dec. 5, 2016, retrieved from https://clinicaltrials.gov/ct2/show/NCT00468052, 24 pages.
ClinicalTrials.gov Identifier: NCT00505804, A Comparison of Dexmedetomidine and Haloperidol in Patients With Intensive Care Unit (ICU)—Associated Agitation and Delirium (Dex), First Posted—Jul. 25, 2007, Last Update Posted—Jan. 24, 2013, retrieved from https://clinicaltrials.gov/ct2/show/NCT00505804, 6 pages.
ClinicalTrials.gov Identifier: NCT00561678, Perioperative Cognitive Function—Dexmedetomidine and Cognitive Reserve, First Posted—Nov. 21, 2007, Last Update Posted—Apr. 23, 2018, retrieved from https://clinicaltrials.gov/ct2/show/NCT00561678, 23 pages.
ClinicalTrials.gov Identifier: NCT00654329, Dexmedetomidine vs Fentanyl for BMT (DexBMT). Children's Research Institute, First Posted Apr. 8, 2018, Results First Posted Apr. 25, 2011, Last Update Posted Apr. 25, 2011, Study Start Date Aug. 2005, https://clinicaltrials.gov/ct2/show/NCT00654329, downloaded May 5, 2018, 6 pages.
ClinicalTrials.gov Identifier: NCT00778063, Study Using Dexmedetomidine to Decreases Emergence Delirium in Pediatric Patients (PED-DEX). Ochsner Health System, First Posted Oct. 23, 2008, Last Update Posted Mar. 15, 2013, Study Start Date Mar. 2009, https://clinicaltrials.gov/ct2/show/NCT00778063, downloaded May 6, 2018, 8 pages.
ClinicalTrials.gov Identifier: NCT00837187, Bioavailability of Dexmedetomidine After Intranasal Administration (INDEX). University of Turku, First Posted Feb. 5, 2009, Last Update Posted Jan. 13, 2010, Study Start Date Mar. 2009, https://clinicaltrials.gov/ct2/show/NCT00837187, downloaded May 6, 2018, 6 pages.
ClinicalTrials.gov Identifier: NCT00857727, Use of Dexmedetomidine to Reduce Emergence Delirium Incident in Children (DexPeds), First Posted—Mar. 9, 2009, Last Update Posted—Nov. 27, 2018, retrieved from https://clinicaltrials.gov/ct2/show/NCT00857727, 18 pages.
ClinicalTrials.gov Identifier: NCT01065701, Comparison of Two Doses of Intranasal Dexmedetomidine as Premedication in Children. The University of Hong Kong, First Posted Feb. 9, 2010, Last Update Posted Oct. 26, 2017, Study Start Date Jul. 2009, https://clinicaltrials.gov/ct2/show/NCT01065701, downloaded May 6, 2018, 5 pages.
ClinicalTrials.gov Identifier: NCT01132794, A Study to Assess the Analgesia and Sedation Using Intranasal Dexmedetomidine in Third Molar Surgery Under Local Anaesthesia. The University of Hong Kong, First Posted May 28, 2010, Last Update Posted Jun. 16, 2010, https://clinicaltrials.gov/ct2/show/NCT01132794, downloaded May 5, 2018, 6 pages.
ClinicalTrials.gov Identifier: NCT01140529, Dexmedetomidine for the Treatment of Delirium After Heart Surgery (DexinDelir), First Posted—Jun. 9, 2010, Last Update Posted—Nov. 1, 2016, retrieved from https://clinicaltrials.gov/ct2/show/NCT01140529, 5 pages.

(56) References Cited

OTHER PUBLICATIONS

ClinicalTrials.gov Identifier: NCT01151865, Dexmedetomidine to Lessen Intensive Care Unit (ICU) Agitation (DahLIA), First Posted—Jun. 29, 2010, Last Update Posted- Jan. 21, 2015, retrieved from https://clinicaltrials.gov/ct2/show/NCT01151865, 9 pages.

ClinicalTrials.gov Identifier: NCT01188551, Dexmedetomidine Versus Fentanyl Following Pressure Equalization Tube Placement. Nationwide Children's Hospital, First Posted Aug. 25, 2010, Last Update Posted Apr. 1, 2014, Study Start Date Jan. 2011, https://clinicaltrials.gov/ct2/show/NCT01188551, downloaded May 5, 2018, 6 pages.

ClinicalTrials.gov Identifier: NCT01255904, A Trial of Oral Chloral Hydrate Versus Intranasal Dexmedetomidine for Sedated Abr Exams. Baylor College of Medicine, First Posted Dec. 8, 2010, Last Update Posted May 16, 2016, Study Start Date Aug. 2011, https://clinicaltrials.gov/ct2/show/NCT01255904, downloaded May 6, 2018, 5 pages.

ClinicalTrials.gov Identifier: NCT01283412, Dexmedetomidine on Postoperative Delirium and Quality of Recovery in Geriatric Patients, First Posted—Jan. 26, 2011, Last Update Posted—Nov. 20, 2013, retrieved from https://clinicaltrials.gov/ct2/show/NCT01283412,4pages.

ClinicalTrials.gov Identifier: NCT01353378, Use of Dexmedetomidine in Children Undergoing Oral Maxillofacial Surgery to Decrease Emergence Delirium, First Posted—May 13, 2011, Last Update Posted—May 5, 2017, retrieved from https://clinicaltrials.gov/ct2/show/NCT01353378, 5 pages.

ClinicalTrials.gov Identifier: NCT01362205, Dexmedetomidine (Precedex) for Severe Alcohol Withdrawal Syndrome (AWS) and Alcohol Withdrawal Delirium (AWD), First Posted—May 30, 2011, Last Update Posted—Nov. 6, 2017, retrieved from https://clinicaltrials.gov/ct2/show/NCT01362205, 36 pages.

ClinicalTrials.gov Identifier: NCT01374737, ED50 of Dexmedetomidine to Prevent Emergence Agitation in Children, First Posted—Jun. 16, 2011, Last Update Posted—Jun. 16, 2011, downloaded Feb. 11, 2018 https://clinicaltrials.gov/ct2/show/NCT01374737, 5 pages.

ClinicalTrials.gov Identifier: NCT01378741, Reducing Delirium After Cardiac Surgery: A Multifaceted Approach of Perioperative Care, First Posted—Jun. 22, 2011, Last Update Posted—Apr. 21, 2015, retrieved from https://clinicaltrials.gov/ct2/show/NCT01378741, 5 pages.

ClinicalTrials.gov Identifier: NCT01512355, The Effect of Dexmedetomidine on Decreasing Emergence Agitation and Delirium in Pediatric Patients Undergoing Strabismus Surgery, First Posted—Jan. 19, 2012, Last Update Posted—Jul. 16, 2015, retrieved from https://clinicaltrials.gov/ct2/show/NCT01512355, 5 pages.

ClinicalTrials.gov Identifier: NCT01513772, The Effect of Dexmedetomidine on the Emergence Agitation in Nasal Surgery, First Posted—Jan. 20, 2012, Last Update Posted—Aug. 9, 2012, retrieved from https://clinicaltrials.gov/ct2/show/NCT01513772, 4 pages.

ClinicalTrials.gov Identifier: NCT01517438, Effects of Serotonin Inhibitors on Patient—controlled Analgesia Related Nausea and Vomiting, First Posted—Jan. 25, 2012, Last Update Posted—Jan. 25, 2012, retrieved from https://clinicaltrials.gov/ct2/show/NCT01517438, 4 pages.

ClinicalTrials.gov Identifier: NCT01517932, Effects of Dexmedetomidine on Stress Response and Postoperative Analgesia, First Posted—Jan. 25, 2012, Last Update Posted—Mar. 20, 2013, retrieved from https://clinicaltrials.gov/ct2/show/NCT01517932, 6 pages.

ClinicalTrials.gov Identifier: NCT01524367, Effect of Single-dose Dexmedetomidine on Emergence Excitement in Adults With Nasotracheal Intubation After Orthognathic Surgery, First Posted—Feb. 2, 2012, Last Update Posted—Feb. 6, 2015, retrieved from https://clinicaltrials.gov/ct2/show/NCT01524367, 6 pages.

ClinicalTrials.gov Identifier: NCT01528891, Dexmedetomidine as a Rapid Bolus in Children for Emergence Agitation, First Posted—Feb. 8, 2012, Last Update Posted—Jan. 20, 2016, downloaded Feb. 11, 2018 https://clinicaltrials.gov/ct2/show/results/NCT01528891, 6 pages.

ClinicalTrials.gov Identifier: NCT01528891, Dexmedetomidine as a Rapid Bolus in Children for Emergence Agitation, First Posted—Feb. 8, 2012, Last Update Posted—Mar. 8, 2018, retrieved from https://clinicaltrials.gov/ct2/show/results/NCT01528891, 15 pages.

ClinicalTrials.gov Identifier: NCT01535287, The Effect of Intramuscular Dexmedetomidine on Emergence Agitation in Children Undergoing With or Without Tube Insertion Under General Anesthesia. First Posted—Feb. 17, 2012, Last Update Posted—Feb. 17, 2012, Study Start Date—Jun. 2010, Estimated Study Completion Date—Jan. 2013, 9 pages.

ClinicalTrials.gov Identifier: NCT01535287, The Effect of Intramuscular Dexmedetomidine on Emergence Agitation in Children Undergoing With or Without Tube Insertion Under General Anesthesia. First Posted—Feb. 17, 2012, Last Update Posted—Jul. 9, 2018, retrieved from https://clinicaltrials.gov/ct2/show/NCT01535287, 24 pages.

ClinicalTrials.gov Identifier: NCT01578161, The Effect of Dexmedetomidine on Emergence Agitation in Children Undergoing a Surgery Under Desflurane Anesthesia, First Posted—Apr. 16, 2012, Last Update Posted—Apr. 16, 2012, downloaded Feb. 11, 2018 https://clinicaltrials.gov/ct2/show/NCT01578161, 6 pages.

ClinicalTrials.gov Identifier: NCT01691001, Effect of Dexmedetomidine on Sevoflurane Requirements and Emergence Agitation in Children Undergoing Ambulatory Surgery, First Posted—Sep. 24, 2012, Last Update Posted—Sep. 24, 2012, retrieved from https://clinicaltrials.gov/ct2/show/NCT01691001, 4 pages.

ClinicalTrials.gov Identifier: NCT01739933, The MENDS2 Study, Maximizing the Efficacy of Sedation and Reducing Neurological Dysfunction and Mortality in Septic Patients With Acute Respiratory Failure (MENDS2), First Posted—Dec. 4, 2012, Last Update Posted—Apr. 5, 2019, retrieved from https://clinicaltrials.gov/ct2/show/NCT01739933, 11 pages.

ClinicalTrials.gov Identifier: NCT01791296, Does Nightly Dexmedetomidine Improve Sleep and Reduce Delirium in ICU Patients? (SKY-DEX), First Posted—Feb. 13, 2013, Last Update Posted—Mar. 17, 2017, retrieved from https://clinicaltrials.gov/ct2/show/NCT01791296, 8 pages.

ClinicalTrials.gov Identifier: NCT01887184, Sedation Using Intranasal Dexmedetomidine in Upper Gastrointestinal Endoscopy. The University of Hong Kong, First Posted Jun. 26, 2013, Last Update Posted Oct. 28, 2014, Study Start Date Jan. 2009, https://clinicaltrials.gov/ct2/show/NCT01887184, downloaded May 5, 2018, 7 pages.

ClinicalTrials.gov Identifier: NCT01895023, Effects of Dexmedetomidine Premedication on Emergence Agitation After Strabismus Surgery in Children. Yao Yusheng, First Posted Jul. 10, 2013, Last Update Posted Jan. 6, 2015, Study Start Date Sep. 2013, https://clinicaltrials.gov/ct2/show/NCT01895023, downloaded May 5, 2018, 7 pages.

ClinicalTrials.gov Identifier: NCT01900405, Intranasal Dexmedetomidine Sedation for Pediatric CT Imaging. University of Sao Paulo, First Posted Jul. 16, 2013, Last Update Posted Jul. 16, 2013, Study Start Date Apr. 2013, downloaded https://clinicaltrials.gov/ct2/show/NCT01900405, downloaded May 6, 2018, 7 pages.

ClinicalTrials.gov Identifier: NCT01901588, Efficacy of Single-Shot Dexmedetomidine Versus Placebo in Preventing Pediatric Emergence Delirium in Strabismus Surgery, First Posted—Mar. 8, 2016, Last Update Posted—Last Update Posted—Jul. 11, 2016, retrieved from https://clinicaltrials.gov/ct2/show/NCT01901588, 5 pages.

ClinicalTrials.gov Identifier: NCT01904760, Dexmedetomidine to Prevent Agitation After Free Flap Surgery, First Posted—Jul. 22, 2013, Last Update Posted—Nov. 13, 2014, retrieved from https://clinicaltrials.gov/ct2/show/NCT01904760, 6 pages.

ClinicalTrials.gov Identifier: NCT01934049, Postoperative Recovery in Elderly Patients Undergoing Hip Hemi-arthroplasty, First Posted—Sep. 4, 2013, Last Update Posted—Sep. 10, 2013, retrieved from https://clinicaltrials.gov/ct2/show/NCT01934049, 7 pages.

ClinicalTrials.gov Identifier: NCT01937611, Intramuscular Dexmedetomidine as Premedication. First Posted—Sep. 9, 2013, Last Update Posted—Sep. 9, 2013, Study Start Date—Mar. 2013, Estimated Study Completion Date—Oct. 2013, 8 pages.

ClinicalTrials.gov Identifier: NCT01966315, The Comparison of Dexmedetomidine and Midazolam for the Sleep in Intensive Care

(56) References Cited

OTHER PUBLICATIONS

Unit, First Posted—Oct. 21, 2013, Last Update Posted—Apr. 23, 2019, retrieved from https://clinicaltrials.gov/ct2/show/NCT01966315, 5 pages.
ClinicalTrials.gov Identifier: NCT02007798, Small-dose Dexmedetomidine Effects on Recovery Profiles of Supratentorial Tumors Patients From General Anesthesia, First Posted—Dec. 11, 2013, Last Update Posted—Jan. 14, 2014, retrieved from https://clinicaltrials.gov/ct2/show/NCT02007798, 8 pages.
ClinicalTrials.gov Identifier: NCT02072083, Intranasal Dexmedetomidine vs Midazolam-ketamine Combination for Premedication of Pediatric Patients. TC Erciyes University, First Posted Feb. 26, 2014, Last Update Posted Apr. 14, 2015, Study Start Date Feb. 2014, https://clinicaltrials.gov/ct2/show/NCT02072083, downloaded May 5, 2018, 6 pages.
ClinicalTrials.gov Identifier: NCT02077712, Intranasal Dexmedetomidine Sedation for Ophthalmic Examinations in Children (DEX-EYE). Sun Yat-sen University, First Posted Mar. 4, 2014, Last Update Posted May 3, 2016, Study Start Date Feb. 2014, https://clinicaltrials.gov/ct2/show/NCT02077712, downloaded May 5, 2018, 7 pages.
ClinicalTrials.gov Identifier: NCT02080169, Safety and Efficacy of Combined Sedation With Midazolam and Dexmedetomidine in ICU Patients, First Posted—Mar. 6, 2014, Last Update Posted—Mar. 6, 2014, retrieved from https://clinicaltrials.gov/ct2/show/NCT02080169, 8 pages.
ClinicalTrials.gov Identifier: NCT02096068, Neuroprotection With Dexmedetomidine in Patients Undergoing Elective Cardiac or Abdominal Surgery (Neuprodex), First Posted—Mar. 26, 2014, Last Update Posted—Aug. 22, 2018, retrieved fromhttps://clinicaltrials.gov/ct2/show/NCT02096068, 9 pages.
ClinicalTrials.gov Identifier: NCT02104297, Effect of Deksmedetomidine and Remifentanil in Extubation Agitation (EA), First Posted—Apr. 4, 2014, Last Update Posted - Apr. 4, 2014, retrieved from https://clinicaltrials.gov/ct2/show/NCT02104297, 5 pages.
ClinicalTrials.gov Identifier: NCT02108171, Intranasal Dexmedetomidine Premedication. Guangzhou First People's Hospital, First Posted Apr. 9, 2014, Last Update Posted Mar. 14, 2016, Study Start Date Mar. 2014, https://clinicaltrials.gov/ct2/show/NCT02108171, downloaded May 5, 2018, 24 pages.
ClinicalTrials.gov Identifier: NCT02117726, Impact of Various Sedation Regimens on the Incidence of Delirium, First Posted—Apr. 21, 2014, Last Update Posted—Jul. 16, 2014, retrieved from https://clinicaltrials.gov/ct2/show/NCT02117726, 7 pages.
ClinicalTrials.gov Identifier: NCT02168439, Intranasal Dexmedetomidine vs Intranasal Midazolam as Anxiolysis Prior to Pediatric Laceration Repair. University of Pittsburgh, Results First Posted Mar. 10, 2017, Last Update Posted Mar. 10, 2017, Study Start Date Jun. 2014, https://clinicaltrials.gov/ct2/show/NCT02168439, downloaded May 6, 2018, 6 pages.
ClinicalTrials.gov Identifier: NCT02169336, Placebo-Controlled Evaluation of Intranasal Dexmedetomidine for Postoperative Analgesia Following Bunionectomy. Recro Pharma, Inc., First Posted Jun. 23, 2014, Last Update Posted Dec. 10, 2015, Study Start Date Jun. 2014, https://clinicaltrials.gov/ct2/show/NCT02169336, downloaded May 6, 2018, 7 pages.
ClinicalTrials.gov Identifier: NCT02169843, Minimizing ICU Neurological Dysfunction With Dexmedetomidine-induced Sleep (MINDDS), First Posted—Jun. 23, 2014, Last Update Posted—Jun. 23, 2014, retrieved from https://clinicaltrials.gov/ct2/show/NCT02169843, 6 pages.
ClinicalTrials.gov Identifier: NCT02211118, Sedation and Physiological Effects of Intranasal Dexmedetomidine in Severe COPD. Dayton VA Medical Center, First Posted Aug. 7, 2014, Last Update Posted Feb. 8, 2017, Study Start Date Oct. 2014, https://clinicaltrials.gov/ct2/show/NCT02211118, 6 pages.
ClinicalTrials.gov Identifier: NCT02222636, The Clinical Research of Intranasal Dexmedetomidine Used in Plastic Surgery of Children. Xijing Hospital, First Posted Aug. 21, 2014, Last Update Posted Aug. 21, 2014, Study Start Date Sep. 2014, https://clinicaltrials.gov/ct2/show/NCT02222636, downloaded May 6, 2018, 6 pages.
ClinicalTrials.gov Identifier: NCT02225210, Effects of Dexmedetomidine Sedation on Delirium and Haemodynamic in Mechanical Ventilated Elderly Patients, First Posted—Aug. 26, 2014, Last Update Posted—Aug. 26, 2014, retrieved from https://clinicaltrials.gov/ct2/show/NCT02225210, 6 pages.
ClinicalTrials.gov Identifier: NCT02239445, Intranasal Dexmedetomidine VS Oral Chloral Hydrate for Rescue Sedation During Magnetic Resonance Imaging. Guangzhou Women and Children's Medical Center, First Posted Sep. 12, 2014, Last Update Posted May 12, 2015, Study Start Date Sep. 2014, https://clinicaltrials.gov/ct2/show/NCT02239445, downloaded May 6, 2018, 7 pages.
ClinicalTrials.gov Identifier: NCT02245256, Efficacy of Low-dose Dexmedetomidine to Prevent Delirium in Liver Transplant Patients, First Posted—Sep. 19, 2014, Last Update Posted—Jan. 25, 2018, retrieved from https://clinicaltrials.gov/ct2/show/NCT02245256, 5 pages.
ClinicalTrials.gov Identifier: NCT02250703, Intranasal Dexmedetomidine Premedication in Children. Results First Posted Jul. 7, 2017, Last Update Posted Jul. 7, 2017, Study Start Date Sep. 2014, downloaded https://clinicaltrials.gov/ct2/show/NCT02250703, downloaded May 6, 2018, 8 pages.
ClinicalTrials.gov Identifier: NCT02253199, The Effect of Age on the Median Effective Dose (ED50) of Intranasal Dexmedetomidine for Rescue Sedation Following Failed Sedation With Oral Chloral Hydrate During Magnetic Resonance Imaging. Guangzhou Women and Children's Medical Center, First Posted Oct. 1, 2014, Last Update Posted Mar. 29, 2016, Study Start Date Oct. 2014, https://clinicaltrials.gov/ct2/show/NCT02253199, downloaded May 5, 2018, 7 pages.
ClinicalTrials.gov Identifier: NCT02267538, Dexmedetomidine and Delirium in Patients After Cardiac Surgery, First Posted—Feb. 2, 2018, Last Update Posted—Mar. 5, 2018, retrieved from https://clinicaltrials.gov/ct2/show/NCT02267538, 12 pages.
ClinicalTrials.gov Identifier: NCT02275182, Impact of Dexmedetomidine on the Post—Operative Cognition Dysfunction(POCD) in Geriatric Patients, First Posted—Oct. 27, 2014, Last Update Posted—Apr. 25, 2018, retrieved from https://clinicaltrials.gov/ct2/show/NCT02275182, 8 pages.
ClinicalTrials.gov Identifier: NCT02284243, Placebo-Controlled Evaluation of Intranasal Dexmedetomidine for Postoperative Analgesia Following Bunionectomy Surgery. Recro Pharma, Inc., First Posted Nov. 5, 2014, Last Update Posted May 2, 2017, Study Start Date Oct. 2014, https://clinicaltrials.gov/ct2/show/NCT02284243, downloaded May 6, 2018, 8 pages.
ClinicalTrials.gov Identifier: NCT02299232, Dexmedetomidine in Children for Magnetic Resonance Imaging (MRI) Sedation (DEX). Sisli Hamidiye Etfal Training and Research Hospital, First Posted Nov. 24, 2014, Last Update Posted Oct. 25, 2017, Study Start Date Feb. 2014, https://clinicaltrials.gov/ct2/show/NCT02299232, downloaded May 6, 2018, 6 pages.
ClinicalTrials.gov Identifier: NCT02366299, Comparison of Dexmedetomidine and Propofol on the Delirium and Neuroinflammation in Patients With SIRS, First Posted—Feb. 19, 2015, Last Update Posted—Feb. 19, 2015, retrieved from https://clinicaltrials.gov/ct2/show/NCT02366299, 4 pages.
ClinicalTrials.gov Identifier: NCT02394418, Effect of Sevoflurane, Propofol and Dexmedetomidine on Delirium & Neuroinflammation in Mechanically Ventilated Patients, First Posted—Mar. 20, 2015, Last Update Posted—Jul. 5, 2017, retrieved from https://clinicaltrials.gov/ct2/show/NCT02394418, 5 pages.
ClinicalTrials.gov Identifier: NCT02412150, Effect of Dexmedetomidine After Thyroidectomy, First Posted—Apr. 9, 2015, Last Update Posted—Mar. 6, 2019, retrieved from https://clinicaltrials.gov/ct2/show/NCT02412150, 4 pages.
ClinicalTrials.gov Identifier: NCT02459509, A Comparison of Two Doses of Intranasal Dexmedetomidine for Premedication in Children. The University of Hong Kong, First Posted Jun. 2, 2015, Last Update Posted Apr. 18, 2016, Study Start Date Jun. 2015, https://clinicaltrials.gov/ct2/show/NCT02459509, downloaded May 6, 2018, 8 pages.

(56) References Cited

OTHER PUBLICATIONS

ClinicalTrials.gov Identifier: NCT02509949, Effects of Dexmedetomidine on Delirium After Living Donor Renal Transplantation in Adult Patients, First Posted—Jul. 28, 2015, Last Update Posted—Jun. 12, 2018, retrieved from https://clinicaltrials.gov/ct2/show/NCT02509949, 4 pages.

ClinicalTrials.gov Identifier: NCT02528513, Midazolam Used Alone or Sequential Use of Midazolam and Propofol/Dexmedetomidine in Mechanically Ventilated Patients, First Posted—Aug. 19, 2015, Last Update Posted—Apr. 28, 2016, retrieved from https://clinicaltrials.gov/ct2/show/NCT02528513, 9 pages.

ClinicalTrials.gov Identifier: NCT02544906, Propofol Versus Dexmedetomidine for Prevention of Sevoflurane Agitation in Recipients of Living Donor Liver Transplantation (Agitation), First Posted—Sep. 9, 2015, Last Update Posted—Sep. 9, 2015 retrieved from https://clinicaltrials.gov/ct2/show/NCT02544906, 4 pages.

ClinicalTrials.gov Identifier: NCT02546765, Dexmedetomidine and IV Acetaminophen for the Prevention of Postoperative Delirium Following Cardiac Surgery (DEXACET), First Posted—Sep. 11, 2015, Last Update Posted—Aug. 1, 2018, retrieved from https://clinicaltrials.gov/ct2/show/NCT02546765, 9 pages.

ClinicalTrials.gov Identifier: NCT02548923, Dexmedetomidine Versus Propofol for Prolonged Sedation in Critically Ill Trauma and Surgical Patients, First Posted—Sep. 14, 2015, Last Update Posted—Sep. 14, 2015, retrieved from https://clinicaltrials.gov/ct2/show/NCT02548923, 5 pages.

ClinicalTrials.gov Identifier: NCT02573558, Intraoperative Sedation and Postoperative Delirium, First Posted—Oct. 12, 2015, Last Update Posted—Apr. 6, 2016, retrieved from https://clinicaltrials.gov/ct2/show/NCT02573558, 5 pages.

ClinicalTrials.gov Identifier: NCT02675049, Efficacy and Optimal Dose Selection of Intranasal Dexmedetomidine During Breast Lumpectomy Under Local Anaesthesia. Tianjin Medical University Cancer Institute and Hospital, First Posted Feb. 5, 2016, Last Update Posted Mar. 1, 2016, Study Start Date Jan. 2016, https://clinicaltrials.gov/ct2/show/NCT02675049, downloaded May 5, 2018, 6 pages.

ClinicalTrials.gov Identifier: NCT02699801, Dexmedetomidine Use in ICU Sedation and Postoperative Recovery in Elderly Patients and Post-cardiac Surgery (DIRECT), First Posted—Mar. 4, 2016, Last Update Posted—Nov. 3, 2016, retrieved from https://clinicaltrials.gov/ct2/show/NCT02699801, 8 pages.

ClinicalTrials.gov Identifier: NCT02720705, Transbucal Dexmedetomidine for Prevention of Sevoflurane Emergence Agitation in Pre-school Children, First Posted—Mar. 28, 2016, Last Update Posted—Dec. 27, 2017, downloaded Feb. 11, 2018 https://clinicaltrials.gov/ct2/show/NCT02720705, 7 pages.

ClinicalTrials.gov Identifier: NCT02720705, Transbucal Dexmedetomidine for Prevention of Sevoflurane Emergence Agitation in Pre-school Children, First Posted—Mar. 28, 2016, Last Update Posted—Nov. 1, 2018, retrieved from https://clinicaltrials.gov/ct2/show/NCT02720705, 6 pages.

ClinicalTrials.gov Identifier: NCT02757495, Can Caudal Dexmedetomidine Prevents Sevoflurane Induced Emergence Agitation in Children, First Posted—May 2, 2016, Last Update Posted—Feb. 27, 2019, retrieved from https://clinicaltrials.gov/ct2/show/NCT02757495, 6 pages.

ClinicalTrials.gov Identifier: NCT02773797, Placebo Controlled Evaluation of Sedation and Physiological Response to Intranasal Dexmedetomidine in Severe COPD. Dayton VA Medical Center, First PostedMay 16, 2016, Last Update Posted May 16, 2016, Study Start Date Aug. 2016, https://clinicaltrials.gov/ct2/show/NCT02773797, 7 pages.

ClinicalTrials.gov Identifier: NCT02780427, ED50 and ED95 of Intranasal Dexmedetomidine in Pediatric Patients Undergoing Transthoracic Echocardiography Study. Guangzhou Women and Children's Medical Center, First Posted May 23, 2016, Last Update Posted Nov. 21, 2017, Study Start Date Jun. 2016, https://clinicaltrials.gov/ct2/show/NCT02780427, downloaded May 6, 2018, 8 pages.

ClinicalTrials.gov Identifier: NCT02793986, Dexmedetomidine vs Propofol Sedation Reduces Postoperative Delirium in Patients Receiving Hip Arthroplasty, First Posted—Jun. 8, 2016, Last Update Posted—Jun. 29, 2017, retrieved from https://clinicaltrials.gov/ct2/show/NCT02793986, 6 pages.

ClinicalTrials.gov Identifier: NCT02809937, Dexmedetomidine and Long-term Outcome in Elderly Patients After Surgery, First Posted—Jun. 22, 2016, Last Update Posted - Jun. 16, 2017, retrieved from https://clinicaltrials.gov/ct2/show/NCT02809937, 10 pages.

ClinicalTrials.gov Identifier: NCT02818569, Repurposing Dexmedetomidine as an Orally Administered Sleep Therapeutic, First Posted—Jun. 29, 2016, Last Update Posted—Aug. 17, 2018, retrieved from https://clinicaltrials.gov/ct2/show/NCT02818569, 5 pages.

ClinicalTrials.gov Identifier: NCT02836431, Pharmacokinetic Study of Dexmedetomidine After Intra-nasal Dosing in Children. Children's Hospital Medical Center, First Posted Jul. 19, 2016, Last Update Posted Aug. 1, 2017, Study Start Date Jan. 2016, https://clinicaltrials.gov/ct2/show/NCT02836431, downloaded May 6, 2018, 8 pages.

ClinicalTrials.gov Identifier: NCT02856594, Minimizing ICU Neurological Dysfunction With Dexmedetomidine-induced Sleep (MINDDS), First Posted—Aug. 5, 2016, Last Update Posted—Jan. 8, 2019, retrieved from https://clinicaltrials.gov/ct2/show/NCT02856594, 6 pages.

ClinicalTrials.gov Identifier: NCT02903407, Pain, Agitation and Delirium (PAD) Protocol in the Duke CICU, First Posted—Sep. 16, 2016, Last Update Posted—Oct. 18, 2018, retrieved from https://clinicaltrials.gov/ct2/show/NCT02903407, 9 pages.

ClinicalTrials.gov Identifier: NCT02917018, Effect of Dexmedetomidine on Stress Response and Emergence Agitation During Laparoscopic Surgery, First Posted—Sep. 28, 2016, Last Update Posted—Jan. 4, 2017, downloaded Feb. 11, 2018 https://clinicaltrials.gov/ct2/show/NCT02917018, 6 pages.

ClinicalTrials.gov Identifier: NCT02923128, Whether Dexmedetomidine Can Improve the Prognosis of Elderly Patients With Postoperative Cognitive Dysfunction, First Posted—Oct. 4, 2016, Last Update Posted—Oct. 11, 2016, retrieved from https://clinicaltrials.gov/ct2/show/NCT02923128, 7 pages.

ClinicalTrials.gov Identifier: NCT02951793, Abuse and Addiction in ICU, First Posted—Nov. 1, 2016, Last Update Posted—May 19, 2017, retrieved from https://clinicaltrials.gov/ct2/show/NCT02951793, 7 pages.

ClinicalTrials.gov Identifier: NCT02955732, Pharmacological Characteristics of Intranasally Given Dexmedetomidine in Paediatric Patients (PINDEX). Turku University Hospital, First Posted Nov. 4, 2016, Last Update Posted Dec. 14, 2017, Study Start Date Jan. 1, 2017, https://clinicaltrials.gov/ct2/show/NCT02955732, downloaded May 6, 2018, 6 pages.

ClinicalTrials.gov Identifier: NCT02985697, Safety and Efficacy of Intranasal Dexmedetomidine. Bon Secours Pediatric Dental Associates, First Posted Dec. 7, 2016, Last Update Posted Dec. 7, 2016, Study Start Date Jan. 2017, https://clinicaltrials.gov/ct2/show/NCT02985697, downloaded May 6, 2018, 8 pages.

ClinicalTrials.gov Identifier: NCT03012984, Dexmedetomidine Supplemented Analgesia and Incidence of Postoperative Delirium, First Posted—Jan. 6, 2017, Last Update Posted—Jul. 31, 2018, retrieved from https://clinicaltrials.gov/ct2/show/NCT03012984, 13 pages.

ClinicalTrials.gov Identifier: NCT03069638, Intranasal Dexmedetomidine Sedation During Intraarticular Joint Injections in Pediatric Population, First Posted—Mar. 3, 2017, Last Update Posted—May 12, 2021, retrieved from https://clinicaltrials.gov/ct2/show/NCT03069638, 8 pages.

ClinicalTrials.gov Identifier: NCT03069638, Intranasal Dexmedetomidine Sedation During Intra-articular Joint Injections in Pediatric Population. University of Oulu, First Posted Mar. 3, 2017, Last Update Posted Mar. 15, 2018, Actual Study Start Date Feb. 1, 2017, https://clinicaltrials.gov/ct2/show/NCT03069638, downloaded May 6, 2018, 7 pages.

ClinicalTrials.gov Identifier: NCT03078946, Dexmedetomidine Versus Morphine and Midazolam in Prevention and Treatment of Delirium After Adult Cardiac Surgery, First Posted—Mar. 14, 2017,

(56) References Cited

OTHER PUBLICATIONS

Last Update Posted—Mar. 14, 2017, retrieved from https://clinicaltrials.gov/ct2/show/NCT03078946, 6 pages.
ClinicalTrials.gov Identifier: NCT03120247, Pharmacokinetics and Pharmacodynamics of Oral Transmucosal Dexmedetomidine. (OTM/DEX/PK), First Posted—Apr. 19, 2017, Last Update Posted—Apr. 19, 2017, downloaded Feb. 11, 2018 https://clinicaltrials.gov/ct2/show/NCT03120247, 7 pages.
ClinicalTrials.gov Identifier: NCT03120247, Pharmacokinetics and Pharmacodynamics of Oral Transmucosal Dexmedetomidine. (OTM/DEX/PK), First Posted—Apr. 19, 2017, Last Update Posted—Oct. 2, 2018, retrieved from https://clinicaltrials.gov/ct2/show/NCT03120247, 6 pages.
ClinicalTrials.gov Identifier: NCT03120442, Postoperative Delirium After Total Knee Arthroplasty Under Regional Anesthesia, First Posted—Apr. 19, 2017, Last Update Posted—Mar. 26, 2019, retrieved from https://clinicaltrials.gov/ct2/show/NCT03120442, 12 pages.
ClinicalTrials.gov Identifier: NCT03131375, Dexmedetomidine Reduces Emergence Delirium in Children Undergoing Tonsillectomy With Propofol Anesthesia, First Posted—Apr. 27, 2017, Last Update Posted—Jul. 9, 2018, retrieved from https://clinicaltrials.gov/ct2/show/NCT03131375, 7 pages.
ClinicalTrials.gov Identifier: NCT03151863, Intranasal Dexmedetomidine for Procedural Pain Management in Elderly Adults in Palliative Care (INDEX). Walid Habre, First Posted May 12, 2017, Last Update Posted May 16, 2017, Estimated Study Start Date Jul. 1, 2017, https://clinicaltrials.gov/ct2/show/NCT03151863, downloaded May 5, 2018, 9 pages.
ClinicalTrials.gov Identifier: NCT03171740, Premedication With Intranasal Dexmedetomidine or Midazolam for Prevention of Emergence Agitation in Children. Brasilia University Hospital, First Posted May 31, 2017, Last Update Posted Sep. 13, 2017, Study Start Date Jun. 1, 2017, https://clinicaltrials.gov/ct2/show/NCT03171740, downloaded May 5, 2018, 8 pages.
ClinicalTrials.gov Identifier: NCT03171740, Premedication With Intranasal Dexmedetomidine or Midazolam for Prevention of Emergence Agitation in Children, First Posted—May 31, 2017, Last Update Posted—Jul. 13, 2018, retrieved from https://clinicaltrials.gov/ct2/show/NCT03171740, 7 pages.
ClinicalTrials.gov Identifier: NCT03172897, Low-dose Dexmedetomidine in Mechanically Ventilated ICU Patients, First Posted—Jun. 1, 2017, Last Update Posted—Jun. 21, 2019, retrieved from https://clinicaltrials.gov/ct2/show/NCT03172897, 10 pages.
ClinicalTrials.gov Identifier: NCT03174678, Dexmedetomidine Premedication in Children, First Posted—Jun. 2, 2017, Last Update Posted—Jun. 2, 2017, retrieved from https://clinicaltrials.gov/ct2/show/NCT03174678, 6 pages.
ClinicalTrials.gov Identifier: NCT03220880, Intranasal Dexmedetomidine Sedation in Children for Non-painful Procedures. Columbia University, First Posted Jul. 18, 2017, Last Update Posted Apr. 10, 2018, Study Start Date Nov. 1, 2018, https://clinicaltrials.gov/ct2/show/NCT03220880, downloaded May 5, 2018, 9 pages.
ClinicalTrials.gov Identifier: NCT03251222, Intranasal Sedation With Dexmedetomidine. University Medical Centre Ljubljana, First Posted Aug. 16, 2017, Last Update Posted Aug. 16, 2017, Actual Study Start Date Jan. 1, 2017, https://clinicaltrials.gov/ct2/show/NCT03251222, downloaded May 6, 2018, 8 pages.
ClinicalTrials.gov Identifier: NCT03251651, Intraoperative Sedatives and Postoperative Deilirium, First Posted—Aug. 16, 2017, Last Update Posted—Apr. 24, 2018, retrieved from https://clinicaltrials.gov/ct2/show/NCT03251651, 6 pages.
ClinicalTrials.gov Identifier: NCT03262090, Effect of Dexmedetomidine on the Prevention of Emergence Agitation in Children Undergoing Day Surgery, First Posted—Aug. 25, 2017, Last Update Posted—Jun. 25, 2019, retrieved from https://clinicaltrials.gov/ct2/show/NCT03262090, 6 pages.
ClinicalTrials.gov Identifier: NCT03290625, Intranasal Sedation With Dexmedetomidine and Ketamine in Pediatric Dentistry (Naso II). Universidade Federal de Goias, First Posted Sep. 25, 2017, Last Update Posted Feb. 20, 2018, Actual Study Start Date Nov. 9, 2017, https://clinicaltrials.gov/ct2/show/NCT03290625, downloaded May 6, 2018, 10 pages.
ClinicalTrials.gov Identifier: NCT03293277, Safety, Pharmacokinetics and Pharmacodynamics of Intranasal Dexmedetomidine in Healthy Subjects. Jiangsu HengRui Medicine Co., Ltd., First Posted Sep. 26, 2017, Last Update Posted Jan. 23, 2018, Study Start Date Jul. 26, 2017, https://clinicaltrials.gov/ct2/show/NCT03293277, downloaded May 5, 2018, 7 pages.
ClinicalTrials.gov Identifier: NCT03293927, Polypharmacy-related Adverse Events in Critically Ill Children, First Posted—Sep. 26, 2017, Last Update Posted—Jul. 18, 2019, retrieved from https://clinicaltrials.gov/ct2/show/NCT03293927, 5 pages.
ClinicalTrials.gov Identifier: NCT03317067, Effects of Dexmedetomidine on Delirium Duration of Non-intubated ICU Patients (4D Trial) (4D), First Posted—Oct. 23, 2017, Last Update Posted—Feb. 4, 2019, retrieved from https://clinicaltrials.gov/ct2/show/NCT03317067, 7 pages.
ClinicalTrials.gov Identifier: NCT03323593, Pharmacokinetics of Different Mode Administration of Intranasal Dexmedetomidine. The University of Hong Kong, First Posted Oct. 27, 2017, Last Update Posted Oct. 27, 2017, Study Start Date May 2013, https://clinicaltrials.gov/ct2/show/NCT03323593, downloaded May 6, 2018, 5 pages.
ClinicalTrials.gov Identifier: NCT03337672, Comparison of Dexmedetomidine and Midazolam for Prevention of Emergence Delirium in Children, First Posted—Nov. 9, 2017, Last Update Posted—Jan. 9, 2019, retrieved from https://clinicaltrials.gov/ct2/show/NCT03337672, 6 pages.
ClinicalTrials.gov Identifier: NCT03346226, How Different Sedatives Affect Hip Fracture Patient's Postoperative Delirium, First Posted—Nov. 17, 2017, Last Update Posted—Dec. 13, 2017, retrieved from https://clinicaltrials.gov/ct2/show/NCT03346226, 9 pages.
ClinicalTrials.gov Identifier: NCT03394430, Comparison of Midazolam or Dexmedetomidine on Epileptiform EEG During Sevoflurane Mask Induction. First Posted Jan. 9, 2018, Last Update Posted Feb. 13, 2018, Estimated Study Start Date Apr. 1, 2018, https://clinicaltrials.gov/ct2/show/NCT03394430, downloaded May 5, 2018, 8 pages.
ClinicalTrials.gov Identifier: NCT03399838, Comparing in Dexmedetomidine With po/pr Midazolam for Procedural Sedation in the Pediatric Emergency Department (PedINDEX). University Hospital Inselspital, Berne, First Posted Jan. 16, 2018, Last Update Posted Jan. 16, 2018, https://clinicaltrials.gov/ct2/show/NCT03399838, downloaded May 6, 2018, 6 pages.
ClinicalTrials.gov Identifier: NCT03417999, Pharmacokinetic Study of Intranasal Dexmedetomidine in Pediatric Patients With Congenital Heart Disease. Children's Hospital of Philadelphia, First Posted Jan. 31, 2018, Last Update Posted Apr. 12, 2018, Estimated Study Start Date May 2018, https://clinicaltrials.gov/ct2/show/NCT03417999, downloaded May 6, 2018, 7 pages.
ClinicalTrials.gov Identifier: NCT03477994, Efficacy of Dexmedetomidine Versus Clonidine to Control Delirium in Patients Undergoing CABG, First Posted—Mar. 27, 2018, Last Update Posted—Jul. 11, 2019, retrieved from https://clinicaltrials.gov/ct2/show/NCT03477994, 6 pages.
ClinicalTrials.gov Identifier: NCT03596775, Effect of Dexmedetomidine on Emergence Agitation and Postoperative Behavior Changes in Children, First Posted—Jul. 24, 2018, Last Update Posted—Sep. 7, 2018, retrieved from https://clinicaltrials.gov/ct2/show/NCT03596775?cond=Dexmedetomidine&sfpd_s=07%2F14%2F2018&sfpd_e=11%2F20%2F2018&rank=29, 7 pages.
ClinicalTrials.gov Identifier: NCT03600727, Propofol and Dexmedetomidine on Inflammation, First Posted—Jul. 26, 2018, Last Update Posted—Jul. 26, 2018, retrieved from https://clinicaltrials.gov/ct2/show/NCT03600727?cond=Dexmedetomidine&sfpd_s=07%2F14%2F2018&sfpd_e=11%2F20%2F2018&rank=21, 6 pages.
ClinicalTrials.gov Identifier: NCT03624595, Low-dose Dexmedetomidine and Postoperative Delirium After Cardiac Surgery, First Posted—Aug. 10, 2018, Last Update Posted—Apr. 24, 2019, retrieved from https://clinicaltrials.gov/ct2/show/NCT03624595?cond=Dexmedetomidine&sfpd_s=07%2F14%2F2018&sfpd_e=11%2F20%2F2018&rank=2, 12 pages.

(56) References Cited

OTHER PUBLICATIONS

ClinicalTrials.gov Identifier: NCT03629262, Dexmedetomidine Supplemented Intravenous Analgesia in Elderly After Orthopedic Surgery, First Posted—Aug. 14, 2018, Last Update Posted—Dec. 11, 2018, retrieved from https://clinicaltrials.gov/ct2/show/NCT03629262?cond=Dexmedetomidine&sfpd_s=07%2F14%2F2018&sfpd_e=11%2F20%2F2018&rank=3, 11 pages.

ClinicalTrials.gov Identifier: NCT03629483, Dexmedetomidine Combined With Ropivacaine for Postoperative Continuous Femoral Nerve Block, First Posted—Aug. 14, 2018, Last Update Posted—Dec. 11, 2018, retrieved from https://clinicaltrials.gov/ct2/show/NCT03629483?cond=Dexmedetomidine&sfpd_s-07%2F14%2F2018&sfpd_e=11%2F20%2F2018&rank=4, 10 pages.

ClinicalTrials.gov Identifier: NCT03655847, Acceptable Hemodynamic Changes in Dexmedetomidine for Single Intravenous Bolus Injection, First Posted—Aug. 31, 2018, Last Update Posted—Feb. 15, 2019, retrieved from https://clinicaltrials.gov/ct2/show/NCT03655847?cond=Dexmed etomidine&sfpd_s=07%2F14%2F2018&sfpd_e=11%2F20%2F2018&rank=9, 7 pages.

ClinicalTrials.gov Identifier: NCT03668951, Pharmacokinetic Study of Dexmedetomidine After Intra-Nasal and Buccal Dosing in Children (DexPK), First Posted—Sep. 13, 2018, Last Update Posted—Sep. 13, 2018, retrieved from https://clinicaltrials.gov/ct2/show/NCT03668951?term=buccal&cond=dexmedetomidine&sfpd_s=07%2F01%2F2018&rank=1, 7 pages.

ClinicalTrials.gov Identifier: NCT03708315, Precedex for Schizophrenia (DEX), First Posted—Oct. 17, 2018, Last Update Posted—Oct. 17, 2018, retrieved from https://clinicaltrials.gov/ct2/show/NCT03708315?cond=Dexmedetomidine&sfpd_s=07%2F14%2F2018&sfpd_e=11%2F20%2F2018&rank=33, 6 pages.

ClinicalTrials.gov Identifier: NCT03742180, Sublingual Ketorolac Compared to Intranasal Dexmedetomidine for Postoperative Analgesia in Pediatric Patients Undergoing Bilateral Myringotomy, First Posted—Nov. 15, 2018, Last Update Posted—Nov. 15, 2018, retrieved from https://clinicaltrials.gov/ct2/show/NCT03742180?te rm=sublingual&cond=dexmedetomidine&sfpd_s=07%2F01%2F2018&rank=1, 6 pages.

ClinicalTrials.gov Identifier: NCT03779282, Ketodex for Emergence Delirium in Children Undergoing Outpatient Strabismus Surgery, First Posted—Dec. 18, 2018, Last Update Posted—Dec. 18, 2018, retrieved from https://clinicaltrials.gov/ct2/show/NCT03779282?term=dexmedetomidine&cond=Agitati on%2C+Emergence, 5 pages.

ClinicalTrials.gov Identifier: NCT03806777, Intra-nasal Dexmedetomidine for Children Undergoing MRI Imaging (DexmedMRI), First Posted—Jan. 16, 2019, Last Update Posted—Jan. 25, 2019, retrieved from https://clinicaltrials.gov/ct2/show/NCT03806777, 7 pages.

ClinicalTrials.gov Identifier: NCT03877120, Treatment of Alcohol Withdrawal Syndrome: Dexmedetomidine Vs Diazepam in a Hospital O'horn, First Posted—Mar. 15, 2019, Last Update Posted—Mar. 15, 2019, retrieved from https://clinicaltrials.gov/ct2/show/NCT03877120, 6 pages.

ClinicalTrials.gov Identifier: NCT03926663, Intranasal Injection of Dexmedetomidine and Bupivacaine in Septoplasty Surgeries, First Posted—Apr. 24, 2019, Last Update Posted—Aug. 1, 2019, retrieved from https://clinicaltrials.gov/ct2/show/NCT03926663, 7 pages.

ClinicalTrials.gov Identifier: NCT03938831, Dexmedetomidine and Delirium in Elderly Patients, First Posted—May 6, 2019, Last Update Posted—May 6, 2019, retrieved from https://clinicaltrials.gov/ct2/show/NCT03938831, 5 pages.

ClinicalTrials.gov Identifier: NCT03957304, Intranasal Dexmedetomidine Dose-finding Study, First Posted—May 21, 2019, Last Update Posted—May 7, 2021, retrieved from https://clinicaltrials.gov/ct2/show/NCT03957304, 9 pages.

ClinicalTrials.gov Identifier: NCT04200235, A Trial of Dexmedetomidine Hydrochloride Nasal Spray in Preoperative Sedation of Children, First Posted—Dec. 16, 2019, Last Update Posted—Sep. 9, 2020, retrieved from https://clinicaltrials.gov/ct2/show/NCT04200235, 8 pages.

ClinicalTrials.gov Identifier: NCT04270708, Intranasal Dexmedetomidine vs Oral Triclofos Sodium for EEG in Children With Autism, First Posted—Feb. 17, 2020, Last Update Posted—Feb. 17, 2020, retrieved from https://clinicaltrials.gov/ct2/show/NCT04270708, 8 pages.

ClinicalTrials.gov Identifier: NCT04383418, A Trial of Dexmedetomidine Hydrochloride Nasal Spray in Preoperative Sedation of Adults, First Posted—May 12, 2020, Last Update Posted—Jul. 15, 2021, retrieved from https://clinicaltrials.gov/ct2/show/NCT04383418, 7 pages.

ClinicalTrials.gov Identifier: NCT04509414, Intranasal Dexmedetomidine for Deep-sedated Pediatric Dental Patients, First Posted—Aug. 12, 2020, Last Update Posted—Aug. 12, 2020, retrieved from https://clinicaltrials.gov/ct2/show/NCT04509414, 8 pages.

ClinicalTrials.gov Identifier: NCT04665453, Dexmedetomidine and Melatonin for Sleep Induction for EEG in Children (MeloDex), First Posted—Dec. 11, 2020, Last Update Posted—Dec. 16, 2020, retrieved from https://clinicaltrials.gov/ct2/show/NCT04665453, 9 pages.

ClinicalTrials.gov Identifier: NCT04669457, Pediatric Delirium, First Posted—Dec. 16, 2020, Last Update Posted—May 11, 2021, retrieved from https://clinicaltrials.gov/ct2/show/NCT04669457, 8 pages.

ClinicalTrials.gov Identifier: NCT04859283, Premedication With Intranasal Dexmedetomidine in Sedation of Patients Undergoing Total Knee Arthroplasty (TKADEX), First Posted—Apr. 26, 2021, Last Update Posted—Sep. 10, 2021, retrieved from https://clinicaltrials.gov/ct2/show/NCT04859283, 7 pages.

ClinicalTrials.gov Identifier: NCT05065775, Bioavailability of Intranasal Dexmedetomidine (INDEX), First Posted—Oct. 4, 2021, Last Update Posted—Oct. 12, 2021, retrieved from https://clinicaltrials.gov/ct2/show/NCT05065775, 7 pages.

ClinicalTrials.gov Identifier: NCT05111431, A Trial of Dexmedetomidine Hydrochloride Nasal Spray in Preoperative Sedation of Children, First Posted—Nov. 8, 2021, Last Update Posted—Dec. 16, 2021, retrieved from https://clinicaltrials.gov/ct2/show/NCT05111431, 7 pages.

Cohen, et al., "Intranasal Dexmedetomidine for Sedation for non-contrast CT Scans in Children." Anesthesiology 2008; 109, A998, 1 page.

Cohen et al., "Oral transmucosal administration of dexmedetomidine for sedation in 4 dogs," Can VetJ. Nov. 2015; 56(11): 1144-1148.

Cohen, et al., "Treatment of post-electroconvulsive therapy agitation with dexmedetomidine." The Journal of ECT (2013); 29(2): e23-e24.

Congdon, et al., "Evaluation of the sedative and cardiovascular effects of intramuscular administration of dexmedetomidine with and without concurrent atropine administration in dogs." Journal of the American Veterinary Medical Association (2011); 239(1): 81-89.

Cozzi, et al., "Intranasal Dexmedetomidine Sedation as Adjuvant Therapy in Acute Asthma Exacerbation With Marked Anxiety and Agitation." Ann Emerg Med. (2016); 69(1): 125-127.

Czinn, et al., "Effectiveness of Intramuscular Dexmedetomidine for Sedation in Young Children Undergoing Diagnostic Testing." The Anesthiology Annual Meeting, American Society of Anestheologists (2011); Abstract A578, 2 pages.

Darrouj et al., "Dexmedetomidine infusion as adjunctive therapy to benzodiazepines for acute alcohol withdrawal," Annals of Pharmacotherapy (2008), 42(11), 1703-1705.

Dewhirst, et al., "Pain management following myringotomy and tube placement: Intranasal dexmedetomidine versus intranasal fentanyl." Int J Pediatr Otorhinolaryngol. (2014); 78 (7): 1090-1094.

Diaper et al., "Pharmacological strategies for detoxification," Br J Clin Pharmacol (2013), 77(2):302-314.

Djaiani et al., "Dexmedetomidine versus Propofol Sedation Reduces Delirium after Cardiac Surgery," Anesthesiology 2016; 124:362-368.

Dogru, et al., "The Effectiveness of Intramuscular Dexmedetomidine on Hemodynamic Responses During Tracheal Intubation and Anesthesia Induction of Hypertensive Patients: A Randomized, Double-Blind, Placebo-Controlled Study." Current Therapeutic Research (2007); 68(5): 292-302.

(56) References Cited

OTHER PUBLICATIONS

Dua, et al., "Comparative evaluation of dexmedetomidine as a premedication given intranasally vs orally in children between 1 to 8 years of age undergoing minor surgical procedures." Pediatric Anesthesia and Critical Care Journal (2016); 4(1): 13-17.
Dundar et al., "Pharmacological treatment of acute agitation associated with psychotic and bipolar disorder: a systematic review and meta-analysis," Hum. Psychopharmacol Clin Exp 2016, 31: 268-285.
Dyck, et al., "The pharmacokinetics and hemodynamic effects of intravenous and intramuscular dexmedetomidine hydrochloride in adult human volunteers." Anesthesiology (1993); 78(5): 813-820.
Ebert et al., "The Effects of Increasing Plasma Concentrations of Dexmedetomidine in Humans," Anesthesiology 2000; 93:382-394.
Economopoulos, 0., "BioXcel Therapeutics CEO Says Wearable Devices Are Another Tool to Combat Alzheimer's Agitation," Benzinga, Apr. 15, 2020, 4 pages, retrieved from: https://www.benzinga.com/general/biotech/20/04/15808398/bioxcel-therapeutics-ceo-says-wearable-devices-are-another-tool-to-combat-alzheimers-agitation.
El-Gohary and Rizk, "Dexmedetomidine for Emergence Agitation after Sevoflurane Anesthesia in Preschool Children Undergoing Day Case Surgery: Comparative Dose-Ranging Study." The Medical Journal of Cairo University (2011); 79(2): 17-23.
El-Hamid and Yassin, "Effect of intranasal dexmedetomidine on emergence agitation after sevoflurane anesthesia in children undergoing tonsillectomy and/or adenoidectomy." Saudi Journal of Anesthesia (2017); 11 (2): 137-143.
Emerick, D., "Automatic pain pathways," Dr. Darren R. Emerick, Apr. 2019, 1 page.
Emerick, D., "Sumo Pharma Version 1.4," Dr. Darren R. Emerick, Apr. 2019, 3 pages.
Emerick, D., "Sumo Pharma Version 1.4a," Dr. Darren R. Emerick, Apr. 2019, 1 page.
Emerick, D., "Sumo Pharma Version 1.5," Dr. Darren R. Emerick, Apr. 2019, 2 pages.
Emerick, D., "Sumo Pharma Version 1.6," Dr. Darren R. Emerick, Apr. 2019, 1 page.
Emery, et al., "Sedative Effects of Intranasal Midazolam and Dexmedetomidine in 2 Species of Tortoises (*Chelonoidis carbonaria* and *Geochelone platynota*)." Journal of Exotic Pet Medicine (2014); 23 (4): 380-383.
Erkola, et al., "Comparison of intramuscular dexmedetomidine and midazolam premedication for elective abdominal hysterectomy." Anesth Analg. (1994); 79(4): 646-653.
EudraCT Clinical Trial No. 2016-001567-37, Efficacy of single dose intranasal dexmedetomidine for conscious sedation in dental practice in dentophobic uncooperative patients with intellectual disability. University Medical Center Groningen, Date of record first entered Jul. 20, 2016, https://www.clinicaltrialsregister.eu/ctr-search/trial/2016-001567-37/NL, downloaded May 6, 2018, 5 pages.
Extended European Search Report for European Patent Application No. 15850725.1, dated May 24, 2018, 11 pages.
Extended European Search Report for European Patent Application No. 17885750.4, dated Jul. 16, 2020, 7 pages.
Extended European Search Report for European Patent Application No. 19824839.5, dated Feb. 28, 2022, 14 pages.
Extended European Search Report for European Patent Application No. 19826778.3, dated May 10, 2022, 6 pages.
Ezz, "Preoperative intranasal dexmedetomidine versus intranasal ketamine for prevention of emergence agitation after sevoflurane in myringotomy patients: A randomized clinical trial." Egyptian Journal of Anaesthesia (2017); 33(2):141-146.
Farag et al., "Using Dexmedetomidine to Manage Patients with Cocaine and Opioid Withdrawal, Who Are Undergoing Cerebral Angioplasty for Cerebral Vasospasm," Anesthesia & Analgesia, Dec. 2006, vol. 103, No. 6, pp. 1618-1620.
Ferguson et al., "Intranasal dexmedetomidine: Procedural sedation in palliative care: A case report," Palliat Med. 2021, 35(8):1625-1628.
Finkel et al., "The use of dexmedetomidine to facilitate acute discontinuation of opioids after cardiac transplantation in children," Critical Care Medicine, Sep. 2005, 33(9):2110-2112.
Finkel et al., "The Use of Dexmedetomidine to Facilitate Opioid and Benzodiazepine Detoxification in an Infant," Anesthesia & Analgesia, 2004, 98:1658-9.
Gagnon D.J., et al., "Transition from Dexmedetomidine to Enteral Clonidine for ICU Sedation: An Observational Pilot Study," Pharmacotherapy, Mar. 2015, vol. 35(3), pp. 251-259.
Garg et al., "Efficacy of dexmedetomidine for prevention of emergence agitation in patients posted for nasal surgery under desflurane anaesthesia: A prospective double-blinded randomised controlled trial," Indian J Anaesth 2018;62:524-30.
Garg et al., "Use of dexmedetomidine with Propofol in modified electroconvulsive therapy: stable hemodynamics, optimum seizure duration and early recovery," Anaesthesia and Anaesthetics, 2018, 2(1): 1-5.
Garrity et al., "Dexmedetomidine-lnduced Sedation Does Not Mimic the Neurobehavioral Phenotypes of Sleep in Sprague Dawley Rat," Sleep 2015;38(1):73-84.
Gaudio, et al., "Alfaxalone anaesthesia in Lemur catta following dexmedetomidine-butorphanol-midazolam sedation." Veterinary Anaesthesia and Analgesia (2018); 45(3):351-356.
Ghai, et al., "Effect of Low Dose Dexmedetomidine on Emergence Delirium and Recovery Profile following Sevoflurane Induction in Pediatric Cataract Surgeries." Journal of Anesthesiology (2015); vol. 2015, Article ID 617074, 7 pages.
Ghali, et al., "Preanesthetic medication in children: A comparison of intranasal dexmedetomidine versus oral midazolam." Saudi J Anaesth. (2011); 5 (4): 387-391.
Gilsbach et al., "Are the pharmacology and physiology of a2adrenoceptors determined by a2-heteroreceptors and autoreceptors respectively?," British Journal of Pharmacology (2012) 165 90-102.
Gioeni et al., "Evaluation of an oral transmucosal administration of dexmedetomidine-butorphanol and dexmedetomidine-methadone in dogs," International Journal of Health and Animal Science Food Safety, vol. IV, No. 1s, Proceeding of Veterinary and Animal Science Days 2017, Jun. 6-8, Milan, Italy, 2 pages.
Giovannitti et al., "Alpha-2 Adrenergic Receptor Agonists: A Review of Current Clinical Applications," Anesth Prog, 2015, 62:31-38.
Granholm, et al., "Evaluation of the clinical efficacy and safety of intramuscular and intravenous doses of dexmedetomidine and medetomidine in dogs and their reversal with atipamezole." Veterinary Anaesthesia and Analgesia (2006); 33(4): 214-223.
Grubb, et al., "Cardiovascular and respiratory effects, and quality of anesthesia produced by alfaxalone administered intramuscularly to cats sedated with dexmedetomidine and hydromorphone." Journal of Feline Medicine and Surgery (2013); 15 (10): 858-865.
Gu et al., "ED50 of Intranasal Dexmedetomidine Sedation for Transthoracic Echocardiography in Children with or without a History of Cardiac Surgery for Cyanotic Congenital Heart Disease," Hindawi BioMed Research International, 2020, vol. 2020, Article ID 1349432, 7 pages.
Guler, et al., "Single-dose dexmedetomidine reduces agitation and provides smooth extubation after pediatric adenotonsillectomy." Pediatric Anesthesia (2005); 15(9): 762-766.
Gumus et al., "Comparison of Effects of Different Dexmedetomidine and Chloral Hydrate Doses Used in Sedation on Electroencephalography in Pediatric Patients," Journal of Child Neurology 2015, vol. 30(8) 983-988.
Gupta, et al., "Comparison between intranasal dexmedetomidine and intranasal midazolam as premedication for brain magnetic resonance imaging in pediatric patients: A prospective randomized double blind trial." J Anaesthesiol Clin Pharmacol. (2017); 33 (2): 236-240.
Guthrie et al., "Pharmacologic interventions for the treatment of opioid dependence and withdrawal," DICP Jul.-Aug. 1990; 24(7-8): 721-734.
Gutirrez, R.E.P., "Clinical case of rapid opiate detoxification under anesthesia," Anestesia Pediatrica e Neonatale, vol. 9, No. 1, Sep.-Oct. 2011, 10 pages.

(56) References Cited

OTHER PUBLICATIONS

Gyanesh, et al., "Comparison between intranasal dexmedetomidine and intranasal ketamine as premedication for procedural sedation in children undergoing MRI: a double-blind, randomized, placebo-controlled trial." J Anesth. (2014); 28 (1): 12-18.
Haenecour et al., "Prolonged Dexmedetomidine Infusion and Drug Withdrawal In Critically Ill Children," J Pediatr Pharmacol Ther 2017;22(6):453-460.
Han, et al., "A randomized study of intranasal vs. intravenous infusion of dexmedetomidine in gastroscopy." Int J Clin Pharmacol Ther. (2014); 52 (9): 756-761.
Hauber, et al., "Dexmedetomidine as a Rapid Bolus for Treatment and Prophylactic Prevention of Emergence Agitation in Anesthetized Children." Anesthesia & Analgesia (2015); 121(5): 1308-1315.
Hitt, et al., "An Evaluation of Intranasal Sufentanil and Dexmedetomidine for Pediatric Dental Sedation." Pharmaceutics (2014); 6 (1): 175-184.
Honey et al., "a2-Receptor Agonists for Treatment and Prevention of Iatrogenic Opioid Abstinence Syndrome in Critically Ill Patients," Ann Pharmacother., 2009;43:1506-1511.
Hong et al., "Dexmedetomidine alleviates smoke-induced bronchial and alveolar epithelial cell injury," Gen Physiol Biophys., May 2020;39(3):293-300.
Hong et al., "Dexmedetomidine preconditioning ameliorates lung injury induced by pulmonary ischemia/reperfusion by upregulating promoter histone H3K4me3 modification of KGF-2," Experimental Cell Research, Sep. 2021, 406, 112762, 11 pages.
Hospira Safety Data Sheet, Precedex (dexmedetomidine hydrochloride) Injection, Solution, Jun. 2, 2014, pp. 1-7.
Hossein, et al., "Comparing the effect of premedication with intra-nasal dexmedetomidine and intra-nasal midazolam on sedation and anxiety level in children undergoing elective surgery." Journal of Anaesthesiology and Pain (2016); 6 (3): 1-10. Abstract.
Hrishi, et al., "A Novel Use of a Novel Drug: Preoperative Nasal Preparation with Dexmedetomidine for Transnasal Transsphenoidal Neurosurgery Approach in Skull Base Neurosurgery." Indian Journal of Neurosurgery (2017); 06 (03): 170-175.
Hsu et al., "Dexmedetomidine Directly Increases Tau Phosphorylation," Journal of Alzheimer's Disease (2015) 44:839-850.
Hsu et al., "Selection of medications for pediatric procedural sedation outside of the operating room," Up To Date, Oct. 10, 2017, 15 pages, retrieved from https://www.uptodate.com/contents/selectionof-medications-for-pediatric-procedural-sedation-outside-of-the-operating-room.
Ibacache, et al., "Single-Dose Dexmedetomidine Reduces Agitation After Sevoflurane Anesthesia in Children." Anesthesia & Analgesia (2004); 98(1): 60-63.
Ibrahim, "A prospective, randomized, double blinded comparison of intranasal dexmedetomodine vs intranasal ketamine in combination with intravenous midazolam for procedural sedation in school aged children undergoing MRI." Anesthesia Essays and Researches (2014); 8 (2): 179-186.
Iirola, et al., "Bioavailability of dexmedetomidine after intranasal administration." European Journal of Clinical Pharmacology (2011); 67 (8): 825-831.
Iirola, et al., "Population pharmacokinetics of dexmedetomidine during long-term sedation in intensive care patients," British Journal of Anaesthesia 108 (3): 460-8 (2012).
International Preliminary Report on Patentability in International Application No. PCT/US2015/055828 dated Apr. 18, 2017, 8 pages.
International Search Report and Written Opinion, for International Application No. PCT/US2017/069030, mailed Feb. 28, 2018, 8 pages.
International Search Report and Written Opinion for International Application No. PCT/US2021/017857 dated Apr. 26, 2021, 9 pages.
International Search Report and Written Opinion of the International Searching Authority for International Application No. PCT/US2019/039268, mailed Sep. 13, 2019, 20 pages.
International Search Report and Written Opinion of the International Searching Authority for International Application No. PCT/US2019/039308, mailed Sep. 13, 2019, 15 pages.
International Search Report and Written Opinion of the International Searching Authority for International Application No. PCT/US2020/0426186, mailed Mar. 1, 2021, 18 pages.
International Search Report and Written Opinion of the International Searching Authority for International Application No. PCT/US2020/051256, mailed Dec. 10, 2020, 18 pages.
International Search Report, PCT appl. No. PCT/US2015/055828, 4 pages (mailed Mar. 1, 2016).
IRCT Registration No. IRCT2015103011398N9, Effect of intranasal administration of dexmedetomidine in providing moderate sedation for patients undergoing ERCP; a randomized control trial. Iran University of Medical Sciences, Registration date Nov. 4, 2015, http://en.irct.ir/trial/11663, downloaded May 5, 2018, 12 pages.
Isik, et al., "Dexmedetomidine decreases emergence agitation in pediatric patients after sevoflurane anesthesia without surgery." Pediatric Anesthesia (2006); 16(7): 748-753.
Jaakola, et al., "Intramuscular dexmedetomidine premedication—an alternative to midazolam-fentanyl-combination in elective hysterectomy?" Acta Anaesthesiol Scand. (1994); 38(3): 238-243.
Jayaram, et al., "A comparative study to evaluate the effect of intranasal dexmedetomidine versus oral alprazolam as a premedication agent in morbidly obese patients undergoing bariatric surgery." J Anaesthesiol Clin Pharmacol. (2013); 29(2): 179-182.
Jiri, et al., "Intramuscular Dexmedetomidine In Burns Victims—Preliminary Results." Anaesthesiology and Intensive Care Medicine (2008); 2: 82-86.
Jia, et al., "A randomised study of intranasal dexmedetomidine and oral ketamine for premedication in children." Anaesthesia (2013); 68 (9): 944-949.
Jia et al., "Application of intranasal dexmedetomidine hydrochloride combined sevoflurane inhalation anesthesia in pediatric lingual frenoplasty," Journal of Xinxiang Medical University (2015), 32(8), 732-734, English Abstract only.
Jun et al., "The effects of intranasal dexmedetomidine premedication in children: a systematic review and meta-analysis," Can J Anesth/J Can Anesth (2017) 64:947-961.
Jung et al., "1877: Dexmedetomidine for Treatment of Refractory Opioid Withdrawal," Critical Care Medicine: Dec. 2016, vol. 44, No. 12 (Suppl.), p. 544.
Jung et al., "Dexmedetomidine for Treatment of Refractory Heroin Withdrawal," Journal of Emergency Nursing, 2017, 43(2):182-184.
Jung, et al., "Effect of dexmedetomidine on emergence agitation in male patients undergoing closed reduction of a nasal bone fracture." RMJ (2015); 40(2): 191-196.
Kambow, et al., "Randomized Double Blind Clinical Trial of Intramuscular Dexmedetomidine V/S Midazolam as Premedication in Paediatric Surgical Patients." J. Evolution Med. Dent. Sci. (2016); 5(42): 2566-2570.
Kang et al., "The correlation of heart rate between natural sleep and dexmedetomidine sedation," Korean J Anesthesiol. Apr. 2019; 72(2): 164-168.
Karaaslan, et al., "Comparison of buccal and intramuscular dexmedetomidine premedication for arthroscopic knee surgery." Journal of Clinical Anesthesia (2006); 18(8):589-593.
Kawaai et al., "Dexmedetomidine decreases the oral mucosal blood flow," British Journal of Oral and Maxillofacial Surgery (2013) 51: 928-931.
Kaya, et al., "The Effects of Intramuscular Dexmedetomidine Premedication on Hemodynamics, Plasma Norepinephrine, Cortisol and Glucose Concentrations." O.M.. Tp Dergisi (2006); 23(1): 9-16.
Keating, G., "Dexmedetomidine: A Review of Its Use for Sedation in the Intensive Care Setting," Drugs (2015) 75:1119-1130.
Keles et al., "The Effect of Oral Dexmedetomidine Premedication on Preoperative Cooperation and Emergence Delirium in Children Undergoing Dental Procedures," Hindawi BioMed Research International, 2017, vol. 2017, Article ID 6742183, 7 pages.
Kelley, et al., "Intramuscular Dexmedetomidine & Midazolam for Preoperative Sedation: A Case Series." Pediatric Anasthesia (Winter

(56) References Cited

OTHER PUBLICATIONS

2013), University of Pittsburgh, Poster Board, 1 page http://www2.pedsanesthesia.org/meetings/2013winter/posters/uploads/373--NM- 293.pdf.
Khenissi, et al., "Comparison of intramuscular alfaxalone and ketamine combined with dexmedetomidine and butorphanol for castration in cats." Journal of Feline Medicine and Surgery (2016); 19(8): 791-797.
Kim, et al., "Appropriate dose of dexmedetomidine for the prevention of emergence agitation after desflurane anesthesia for tonsillectomy or adenoidectomy in children: up and down sequential allocation." BMC Anesthesiology (2015); 15: 79, 6 pages.
Kim, et al., "Dexmedetomidine for sedation in pediatric patients who received more than 20 sessions of radiation therapy-two cases report." Korean Journal of Anesthesiology (2016); 69 (6): 627-631.
Kim et al., "Risk Factors of Emergence Agitation in Adults Undergoing General Anesthesia for Nasal Surgery," Clinical and Experimental Otorhinolaryngology vol. 8, No. 1, 46-51, Mar. 2015.
Kobayashi, et al., "Efficacy of Dexmedetomidine for Controlling Delirium in Intensive Care Unit Patients." Japanese Journal of Anesthesiology [Masui] (2007); 56(10): 1155-1160.
Kobayashi, et al., "Mechanism of the Inhibitory Effect of Surfactants on Intramuscular Absorption of Drugs." Chemical and Pharmaceutical Bulletin (1977); 25(7): 1547-1554.
Konia, M., "Oral dexmedetomidine for preoperative sedation in an adult uncooperative autistic patient," Journal of Clinical Anesthesia (2016) 34, 29-31.
Korpivaara et al., "Dexmedetomidine oromucosal gel for noise-associated acute anxiety and fear in dogs—a randomised, double-blind, placebo-controlled clinical study," Veterinary Record (2017) 180, 356, 7 pages.
Korpivaara et al., "Effect of dexmedetomidine oromucosal gel for alleviation of canine acute fear and anxiety associated with noise at sub-sedative doses—A pilot study," BSAVA Congress 2014, Poster, 1 page.
Kostoglou, et al., "Effect of 13-carotene on health status and performance of sows and their litters." Journal of Animal Physiology and Animal Nutrition (2000); 83 (3): 150-157.
Krimins, et al., "Hemodynamic effects in dogs after intramuscular administration of a combination of dexmedetomidine-butorphanol-tiletamine-zolazepam or dexmedetomidine-butorphanol-ketamine." American Journal of Veterinary Research (2012); 73(9): 1363-1370. Abstract.
Kastner, et al., "Clinical comparison of preanaesthetic intramuscular medetomidine and dexmedetomidine in domestic sheep." DTW. Deutsche Tierarztliche Wochenschrift (2001); 108 (10): 409-413.
Kumar, et al., "Efficacy of intranasal dexmedetomidine versus oral midazolam for paediatric premedication." Indian J Anaesth (2017); 61: 125-130.
Kumar et al., "Role of dexmedetomidine for sedation in a patient with schizophrenia for strabismus surgery," Indian J Anaesth. Nov. 2016; 60(11): 856-857.
Kumari, et al., "Clinico-anesthetic and Hemodynamic Effects of Midazolam and Dexmedetomidine-Midazolam with Propofol in Dogs During Ovariohysterectomy." The Philippine Journal of Veterinary Medicine (2017); 54(1): 46-53.
Kundra et al., "Oral ketamine and dexmedetomidine in adults' burns wound dressing—A randomized double blind cross over study," Burns 39 (2013) 1150-1156.
Kurlansky, et al., "Role of the carrier solution in cyclosporine pharmacokinetics in the baboon." The Journal of Heart Transplantation (1986); 5(4): 312-316.
Lami et al., "Transmucosal dexmedetomidine for computed tomography sedation," Paediatr Anaesth., 2008, 18:349-350.
Lehman et al., "Practice Guideline for the Treatment of Patients With Schizophrenia," American Psychiatric Association Practice Guidelines, Second Edition, 2010, 184 pages.
Lei et al., "Incidence and risk factors of bradycardia in pediatric patients undergoing intranasal dexmedetomidine sedation," Acta Anesthesiologica Scandinavica (2020), 64:464-471.
Levnen, et al., "Dexmedetomidine Premedication Attenuates Ketamine-induced Cardiostimulatory Effects and Postanesthetic Delirium." Anesthesiology (1995); 82: 1117-1125.
Li, et al., "A comparison of intranasal dexmedetomidine for sedation in children administered either by atomiser or by drops." Anaesthesia (2016); 71: 522-528.
Li et al., "Dexmedetomidine inhibits inflammation in microglia cells under stimulation of LPS and ATP by c-Fos/NLRP3/caspase-1 cascades," EXCLI Journal 2018; 17:302-311.
Li et al., "Impact of dexmedetomidine on the incidence of delirium in elderly patients after cardiac surgery: A randomized controlled trial," PLoS ONE 12(2): e0170757, 15 pages.
Li, et al., "Intranasal dexmedetomidine for sedation in children undergoing transthoracic echocardiography study—a prospective observational study." Pediatric Anesthesia (2015); 25 (9): 891-896.
Li, et al., "Intranasal dexmedetomidine with and without buccal midazolam for procedural sedation in autistic children: a double-blind randomised controlled trial." The Lancet (2017); 390 (4): S26.
Lili, et al., "The application of dexmedetomidine in children undergoing vitreoretinal surgery." Journal of Anesthesia (2012); 26(4): 556-561.
Lin, et al., "Efficacy of premedication with intranasal dexmedetomidine on inhalational induction and postoperative emergence agitation in pediatric undergoing cataract surgery with sevoflurane." Journal of Clinical Anesthesia (2016); 33: 289-295.
Liu et al., "Safety and sedative effect of intranasal dexmedetomidine in mandibular third molar surgery: a systematic review and meta-analysis," Drug Design, Development and Therapy (2019), 13:1301-1310.
Liu et al., "Comparison of sedative effects of two methods of intranasal dexmedetomidine in cardiac ultrasonography in infants with congenital heart disease," Practical Medicine and Clinic. 2015, 18(12), 1452-1454, English Abstract only.
Liu et al., "Determination of the 90% effective dose of intranasal dexmedetomidine for sedation during electroencephalography in children," Acta Anaesthesiologica Scandinavica (2019), 63, 847-852.
Liu X., et al., "Dexmedetomidine Versus Propofol Sedation Improves Sublingual Microcirculation After Cardiac Surgery: A Randomized Controlled Trial," Journal of Cardiothoracic and Vascular Anesthesia, 2016, vol. 30(6), pp. 1509-1515.
Liyan, Chu et al., "Effect of dexmedetomidine on minimum alveolar concentration of sevoflurane in children undergoing inhalation anesthesia," Beijing Yixue I Beijing Medical Journal, 2017, vol. 39, Issue 6, pp. 581-584 (English abstract only).
Li et al., "Comparison of preoperative application of different doses of dexmedetomidine intranasal in children undergoing outpatient surgery," Sichuan Yixue (2015), 36(09), 1209-1211. DOI: 1 0.16252/j.cnki.issn1 004-0501-2015.09.002.
Li et al., "Pharmacokinetic and pharmacodynamic study of intranasal and intravenous dexmedetomidine," British Journal of Anaesthesia (2018), 120(5), 960-968.
Li et al., "The 95% effective dose of intranasal dexmedetomidine sedation for pulmonary function testing in children aged 1-3 years: A biased coin design up-and- down sequential method," Journal of Clinical Anesthesia (2020), 63, 109746, 5 pages.
Louis et al., "Effects of dexmedetomidine on delirium duration of non-intubated ICU patients (4D trial): study protocol for a randomized trial," Trials (2018) 19:307, 11 pages.
Lu, et al., "Intranasal Dexmedetomidine as a Sedative Premedication for Patients Undergoing Suspension Laryngoscopy: A Randomized Double-Blind Study." PLoS ONE (2016); 11(5): e0154192.
Maccioli et al., "Dexmedetomidine to Facilitate Drug Withdrawal," Anesthesiology, Feb. 2003, V 98, No. 2, pp. 575-575.
Madhav et al., "Orotransmucosal drug delivery systems: A review," Journal of Controlled Release (2009) 140: 2-11.
Mahmoud et al., "Dexmedetomidine: review, update, and future considerations of paediatric perioperative and periprocedural applications and limitations," British Journal of Anaesthesia 2015, 171-82, doi: 10.1093/bja/aev226.

(56) References Cited

OTHER PUBLICATIONS

Malhotra, et al., "Comparative evaluation of dexmedetomidine and midazolam-ketamine combination as sedative agents in pediatric dentistry: A double-blinded randomized controlled trial." Contemp Clin Dent (2016); 7: 186-192.
Manaa, et al., "Fentanyl versus dexmedetomidine effect on agitation after sevoflurane anaesthesia." Saudi J Anaesth. (2007); 1(2): 57-61, 10 pages.
Martin et al., "The Role of the a2-Adrenoceptor Agonist Dexmedetomidine in Postsurgical Sedation in the Intensive Care Unit," J Intensive Care Med 2003; 18:29-41.
Mason, et al., "Intramuscular dexmedetomidine: an effective route of sedation preserves background activity for pediatric electroencephalograms." J Pediatr. (2012); 161(5): 927-932.
Mason, et al., "Intramuscular dexmedetomidine for pediatric electroencephalogram (EEG) sedation: 10AP3-7." European Journal of Anaesthesiology (EJA) (2012); 29: p. 161.
Mason, et al., "Intramuscular Dexmedetomidine Sedation for Pediatric MRI and CT." American Journal of Roentgenology (2011); 197: 720-725.
Mazy et al., "Spinal anesthesia for lengthy lower limb orthopedic surgeries: dexmedetomidine plus fentanyl versus dexmedetomidine," Ain-Shams Journal of Anesthesiology (2019) 11:10, 8 pages.
Micieli, et al., "Sedative and cardiovascular effects of intranasal or intramuscular dexmedetomidine in healthy dogs." Vet Anaesth Analg. (2017); 44(4): 703-709.
Miller et al., "Comparison of Intranasal Dexmedetomidine and Oral Pentobarbital Sedation for Transthoracic Echocardiography in Infants and Toddlers: A Prospective, Randomized, Double-Blind Trial," Anesthesia & Analgesia, Jun. 2018, vol. 126, No. 6, pp. 2009-2016.
Miller et al., "Does intranasal dexmedetomidine provide adequate plasma concentrations for sedation in children: a pharmacokinetic study," British Journal of Anaesthesia (2018), 120(5), 1056-1065.
Miller, et al., "Dosing and efficacy of intranasal dexmedetomidine sedation for pediatric transthoracic echocardiography: a retrospective study." Canadian Journal of Anesthesia (2016); 63 (7): 834-841.
Misra et al., "Effect of preoperative dexmedetomidine nebulization on the hemodynamic response to laryngoscopy and intubation: a randomized control trial," Korean Journal of Anesthesiology 2021; 7 4(2): 150-157.
Mizrak, et al., "Dexmedetomidine Use during Strabismus Surgery in Agitated Children." Med Prine Pract (2011); 20(5): 427-432.
Mizrak, et al., "Premedication with dexmedetomidine and midazolam attenuates agitation after electroconvulsive therapy." J Anesth. (2009); 23(1): 6-10.
Mohite et al., "Role of dexmedetomidine in pediatric dental sedation," J Dent Anesth Pain Med., Apr. 2019;19(2):83-90.
Mohr et al., "Treatment of acute agitation in psychotic disorders," Neuroendocrinology Letters, 2005, vol. 26, No. 4, pp. 327-335.
Montoya et al., "Validation of the Excited Component of the Positive and Negative Syndrome Scale (PANSS-EC) in a naturalistic sample of 278 patients with acute psychosis and agitation in a psychiatric emergency room," Health and Quality of Life Outcomes, 2011, 9:18, 11 pages.
Moshiri et al., "Premedication effect of dexmedetomidine and alfentanil on seizure time, recovery duration, and hemodynamic responses in electroconvulsive therapy," Annals of Cardiac Anaesthesia, Apr.-Jun. 2016, vol. 19, Issue 2, pp. 263-268.
Mostafa, et al., "Effect of Different Doses of Dexmedetomidine on Stress Response and Emergence Agitation after Laparoscopic Cholecystectomy: Randomized Controlled Double-Blind Study." J Anesth Clin Res (2017); 8: 707, 6 pages.
Mountain et al., "Dexmedetomidine as a Pediatric Anesthetic Premedication to Reduce Anxiety and to Deter Emergence Delirium," AANA Journal, Jun. 2011, vol. 79, No. 3, pp. 219-224.
Mukherjee, et al., "Emergence agitation prevention in paediatric ambulatory surgery: A comparison between intranasal Dexmedetomidine and Clonidine." J Res Pharm Pract. (2015); 4(1): 24-30.
Mult, A., "Prolonged Dexmedetomidine Infusion as an Adjunct in Treating Sedation-Induced Withdrawal," Anesth Analg 2003; 96:1054-1055.
Muszkat et al., "Alpha2-Adrenergic Receptor-Induced Vascular Constriction in Blacks and Whites," Hypertension, 2004, vol. 43, pp. 31-35.
Na, et al., "Randomized controlled trial on influence of nasal administration of dexmedetomidine after induction of anesthesia on agitation of children in ophthalmologic surgery." Adverse Drug Reactions Journal (2016); 18 (2): 95-98. Abstract.
Naples, et al., "Comparison of the Anesthetic Effects of Oral Transmucosal Versus Injectable Medetomidine in Combination with Tiletamine-Zolazepam for Immobilization of Chimpanzees (*Pan troglodytes*)." Journal of Zoo and Wildlife Medicine (2010); 41 (1): 50-62.
Nasr et al., "Ultra-rapid opiate detoxification using dexmedetomidine under general anesthesia," J Opioid Manag., 2011;7(5):337-344.
Nawrat, A., "Triple combo: calming Alzheimer's agitation with AI, wearables and a novel drug," Medical Device Network, Jan. 28, 2020, 4 pages, retrieved from https://www.medicaldevice-network.com/analysis/wearable-ai-device-for- agitation/#:~: text =.
Neville, et al., "Double-blind Randomized Controlled Trial of Intranasal Dexmedetomidine Versus Intranasal Midazolam as Anxiolysis Prior to Pediatric Laceration Repair in the Emergency Department." Acad Emerg Med. (2016); 23 (8): 910-917.
Ni, et al., "Effect of Dexmedetomidine on Preventing Postoperative Agitation in Children: A Meta-Analysis." PLoS ONE (2015); 10 (5): e0128450.
Nitturi et al., "A Comparative Evaluation of Intranasal Dexmedetomidine and Intranasal Midazolam for Premedication in Pediatric Surgery," IAIM, 2018; 5(1): 82-94.
Niyogi et al., "Attenuation of haemodynamic responses to laryngoscopy and endotracheal intubation with dexmedetomidine: A comparison between intravenous and intranasal route," Indian J Anaesth 2019;63:915-923.
Nizari et al., "Non-amyloidogenic effects of a2 adrenergic agonists: implications for brimonidine-mediated neuroprotection," Cell Death Dis., 2016; 7(12): e2514, 13 pages.
Nooh, et al., "Intranasal atomized dexmedetomidine for sedation during third molar extraction." Int J Oral Maxillofac Surg. (2013); 42 (7): 857-862.
Nuamah et al., "The past, present and future of opioid withdrawal assessment: a scoping review of scales and technologies," BMC Medical Informatics and Decision Making (2019) 19:113, 11 pages.
O'Brien, et al., "Dexmedetomidine and the successful management of electroconvulsive therapy postictal agitation: a case report." The Journal of ECT (2010); 26(2): 131-133.
Oschman et al., "Dexmedetomidine for opioid and benzodiazepine withdrawal in pediatric patients," Am J Health-Syst Pharm. 2011; 68:1233-8.
Ouchi et al., "Dexmedetomidine Dose Dependently Enhances the Local Anesthetic Action of Lidocaine in Inferior Alveolar Nerve Block a Randomized Double-Blind Study," Reg Anesth Pain Med 2016;41: 348-355.
Pant D., et al., "Comparison of Sublingual Midazolam and Dexmedetomidine for Premedication in Children," Minerva Anestesiologica, 2014, vol. 80(2), pp. 167-175.
Parikh et al., "Single Dose Pharmacokinetics of Fentanyl Sublingual Spray and Oral Transmucosal Fentanyl Citrate in Healthy Volunteers: A Randomized Crossover Study," Clinical Therapeutics, 2013, vol. 35, No. 3, pp. 236-243.
Park et al., "Dexmedetomidine Oral Mucosa Patch for Sedation Suppresses Apoptosis in Hippocampus of Normal Rats," Int Neurourol J 2017;21 Suppl 1:S39-47.
Parmar et al., "A Review On Sublingual Spray: Novel Drug Delivery System," IJPSR, 2017; vol. 8(11): pp. 4533-4539.
Pasin L., et al., "Dexmedetomidine vs Midazolam as Preanesthetic Medication in Children: a Meta-Analysis of Randomized Controlled Trials," Pediatric Anesthesia, 2015, vol. 25, pp. 468-476.
Patel, et al., "Vasovagal syncope and severe bradycardia following intranasal dexmedetomidine for pediatric procedural sedation." Paediatr Anaesth. (2014); 24 (4): 446-448.

(56) References Cited

OTHER PUBLICATIONS

Pavithra, et al., "Comparison of two doses of intranasal dexmedetomidine as premedication in children." Pediatric Anesthesia and Critical Care Journal (2017); 5(2): 86-94.
Peker, et al., "Buccal versus intramuscular dexmedetomidine premedication for arthroscopic knee surgery under spinal anesthesia: A-600." European Journal of Anaesthesiology (EJA) (2006); 23: p. 156.
Peng, et al., "Premedication with dexmedetomidine in pediatric patients: a systematic review and meta-analysis." Clinics (2014); 69(11): 777-786.
Penttila et al., "Cardiovascular and parasympathetic effects of dexmedetomidine in healthy subjects," Canadian Journal of Physiology and Pharmacology, 2004, 82(5): 359-362.
Pestieau, et al., "The effect of dexmedetomidine during myringotomy and pressure-equalizing tube placement in children." Pediatric Anesthesia (2011); 21 (11): 1128-1135.
Phan et al., "Clinical Uses of Dexmedetomidine in Pediatric Patients," Pediatr Drugs, 2008;10(1):49-69.
Pinelas, et al., "Effects of different doses of dexmedetomidine on anaesthetic induction with alfaxalone—a clinical trial." Veterinary Anaesthesia and Analgesia (2013); 41(4): 378-385.
Pons, et al., "Effects of dexmedetomidine administered at acupuncture point GV20 compared to intramuscular route in dogs." J Small Anim Pract. (2016); 58(1): 23-28.
Porters, et al., "Sedative and antinociceptive effects of dexmedetomidine and buprenorphine after oral transmucosal or intramuscular administration in cats." Veterinary Anaesthesia and Analgesia (2014); 41 (1): 90-96.
Porters, et al., "Pharmacokinetics of oral transmucosal and intramuscular dexmedetomidine combined with buprenorphine in cats." Journal of Veterinary Pharmacology and Therapeutics (2014); 38 (2): 203-208.
Posner, "Measuring Alertness," Ann. N.Y. Acad. Sci. (2008) 1129: 193-199.
Prabhu and Mehandale, "Comparison of oral dexmedetomidine versus oral midazolam as premedication to prevent emergence agitation after sevoflurane anaesthesia in paediatric patients." Indian J Anaesth. (2017); 61(2): 131-136.
Precedex Label, Highlights of Prescribing Information, Mar. 2016, 23 pages.
Proctor et al., "Oral Dexmedetomidine Attenuates Hemodynamic Responses during Emergence from General Anesthesia in Chronically Instrumented Dogs," Anesthesiology, 1991, 74:108-114.
Proctor et al., "Premedication with Oral Dexmedetomidine Alters Hemodynamic Actions of Intravenous Anesthetic Agents in Chronically Instrumented Dogs," Anesthesiology, 1992, 77:554-562.
Purushotham et al., "Intranasal Dexmedetomidine Versus Oral Midazolam as Premedication in Anaesthesia in Children," RJPBCS, Jul.-Aug. 2017, 8(4), pp. 1219-1241.
Qi, et al., "The observation of the sedation effects of intranasal methods of dexmedetomidine for magnetic resonance imaging in children." BIO Web of Conferences 8, 01043 (2017), 4 pages.
Qiao, et al., "Intranasal atomised dexmedetomidine optimises surgical field visualisation with decreased blood loss during endoscopic sinus surgery: a randomized study." Rhinology (2016); 54: 38-44.
Qiao et al., "Pediatric premedication: a double-blind randomized trial of dexmedetomidine or ketamine alone versus a combination of dexmedetomidine and ketamine," BMC Anesthesiology (2017) 17:158, 7 pages.
Qiu et al., "Sedative effects of different doses of intranasal dexmedetomidine in different age groups of children," Journal of Medical Postgraduates 2014;(4):394-397, English abstract only.
Rahman et al., "The use of dexmedetomidine for refractory agitation in substance abuse patient," Crit Care & Shock (2010) 13:59-60.
Rajalakshmi, et al., "A Comparative Study Between Intranasal Dexmedetomidine and Intranasal Ketamine as a Premedication in Paediatric Surgeries." Indian Journal of Applied Research (2014); 4 (12): 379-381.
Raszplewicz, et al., "Comparison of sedation scores and propofol induction doses in dogs after intramuscular premedication with butorphanol and either dexmedetomidine or medetomidine." Veterinary Anaesthesia and Analgesia (2013); 40(6): 584-589.
Rathbone et al., "Mechanisms, barriers and pathways of oral mucosal drug permeation," Advanced Drug Delivery Reviews, (1993) 12: 41-60.
Ravipati, et al., "Dexmedetomidine decreases the requirement of ketamine and propofol during burns debridement and dressings." Clinical Investigation (2014); 58(2): 138-142.
Ray et al., "Dexmedetomidine for sedation during electroencephalographic analysis in children with autism, pervasive developmental disorders, and seizure disorders," Journal of Clinical Anesthesia (2008) 20, 364-368.
Reade and Finfer, "Sedation and delirium in the intensive care unit," New England Journal of Medicine, 2014; vol. 370 (5): pp. 444-454.
Riker et al., "Dexmedetomidine vs Midazolam for Sedation of Critically Ill Patients a Randomized Trial," JAMA, 2009;301 (5):489-499.
Roberts et al., "Characterizing the experience of agitation in patients with bipolar disorder and schizophrenia," BMC Psychiatry (2018) 18:104.
Rojas-Gomez and Nystrom, "Sedation and Physiological Response to Intranasal Dexmedetomidine (IN-DEX) in Patients with Severe Chronic Obstructive Pulmonary Disease (COPD)." ATS Journals 2016: Abstract A3548; American Journal of Respiratory and Critical Care Medicine (2016); 193: 1.
Roosens et al., "The use of dexmedetomidine in extreme agitation," Tijdschrift Voor Psychiatrie (2017) 59:9, 554-558, with English abstract.
Rosen et al., "The Pittsburgh Agitation Scale," American Journal of Geriatric Psychiatry, 1994, 1 page.
Ryu et al., "Sedation Protocol Using Dexmedetomidine for Third Molar Extraction," J Oral Maxillofac Surg, 2016 74:926.e1-926.e7, 7 pages.
Saad et al., "Intranasal dexmedetomidine versus intranasal midazolam as pre-anesthetic medication in pediatric age group undergoing adenotonsillectomy," Ain-Shams Journal of Anesthesiology (2020) 12:40, 10 pages.
Saito et al., "Usefulness of dexmedetomidine to prevent emergence agitation in a patient with Krabbe disease: a case report," JA Clinical Reports (2018) 4:34, 4 pages.
Sakurai et al., "Buccal administration of dexmedetomidine as a preanesthetic in children," Journal of Anesthesia, 2010, 24:49-53.
Santana and Mills, "Retrospective study of intranasal dexmedetomidine as a prophylactic against emergence delirium in pediatric patients undergoing ear tube surgery." International Journal of Pediatric Otorhinolaryngology (2017); 100: 39-43.
Santangelo, et al., "Transnasal administration of a combination of dexmedetomidine, midazolam and butorphanol produces deep sedation in New Zealand White rabbits." Veterinary Anaesthesia and Analgesia (2016); 43 (2): 209-214.
Santos, et al., "Sedative and cardiorespiratory effects of dexmedetomidine and buprenorphine administered to cats via oral transmucosal or intramuscular routes." Veterinary Anaesthesia and Analgesia (2010); 37 (5): 417-424.
Santos, et al., "Effects of intramuscular dexmedetomidine in combination with ketamine or alfaxalone in swine." Veterinary Anaesthesia and Analgesia (2016); 43 (1):81-85.
Sato, et al., "Effect of single-dose dexmedetomidine on emergence agitation and recovery profiles after sevoflurane anesthesia in pediatric ambulatory surgery." Journal of Anesthesia (2010); 24(5): 675-682.
Savla, et al., "Effect of intranasal dexmedetomidine or oral midazolam premedication on sevoflurane EC50 for successful laryngeal mask airway placement in children: a randomized, double-blind, placebo-controlled trial." Pediatric Research (2014); 24 (4):433-439.
Sazuka et al., "Dexmedetomidine dose dependently decreases oral tissue blood flow during sevoflurane and propofol anesthesia in rabbits," Journal of Oral and Maxillofacial Surgery, 2012, 70(8): 1808-1814.

(56) References Cited

OTHER PUBLICATIONS

Scheinin, et al., "Intramuscular Dexmedetomidine as Premedication for General Anesthesia: A Comparative Multicenter Study." Anesthesiology (1993); 78: 1065-1075.
Scheinin, et al., "Pharmacodynamics and pharmacokinetics of intramuscular dexmedetomidine." Clinical Pharmacology & Therapeutics (1992); 52(5): 537-546.
Schmidt, et al., "Effects of preanesthetic administration of midazolam, clonidine, or dexmedetomidine on postoperative pain and anxiety in children." Pediatric Anesthesia (2007); 17(7): 667-674.
Schnellbacher, et al., "The Efficacy of Intranasal Administration of Dexmedetomidine and Ketamine to Yellow-Bellied Sliders (*Trachemys scripta scripta*)." Journal of Herpetological Medicine and Surgery (2012); 22 (3-4): 91-98.
Segovia, et al., "Pre-anaesthetic medication with intranasal dexmedetomidine and oral midazolam as an anxiolytic. A clinical trial." Analesdepediatria (2013); 81 (4): 226-231.
Sethi, et al., "Conscious sedation in a psychiatric patient: A challenge." J Anaesthesiol Clin Pharmacol. (2017); 33(3): 416-417.
Shah, et al., "Physiologic and biochemical effects of electroacupuncture combined with intramuscular administration of dexmedetomidine to provide analgesia in goats." American Journal of Veterinary Research (2016); 77 (3): 252-259.
Shams and El-Masry, "Ketofol-Dexmedetomidine combination in ECT: A punch for depression and agitation." Indian Journal of Anaesthesia (2014); 58(3): 275-280.
Sharan et al., "A comparison of dexmedetomidine with propofol versus esmolol with propofol to attenuate the hemodynamic stress responses after electroconvulsive therapy," Indian J Psychiatry, Jul. 2017-Sep. 59(3): 366-369.
Shehabi, et al., "The effect of dexmedetomidine on agitation during weaning of mechanical ventilation in critically ill patients." Anaesthesia and Intensive Care (2010); 38 (1): 82-90.
Sheta, et al., "Intranasal dexmedetomidine vs midazolam for premedication in children undergoing complete dental rehabilitation: a double-blinded randomized controlled trial." Pediatric Anesthesia (2014); 24 (2): 181-189.
Shetty and Aggarwal, "Efficacy of Intranasal Dexmedetomidine for Conscious Sedation in Patients Undergoing Surgical Removal of Impacted Third Molar: A Double-Blind Split Mouth Study." Journal of Maxillofacial and Oral Surgery (2016); 15 (4): 512-516.
Shi, et al., "Intranasal Dexmedetomidine in Termination of First Trimester Pregnancy of Suction Evacuation." J Anesth Clin Res (2017); 8 (11): 1000781, 7 pages.
Singh et al., "A comparative evaluation of analgo-sedative effects of oral dexmedetomidine and ketamine: a triple-blind, randomized study," Anesthesia 24 (2014) 1252-1259.
Singla, et al., "Comparison of dexmedetomidine versus midazolam for intranasal premedication in children posted for elective surgery: a double-blind, randomised study." Southern African Journal of Anaesthesia and Analgesia (2015); 21 (6):154-157.
Sivrikaya, et al., "Intranasal Dexmedetomidine Versus Midazolam Premedication in Paediatric Patients: A Prospective Study." Ecronicon Anaesthesia (2015); 2 (3): 139-147.
Slingsby, et al., "Thermal antinociception after dexmedetomidine administration in cats: a comparison between intramuscular and oral transmucosal administration." J Feline Med Surg. (2009); 11(10): 829-834.
Sobel, et al., "Intramuscular administration of human tissue-type plasminogen activator in rabbits and dogs and its implications forcoronary thrombolysis." Circulation (1987); 75 (6): 1261-1272.
Song, et al., "Dexmedetomidine Injection during Strabismus Surgery Reduces Emergence Agitation without Increasing the Oculocardiac Reflex in Children: A Randomized Controlled Trial." PLoS ONE (2016); 11(9): e0162785, 12 pages.
Spalink, et al., "Intranasal dexmedetomidine for adrenergic crisis in familial dysautonomia." Clinical Autonomic Research (2017); 27 (4): 279-282.

Srinivasa, et al., "Study of Dexmedetomidine as intramuscular premedication in outpatient cataract surgery: A placebo—controlled study." IAIM (2016); 3(2): 60-68.
Staines, R., "BioXcel to trial Apple Watch-drug combination to prevent Alzheimer's agitation episodes," PharmaPhorum, Sep. 19, 2019, 2 pages, retrieved from: https://pharmaphorum.com/news/bioxcel-to-trial-apple-watch-drug-combination-to-prevent-alzheimers-agitation-episodes/.
Su et al., "Dexmedetomidine for prevention of delirium in elderly patients after non-cardiac surgery: a randomised, double-blind, placebo-controlled trial," Lancet 2016; 388: 1893-1902.
Sulton, et al., "The Use of Intranasal Dexmedetomidine and Midazolam for Sedated Magnetic Resonance Imaging in Children: A Report From the Pediatric Sedation Research Consortium." Pediatric Emergency Care (2017); 00: 00-00, 5 pages, Published Ahead of Print.
Sun et al., "Dexmedetomidine inhibits astrocyte pyroptosis and subsequently protects the brain in in vitro and in vivo models of sepsis," Cell Death and Disease (2019) 10:167, 13 pages.
Sun, et al., "Low-Dose Intramuscular Dexmedetomidine as Premedication: A Randomized Controlled Trial." Med Sci Monit (2014); 20: 2714-2719.
Sundaram and Mathian, "A Comparative Evaluation of Intranasal Dexmedetomidine and Intranasal Midazolam for Premedication in Children: A Double Blind Randomised Controlled Trial." JIDA (2011); 5 (7): 777-781.
Surendar, et al., "A comparative evaluation of intranasal dexmedetomidine, midazolam and ketamine for their sedative and analgesic properties: a triple blind randomized study." J Clin Pediatr Dent. (2014); 38 (3): 255-261.
Sutcliffe, et al., "Efficacy of Selective PDE4D Negative Allosteric Modulators in the Object Retrieval Task in Female Cynomolgus Monkeys (*Macaca fascicularis*)." PLoS ONE (2014); 9 (7): e102449, pp. 1-16.
Talon, et al., "Intranasal Dexmedetomidine Premedication is Comparable With Midazolam in Burn Children Undergoing Reconstructive Surgery." Journal of Burn Care & Research (2009); 30 (4): 599-605.
Tammam and Wahba, "Quality of MRI pediatric sedation: Comparison between intramuscular and intravenous dexmedetomidine." Egyptian Journal of Anaesthesia (2013);29: 47-52.
Tammam, "Comparison of the efficacy of dexmedetomidine, ketamine, and a mixture of both for pediatric MRI sedation." Egyptian Journal of Anaesthesia (2013); 29(3): 241-246.
Tang et al., "Dexmedetomidine Controls Agitation and Facilitates Reliable, Serial Neurological Examinations in a Non-Intubated Patient with Traumatic Brain Injury," Neurocrit Care., 2011; 15(1):175-181 (Published online: Mar. 3, 2010).
Tang, et al., "Intranasal Dexmedetomidine on Stress Hormones, Inflammatory Markers, and Postoperative Analgesia after Functional Endoscopic Sinus Surgery." Mediators of Inflammation (2015); Article ID 939431, 9 pages.
Tang et al., "The effect of intranasal administration of dexmedetomidine to assist local anesthesia in patients with endoscopic nasal surgery," Chinese Journal of Anesthesiology, 2016, 36(2), English abstract only, 4 pages.
Tayari, et al., "Methadone and Dexmedetomidine Combination as Premedicant Agents for Ovariectomy in Cats." American Journal of Animal and Veterinary Sciences (2015);10(2):101-111.
Tazeroualti, et al., "Oral clonidine vs midazolam in the prevention of sevoflurane-induced agitation in children. A prospective, randomized, controlled trial." British Journal of Anaesthesia (2007); 98 (5): 667-671.
Tetef, S., "Effectiveness of Transmucosal Sedation for Special Needs Populations in the Ambulatory Care Setting," AORN Journal, Dec. 2014, 100(6):651-669.
Tobi et al., "Emergence Delirium in a Schizophrenic Patient who Underwent Craniotomy for Elevation of Depressed Skull Fracture under General Anaesthesia: A Case Report," International Journal for Case Reports, 2018, vol. 2, No. 2:8, 3 pages.
Tobias, J.D., "Dexmedetomidine to Control Agitation and Delirium from Toxic Ingestions in Adolescents." J Pediatr Pharmacol Ther. (2010); 15(1): 43-48.

(56) References Cited

OTHER PUBLICATIONS

Tobias, J.D., "Dexmedetomidine to treat opioid withdrawal in infants following prolonged sedation in the pediatric ICU," J Opioid Manag., 2006;2(4):201-205.
Tobias, J.D., "Subcutaneous dexmedetomidine infusions to treat or prevent drug withdrawal in infants and children," Journal of Opioid Management, 2008, 4(4):187-191.
Tomita et al., "The Effect of Dexmedetomidine on Oral Mucosal Blood Flow and the Absorption of Lidocaine," Anesth Prog 2018, 65: 168-176.
Trevisan et al., "Intranasal dexmedetomidine and intravenous ketamine for procedural sedation in a child with alpha-mannosidosis: a magic bullet?" Italian Journal of Pediatrics (2019) 45:119, 6 pages.
Tug, et al., "Comparison of Two Different Intranasal Doses of Dexmedetomidine in Children for Magnetic Resonance Imaging Sedation." Paediatr Drugs (2015); 17 (6): 479-485.
UK Competent Authority, Chemicals Regulation Directorate, Health and Safety Executive, United Kingdom "CLH report, Proposal for Harmonised Classification and Labelling Based on Regulation (EC) No 1272/2008 (CLP Regulation), Annex VI, Part 2, Substance Name: Medetomidine," CLH Report for Medetomidine, Version No. 1, Oct. 2014, pp. 1-64.
UMIN-CTR Clinical Trial Identifier: UMIN000020446, Intranasal Premedication with Dexmedetomidine and midazolam in ophthalmic surgery for pediatrics, are they really equally effective? Mansoura Faculty of Medicine, mansoura university, Date of disclosure of study Feb. 1, 2016, Last modified Jan. 5, 2016, Registered Jan. 5, 2016, https://upload.umin.ac.jp/cgi-open-bin/ctr_e/ctr_view.cgi?recptno=R000023623, downloaded May 5, 2018, 5 pages.
Upadhyay et al., "Dexmedetomidine Infusion to Facilitate Opioid Detoxification and Withdrawal in a Patient with Chronic Opioid Abuse," Indian Journal of Palliative Care, Sep.-Dec. 2011, 17:(3)251-254.
Upadhyay et al., "Prolonged dexmedetomidine infusion to facilitate drug detoxification and withdrawal in patients with multiple drugs addiction," Crit Care & Shock (2011) 14:84-88.
Uusalo et al., "Feasibility of Intranasal Dexmedetomidine in Treatment of Postoperative Restlessness, Agitation, and Pain in Geriatric Orthopedic Patients," Drugs &Aging (2021) vol. 38, pp. 441-450.
Uusalo et al., "Pharmacokinetics and Sedative Effects of Intranasal Dexmedetomidine in Ambulatory Pediatric Patients," Anesth Analg. Apr. 2020;130(4):949-957.
Vega et al., "Prevention of Opioid Withdrawal Syndrome After Pediatric Heart Transplantation: Usefulness of Dexmedetomidine," Scientific Letters/Rev Esp Cardiol, 2013;66(7):593-595.
Virkkila, et al., "Dexmedetomidine as intramuscular premedication for daycase cataract surgery." Anaesthesia (1994); 49(10): 853-858.
Virkkila, et al., "Dexmedetomidine as intramuscular premedication in outpatient cataract surgery." Anaesthesia (1993); 48(6): 482-487.
Walsh, et al., "Use of intranasal dexmedetomidine for preoperative sedation in the pediatric population: a case series." Anesthesiology 2008; 109, A1378, 1 page.
Wang et al., "Comparison of Intranasal Dexmedetomidine and Oral Midazolam for Premedication in Pediatric Dental Patients under General Anesthesia: A Randomised Clinical Trial," BioMed Research International, 2020, vol. 2020, Article ID 5142913, 7 pages.
Wang et al., "Effects of dexmedetomidine nasal spray on preoperative sedation and analgesia and postoperative agitation in children with ventricular septal defect closure," Chinese Journal of Experimental Surgery, 2016, 33(3), English abstract only, 4 pages.
Wang et al., "Pharmacokinetics of Intranasally Administered Dexmedetomidine in Chinese Children," Front. Pharmacal., Jul. 2019, 10:756, 9 pages.
Wang, et al., "The sedative effects and the attenuation of cardiovascular and arousal responses during anesthesia induction and intubation in pediatric patients: a randomized comparison between two different doses of preoperative intranasal dexmedetomidine." Paediatr Anaesth (2014); 24 (3): 275-281.
Whittington et al., "Dexmedetomidine increases tau phosphorylation under normothermic conditions in vivo and in vitro," Neurobiology of Aging (2015) 36: 2414-2428.
Whittington et al., "Dexmedetomidine induces tau hyperphosphorylation in the mouse hippocampus," Alzheimer's & Dementia, Jul. 2012, vol. 8, Issue 4, Supplement, pp. P461-P462.
Wikipedia, Bipolar I disorder, Mar. 30, 2018, 5 pages, retrieved from https://en.wikipedia.org/w/index.php?title=Bipolar_1_disorder&oldid=833316388.
Wilson et al., "The Psychopharmacology of Agitation: Consensus Statement of the American Association for Emergency Psychiatry Project BETA Psychopharmacology Workgroup," West J Emerg Med. 2012; 13(1):26-34.
Winstock et al., "'Should I stay or should I go?' Coming off methadone and buprenorphine treatment," International Journal of Drug Policy (2011) 22:77-81.
Wong and Freeman, "Cutaneous allergic reaction to intramuscular vitamin K1." Australian Journal of Dermatology (1999); 40 (3): 147-152.
Written Opinion of the International Searching Authority, PCT appl. No. PCT/US2015/055828, 7 pages (mailed Mar. 1, 2016).
Wu et al., "Efficacy and safety of intravenous dexmedetomidine in adjuvant general anesthesia," Chinese Journal of Anesthesiology, 2007, Issue 9, 773-776, English abstract only, 4 pages.
Wu, et al., "Intranasally Administered Adjunctive Dexmedetomidine Reduces Perioperative Anesthetic Requirements in General Anesthesia." Yonsei Med J (2016); 57 (4): 998-1005.
Wu et al., "Neuroprotective effect of dexmedetomidine in a murine model of traumatic brain injury," Scientific Reports, (2018) 8:4935, 10 pages.
Xu et al., "ED50 of dexmedetomidine nasal drip in induction of hypnosis in children during computed tomography," Zhonghua Yi Xue Za Zhi. Jun. 24, 2014;94(24):1886-8, English abstract only.
Xu, et al., "Effects of dexmedetomidine on the recovery profiles from general anesthesia in patients undergoing endoscopic sinus surgery." Int J Clin Exp Med (2016); 9(5): 8405-8410.
Xu et al., "Effects of Two Intranasal Dexmedetomidine Doses as Premedication on Sevoflurane EC 50 for Successful Laryngeal Mask Airway Placement in Children," Zhongguo Yi Xue Ke Xue Yuan Xue Bao. Dec. 20, 2016;38(6):627-631, English abstract only.
Xu et al., "Efficacy and Safety of Intranasal Dexmedetomidine During Recovery From Sevoflurane Anesthesia in Children: A Systematic Review and Meta-analysis," Clin Neuropharmacol, 2021; 44:157-168.
Yamane et al., "Effect of Dexmedetomidine Injected Into the Oral Mucosa in Combination With Lidocaine on Local Anesthetic Potency in Humans: A Crossover Double-Blind Study," J Oral Maxillofac Surg, 2015 73:616-621.
Yang et al., "Analysis of 17 948 pediatric patients undergoing procedural sedation with a combination of intranasal dexmedetomidine and ketamine," Paediatr Anaesth., 2019; 29(1):85-91.
Yang et al., "Effect of dexmedetomidine on postoperative cognitive dysfunction and inflammation in patients after general anaesthesia, A PRISMA-compliant systematic review and meta-analysis," Medicine (2019) 98:18(e15383), 10 pages.
Yang et al., "Fifty Percent Effective Dose of Intranasal Dexmedetomidine Sedation for Transthoracic Echocardiography in Children With Cyanotic and Acyanotic Congenital Heart Disease," Journal of Cardiothoracic and Vascular Anesthesia (2020), 34, 966-971.
Yao, et al., "Intranasal dexmedetomidine premedication reduces minimum alveolar concentration of sevoflurane for laryngeal mask airway insertion and emergence delirium in children: a prospective, randomized, double-blind, placebo-controlled trial." Pediatric Anesthesia (2015); 25 (5): 492-498.
Yingyi, et al., "ED50 of dexmedetomidine nasal drip in induction of hypnosis in children during computed tomography." Zhonghua Yi Xue Za Zhi (2014); 94(24): 1886-1888.
Yuen, et al., "A Comparison of Intranasal Dexmedetomidine and Oral Midazolam for Premedication in Pediatric Anesthesia: A Double-Blinded Randomized Controlled Trial." Anesthesia & Analgesia (2008); 106 (6): 1715-1721.

(56) References Cited

OTHER PUBLICATIONS

Yuen, et al., "A Double-Blind, Crossover Assessment of the Sedative and Analgesic Effects of Intranasal Dexmedetomidine." Anesthesia & Analgesia (2007); 105 (2): 374-380.

Yuen, et al., "A randomised comparison of two intranasal dexmedetomidine doses for premedication in children." Anaesthesia (2012); 67 (11): 1210-1216.

Yuen, et al., "Optimal timing for the administration of intranasal dexmedetomidine for premedication in children." Anaesthesia (2010); 65 (9): 922-939.

Yun, et al., "Effects of intranasal dexmedetomidine for children undergoing cleft lip and palate repair surgery." International Journal of Somatology (2016); 43 (4): 401-405.

Ozcengiz et al., "Oral melatonin, dexmedetomidine, and midazolam for prevention of postoperative agitation in children," J Anesth (2011) 25:184-188.

Zhang, et al., "Median Effective Dose of Intranasal Dexmedetomidine for Rescue Sedation in Pediatric Patients Undergoing Magnetic Resonance Imaging." Anesthesiology (2016); 125 (6): 1130-1135.

Zhang et al., "The Effect of Dexmedetomidine on Cognitive Function and Protein Expression of A13, p-Tau, and PSD95 after Extracorporeal Circulation Operation in Aged Rats," Hindawi BioMed Research International, Jan. 2018, vol. 2018, Article ID 4014021, 8 pages.

Zhang et al., "The Safety and Efficacy of Intranasal Dexmedetomidine During Electrochemotherapy for Facial Vascular Malformation: A Double-Blind, Randomized Clinical Trial," J Oral Maxillofac Surg, 2013 71:1835-1842.

Zheng et al., "Administration of Dexmedetomidine inhibited NLRP3 inflammasome and microglial cell activities in hippocampus of traumatic brain injury rats," Bioscience Reports, Accepted Manuscript, Sep. 19, 2018, 29 pages.

Zornow, et al., "Dexmedetomidine Decreases Cerebral Blood Flow Velocity in Humans." Journal of Cerebral Blood Flow & Metabolism (1993); 13(2): 350-353.

Zub et al., "Preliminary experience with oral dexmedetomidine for procedural and anesthetic premedication," Pediatric Anesthesia 2005 15: 932-938.

IGALMI (dexmedetomidine) label, Highlights of Prescribing Information, Apr. 28, 2022, 21 pages.

Boyer, Jeanne, "Treating Agitation With Dexmedetomidine in the ICU." Dimensions of Critical Care Nursing (2009); 28(3): 102-109.

cognitivevitality.org. "Dexmedetomidine" Mar. 19, 2019, 11 pages, retrieved from https://www.alzdiscovery.org/uploads/cognitive_vitality_media/Dexmedetomidine-Cognitive-Vitality-For-Researchers.pdf.

Weerink et al., "Clinical Pharmacokinetics and Pharmacodynamics of Dexmedetomidine." Clinical Pharmacokinetics (2017); 56: 893-913.

* cited by examiner

NON-SEDATING DEXMEDETOMIDINE TREATMENT REGIMENS

FIELD

Disclosed herein are methods of treating a human subject having a condition (e.g., agitation) which can be improved using an alpha-2 adrenergic receptor agonist. The methods comprise administering dexmedetomidine or a pharmaceutically acceptable salt thereof at a suitable dose, and via an appropriate route of administration, to achieve a plasma concentration profile that provides a rapid improvement to the subject's condition without also inducing significant sedation. The administration regimens are also selected to provide maximum therapeutic benefit to the subject, without incurring any significant side effects, such as undesirable cardiovascular events. The disclosed methods are particularly suitable for the treatment of agitation or signs of agitation, especially when associated with schizophrenia or a bipolar illness, such as bipolar I disorder or bipolar II disorder.

BACKGROUND

On Dec. 17, 1999, the U.S. Food and Drug Administration approved a dexmedetomidine product, PRECEDEX®, formulated as an intravenous solution for continuous infusion, and indicated as a sedative agent for initially intubated and mechanically ventilated patients during treatment in an intensive care setting. PRECEDEX® was later approved as a sedative agent for non-intubated patients prior to and/or during surgical and other procedures.

Dexmedetomidine has also been administered intravenously and via other routes to treat a range of conditions, often peri- or post-surgery, including the treatment of pain, anxiety, delirium, withdrawal symptoms, sleep disorders and agitation. However, administration of dexmedetomidine in an appropriate dosage form to provide effective, rapid, relief for the subject without also causing significant sedation is a challenging task. The utilization of dexmedetomidine has also been limited in clinical practice due to its common side effects, such as hypotension and bradycardia. For example, significant cardiovascular side-effects have occurred at therapeutic doses following administration of dexmedetomidine hydrochloride via a sublingual spray or tablets, or intravenously. Thus, a continuing, unmet need exists for an effective dexmedetomidine product which does not cause significant sedation, and desirably is effective without also producing significant adverse effects, such as cardiovascular events. The unmet need is particularly acute for non-addictive medicines that can effectively treat agitation or signs of agitation without also producing the aforementioned adverse effects and sedation.

SUMMARY

The present disclosure is related to the discovery that an agitated human subject with schizophrenia or bipolar I or II disorder and a hepatic impairment can be treated with an oromucosal formulation comprising dexmedetomidine or a pharmaceutically acceptable salt thereof in a lower dose than a similar human subject without a hepatic impairment.

The present disclosure provides a method of using dexmedetomidine, comprising: administering an initial dose of dexmedetomidine or a pharmaceutically acceptable salt thereof in an oromucosal formulation to a human subject having an agitation associated with schizophrenia or bipolar I or II disorder;

optionally administering a second dose of dexmedetomidine or the pharmaceutically acceptable salt thereof in the oromucosal formulation to the human subject at least two hours after and within 24 hours of the initial dose; and optionally administering a third dose of dexmedetomidine or the pharmaceutically acceptable salt thereof in the oromucosal formulation to the human subject at least two hours after the second dose and within 24 hours of the initial dose;

wherein the administration of the dexmedetomidine does not exceed a maximum total daily dosage;

wherein the human subject has a hepatic impairment;

wherein the second dose and the third dose are 60 mcg of dexmedetomidine each;

wherein the initial dose is 90 mcg of dexmedetomidine and the maximum total daily dosage is 210 mcg of dexmedetomidine if the agitation is mild or moderate and if the hepatic impairment is mild or moderate;

wherein the initial dose is 120 mcg of dexmedetomidine and the maximum total daily dosage is 240 mcg of dexmedetomidine if the agitation is severe and if the hepatic impairment is mild or moderate;

wherein the initial dose is 60 mcg of dexmedetomidine and the maximum total daily dosage is 180 mcg of dexmedetomidine if the agitation is mild or moderate and if the hepatic impairment is severe; and wherein the initial dose is 90 mcg of dexmedetomidine and the maximum total daily dosage is 210 mcg of dexmedetomidine if the agitation is severe and if the hepatic impairment is severe.

In some embodiments of the method, the second dose of dexmedetomidine is optional, and in some other embodiments of the methods the second dose of dexmedetomidine is not optional.

In some embodiments of the method, the third dose of dexmedetomidine is optional and in some other embodiments of the methods the third dose of dexmedetomidine is not optional.

In some embodiments of the method, agitation that is mild or moderate is defined as a Positive and Negative Syndrome Scale-Excited Component (PEC) score of 19 or lower. In some embodiments of the method, agitation that is mild is defined as a PEC score of 13 or lower. In some embodiments of the method, agitation that is moderate is defined as a PEC score of 14 to 19 inclusive. In some embodiments of the method, agitation that is severe is defined as a PEC score of 20 or higher.

In some embodiments of the method, the hepatic impairment is mild that is defined as Child-Pugh Class A. In some embodiments of the method, the hepatic impairment is moderate that is defined as Child-Pugh Class B. In some embodiments of the method, the hepatic impairment is severe that is defined as Child-Pugh Class C.

In some embodiments of the method, the third dose is administered at least two hours after the second dose and within 24 hours of the initial dose.

In some embodiments of the method, the agitation is mild or moderate and the hepatic impairment is mild or moderate, and wherein the initial dose is 90 mcg of dexmedetomidine and the maximum total daily dosage is 210 mcg of dexmedetomidine. In some embodiments of the method, the third dose is administered at least two hours after the second dose and within 24 hours of the initial dose.

In some embodiments of the method, the agitation is severe and the hepatic impairment is mild or moderate, and wherein the initial dose is 120 mcg of dexmedetomidine and the maximum total daily dosage is 240 mcg of dexmedetomidine. In some embodiments of the method, the third dose is administered at least two hours after the second dose and within 24 hours of the initial dose.

In some embodiments of the method, the agitation is mild or moderate and the hepatic impairment is severe, and wherein the initial dose is 60 mcg of dexmedetomidine and the maximum total daily dosage is 180 mcg of dexmedetomidine. In some embodiments of the method, the third dose is administered at least two hours after the second dose and within 24 hours of the initial dose.

In some embodiments of the method, the agitation is severe and the hepatic impairment is severe, and wherein the initial dose is 90 mcg of dexmedetomidine and the maximum total daily dosage is 210 mcg of dexmedetomidine. In some embodiments of the method, the third dose is administered at least two hours after the second dose and within 24 hours of the initial dose.

A method of using an oromucosal formulation of dexmedetomidine for an acute treatment of an agitation associated with schizophrenia or bipolar I or II disorder in a human subject, wherein the human subject does not have a hepatic impairment, the method comprising:
  administering an initial dose of dexmedetomidine or a pharmaceutically acceptable salt thereof in the oromucosal formulation to the human subject;
  optionally administering a second dose of dexmedetomidine or the pharmaceutically acceptable salt thereof in the oromucosal formulation to the human subject at least two hours after and within 24 hours of the initial dose; and
  optionally administering a third dose of dexmedetomidine or the pharmaceutically acceptable salt thereof in the oromucosal formulation to the human subject at least two hours after the second dose and within 24 hours of the initial dose;
  wherein the administration of the dexmedetomidine does not exceed a maximum total daily dosage;
  wherein the initial dose, the second dose, the third dose, and the maximum total daily dosage are 120 mcg, 60 mcg, 60 mcg, and 240 mcg of dexmedetomidine, respectively, if the human subject is younger than 65 years of age and if the agitation is mild or moderate;
  wherein the initial dose, the second dose, the third dose, and the maximum total daily dosage are 180 mcg, 90 mcg, 90 mcg, and 360 mcg of dexmedetomidine, respectively, if the human subject is younger than 65 years of age and if the agitation is severe; and
  wherein the initial dose, the second dose, the third dose, and the maximum total daily dosage are 120 mcg, 60 mcg, 60 mcg, and 240 mcg of dexmedetomidine, respectively, if the human subject is 65 years of age or older and if the agitation is mild, moderate, or severe.

A method of using an oromucosal formulation of dexmedetomidine for an acute treatment of an agitation associated with schizophrenia or bipolar I or II disorder in a human subject, the method comprising:
  administering an initial dose of dexmedetomidine or a pharmaceutically acceptable salt thereof in the oromucosal formulation to the human subject;
  optionally administering a second dose of dexmedetomidine or the pharmaceutically acceptable salt thereof in the oromucosal formulation to the human subject at least two hours after and within 24 hours of the initial dose; and
  optionally administering a third dose of dexmedetomidine or the pharmaceutically acceptable salt thereof in the oromucosal formulation to the human subject at least two hours after the second dose and within 24 hours of the initial dose;
  wherein the administration of the dexmedetomidine does not exceed a maximum total daily dosage;
  wherein the initial dose, the second dose, the third dose, and the maximum total daily dosage are 120 mcg, 60 mcg, 60 mcg, and 240 mcg of dexmedetomidine, respectively, if the human subject is younger than 65 years of age and if the agitation is mild or moderate;
  wherein the initial dose, the second dose, the third dose, and the maximum total daily dosage are 180 mcg, 90 mcg, 90 mcg, and 360 mcg of dexmedetomidine, respectively, if the human subject is younger than 65 years of age and if the agitation is severe; and
  wherein the initial dose, the second dose, the third dose, and the maximum total daily dosage are 120 mcg, 60 mcg, 60 mcg, and 240 mcg of dexmedetomidine, respectively, if the human subject is 65 years of age or older and if the agitation is mild, moderate, or severe.

In any embodiments of the method, the oromucosal formulation further comprises at least one water-soluble polymer. In some embodiments, the at least one water-soluble polymer is selected from the group consisting of hydroxypropyl cellulose, hydroxypropyl methylcellulose, hydroxyethyl cellulose, carboxy methylcellulose, methylcellulose, polyethylene oxide (PEO), and mixtures thereof. In some embodiments, the at least one water-soluble polymer is hydroxypropyl cellulose.

treated with a sublingual film containing dexmedetomidine hydrochloride (60 µg, 80 µg, 120 µg and 180 µg) versus a placebo group. The error bars in the figure represent "standard error." The preparation of dexmedetomidine hydrochloride sublingual film (60 µg) is exemplified in Example 1 and dexmedetomidine hydrochloride sublingual films (80 µg, 120 µg and 180 µg) are exemplified in Example 2.

Figure 5A:
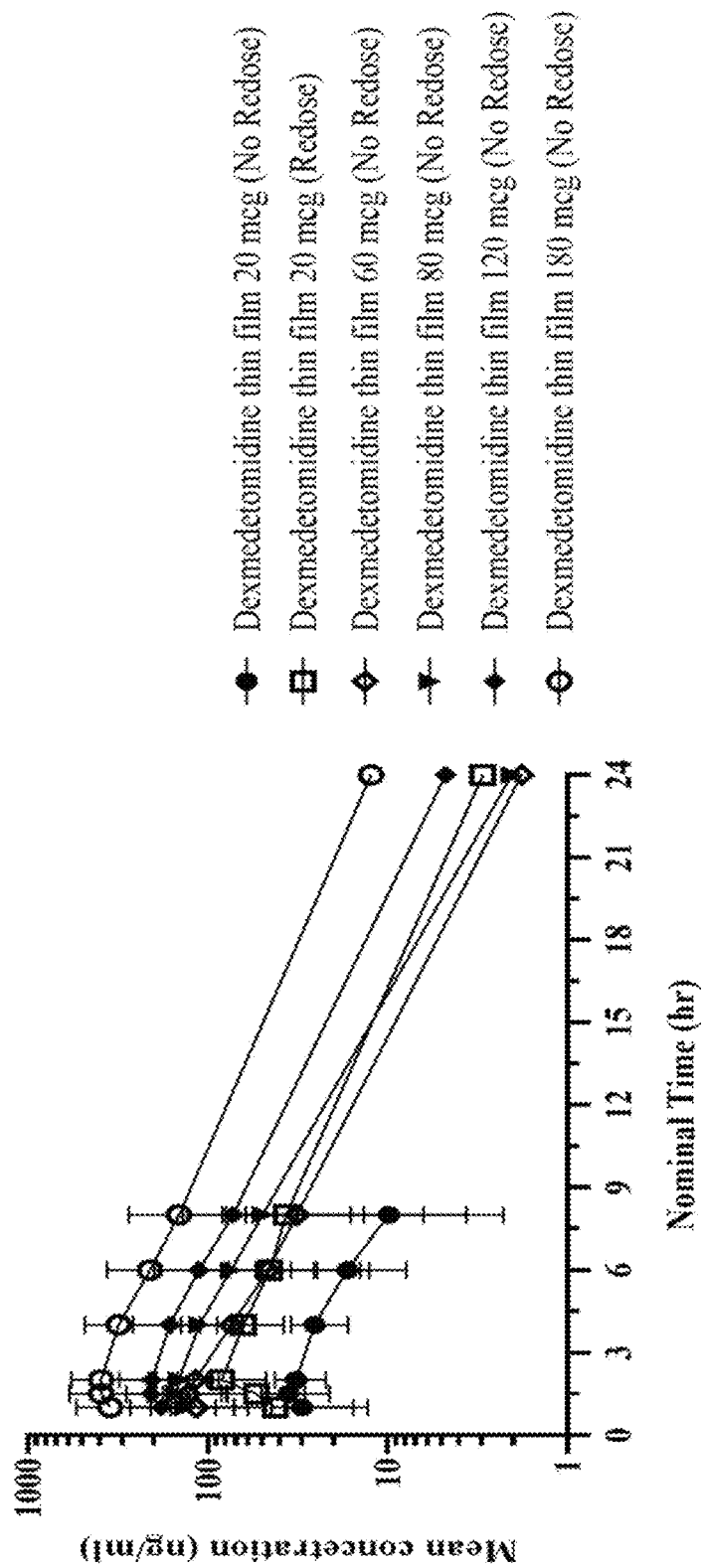

FIG. 5A depicts the mean dexmedetomidine plasma concentration vs. nominal time sorted by dose and redose (Semilog Scale) in schizophrenic patients (Pharmacokinetic Population) treated with a sublingual film containing dexmedetomidine hydrochloride (20 µg, 20 µg (redose), 60 µg, 80 µg, 120 µg and 180 µg) versus a placebo group. The preparation of dexmedetomidine hydrochloride sublingual films (20 µg and 60 µg) are exemplified in Example 1 and dexmedetomidine hydrochloride sublingual films (80 µg, 120 µg and 180 µg) are exemplified in Example 2.

Figure 5B:
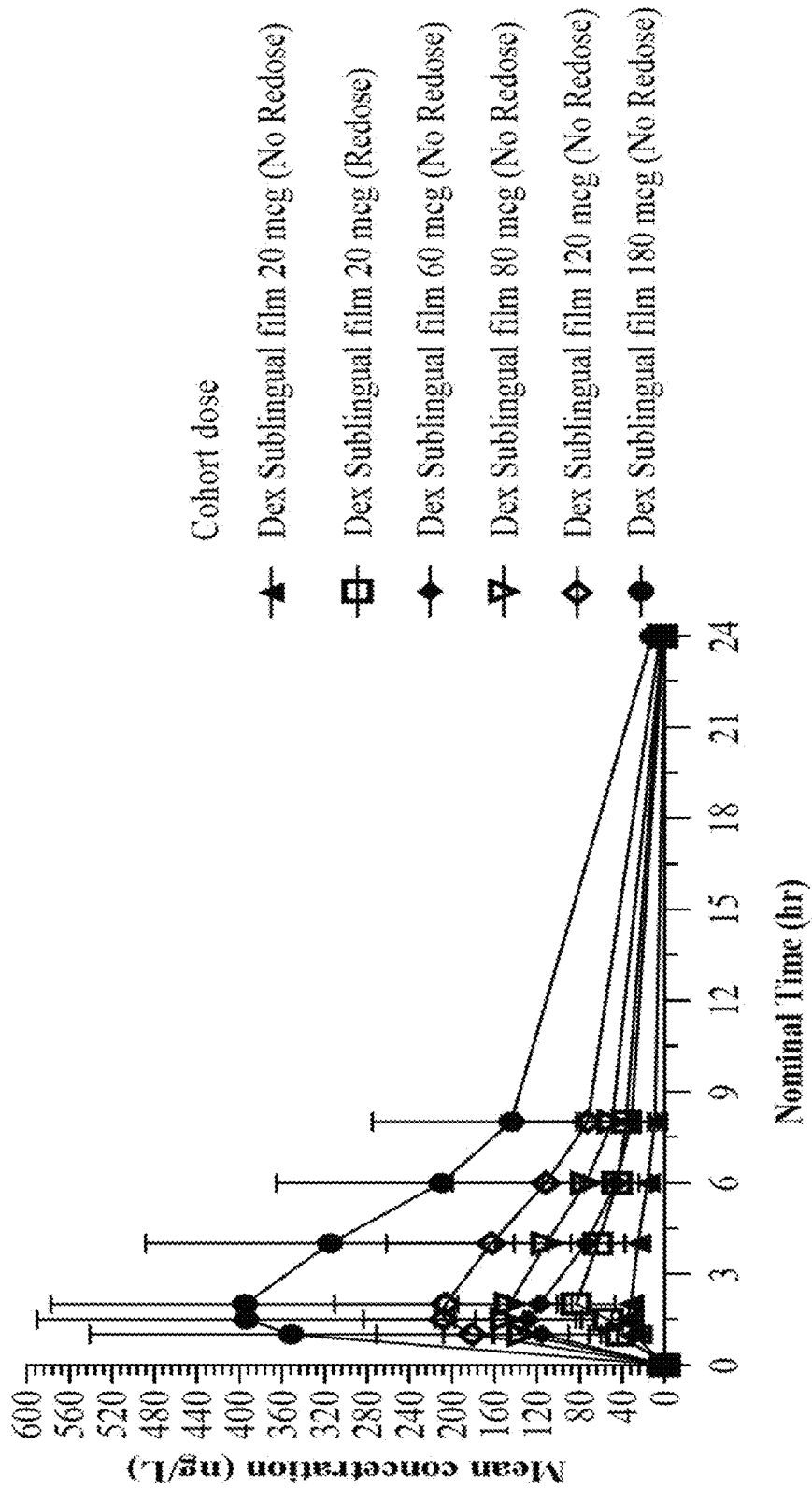

FIG. 5B depicts the mean dexmedetomidine plasma concentration vs. nominal time sorted by dose and redose (Linear Scale) in schizophrenic patients (Pharmacokinetic Population) treated with a sublingual film containing dexmedetomidine hydrochloride (20 µg, 20 µg (redose), 60 µg, 80 µg, 120 µg and 180 µg) versus a placebo group. The preparation of dexmedetomidine hydrochloride sublingual films (20 µg and 60 µg) are exemplified in Example 1 and dexmedetomidine hydrochloride sublingual films (80 µg, 120 µg and 180 µg) are exemplified in Example 2.

Figure 6A:
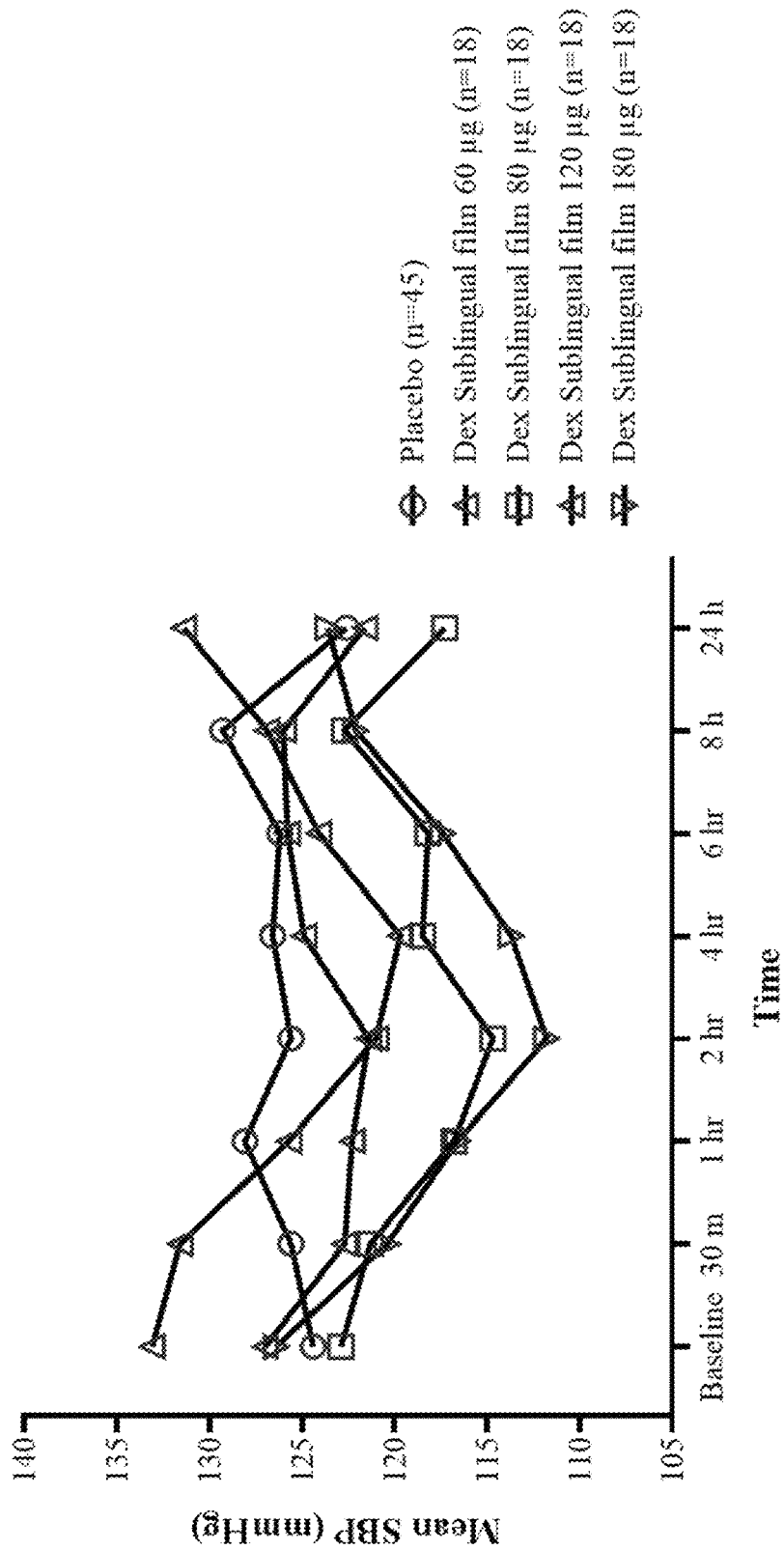

FIG. 6A depicts the mean values for resting systolic blood pressure (SBP) over time in schizophrenic patients (Safety Population) treated with a sublingual film containing dexmedetomidine hydrochloride (60 µg, 80 µg, 120 µg and 180 µg) versus a placebo group. The preparation of dexmedetomidine hydrochloride sublingual film (60 µg) is exemplified in Example 1 and dexmedetomidine hydrochloride sublingual films (80 µg, 120 µg and 180 µg) are exemplified in Example 2.

Figure 6B:
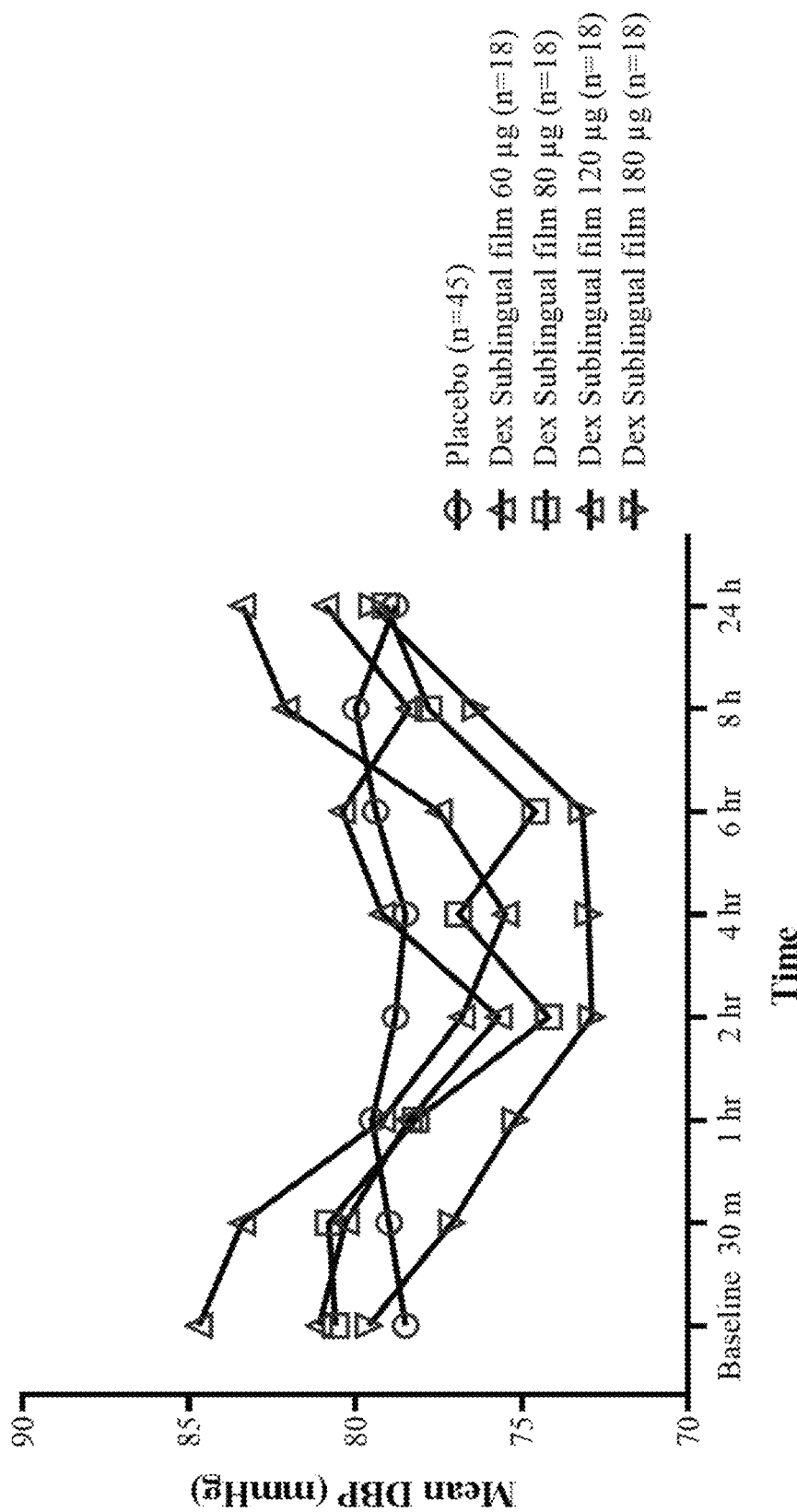

FIG. 6B depicts the mean values for resting diastolic blood pressure (DBP) over time in schizophrenic patients (Safety Population) treated with a sublingual film containing dexmedetomidine hydrochloride (60 µg, 80 µg, 120 µg and 180 µg) versus a placebo group. The preparation of dexmedetomidine hydrochloride sublingual film (60 µg) is exemplified in Example 1 and dexmedetomidine hydrochloride sublingual films (80 µg, 120 µg and 180 µg) are exemplified in Example 2.

Figure 6C:
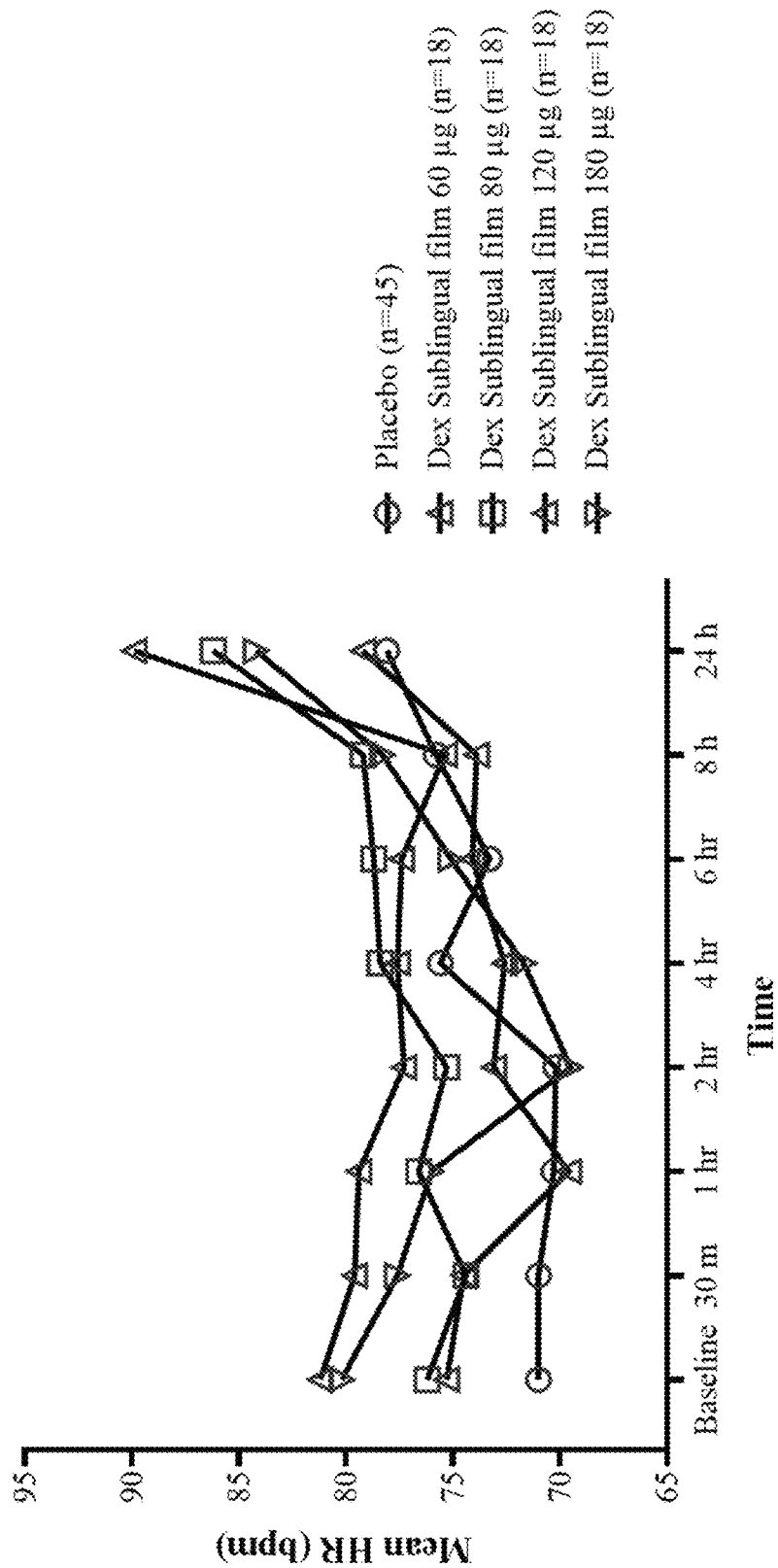

FIG. 6C depicts the mean values for resting heart rate (HR) over time in schizophrenic patients (Safety Population) treated with a sublingual film containing dexmedetomidine hydrochloride (60 µg, 80 µg, 120 µg and 180 µg) versus a placebo group. The preparation of dexmedetomidine hydrochloride sublingual film (60 µg) is exemplified in Example 1 and dexmedetomidine hydrochloride sublingual films (80 µg, 120 µg and 180 µg) are exemplified in Example 2.

Figure 7A:
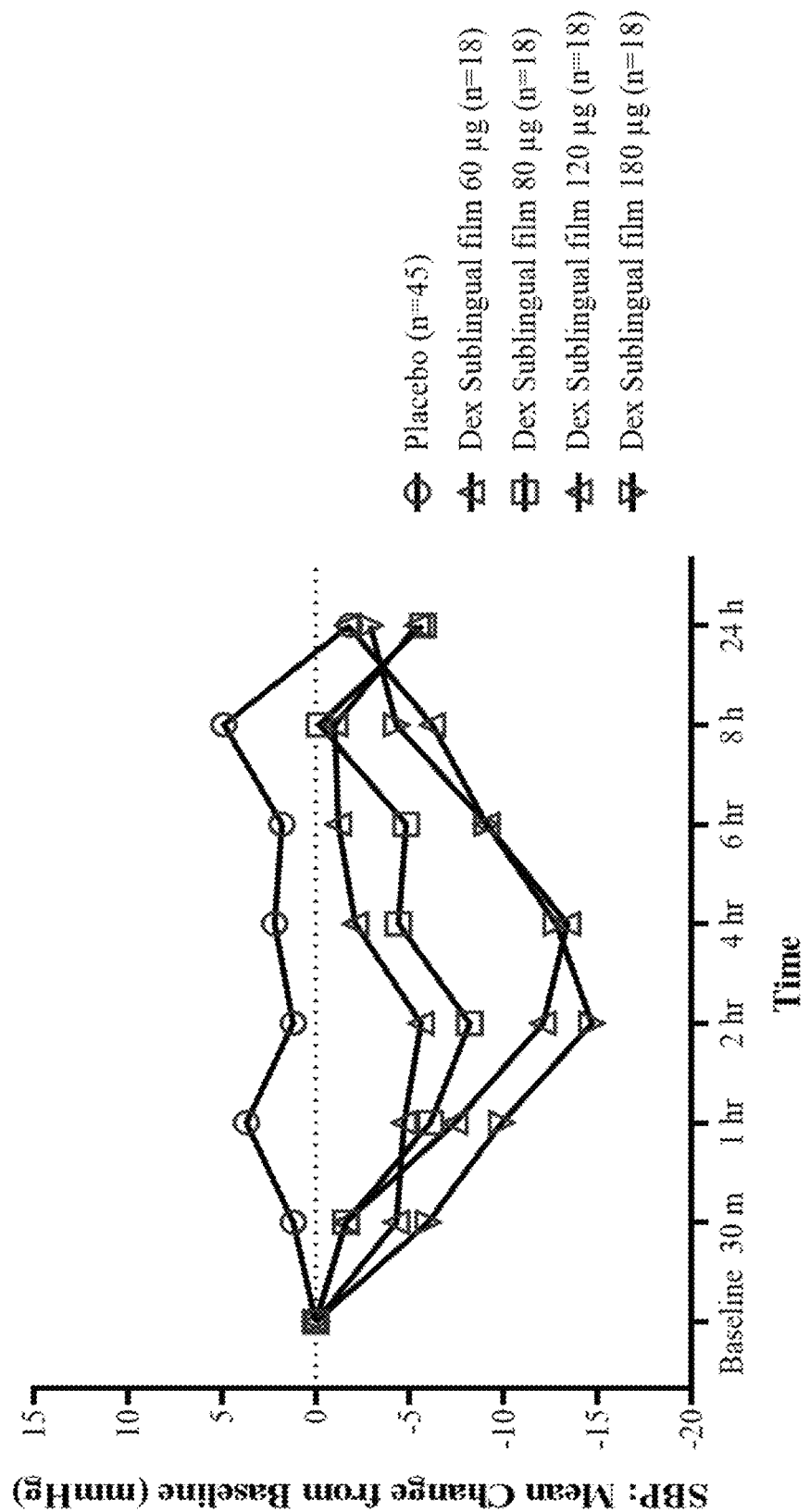

FIG. 7A depicts the mean change from baseline for resting systolic blood pressure (SBP) over time in schizophrenic patients (Safety Population) treated with a sublingual film containing dexmedetomidine hydrochloride (60 µg, 80 µg, 120 µg and 180 µg) versus a placebo group. The preparation of dexmedetomidine hydrochloride sublingual film (60 µg) is exemplified in Example 1 and dexmedetomidine hydrochloride sublingual films (80 µg, 120 µg and 180 µg) are exemplified in Example 2.

Figure 7B:
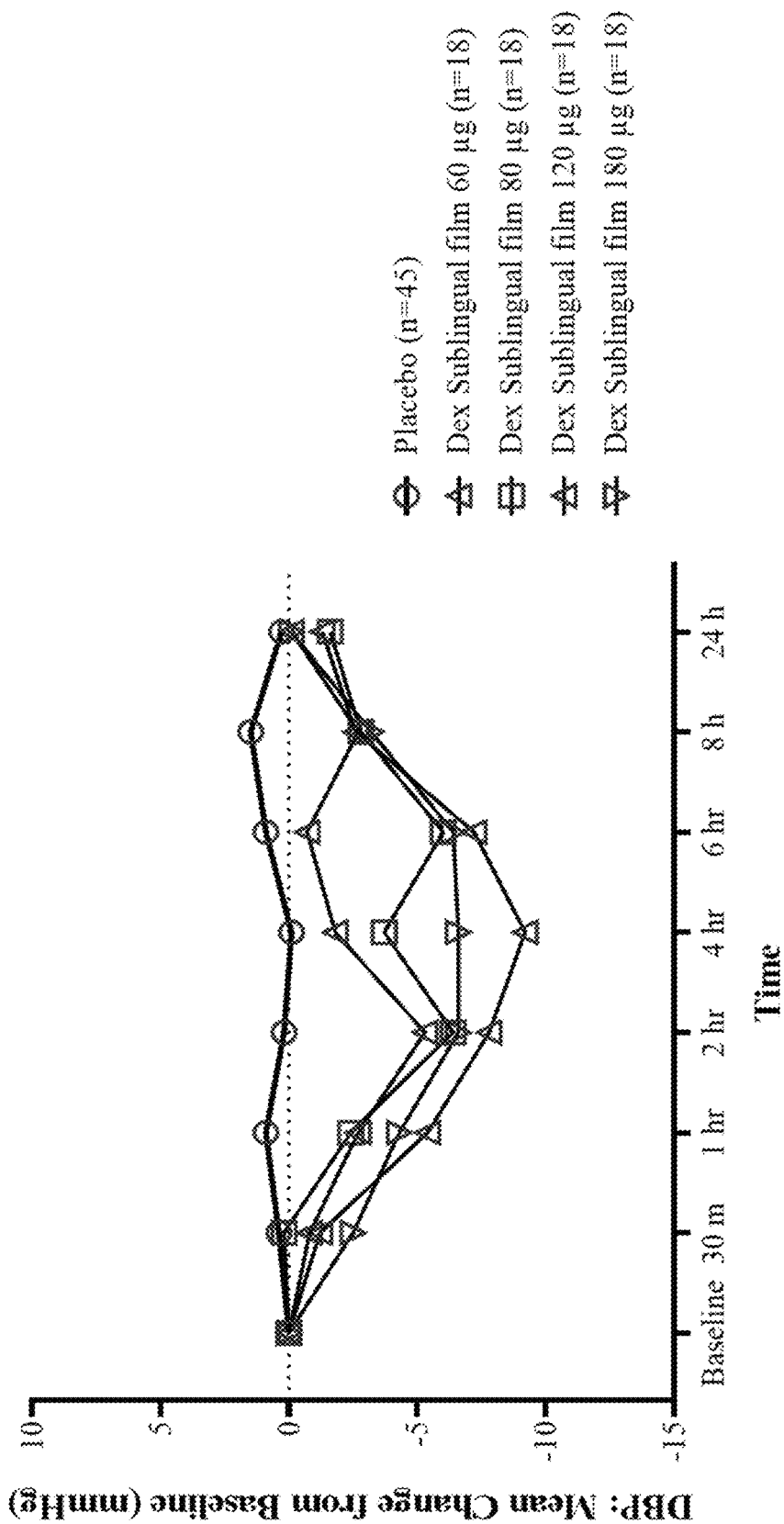

FIG. 7B depicts the mean change from baseline for resting diastolic blood pressure (DBP) over time in schizophrenic patients (Safety Population) treated with a sublingual film containing dexmedetomidine hydrochloride (60 µg, 80 µg, 120 µg and 180 µg) versus a placebo group. The preparation of dexmedetomidine hydrochloride sublingual film (60 µg) is exemplified in Example 1 and dexmedetomidine hydrochloride sublingual films (80 µg, 120 µg and 180 µg) are exemplified in Example 2.

Figure 7C:
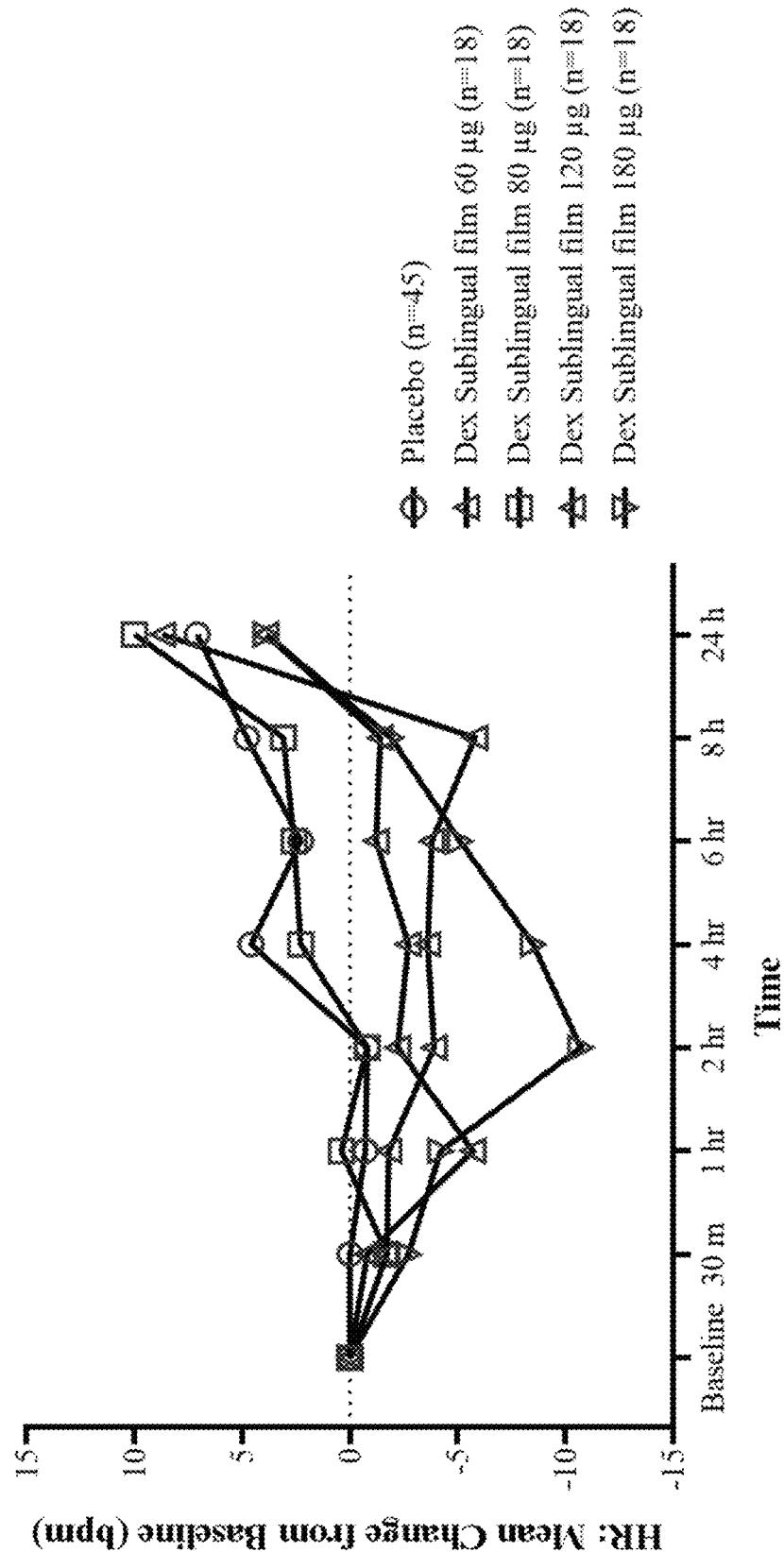

FIG. 7C depicts the mean change from baseline for resting heart rate (HR) over time in schizophrenic patients (Safety Population) treated with a sublingual film containing dexmedetomidine hydrochloride (60 µg, 80 µg, 120 µg and 180 µg) versus a placebo group. The preparation of dexmedetomidine hydrochloride sublingual film (60 µg) is exemplified in Example 1 and dexmedetomidine hydrochloride sublingual films (80 µg, 120 µg and 180 µg) are exemplified in Example 2.

Figure 8:
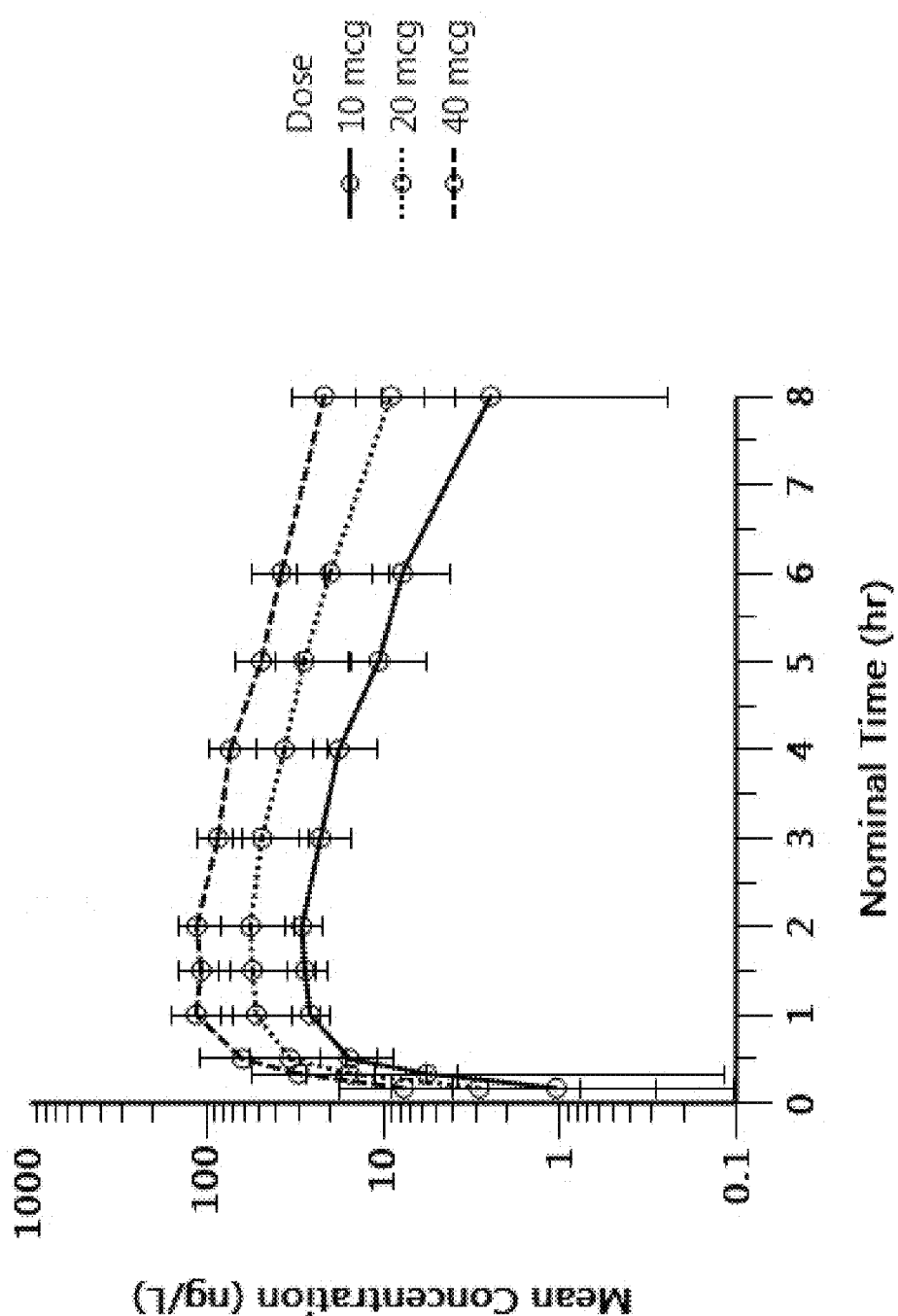

FIG. 8 shows the mean dexmedetomidine plasma log concentration vs. time for dose levels 10 µg, 20 µg and 40 µg of dexmedetomidine sublingual film (Semi-log scale). Error bars represent 1 standard deviation.

Figure 9A:
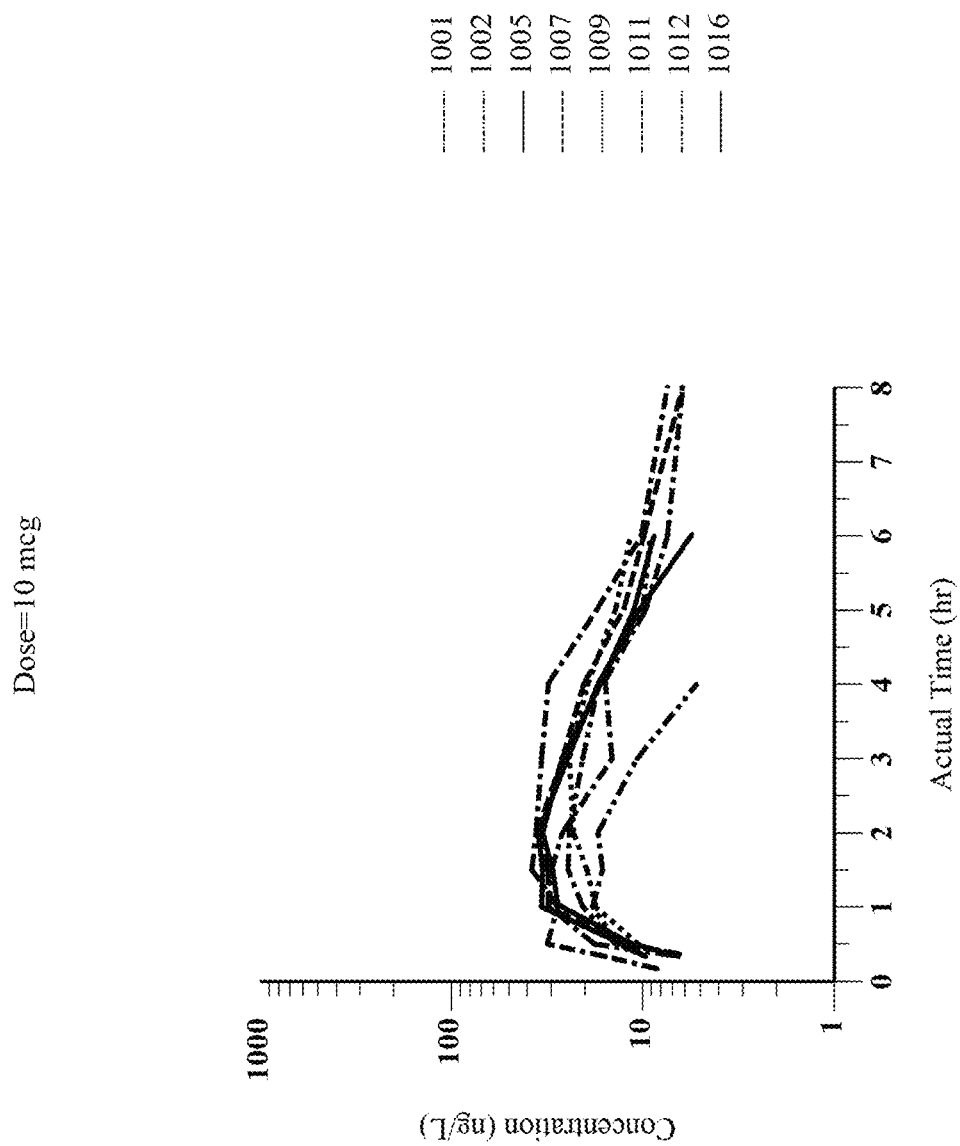

FIG. 9A depicts individual dexmedetomidine concentration-time profiles for all subjects by dose after administration of dexmedetomidine sublingual film (10 µg) Semi-log Scale. Dexmedetomidine sublingual film is exemplified in Example 1.

Figure 9B:
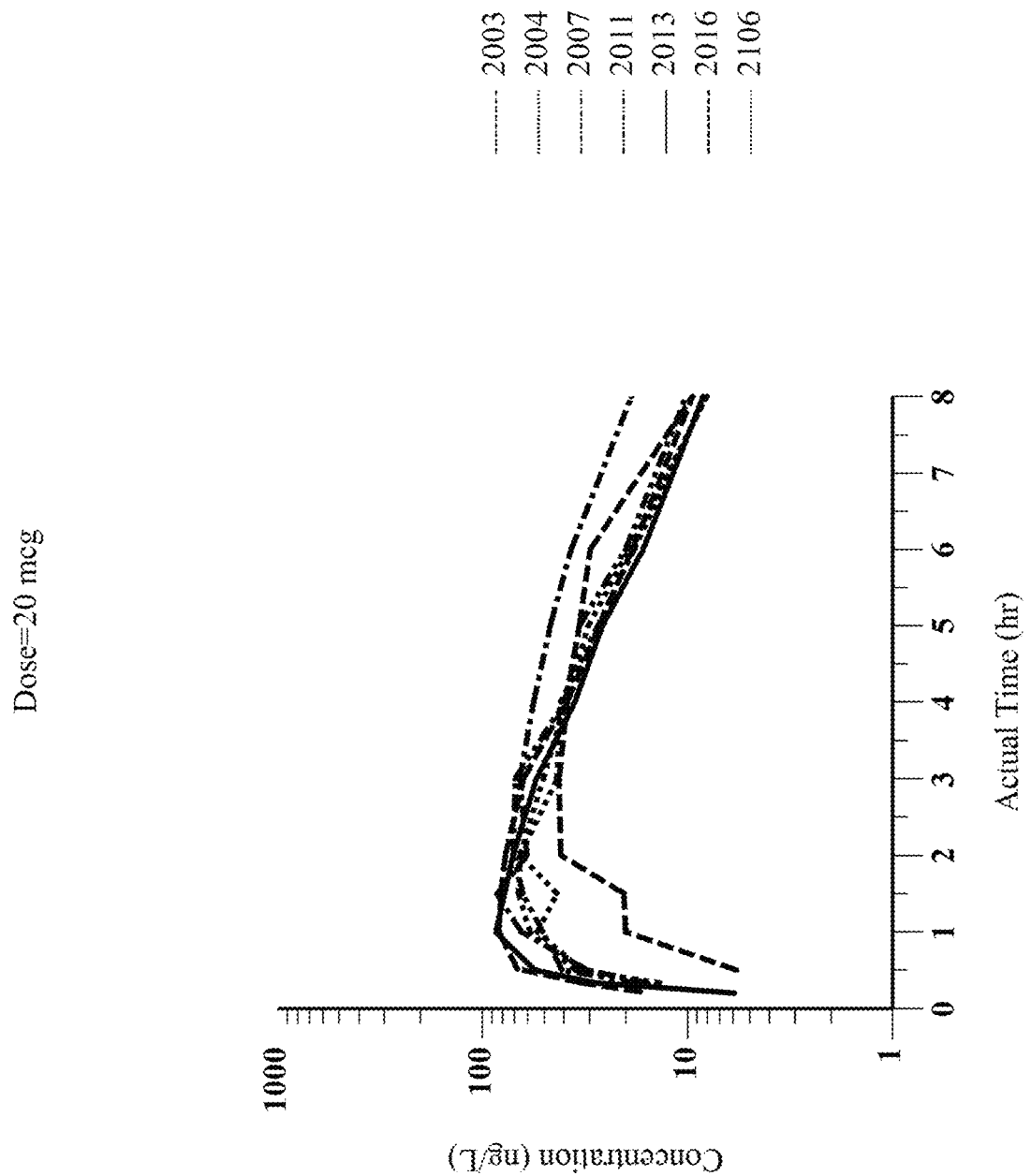

FIG. 9B depicts individual dexmedetomidine concentration-time profiles for all subjects by dose after administration of dexmedetomidine sublingual film (20 µg) Semi-log Scale. Dexmedetomidine sublingual film is exemplified in Example 1.

Figure 9C:
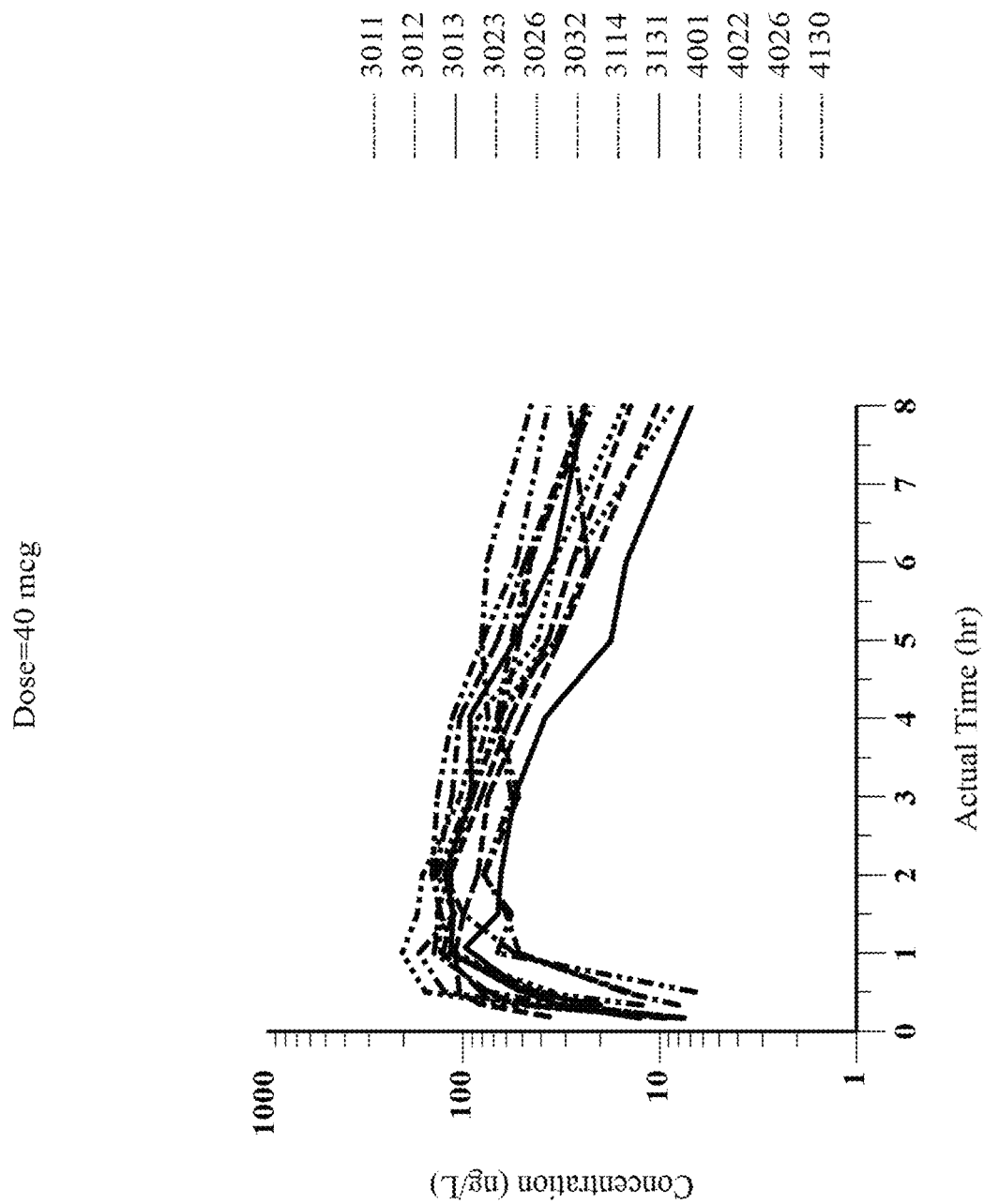

FIG. 9C depicts individual dexmedetomidine concentration-time profiles for all subjects by dose after administration of dexmedetomidine sublingual film (40 µg) Semi-log Scale. The preparation of Dexmedetomidine sublingual film is exemplified in Example 1.

Figure 10:
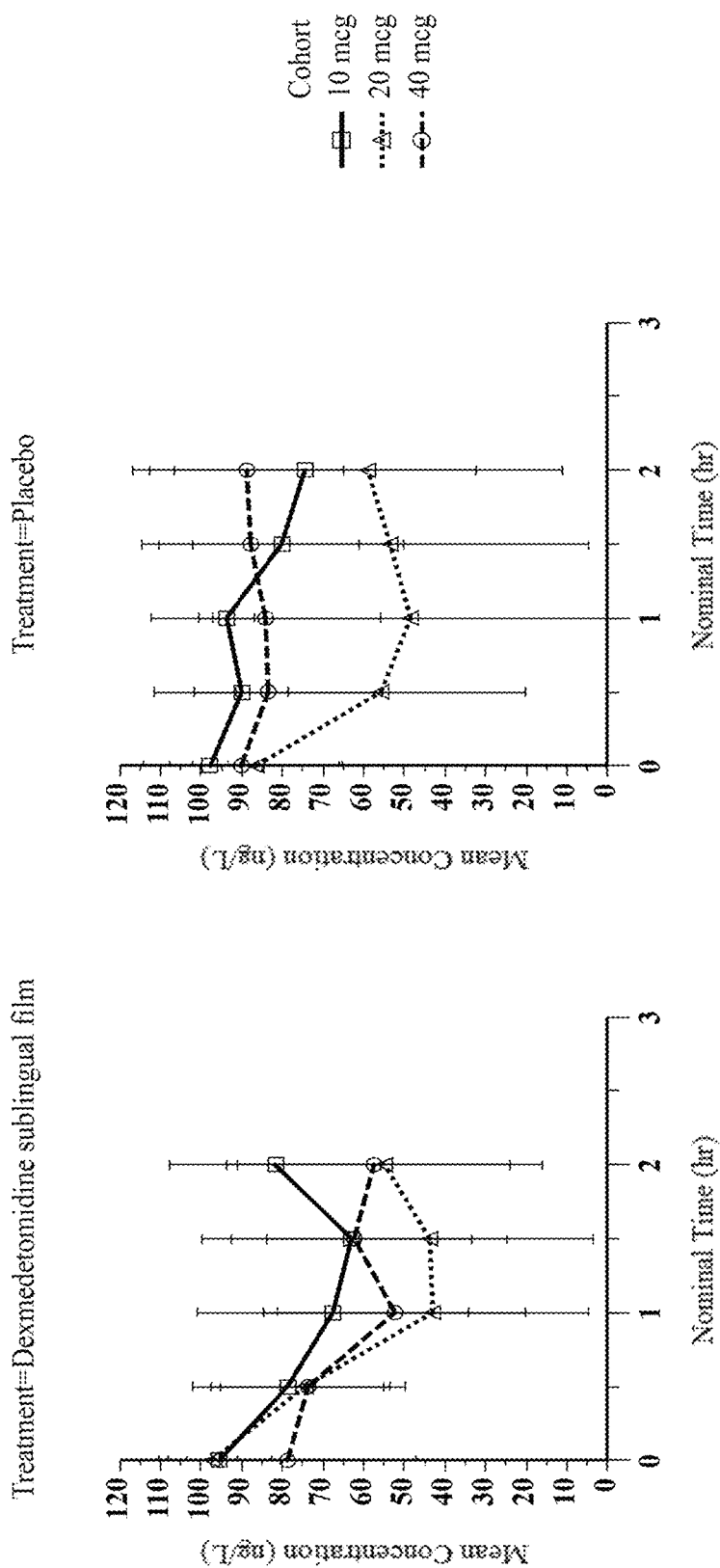

FIG. 10 depicts the mean VAS/S score vs. nominal time after administration of dexmedetomidine sublingual film (10 µg, 20 µg, 40 µg) and placebo. Dexmedetomidine sublingual film (10 µg and 20 µg) and the preparation of dexmedetomidine sublingual film (40 µg) are exemplified in Example 1.

Figure 11:
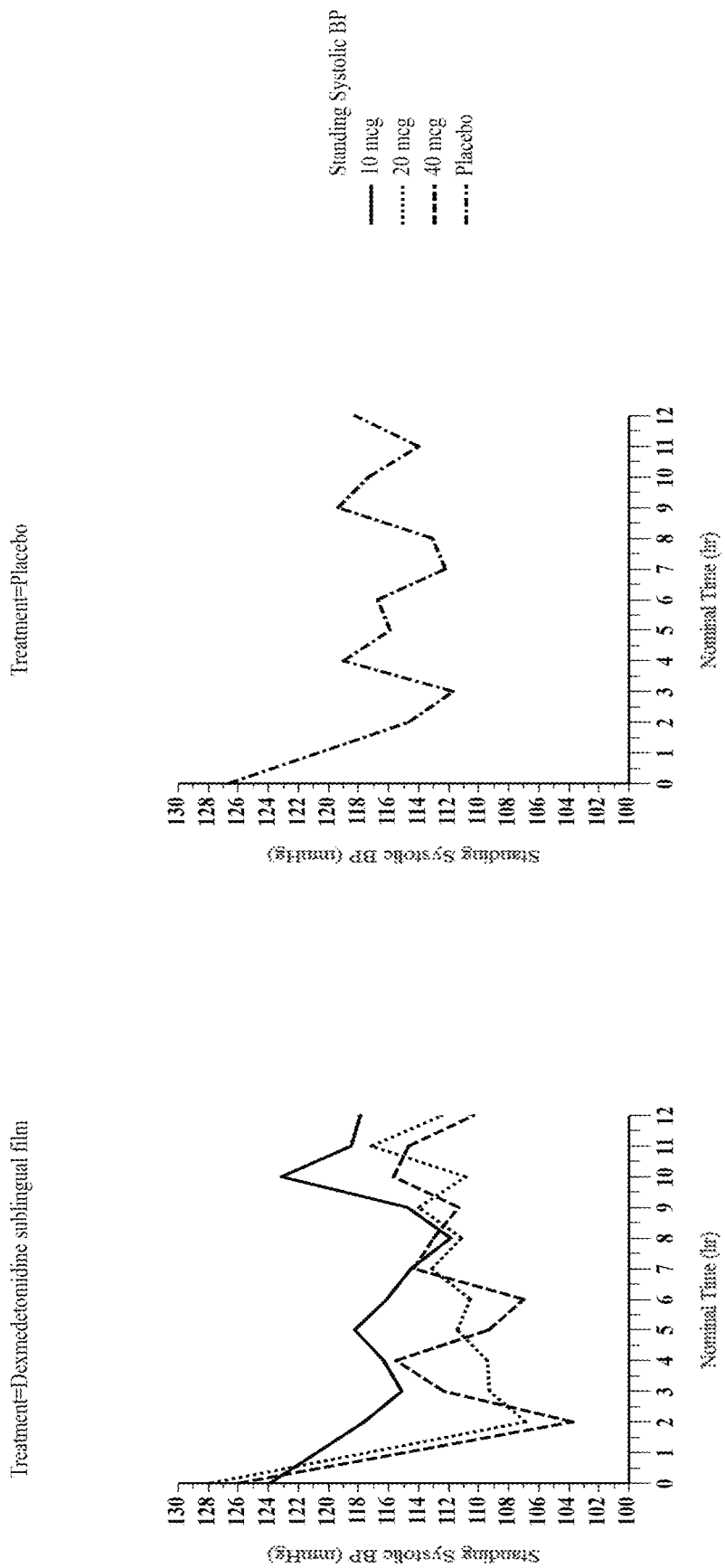

FIG. 11 depicts standing systolic BP vs nominal time after administration of dexmedetomidine sublingual film (10 µg, 20 µg, 40 µg) and placebo. Dexmedetomidine sublingual film (10 µg and 20 µg) and the preparation of dexmedetomidine sublingual film (40 µg) are exemplified in Example 1.

Figure 12:
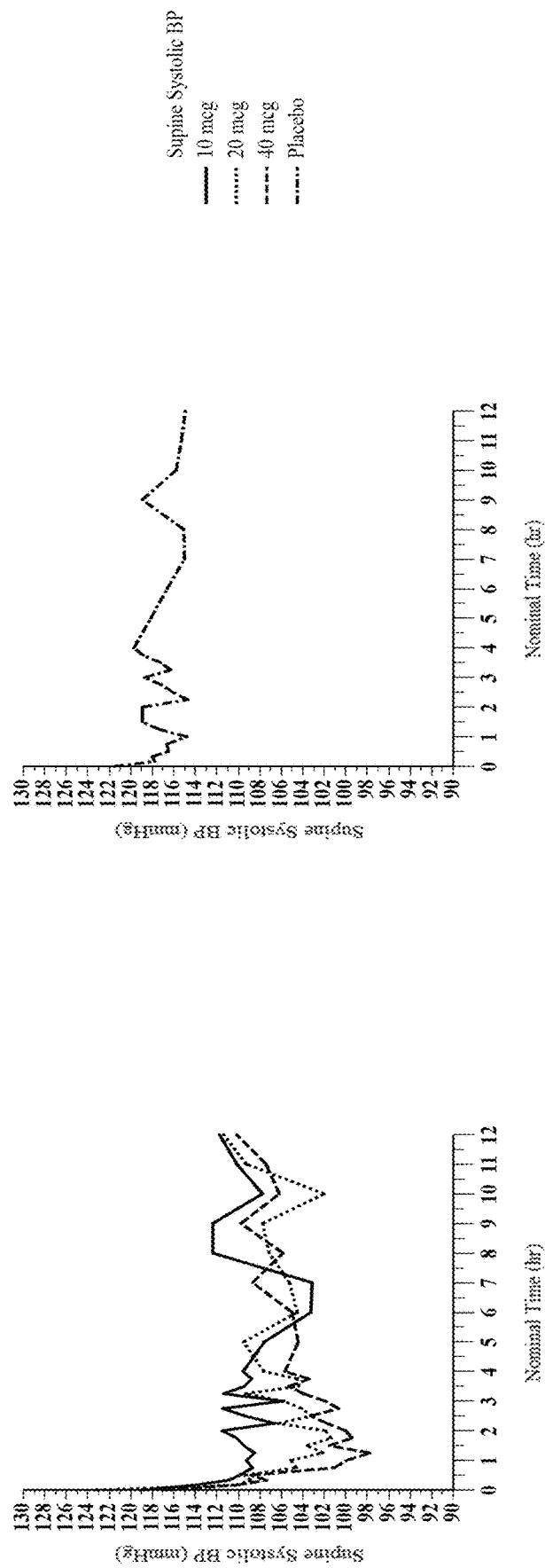

FIG. 12 depicts supine systolic BP. vs nominal time after administration of dexmedetomidine sublingual film 10 µg, 20 µg and 40 µg and placebo. Dexmedetomidine sublingual film (10 µg and 20 µg) and the preparation of dexmedetomidine sublingual film (40 µg) are exemplified in Example 1.

Figure 13:
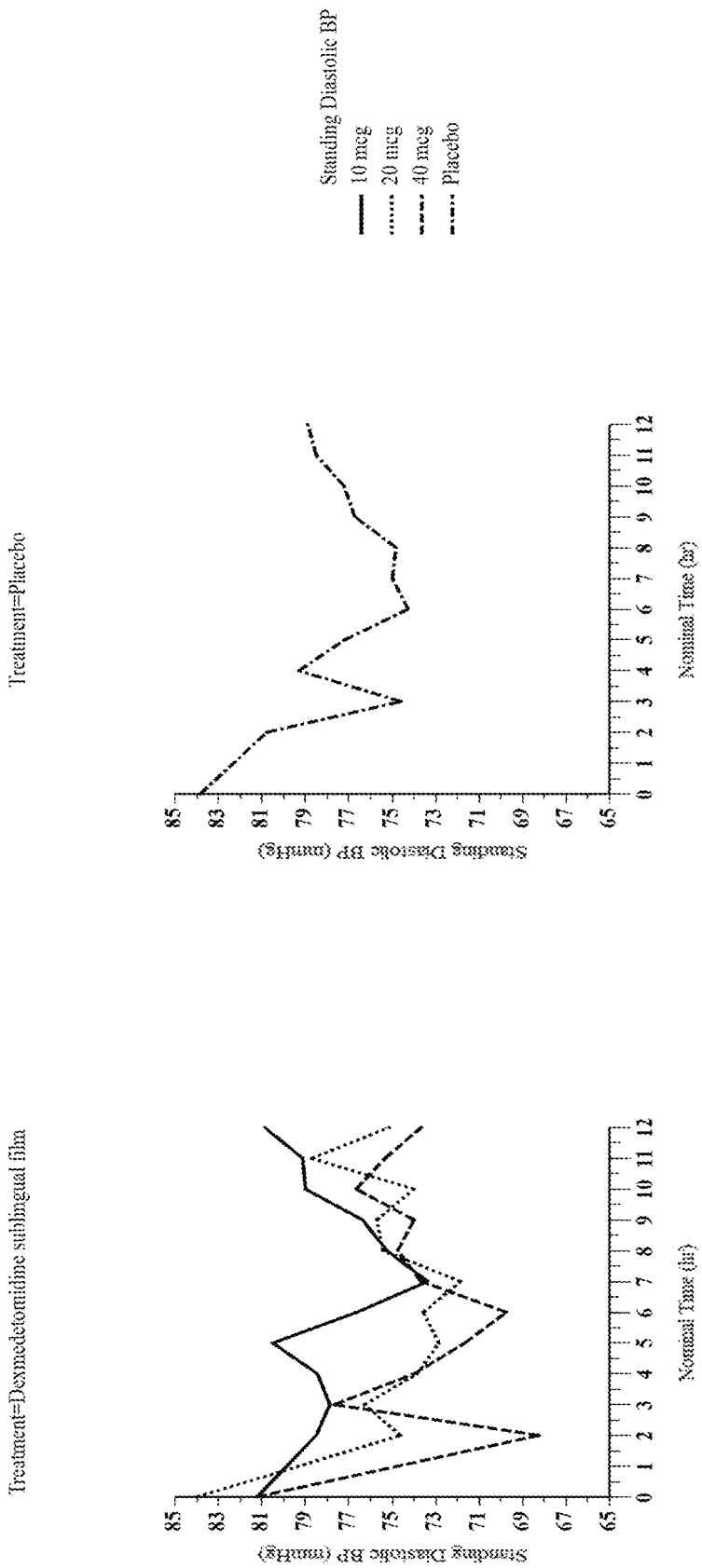

FIG. 13 depicts standing diastolic BP vs nominal time after administration of dexmedetomidine sublingual film 10 µg, 20 µg and 40 µg and placebo. Dexmedetomidine sublingual film (10 µg and 20 µg) and the preparation of dexmedetomidine sublingual film (40 µg) are exemplified in Example 1.

Figure 14:
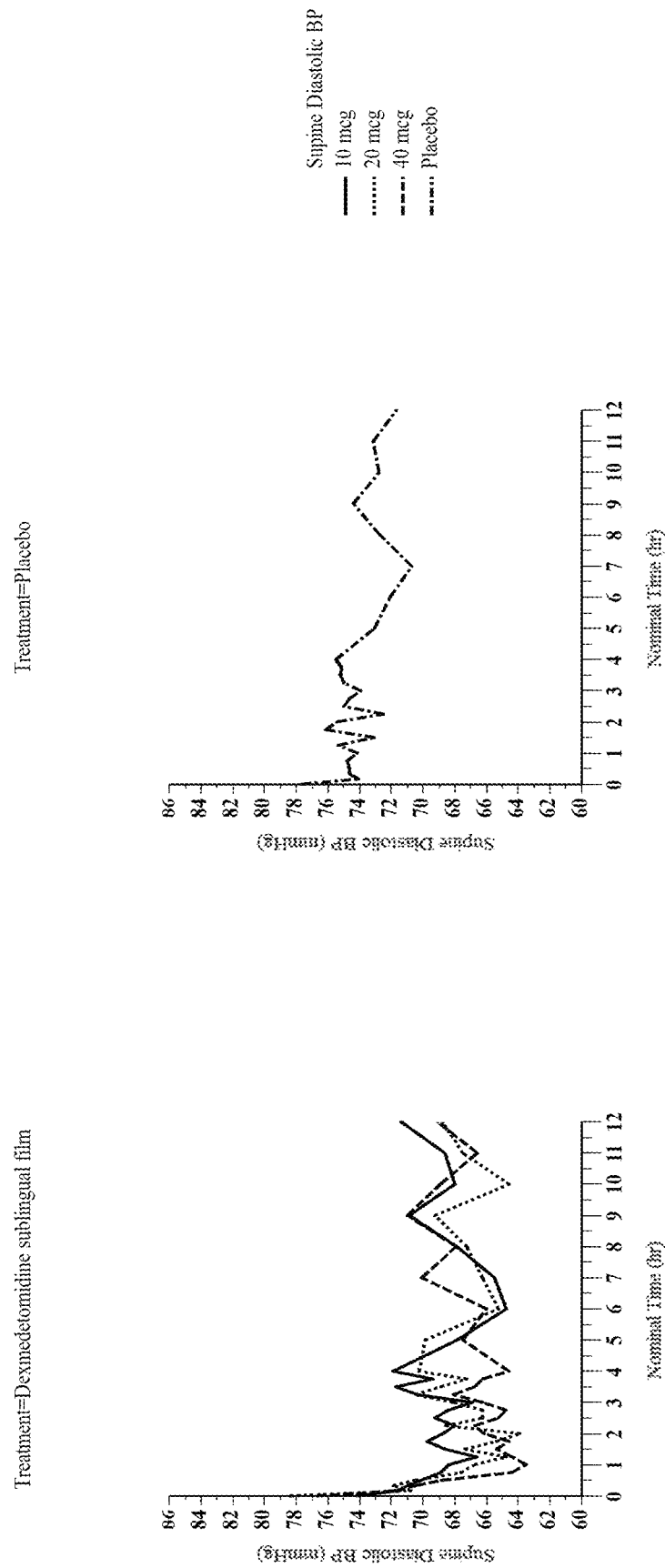

FIG. 14 depicts supine diastolic BP vs nominal time after administration of dexmedetomidine sublingual film 10 µg, 20 µg and 40 µg and placebo. Dexmedetomidine sublingual film (10 µg and 20 µg) and the preparation of dexmedetomidine sublingual film (40 µg) are exemplified in Example 1.

Figure 15:
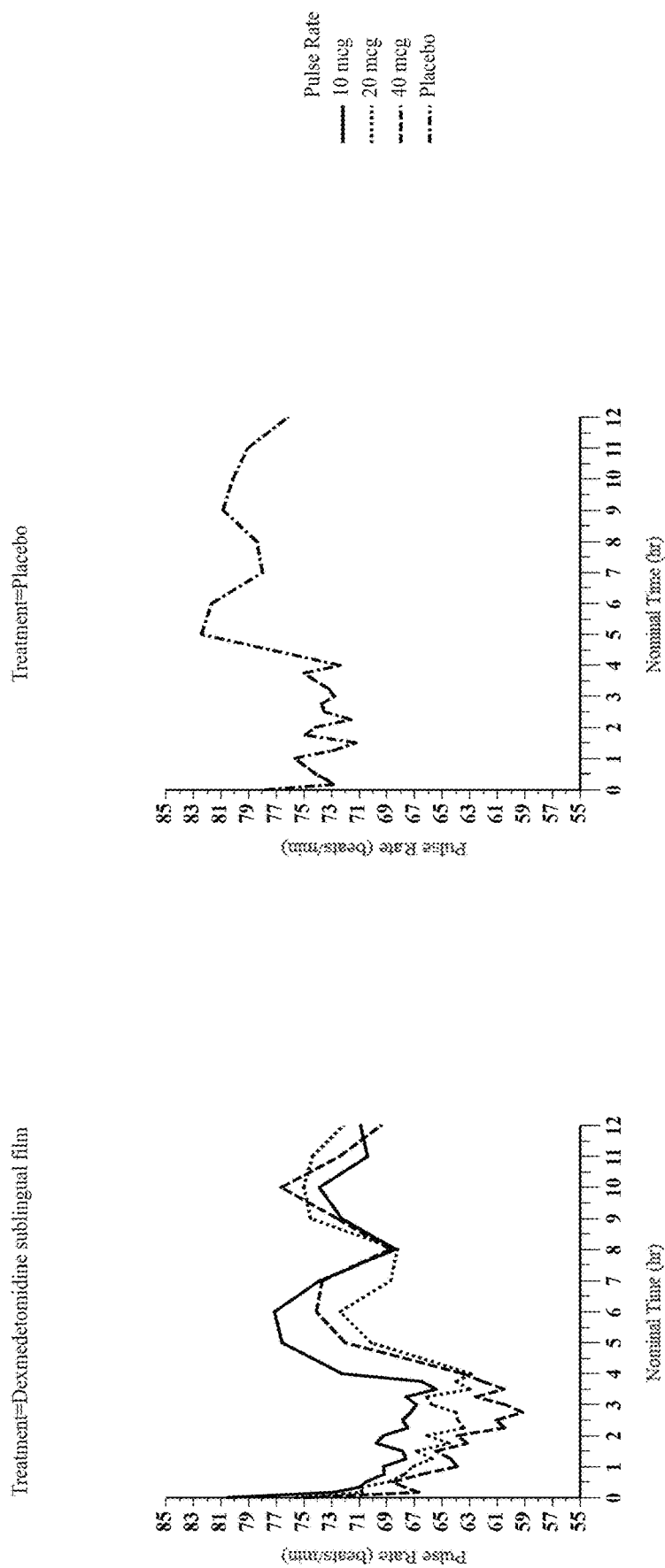

FIG. 15 depicts pulse rate vs nominal time after administration of dexmedetomidine sublingual film 10 µg, 20 µg and 40 µg and placebo. Dexmedetomidine sublingual film (10 µg and 20 µg) and the preparation of dexmedetomidine sublingual film (40 µg) are exemplified in Example 1.

Figure 16:
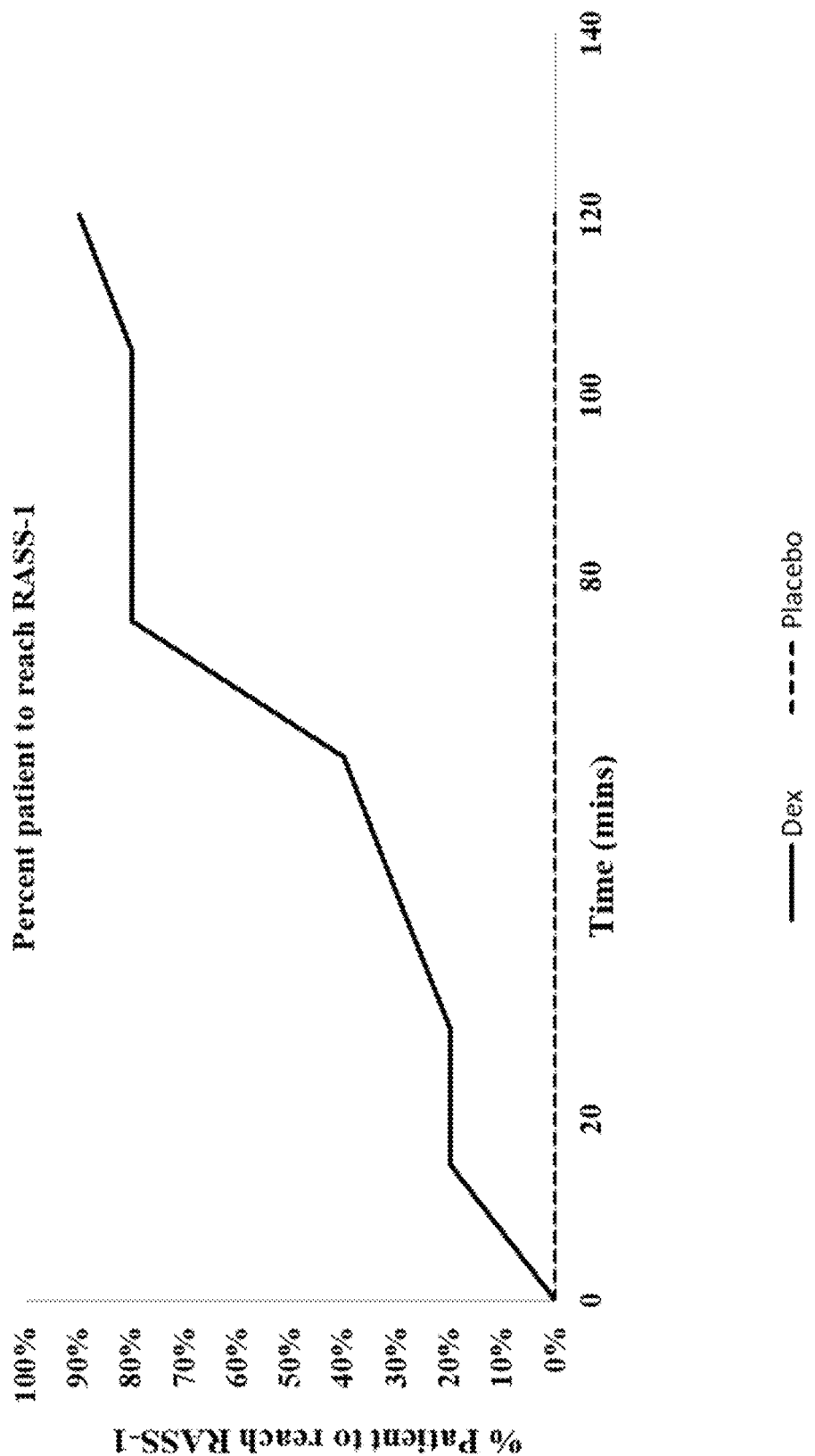

FIG. 16 depicts the percentage of schizophrenic patients achieving RASS-1 in the treatment arm (IV dexmedetomidine hydrochloride treated group) versus placebo group.

Figure 17:
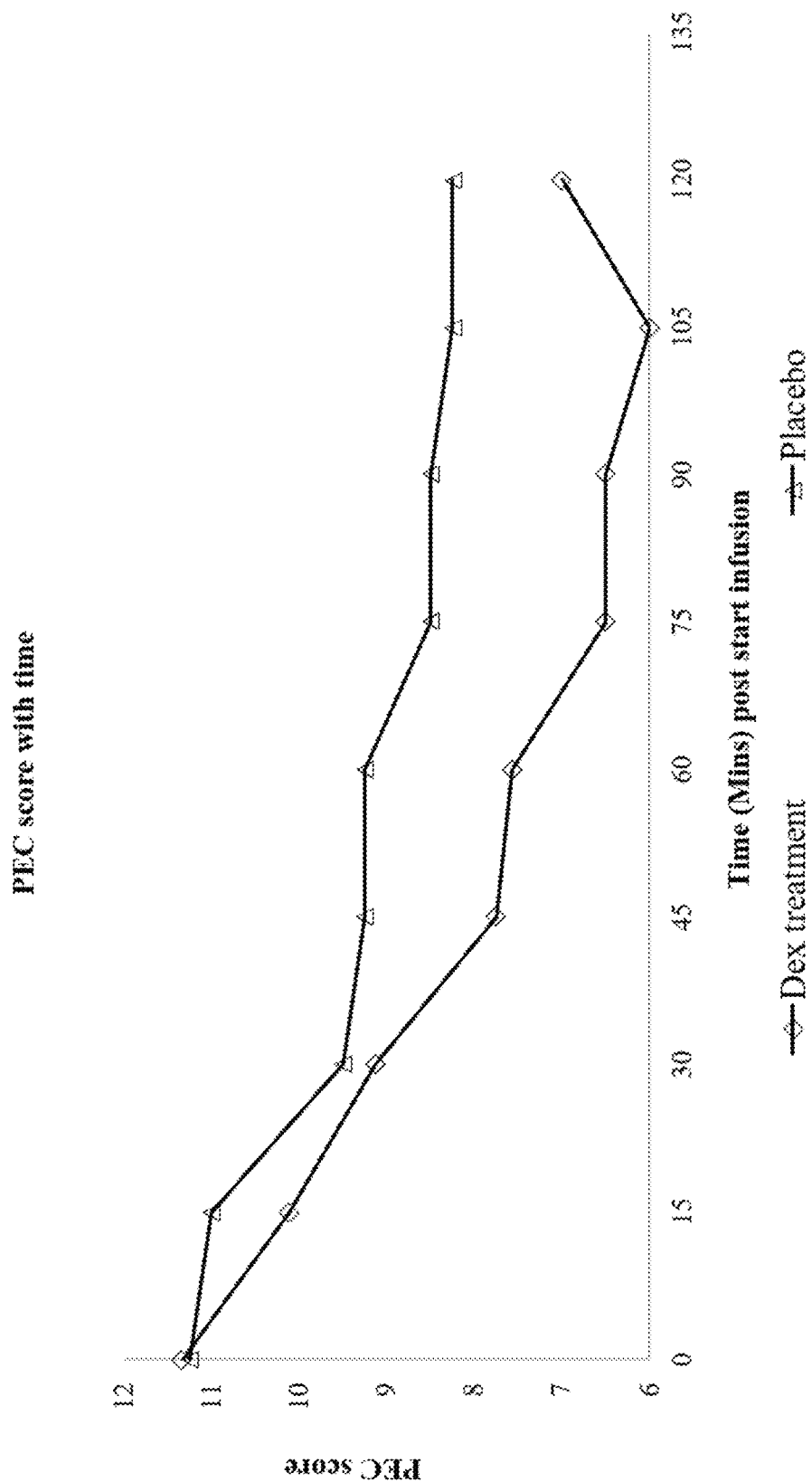

FIG. 17 depicts the mean drop in PEC score with time in schizophrenic patients in the treatment arm (IV dexmedetomidine hydrochloride treated group) versus placebo group.

Figure 18:
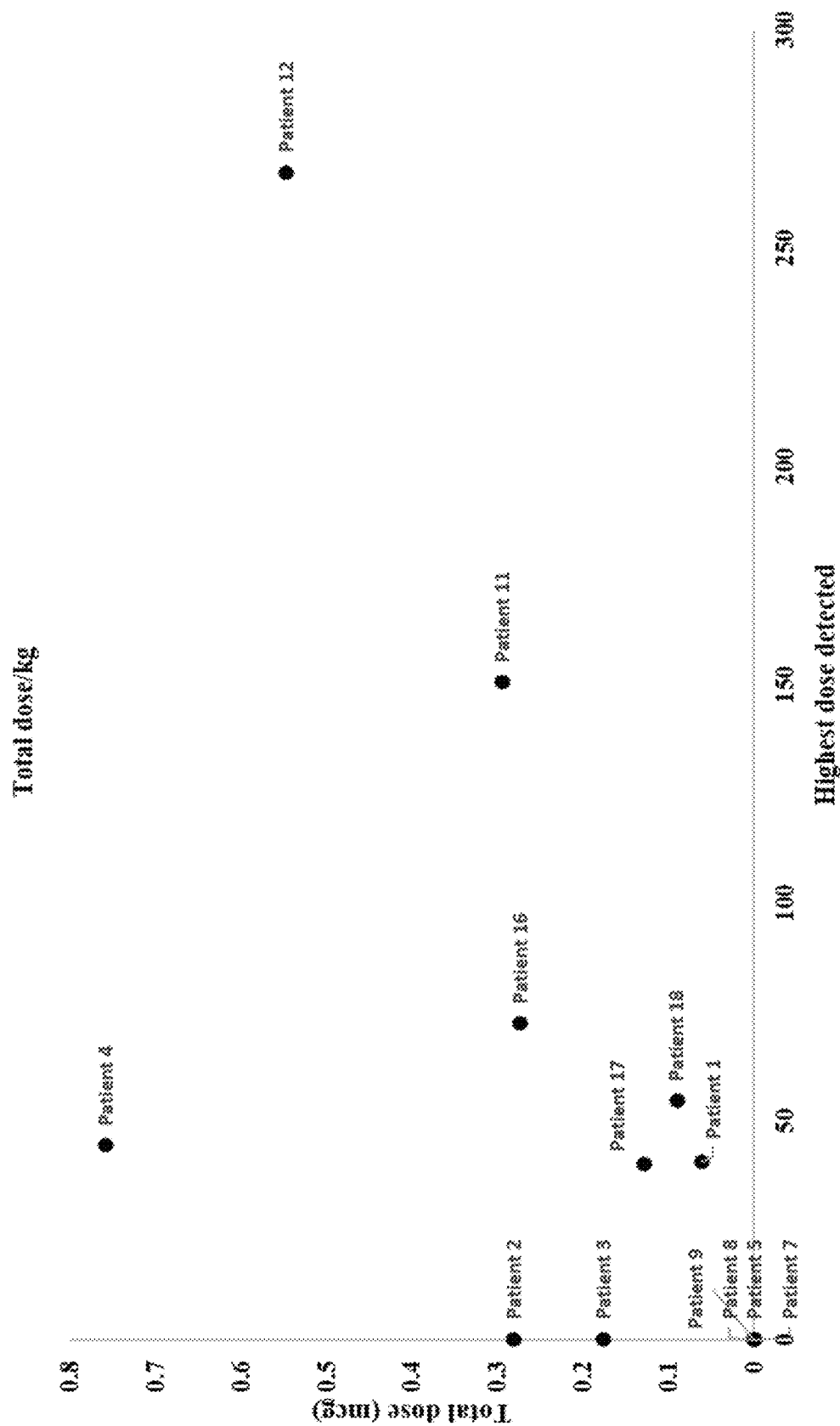

FIG. 18 depicts the maximum doses of IV dexmedetomidine hydrochloride received by schizophrenic patients for the treatment of agitation.

Figure 19:
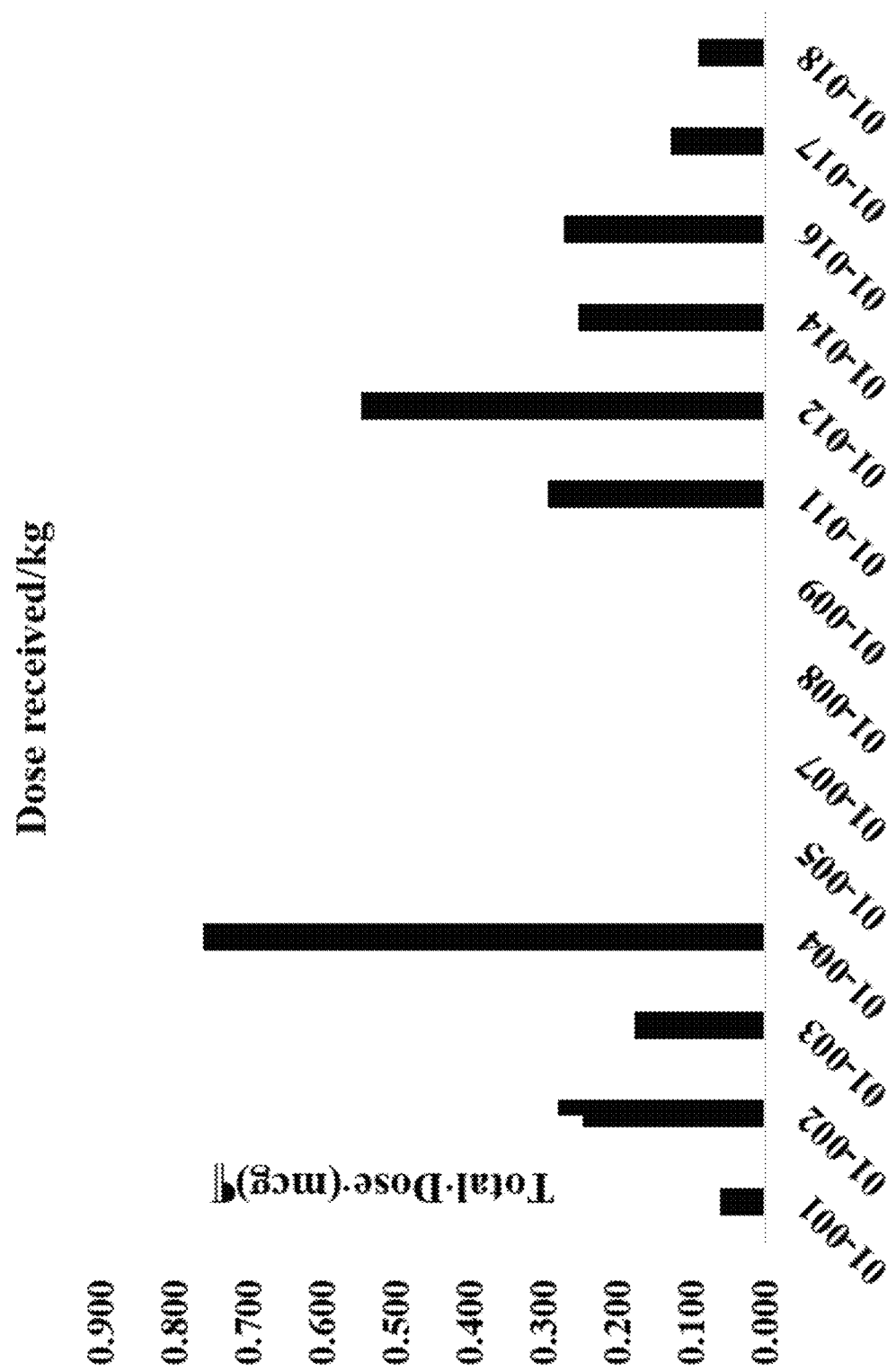

FIG. 19 depicts the total intravenous dose of dexmedetomidine hydrochloride received by schizophrenic patients for the treatment of agitation.

Figure 20:
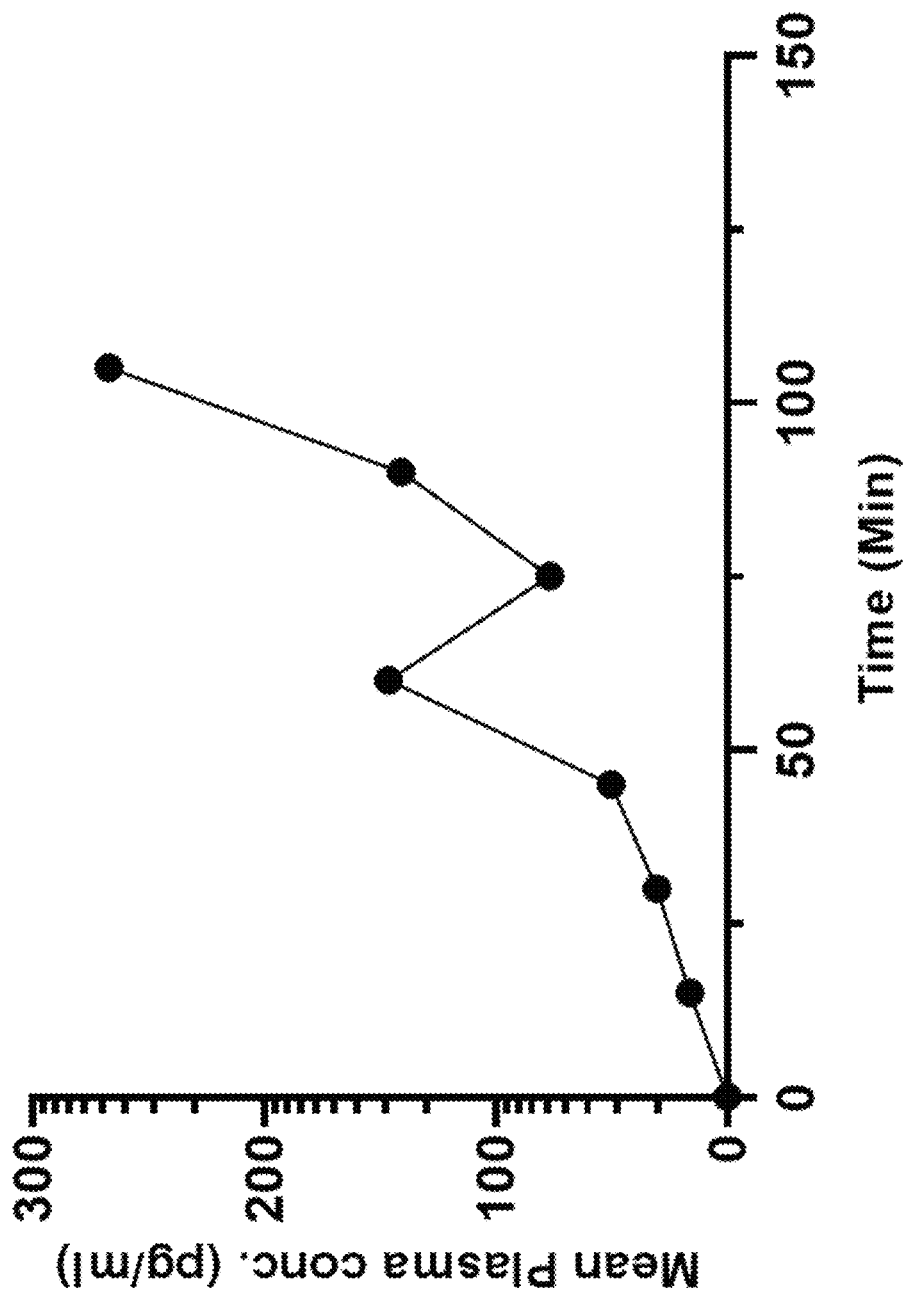

FIG. 20 depicts the mean plasma concentration (pg/ml) vs actual time in schizophrenic patients treated with dexmedetomidine hydrochloride.

Figure 21A:
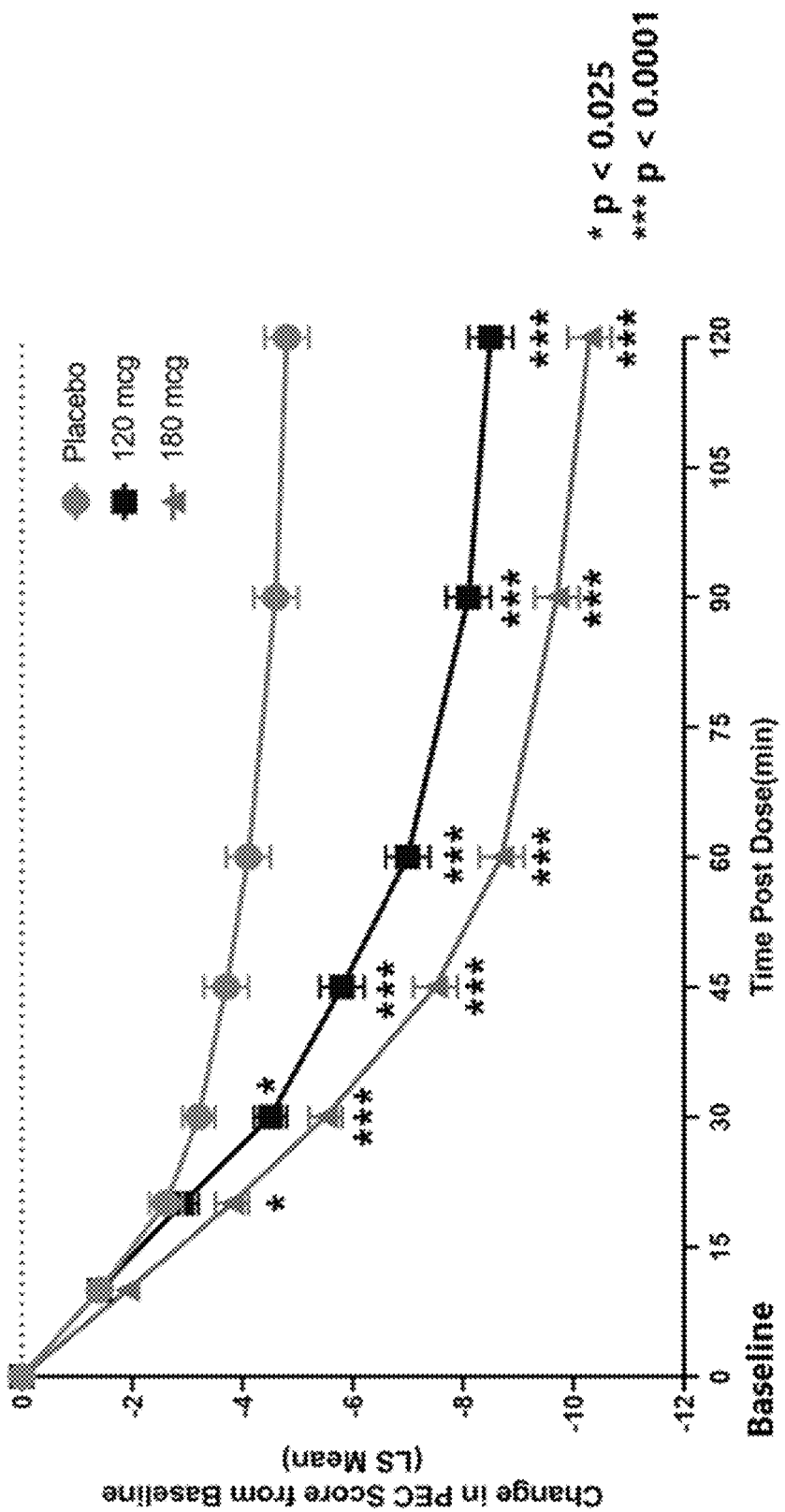

FIG. 21A depicts the change in PEC score from baseline in schizophrenia patients until 2 hours post-dose of 120 μg and 180 μg dexmedetomidine sublingual thin film (as exemplified in Example 2) compared to placebo.

Figure 21B:
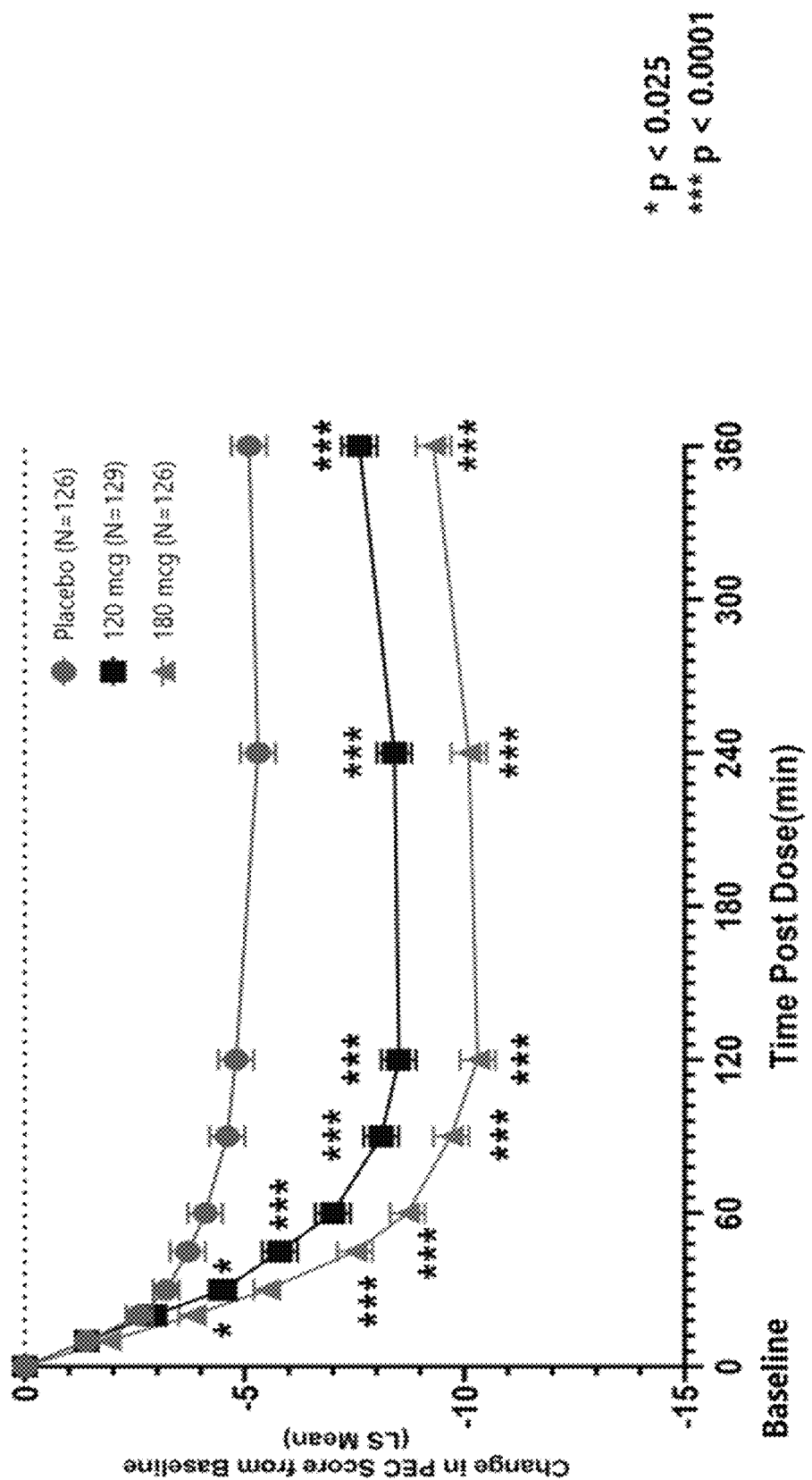

FIG. 21B depicts the change in PEC score from baseline in schizophrenia patients until 6 hours post-dose of 120 μg and 180 μg dexmedetomidine sublingual film (as exemplified in Example 2) compared to placebo.

Figure 22:
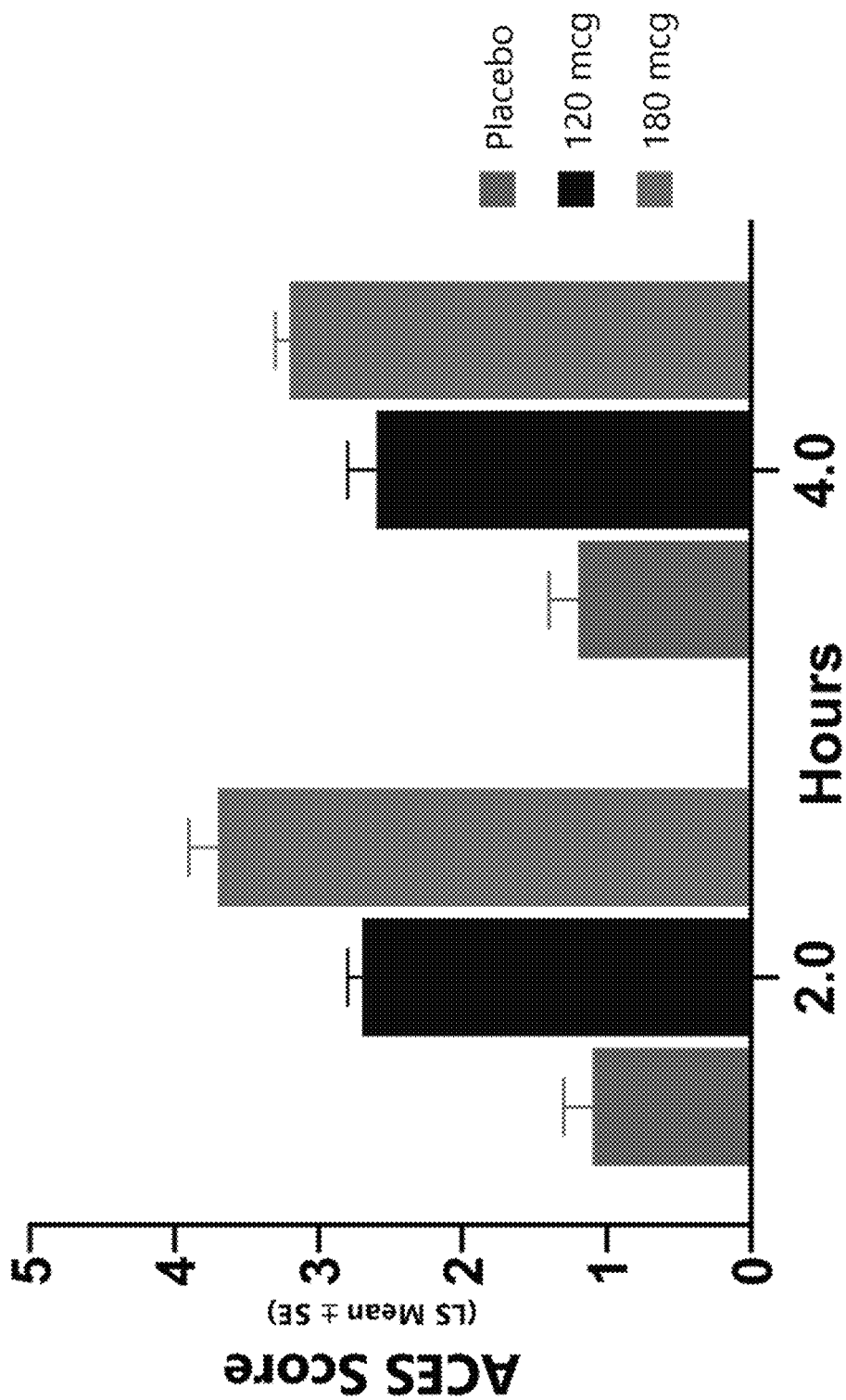

FIG. 22 depicts calming improvement in schizophrenia patients at 2 hours and 4 hours following administration of 120 μg (middle bar) and 180 μg dexmedetomidine (right bar) sublingual film (as exemplified in Example 2) compared to placebo (left bar), as measured by Agitation and Calmness Evaluation Scale (ACES).

Figure 23:
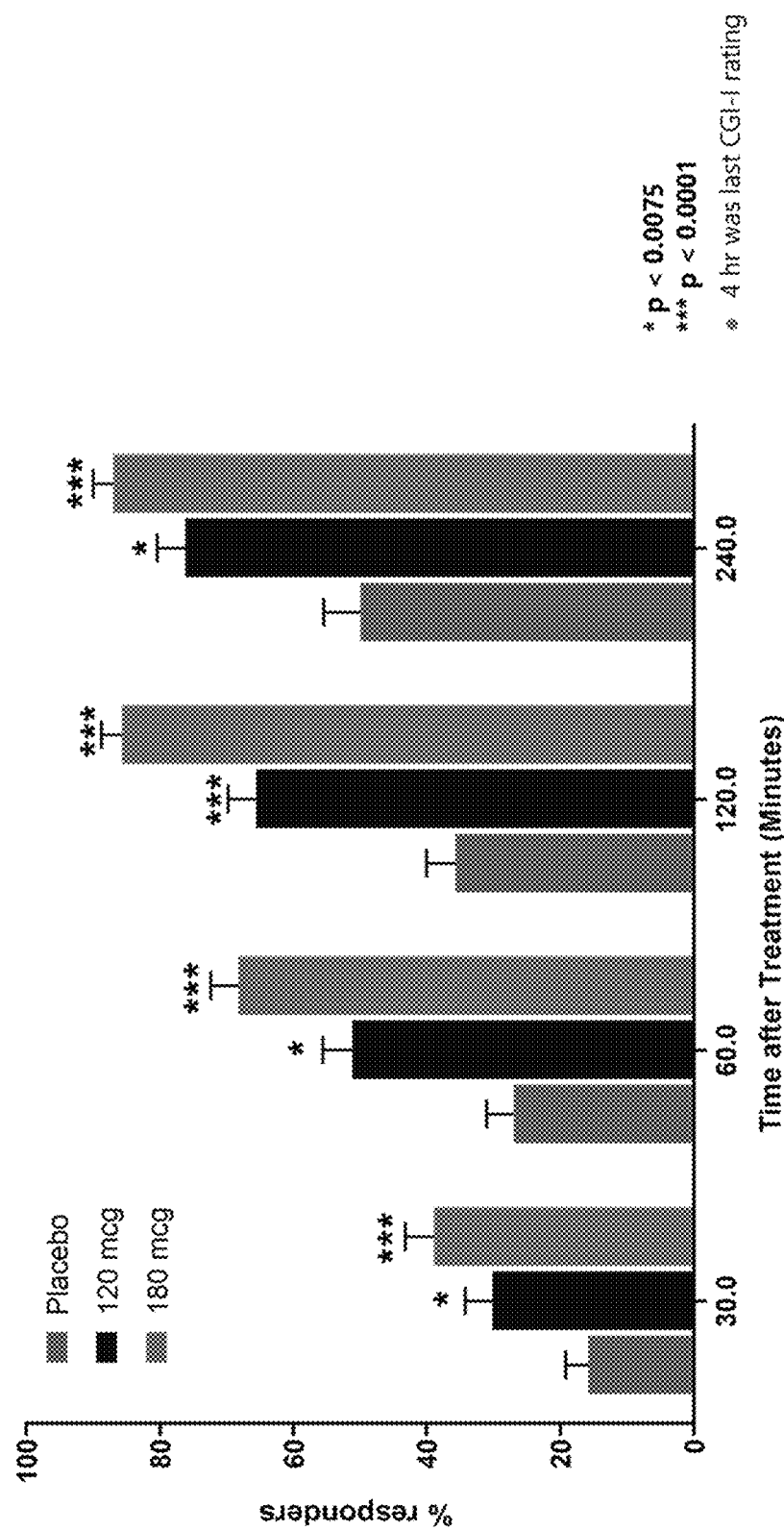

FIG. 23 depicts percent response in schizophrenia patients at 30 minutes, 60 minutes, 120 minutes and 240 minutes following administration of 120 μg (middle bar) and 180 μg dexmedetomidine (right bar) sublingual film (as exemplified in Example 2) compared to placebo (left bar), as measured by Clinical Global Impression-Improvement (CGI).

Figure 24A:
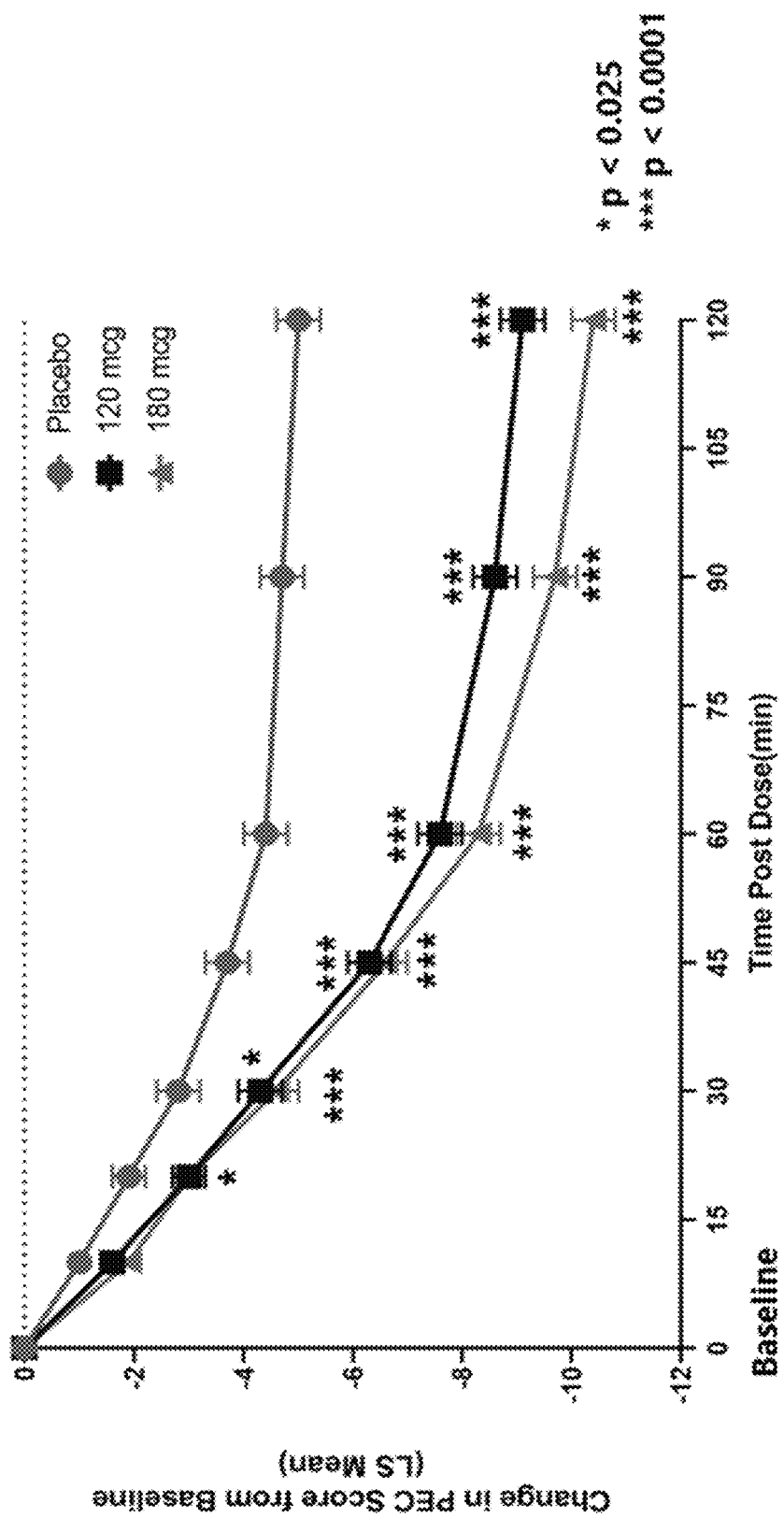

FIG. 24A depicts the change in PEC score from baseline in bipolar patients until 2 hours post-dose of 120 μg and 180 μg dexmedetomidine sublingual film (as exemplified in Example 2) compared to placebo.

Figure 24B:
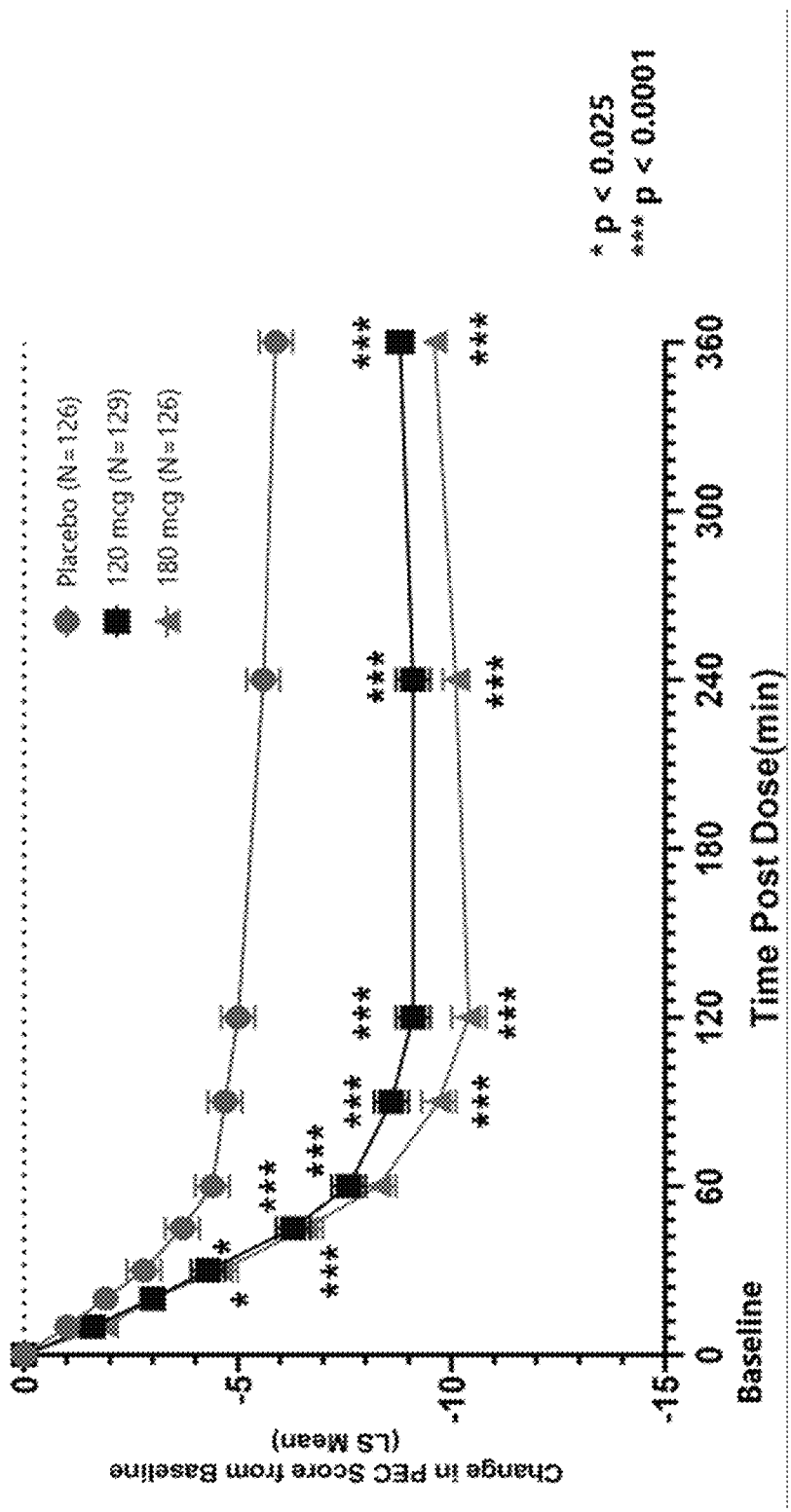

FIG. 24B depicts the change in PEC score from baseline in bipolar patients until 6 hours post-dose of 120 μg and 180 μg dexmedetomidine sublingual film (as exemplified in Example 2) compared to placebo.

Figure 25:
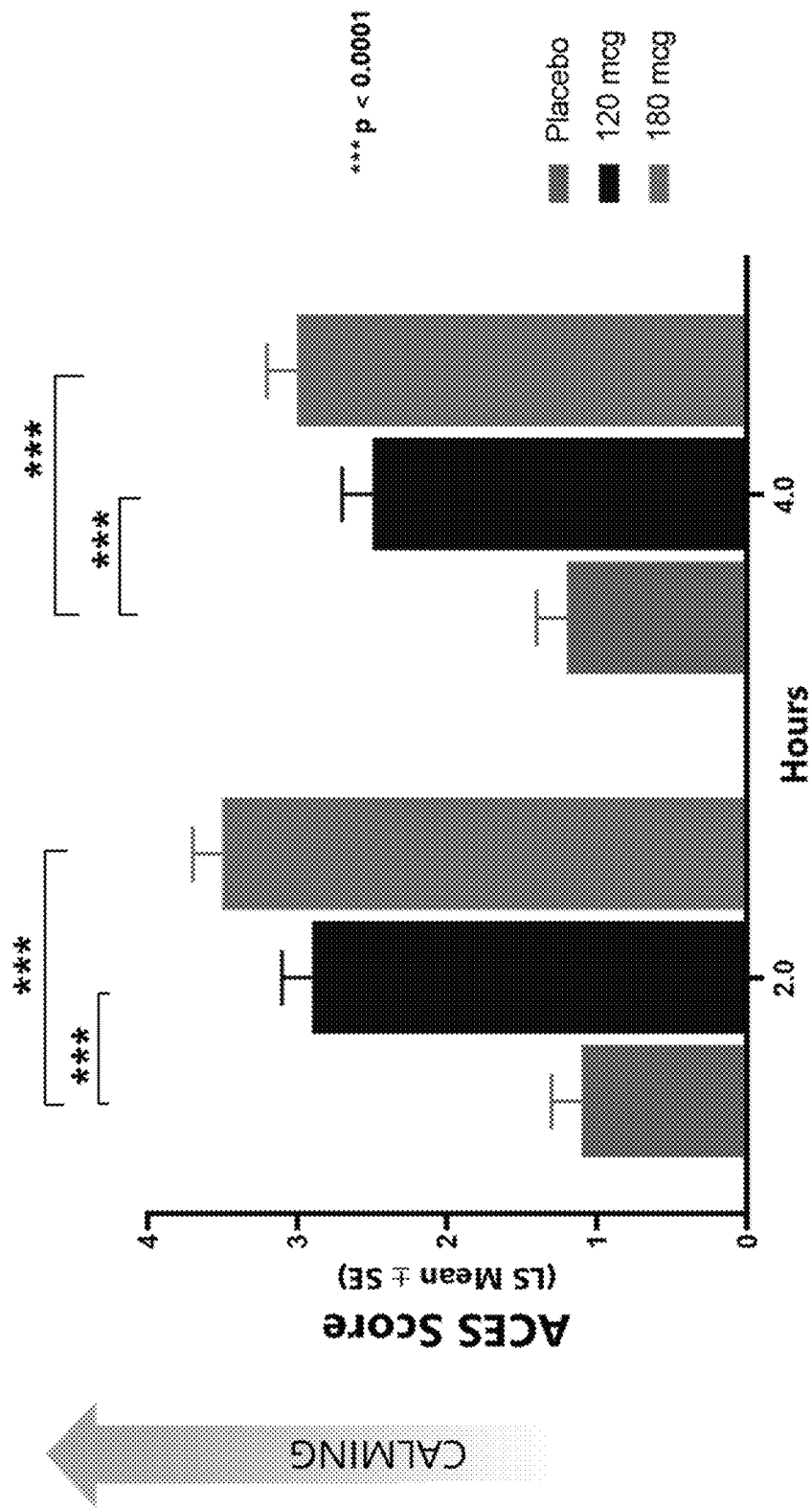

FIG. 25 depicts calming improvement in bipolar patients at 2 hours and 4 hours following administration of 120 μg (middle bar) and 180 μg dexmedetomidine (right bar) sublingual film (as exemplified in Example 2) compared to placebo (left bar), as measured by Agitation and Calmness Evaluation Scale (ACES).

Figure 26:
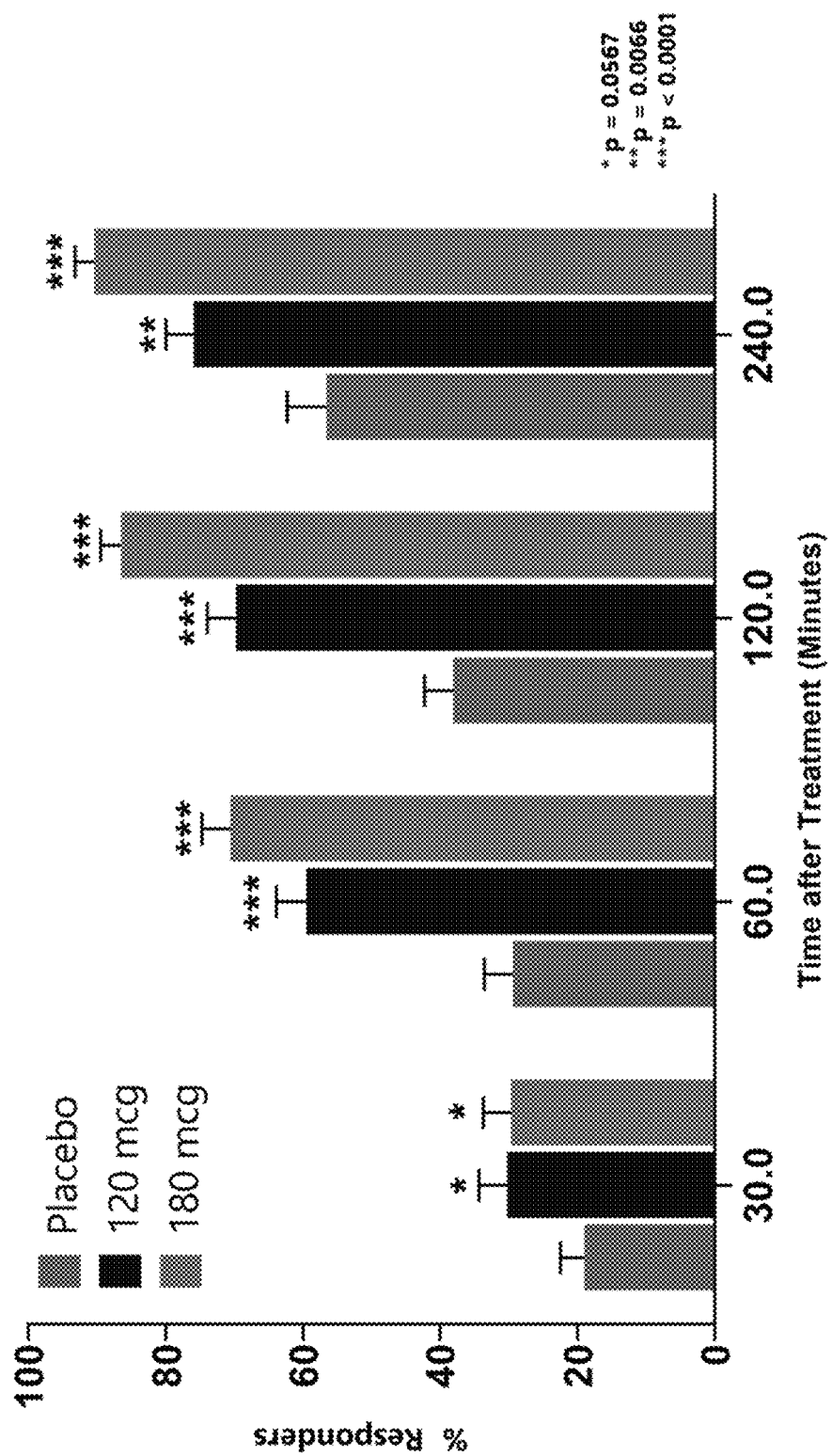

FIG. 26 depicts percent response in bipolar patients at 30 minutes, 60 minutes, 120 minutes and 240 minutes following administration of 120 μg (middle bar) and 180 μg dexmedetomidine (right bar) sublingual film (as exemplified in Example 2) compared to placebo (left bar), as measured by Clinical Global Impression-Improvement (CGI).

DETAILED DESCRIPTION

Abbreviations

ACES: Agitation-Calmness Evaluation Scale;
AD: Alzheimer disease;
AE: Adverse event;
AUC: Area under the curve;
AUClast: area under the curve, calculated to the last observable time point;
AUC0-Inf: Area under the plasma concentration-time curve from time of administration to infinity
BID: twice a day;
BMI: Body mass index;
CGI-I: Clinical Global Impression-Improvement
CGI-S: Clinical Global Impression-Severity
Cmax: maximum plasma concentration;
COWS: Clinical Opiate Withdrawal Scale;
CMAI: Cohen Mansfield Agitation Inventory
CMC: Carboxy methylcellulose
C-SSRS: Columbia Suicide Severity Rating Scale
CT: Computed tomography;
CTCAE: Common Terminology Criteria for Adverse Events;
DBP: Diastolic Blood Pressure
Dex or DEX: Dexmedetomidine
DLB: Dementia with Lewy bodies;
DLT: Dose Limiting Toxicity;
DSM: Diagnostic and Statistical Manual of Mental Disorders;
DT: Disintegration time;
ECG: Electrocardiogram;
FTD: Fronto temporal disease;
HPC: Hydroxypropyl cellulose;
HPMC: Hydroxyl propyl methyl cellulose
HR: Heart rate
ICH: International Conference on Harmonisation;
ICU— Intensive care unit;
IUD: intrauterine device
IPD: In-patient Departments;
ITT: Intent to treat Population
LAR: Legally authorized representative;
LSM: Least square mean
LS: Least square;
MedDRA: Medical Dictionary for Regulatory Activities;
MMRM: Mixed model repeated measures;
MMSE: Mini-Mental State Examination;
MRI: Magnetic resonance imaging;
MW: Molecular weight;
mm: Millimeter;
mcg: microgram;
mg: Milligrams;
μg: microgram;
ml: milliliter;
mmHG: millimeters of mercury;
msec: millisecond;
ng: nanogram;
OPD: Out-Patient Department;
PANSS: Positive and Negative Syndrome Scale;
PAS: Pittsburgh Agitation Scale;
PCRS: Placebo-Control Reminder Script;
PEC: PANSS Excitement Component;
PEO: Polyethylene oxide;
PD: Pharmacodynamic;
PK: Pharmacokinetics
PVA: Polyvinyl alcohol;
QTcF: QT interval corrected for heart rate using Fridericia's formula;
QID: Quater in die
RASS: Richmond Agitation Sedation Scale;
SAE: Serious adverse event; SOWS-Gossop: Short Opiate Withdrawal Scale of Gossop;
SAP: Statistical Analysis Plan;
SBP: Systolic Blood Pressure
SD=standard deviation;
SE=standard error
SL: Sublingual;

$T_{1/2}$: Elimination half-life;
TEAE: treatment emergent adverse event;
Tmax: Time of maximum plasma concentration;
Wt %: Weight percentage
ULN: upper limit of normal
VAS: Visual Analog Scale;
YMRS: Young Mania Rating Scale Definitions As used herein, "about" means plus or minus 10% of the indicated numerical value.

The terms "formulation" and "composition" are used interchangeably, except where otherwise clearly intended to have different meanings.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range can be an endpoint for the range encompassed thereby (e.g., the range 50-80 includes the ranges with endpoints such as 55-80, 50-75, etc.).

The term "a" or "an" refers to one or more of that entity. As such, the terms "a" (or "an"), "one or more" and "at least one" are used interchangeably herein. In addition, reference to e.g., "an agent" by the indefinite article "a" or "an" does not exclude the possibility that more than one of the agents are present, unless the context clearly requires that there is one and only one of the agents.

As used herein, the verb "comprise" as is used in this description and in the claims and its conjugations are used in its non-limiting sense to mean that items following the word are included, but items not specifically mentioned are not excluded. The present invention may suitably "comprise," "consist of," or "consist essentially of," the steps, elements, and/or reagents described in the claims.

The term "pharmaceutically acceptable carrier" refers to a pharmacologically inert substance to be used as a carrier. As used herein, the phrase "carrier" and "excipients" are used interchangeably, except where otherwise clearly intended to have different meanings.

The term "agitation," as used herein, means irritability, emotional outburst, impaired thinking, or excess motor and verbal activity that may occur due to either dysfunction of specific brain regions such as frontal lobes or due to dysfunction of neurotransmitter systems such as dopamine and nor-epinephrine. In the present invention, agitation also includes aggression and hyper-arousal in post-traumatic stress disorder. The agitation can be acute or chronic.

The term "the signs of agitation" includes excessive motor activity (examples include: pacing, rocking, gesturing, pointing fingers, restlessness, performing repetitious mannerisms), verbal aggression (e.g., yelling, speaking in an excessively loud voice, using profanity, screaming, shouting, threatening other people), physical aggression (e.g., grabbing, shoving, pushing, clenching hands into fists, resisting, hitting others, kicking objects or people, scratching, biting, throwing objects, hitting self, slamming doors, tearing things), and destroying property.

The term "without significant sedation" and the like means that the patient experiences a level of sedation not greater than Level 3 on the Ramsay Sedation Scale. Level 3 means sedated but responds to commands. In some embodiments, the dexmedetomidine can be dosed to achieve a Richmond Agitation Sedation Scale (RASS) of −1 ("light sedation").

The term "dissolvable" means the films herein are readily disintegrated, e.g., at least within about 20 minutes, following administration to the oral mucosa. Disintegration is achieved by saliva and/or other aqueous materials on the mucosal surface.

The term "neuropsychiatric conditions" includes, but is not limited to, schizophrenia, bipolar illness (bipolar disorder, bipolar mania), depression, delirium or other related neuropsychiatric conditions.

The term "an effective amount" is interchangeable with "therapeutically effective dose," or "therapeutically effective amount," and refers to an amount sufficient to produce the desired effect. An effective amount is sufficient to cause an improvement in a condition (e.g., agitation) of the subject.

The terms "treating," and "treatment," as used herein refer to curative therapy, prophylactic therapy, and/or preventative therapy and can be used interchangeably.

The term "significantly reduced" refers to a reduction level by at least 10% or higher, preferably 20% or higher, more preferably 40% or higher, even more preferably 60% or higher, still more preferably 80% or higher, and 90% or higher, as compared to a control. For example, in the context of agitation, the a skilled artisan will readily understand that the reduction can be measured in terms of well-known agitation scales, such as PEC score and CGI-I (described in more detail in the examples). As an example, when agitation is significantly reduced in a patient, the reduction can be interpreted as those who achieve at least a 10%, 20%, 30%, 40%, 50%, 60%, 70%, 80%, 90%, or 100% or greater reduction in PEC total score from baseline (e.g., measured at 2 hours post-dose). In some embodiments, significantly reduced agitation refers to at least a 40% reduction in PEC total score from baseline. Similarly, a significant reduction in agitation can be measured on the CGI-I scale and may refer to a patient that has a score of 1 or 2 on the CGI-I scale (e.g., measured at 1, 2, or 4 hours post-dose) or the Agitation-Calmness Evaluation Scale (ACES) scale and may refer to a patient that has a score of e.g., 3 or higher.

The term "pharmaceutically acceptable salt" refers to a salt known to be non-toxic and commonly used in the pharmaceutical literature. Typical inorganic acids used to form such salt include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyl alkandioic acids, aromatic acids, aliphatic and aromatic sulfonic acids may also be used. A preferred salt is the hydrochloride salt.

The term "film" herein includes thin films, sheets and wafers, in any shape, including rectangular, square, or other desired shape. The film can be of any desired thickness and size, such that it can be conveniently placed sub-lingually in the patient. For example, the film can be a relatively thin film having a thickness of from about 20 micrometers to about 200 micrometers or can be a somewhat thicker film having a thickness of from about 20 micrometers to about 1000 micrometers. In certain embodiments, the film can be even thicker, e.g., having a thickness greater than about 30 millimeters.

As used herein, the phrase "water-soluble polymer" refers to (i) a polymer that is at least partially soluble in water, and desirably fully or predominantly soluble in water, and/or (ii) a polymer that absorbs water. Polymers that absorb water are referred to herein as water-swellable polymers.

The term "self-supporting" means the films herein maintain structural integrity upon handling without the need for a backing layer. Some flexibility in the film is contemplated and can be desirable.

As used herein, the phrase "disposed within a polymer matrix" means that dexmedetomidine or a pharmaceutically acceptable salt thereof is incorporated directly into the polymer solution prior to the formation of the solid polymer matrix film composition.

As used herein, the phrase "deposited on the surface of a polymer matrix" means that dexmedetomidine or a pharmaceutically acceptable salt thereof is formulated as liquid composition separate from the preparation of the solid polymer matrix, and deposited onto the solid polymer, e.g., as one or more (e.g., 1, 2, or 3) micro-deposits, where it dries. The dried product is sometimes referred to herein as the "micro-deposited matrix film." The drug liquid formulation can be in any form, including as a solution, emulsion, suspension, or dispersion.

The term "intranasal administration" means administration by the nasal route, whereby a drug is insufflated through the nose. The administration can be either topical or systemic, meaning the locally delivered drug can go on to exhibit either purely local or systemic effects.

The term "parenteral" refers to administration of a drug by injection under one or more layer of skin or mucous membrane, and can include, for example, subcutaneous, intravenous, intraperitoneal or intramuscular injection.

The term "proportion of treatment responders" is defined as those subjects exhibiting about a 40% drop in PEC score at 2 hours.

The term "clinically significant cardiovascular effects" means herein a lowering in blood pressure (hypotension) and/or heart rate (bradycardia) to the extent that medical intervention is required to address the cardiovascular side effects, where the term "medical intervention" means an intervention that more serious than administering fluids, such as an energy drink.

The disclosure of International Patent Application PCT/US2020/042618 is incorporated herein by reference in its entirety.

Active Agent

Dexmedetomidine has the IUPAC name (+) 4-(S)-[1-(2,3-dimethylphenyl)ethyl]-1H-imidazole. As the monohydrochloride salt, it is predominantly used as a medication for the sedation of patients during treatment in an intensive care setting or to sedate patients prior to and/or during surgical and other procedures. Such medication is currently sold under the registered trade name "PRECEDEX."

Pharmaceutically acceptable salts of dexmedetomidine that can be used herein include generally any suitable salt that has been or can be approved by the US FDA or other appropriate foreign or domestic agency for administration to a human. Non-limiting examples of suitable pharmaceutically acceptable salts include salts of inorganic acids such as hydrochloric, hydrobromic, nitric, carbonic, monohydrocarbonic, phosphoric, monohydrogen phosphoric, dihydrogen phosphoric, sulfuric, hydrogen sulfuric, and hydroiodic acid. Other examples include salts derived from non-toxic organic acids, including acetic, propionic, isobutyric, maleic, malonic, benzoic, succinic, suberic, fumaric, lactic, mandelic, phthalic, benzenesulfonic, p-toluenesulfonic, citric, tartaric, and methanesulfonic acids, or combinations of these acid salts. Exemplary salts include dexmedetomidine hydrochloride, dexmedetomidine hydrobromide, dexmedetomidine sulfate, dexmedetomidine sulfonate, dexmedetomidine phosphate, dexmedetomidine nitrate, dexmedetomidine formate, dexmedetomidine citrate, dexmedetomidine tartrate, dexmedetomidine malate, dexmedetomidine benzoate, dexmedetomidine salicylate, dexmedetomidine ascorbate or the like. In other embodiments, deuterated forms of dexmedetomidine or a pharmaceutically acceptable salt thereof can be included.

Dosage

In some embodiments, the dosage of dexmedetomidine or a pharmaceutically acceptable salt thereof administered may conveniently be in the range of between about 0.5 µg (mcg) to about 1200 µg, depending on the route of administration etc. Examples of suitable dosages include: about 0.5 µg to about 1200 µg, about 0.5 µg to about 500 µg, about 0.5 µg to about 450 µg, about 0.5 µg to about 405 µg, about 0.5 µg to about 360 µg, about 0.5 µg to about 270 µg, about 0.5 µg to about 180 µg, and about 0.5 µg to about 120 µg. In some embodiments, the dose is 180 µg, 120 µg, 90 µg, or 60 µg.

In embodiments of the method, the dosage of dexmedetomidine is defined as the amount of dexmedetomidine free base or an equivalent amount of pharmaceutically acceptable salt thereof administered.

The dose can be administered one or more times a day including once, twice, three times, four times, five times or six times per day. In some embodiments, the dose can be administered one time a day or two times a day, and in other embodiments, the dose can be administered three times a day so long as the maximum total daily (i.e., a 24 hour period) dose is not exceeded. In some embodiments, the first (i.e., initial) daily dose is higher than the optional second dose or optional third dose. In some embodiments, the first (i.e., initial) daily dose is 180 µg, 120 µg, 90 µg, or 60 µg. In some embodiments subsequent doses (e.g., a second dose, a third dose) are 60 µg. In some embodiments, a dose of 90 µg or 60 µg can be provided by cutting an oromucosal formulation (e.g., an oromucosal film) comprising 180 µg or 120 µg, respectively, in half.

In some embodiments, dexmedetomidine or a pharmaceutically acceptable salt thereof can be administered at a dose of about 10 µg to about 300 µg, e.g., about 10 µg to 270 µg, about 20 µg to about 240 µg, about 30 µg to about 180 µg, about 40 µg to about 140 µg, about 60 µg to about 120 µg, about 70 µg to about 100 µg, about 80 µg to about 100 µg of unit dose total weight of pharmaceutical composition. These doses can be provided via one or more units to deliver the total dose. Examples of suitable doses include (in µg): about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245 and about 250.

In an embodiment, dexmedetomidine or a pharmaceutically acceptable salt thereof are administered oromucosally (e.g., sublingually or buccally) at a dose of about 10 µg to about 300 µg, e.g., about 10 µg to 270 µg, about 20 µg to about 240 µg, about 30 µg to about 180 µg, about 40 µg to about 140 µg, about 50 µg to about 120 µg, about 60 µg to about 120 µg, about 70 µg to about 100 µg, about 80 µg to about 100 µg of unit dose total weight of sublingual film composition. These doses can be provided via one or more units to deliver the total dose. Examples of suitable doses include (in µg): about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245 and about 250.

In some embodiments, dexmedetomidine or a pharmaceutically acceptable salt thereof can be administered at a dose of about 120 µg to about 405 µg, e.g., about 120 µg to about 270 µg, including about 120 µg and about 180 µg of unit dose total weight of pharmaceutical composition. These doses can be provided via one or more units to deliver the total dose. Examples of suitable doses include (in µg): about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400 and about 405.

In another embodiment, dexmedetomidine or a pharmaceutically acceptable salt thereof can be administered oromucosally (e.g., sublingually or buccally) at a dose of about 120 µg to about 405 µg, e.g., about 120 µg to about 270 µg, including about 120 µg and about 180 µg of unit dose total weight of sublingual film composition. These doses can be provided via one or more units to deliver the total dose. Examples of suitable doses include (in µg): about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400 and about 405.

The exemplary dosage of dexmedetomidine or a pharmaceutically acceptable salt thereof to be administered to a particular patient, will depend on the type and extent of the condition, the overall health status of the particular patient, the particular form of dexmedetomidine or a pharmaceutically acceptable salt thereof being administered, and the particular formulation used to treat the patient.

Pharmaceutical Compositions

According to the present disclosure, dexmedetomidine or a pharmaceutically acceptable salt thereof can be administered to the human subject through the oromucosa (e.g., sublingually, buccally). Formulations suitable for use according to the present disclosure are outlined below. Additional formulations suitable for use according to the present disclosure are described in US 2020/0000717, which is hereby incorporated by reference in its entirety for all purposes.

Dexmedetomidine or a pharmaceutically acceptable salt thereof can be formulated, according to the present disclosure, into dosage forms suitable for sublingual or buccal administration. Such dosage forms include tablets, powders, pills, films, capsules, liquids, gels, syrups, slurries, suspensions, and the like. In one embodiment, dexmedetomidine or a pharmaceutically acceptable salt thereof is formulated as a film product.

Carriers suitable for inclusion in sublingual or buccal formulations include, but are not limited to, sugars, starches, cellulose and its derivatives, malt, gelatin, talc, calcium sulphate, vegetable oils, synthetic oils, polyols, alginic acid, phosphate buffered solutions, emulsifiers, isotonic saline, pyrogen—free water and combinations thereof. Carriers which readily dissolve in saliva can be used.

Sublingual or buccal formulations may also include other pharmaceutically acceptable carriers and/or excipients such as binders, lubricants, diluents, coatings, disintegrants, barrier layer components, glidants, colouring agents, solubility enhancers, gelling agents, fillers, proteins, co-factors, emulsifiers, solubilising agents, suspending agents and mixtures thereof. Particular excipients, which can be used according to this disclosure, are known in the art, for example as described in Handbook of Pharmaceutical Excipients, fifth edition, 2005 edited by Rowe et al., Mcgraw Hill.

Films

Suitable films for sublingual or buccal administration (i.e. oromucosal administration) according to the present disclosure comprise dexmedetomidine or a pharmaceutically acceptable salt thereof either (i) disposed within a polymer matrix or (ii) deposited on the surface of a polymer matrix, e.g., on the surface of a "placebo" film.

The polymer component consists of one or more water-soluble polymers within the film matrix and/or as part of the drug-containing deposit (e.g., one or more droplets) on the surface of the polymer. In some embodiments of the disclosure, the polymer component consists of a single water-soluble polymer. In some embodiments, the polymer component consists of two or more water-soluble polymers, including two or more of the same water-soluble polymers having different molecular weights.

The polymer component in the film matrix is of a suitable composition and present in a sufficient amount to ensure rapid disintegration of the film matrix in the oral mucosa. For example, the presence of the polymer component may allow the film matrix to disintegrate completely oromucosally in about 15 seconds to about 180 seconds, for example, about 30 seconds to about 180 seconds, including about 120 seconds. The polymer component in the film matrix also provides the film with sufficient strength (i.e. the film is self-supporting).

When present in one or more droplets of the dexmedetomidine composition deposited onto the surface of the polymer matrix/substrate, the polymer component may, for example, consist of the water-soluble polymer hydroxypropyl cellulose, although different water-soluble polymers are also contemplated as described hereinafter under the definition "first water-soluble polymer" and "second water soluble polymer." For example, the polymer component may consist of one, two or three hydroxypropyl celluloses having different molecular weights. The molecular weights of the different hydroxypropyl celluloses may conveniently range from (i) less than about 60,000 daltons (e.g., about 5,000 daltons to about 49,000 daltons) (ii) about 90,000 daltons to about 200,000 daltons and (iii) about 200,000 daltons to about 500,000 daltons. The two or more hydroxypropyl celluloses can be mixed in any suitable ratio to achieve the desired droplet viscosity. The viscosity of the dexmedetomidine composition solution or suspension can be measured using a Brookfield viscometer with a small sample adapter at a temperature of 25° C. and may range from about 5 cps to about 3700 cps. For example, it may range from about 5 cps to about 500 cps, about 6 cps to about 200 cps, about 6 cps to about 100 cps or about 6 cps to about 50 cps. In some embodiments of the present disclosure, the viscosity of the dexmedetomidine composition solution or suspension is from about 6 cps to about 20 cps at 25° C. and a shear rate of about 7 (1/s).

When present in a monolithic (i.e. placebo or drug-containing) film, the polymer component may, for example, consist of one water soluble polymer or two different water-soluble polymers. When two different water-soluble polymers are present, one of the water-soluble polymers may include the same polymer but present in the polymer component as a combination of different molecular weights. For example, the polymer component may consist of one, two or three hydroxypropyl celluloses having different molecular weights, although different water-soluble polymers are also contemplated as described hereinafter under the definition "first water-soluble polymer" and "second water soluble polymer" such as polyethylene oxide. The molecular weights of the different hydroxypropyl celluloses may conveniently range from (i) less than about 60,000 daltons (e.g., about 5000 daltons to about 49000 daltons) (ii) about 90000 daltons to about 200000 daltons and (iii) about 200,000 daltons to about 500,000 daltons (e.g., about 300000 daltons to about 450000 daltons). The two or more hydroxypropyl celluloses (e.g., low and high molecular weight hydroxypropyl celluloses) can be mixed in any suitable ratio to achieve the desired film properties. When present in a monolithic (i.e. placebo or drug-containing) film or microdeposited film matrix composition, the polymer component may conveniently consist of one or more water-soluble polymers having a molecular weight less than about 60,000 daltons (e.g., about 5,000 daltons to about 49,000 daltons), and/or from about 90000 daltons to about 200,000 daltons and/or about 200,000 daltons to about 500,000 daltons (e.g., about 300000 daltons to about 450000 daltons). When a structurally different water-soluble polymer is also present, it may conveniently have a higher molecular weight, for example a molecular weight greater than about 500,000 daltons.

In some embodiments, the disclosure provides pharmaceutical film compositions, comprising: (i) dexmedetomidine or a pharmaceutically acceptable salt thereof; (ii) a polymer component consisting of a first water-soluble polymer having a molecular weight less than about 60,000 daltons (e.g., about 5,000 daltons to about 49,000 daltons), and one or more second-water soluble polymers having a molecular weight greater than about 60,000 daltons; and, optionally, (iii) one or more pharmaceutically acceptable carriers.

In some embodiments, the disclosure provides pharmaceutical film compositions consisting essentially of: (i) dexmedetomidine or a pharmaceutically acceptable salt thereof, (ii) a polymer component consisting of a first water-soluble polymer having a molecular weight less than about 60,000 daltons (e.g., about 5,000 daltons to about 49,000 daltons), and one or more second-water soluble polymers having a molecular weight greater than about 60,000 daltons; and, optionally, (iii) one or more pharmaceutically acceptable carriers.

In some embodiments, the disclosure provides pharmaceutical film compositions consisting of: (i) dexmedetomidine or a pharmaceutically acceptable salt thereof, (ii) a polymer component consisting of a first water-soluble polymer having a molecular weight less than about 60,000 daltons (e.g., about 5,000 daltons to about 49,000 daltons), and one or more second water-soluble polymers having a molecular weight greater than about 60,000 daltons; and, optionally, (iii) one or more pharmaceutically acceptable carriers.

Examples of one or more first water-soluble polymers are selected from the group consisting of hydroxypropyl cellulose (HPC), hydroxyethyl cellulose, hydroxypropyl methylcellulose (HPMC), carboxymethyl cellulose, methyl cellulose and mixtures thereof, including mixtures of the same polymer having different molecular weights.

Examples of one or more second water-soluble polymers are selected from the group consisting of hydroxypropyl cellulose, hydroxypropyl methylcellulose, hydroxyethyl cellulose, carboxy methylcellulose, methylcellulose and mixtures thereof, including mixtures of the same polymer having different molecular weights. Polyethylene oxide (PEO) may also be present herein as a second water-soluble polymer or can be described separately hereinafter in the pharmaceutical film compositions as an example of a pharmaceutically acceptable carrier, or more particularly, as a mucoadhesive agent.

In one embodiment, the weight ratio of said first water-soluble polymer to said second water-soluble polymer(s) (including PEO when present in the film) in the entire film composition is from about 2:1 to about 1:50, for example about 1:1 to about 1:40, including about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:21, about 1:22, about 1:23, about 1:24, about 1:25, about 1:26, about 1:27, about 1:28, about 1:29, about 1:30, about 1:31, about 1:32, about 1:33, about 1:34, about 1:35, about 1:36, about 1:37, about 1:38, about 1:39, or about 1:40.

In a further embodiment, the weight ratio of said first water-soluble polymer to said second water-soluble polymer(s) (including PEO when present in the film) in the entire film composition is from about 1:10 to about 1:30, about 1:15 to about 1:25 or about 1:15 to about 1:20. In some embodiments, a ratio of about 1:15 to about 1:20 provides beneficial functional effects.

Examples of other water-soluble polymers which can be included in the film with the first water-soluble polymer/second water-soluble polymer or replace such polymer(s) include povidone (polyvinylpyrrolidone), copovidone (co-polymers of N-vinyl-2-pyrrolidone and vinyl acetate), polyvinyl alcohol, polyethylene glycol, polyacrylic acid, methylmethacrylate copolymer, carboxyvinyl copolymers, polydextrose, pullulan, carboxymethyl cellulose, sodium alginate, chitosan, xanthan gum, tragacanth gum, guar gum, acacia gum, arabic gum, starch, carrageenan, gelatin and mixtures thereof. The water-soluble polymer component, including water-soluble polymer carriers when present, may conveniently comprise about 40% to about 99.8%, about 50% to about 99.7%, about 60% to about 99.6% of the film composition, based on the weight of the film on a dry weight basis.

In some embodiments, the polymer component for the film composition comprises a first water-soluble polymer present in an amount of from about 2% to about 15% on a dry weight basis of the polymer component (e.g., at about 3% to about 8% w/w of the total film weight). This water-soluble polymer may conveniently have a molecular weight from about 5,000 daltons to about 49,000 daltons. Examples of suitable such water-soluble polymers include those selected from the group consisting of hydroxypropyl cellulose, hydroxyethyl cellulose, hydroxypropyl methylcellulose, carboxymethyl cellulose, methyl cellulose, and mixtures thereof.

In some embodiments, low molecular weight hydroxypropyl cellulose can be present in the film at about 3% to about 8% w/w of the total film weight.

In some embodiments, the one or more second water-soluble polymers (including water-soluble polymer carriers such as polyethylene oxide) may, for example, be present in an amount of from about 50 to about 98 weight percent on dry weight basis of the polymer component. The one or more second water-soluble polymers each has a molecular weight greater than 60,000 daltons; for example, from about 90,000 daltons to about 1,500,000 daltons, especially when the polymer is selected from the group consisting of polyethylene oxide, hydroxypropyl cellulose, hydroxypropyl methylcellulose, hydroxyethyl cellulose, carboxy methylcellulose, methylcellulose, and mixtures thereof.

In some embodiments, the one or more second water-soluble polymers may together be present in the film at about 25% to about 40% w/w of the total film weight when the one or more second water-soluble polymers each has a molecular weight from about 90,000 daltons to about 200,000 daltons and/or from about 200,000 daltons to about 500,000 daltons, and the polymer is selected from the group consisting of hydroxypropyl cellulose, hydroxypropyl methylcellulose, hydroxyethyl cellulose, carboxy methylcellulose, methylcellulose, and mixtures thereof.

In some embodiments, a polyethylene oxide can be present in the film at about 50% to about 60% w/w of the total film weight.

In one embodiment, the polymer component for the film composition consists of a low molecular weight, water-soluble polymer (e.g., having a molecular weight less than about 60,000 daltons) and one or more high molecular weight polymers (e.g., having a molecular weight greater about 60,000, up to about 1,500,000 daltons when a polyethylene oxide is included in the polymer mixture or up to about 500,000 daltons when a polyethylene oxide is not included in the polymer mixture). This polymer combination, especially when the polymers are a combination of hydroxypropyl cellulose and polyethylene oxide, lends certain advantages to the tensile strength and pharmacokinetics of the film composition.

In some embodiments, the oromucosal formulation is a film composition comprising (e.g., consisting essentially of):
(i) a therapeutically effective amount of dexmedetomidine or a pharmaceutically acceptable salt thereof,
(ii) a polymer component consisting of one or more water-soluble polymers; and
(iii) one or more pharmaceutically acceptable carriers.

In one embodiment, the oromucosal formulation is a film composition comprising (e.g., consisting essentially of):
(i) therapeutically effective amount of dexmedetomidine or a pharmaceutically acceptable salt thereof;
(ii) a polymer component consisting of: (a) one or more first water-soluble polymer (e.g., hydroxypropyl cellulose, hydroxypropyl methylcellulose, hydroxyethyl cellulose, carboxy methylcellulose, methylcellulose, and mixtures thereof) having a molecular weight from about 5,000 daltons to about 49,000 daltons, for example, in about 2 to about 15 weight percent on dry weight basis of the total polymer component; and (b) one or more second water-soluble polymers (e.g., polyethylene oxide, hydroxypropyl cellulose, hydroxypropyl methylcellulose, hydroxyethyl cellulose, carboxy methylcellulose, methylcellulose, and mixtures thereof) having a molecular weight greater than 60,000 daltons, such as greater than 100000 daltons, for example in about 50 to about 98 weight percent on dry weight basis of the total polymer component; and
(iii) one or more pharmaceutically acceptable carriers.

The molecular weight of hydroxypropyl cellulose, when present in the film of the present disclosure, can be varied, and can be present as both a low molecular weight, water-soluble polymer and as one or more high molecular weight, water-soluble polymers. In some embodiments, the molecular weight can be less than about 60,000 daltons (e.g., about 5,000 daltons to about 49,000 daltons). In other embodiments the molecular weight can be in the range from about 90,000 daltons to about 200,000 daltons. In yet other embodiments, the molecular weight can be in the range from about 200,000 daltons to about 500,000 daltons.

Hydroxypropyl cellulose, when part of the film composition including polyethylene oxide, may conveniently be present in the range from about 10% to about 90% by weight on a dry weight basis of the polymer component, e.g., about 20% to about 80% by weight on dry weight basis of the polymer component, e.g., about 20% to about 50% by weight on dry weight basis of the polymer component, e.g., about 25% to about 45% by weight on dry weight basis of the polymer component.

The molecular weight of polyethylene oxide, when present in the film of the present disclosure, may also be varied. In some embodiments, a water-soluble, high molecular weight polyethylene oxide can be used, for example, to increase muco-adhesivity of the film. In certain embodiments, the molecular weight may range from about 100,000 daltons to about 1,500,000 daltons, including about 100,000, 200,000, 300,000, 600,000, 900,000 or 1,000,000 daltons. In some embodiments, it can be desirable to use a combination of polyethylene oxide having a molecular weight of about 600,000 daltons to about 900,000 daltons with polyethylene oxide having a molecular weight of about 100,000 daltons to about 300,000 daltons in the polymer component.

Polyethylene oxide, when part of the film composition, may conveniently be present range from about 30% to about 90% by weight on a dry weight basis of the total polymer component, e.g., about 40% to about 85% by weight on a dry weight basis of the polymer component, e.g., about 55% to about 80% by weight on a dry weight basis of the polymer component.

Such film compositions may contain the drug dispersed within the film, or micro-deposited onto a surface of the film. When micro-deposited on the surface of a "placebo" film, the drug may conveniently be added as part of a dexmedetomidine composition as one or more droplets in a liquid carrier, such as a solvent (e.g., an alcohol such as ethanol), optionally together with one or more (e.g., one, two, three, or four) water-soluble polymers and/or pharmaceutically acceptable carriers. Suitable water-soluble polymers include (1) a low molecular weight, water-soluble polymer, for example a low molecular weight, water-soluble polymer having a molecular weight of less than about 60,000 daltons (e.g., a molecular weight of about 5,000 daltons to about 49,000 daltons and optionally (2) one or more (e.g., one or two) high molecular weight, water-soluble polymers, for example a high molecular weight, water-soluble polymer having a molecular weight of greater than about 60,000 daltons (e.g., a molecular weight of from about 60,000 daltons to about 150,000 daltons such as hydroxypropyl cellulose (77,000 MW), hydroxypropyl cellulose (80,000 MW), hydroxypropyl cellulose (90,000 MW), or hydroxypropyl cellulose (140,000 MW)) and/or a high molecular weight, water-soluble polymer having a molecular weight of greater than about 60,000 daltons (e.g., a molecular weight of from about 200,000 daltons to about 900,000 daltons such as hydroxypropyl cellulose (340,000 MW), hydroxypropyl cellulose (370,000 MW), polyethylene oxide (200,000 MW) or polyethylene oxide (600,000 MW)). Each water-soluble polymer may independently be selected from the group consisting of hydroxypropyl cellulose, hydroxypropyl methylcellulose, hydroxyethyl cellulose, carboxymethyl cellulose, polyethylene oxide and methyl cellulose, e.g., hydroxypropyl cellulose and/or polyethylene oxide.

In some embodiments, the dexmedetomidine composition comprises dexmedetomidine hydrochloride, a low molecular weight polymer which is hydroxypropyl cellulose and one or two high molecular weight polymers which are each hydroxypropyl cellulose in an ethanol solvent.

In one embodiment, the dexmedetomidine composition comprises dexmedetomidine or a pharmaceutically acceptable salt thereof (e.g., dexmedetomidine hydrochloride), hydroxypropyl cellulose (40,000 MW) and one or both of hydroxypropyl cellulose (140,000 MW) and hydroxypropyl cellulose (370,000 MW).

In another embodiment, the dexmedetomidine composition comprises dexmedetomidine or a pharmaceutically acceptable salt thereof (e.g., dexmedetomidine hydrochloride), and only two hydroxypropyl celluloses, namely hydroxypropyl cellulose (40,000 MW) and hydroxypropyl cellulose (140,000 MW).

In some embodiments, the deposition composition can be in any form, including as a solution, emulsion, suspension or dispersion. For example, the dexmedetomidine composition can be added as one or more droplets in an ethanol-based solution, optionally containing a pH-neutralizing agent such as sodium hydroxide. In some embodiments, the film substrate surface contains two or more micro-deposited spots of dexmedetomidine hydrochloride (e.g., two microdeposited spots) in a polymer matrix. The viscosity of deposition solution/suspension may range from about 6 cps to about 3700 cps as measured at 25° C. using a Brookfield viscometer with a small sample adapter. As an example, it may range from about 5 cps to about 500 cps, about 6 cps to about 200 cps, about 6 cps to about 100 cps or about 6 cps to about 50 cps.

In some embodiments of the present disclosure, the viscosity of the dexmedetomidine composition is from about 6 cps to about 20 cps at 25° C. and a shear rate of about 7 (l/s).

Following drying to remove the solvent, the film comprises a film substrate (e.g., a placebo) with the dexmedetomidine composition as previously described but absent the solvent deposited (e.g., micro-deposited) on the surface of the film substrate. The dried composition containing dexmedetomidine or a pharmaceutically acceptable salt thereof (e.g., dexmedetomidine hydrochloride) may cover the whole of the film substrate surface or only part of the film substrate surface.

In some embodiments, the dried dexmedetomidine composition appears as one or more discrete drug-containing droplets on the film substrate surface. Alternatively, stenciling can be used to achieve a one or more defined and discrete regions of drug-containing composition on the surface of the film substrate.

In some embodiments, the disclosure provides a dry film product comprising a film substrate with one or more discrete drug-containing droplets on the film substrate surface, wherein each such drug-containing droplet comprises dexmedetomidine or a pharmaceutically acceptable salt thereof, and hydroxypropyl cellulose of two molecular weights: hydroxypropyl cellulose (40,000 MW) available as HPC-SSL, and hydroxypropyl cellulose (140,000 MW) marketed under the tradename of Klucel™ Type JF NF, and wherein the film substrate comprises hydroxypropyl cellulose of three molecular weights: hydroxypropyl cellulose (40,000 MW), hydroxypropyl cellulose (140,000 MW), and hydroxypropyl cellulose (370,000 MW) marketed under the tradename of Klucel™ Type GF NF. In some embodiments, the film substrate also comprises polyethylene oxide (600,000 MW) available under the name of Sentry Polyox WSR 205 LEO NF.

In some embodiments, the dry film product comprises a deposition composition (also referred to herein as a "dexmedetomidine composition") comprising: (i) dexmedetomidine hydrochloride, present at about 9% to about 50% w/w of the deposition composition, e.g., about 15% to about 25% w/w of the deposition composition; (ii) hydroxypropyl cellulose (40,000 MW), present at about 5% to about 85% w/w of the deposition composition; (iii) hydroxypropyl cellulose (140,000 MW) present at about 5% to 85% w/w of the deposition composition; and (iv) hydroxypropyl cellulose (370,000 MW) present at about 0% to about 65% w/w of the deposition composition. The film also comprises a polymer matrix, wherein the polymer matrix comprises: (i) hydroxypropyl cellulose (40,000 MW) present at about 3% to about 40% w/w of the polymer matrix; (ii) hydroxypropyl cellulose (140,000 MW) present at about 3% to about 40% w/w of the polymer matrix; (iii) hydroxypropyl cellulose (370,000 MW) present at about 0% to about 30% w/w of the polymer matrix, and (iv) polyethylene oxide (600,000 MW) present at about 55% to about 75% w/w of the polymer matrix.

In some embodiments, the dry film product (e.g., a micro-deposited film product) comprises (i) dexmedetomidine hydrochloride, present at about 1% to about 50% w/w of the total film weight; (ii) hydroxypropyl cellulose (40,000 MW), present at about 2% to about 30% w/w of the total film weight; (iii) hydroxypropyl cellulose (140,000 MW) present at about 2% to about 30% w/w of the total film weight; (iv) hydroxypropyl cellulose (370,000 MW) present at about 10% to about 50% w/w of the total film weight, (v) polyethylene oxide (600,000 MW) present at about 40% to about 75% w/w of the total film weight and (vi) optionally other pharmaceutically acceptable carriers.

In some embodiments, the films disclosed herein combine several types of hydroxypropyl cellulose (HPC) to provide a film with advantageous properties. For example, the film composition may contain two or three of hydroxypropyl cellulose (40,000 MW), hydroxypropyl cellulose (140,000 MW) and hydroxypropyl cellulose (370,000 MW) in combination. In certain embodiments, polyethylene oxide (600,000 MW) is included with these types of HPC when part of a monolithic film.

In certain film compositions of the present disclosure, a low molecular weight hydroxypropyl cellulose (e.g., 40,000 MW) is present at about 3% to about 8% (e.g., about 5%) w/w of the total film weight, a high molecular weight hydroxypropyl cellulose (e.g., 140,000 MW) is present at about 3% to about 8% (e.g., about 5%) w/w of the total film weight, a high molecular weight hydroxypropyl cellulose (e.g., 370,000 MW) is present at about 20% to about 40% w/w of the total film weight, and a polyethylene oxide (e.g., 600,000 MW) is present at about 40% to about 70%, (e.g., about 50% to about 60%) w/w of the total film weight. In some embodiments, the two high molecular weight, water-soluble polymers are together present at about 25% to about 40% w/w of the total film weight.

The selection and ratio of water-soluble polymers can be made to effect complete dissolution of the film composition in oral mucosal fluids within seconds to minutes, e.g., in about 0.25 minutes to about 15 minutes, thus ensuring delivery of a therapeutically effective amount of dexmedetomidine or a pharmaceutically acceptable salt thereof via the oral mucosa. For example, the film compositions may reside in the sublingual or buccal region of the mouth up to about 15 minutes, up to about 10 minutes, or up to about 5 minutes, including for a period of from about 30 seconds to about 15 minutes, about 1 minute to about 10 minutes, or about 1 minute to about 5 minutes.

The standard basket or paddle apparatus described in any pharmacopoeia can be used for in vitro dissolution testing. The selection of dissolution medium will essentially depend as per the sink conditions and highest dose of drug. The temperature of dissolution medium should be maintained at 37±0.5° C. and rpm at 50 (see Bala et al., Int J Pharm Investigation, 2013, vol. 3 (2), pages 67-76).

Films disclosed herein have several functional advantages to promote rapid onset of drug effect. In some embodiments, thin films compositions of the disclosure have a disintegration time (DT) of about 15 seconds to about 180 seconds, about 15 seconds to about 160 seconds, about 25 seconds to about 150 seconds, about 15 seconds to about 140 seconds, about 15 seconds to about 120 seconds, about 40 seconds to about 120 seconds, about 50 seconds to about 120 seconds, for example about 120 seconds, when applied sublingually or buccally. A disintegration time in this time-frame provides optimal onset of drug effects.

In some embodiments, thin film compositions of the invention have mucoadhesion properties that provide practical benefits of localizing the film to the sublingual location and reducing, or preventing, effective removal prior to dissolution. This quality is particularly advantageous in a clinical setting with an agitated subject. Thus, in some embodiments, thin film compositions have a mucoadhesion force (the mucoadhesion strength or shear strength) of about 50 μg or above, about 100 μg or above, about 200 μg or above, about 300 μg or above, about 400 μg or above, about 500 μg or above, about 600 μg or above, about 700 μg or above, about 800 μg or above, about 900 μg or above, about 1000 μg or above. In some embodiments, the mucoadhesion force is in a range of about 300 μg to about 4000 μg, about 500 μg to about 3000 μg, or about 1000 μg to about 2000 g.

Burst strength of the film also contributes to drug delivery. Certain thin film compositions of the invention have a burst strength at or above 50 μg, 100 μg, 200 μg, 300 μg, 400 μg, 500 μg, 600 μg, 700 μg, 800 μg, 900 μg, 1000 μg, 1100 μg, 1200 μg, 1300 μg, 1400 μg, 1500 μg, 1600 μg, 1700 μg, 1800 μg, 1900 μg, 2,000 μg, 2,500 μg, 3,000 μg, 3,500 μg, 4,000 μg, 4,500 μg, 5,000 μg, 5,500 μg, 6,000 μg, 6,500 μg, 7,000 μg, 7,500 μg, 8,000 μg, 8,500 μg, 9,000 μg, 9,500 μg, 10,000 μg or 15,000 g. For example, the burst strength can be in a range of about 200 μg to about 15000 μg, about 300 μg to about 10,000 μg, or 400 μg to about 5,000 μg.

Pharmaceutically Acceptable Carriers

The film compositions can further comprise one or more pharmaceutically acceptable carriers that includes, but is not limited to, liquid carriers, flavours, sweeteners, refreshing agents, antioxidants, pH adjusting agents, permeation enhancers, mucoadhesive agents, plasticizers, bulking agents, surfactants/non-ionic solubilizers, stabilizers, antifoam agents, colors or the like. In certain embodiments, the film compositions are substantially free of acidic buffer or other acidic agents.

Liquid Carriers

According to some embodiments, the pharmaceutically acceptable carrier includes a liquid carrier. The liquid carrier comprises one or more solvents useful in the preparation of the polymer matrix (drug containing or placebo) and deposition composition on the polymer matrix. In some embodiments, the solvent can be water. In some embodiments, the solvent may a polar organic solvent including, but are not limited to, ethanol, isopropanol, acetone, butanol, benzyl alcohol and mixtures thereof. In some embodiments, the solvent can be a non-polar organic solvent, such as methylene chloride, toluene, ethyl acetate and mixtures thereof. Certain solvents are alcohols, especially ethanol, water and mixtures thereof. Desirably, the solvent content in the wet polymer matrix is at least about 30% by weight of the total wet weight of the total film composition prior to drying. The subsequent dried film composition will desirably contain less than about 10% by weight of solvent, more desirably less than about 8% by weight of solvent, even more desirably less than about 6% by weight of solvent and most desirably less than about 2% by weight of solvent.

Flavors/Sweeteners Refreshing Agents

It can be beneficial to add a sweetener, flavoring agent, refreshing agent, taste-masking agent or a combination thereof to the film compositions to improve the film composition taste. Flavors can be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. Non-limiting flavor oils include: spearmint oil, cinnamon oil, peppermint oil, clove oil, bay oil, thyme oil, cedar leaf oil, oil of nutmeg, oil of sage, and oil of bitter almonds. In one embodiment, the flavor is a peppermint oil flavour available as peppermint oil, NF.

The amount can be varied in order to obtain the result desired in the final product. Such variations are within the capabilities of those skilled in the art without the need for undue experimentation. In general, amounts of about 0.1% to about 30 wt % can be used in the films to supply flavoring. Suitable sweeteners include both natural and artificial sweeteners. Non-limiting examples of suitable sweeteners include, e.g.: water-soluble sweetening agents such as monosaccharides, disaccharides and polysaccharides such as xylose, ribose, glucose (dextrose), mannose, galactose, fructose (levulose), sucrose (sugar), high fructose corn syrup, maltose, invert sugar (a mixture of fructose and glucose derived from sucrose), partially hydrolyzed starch, corn syrup solids, and dihydrochalcones; water-soluble artificial sweeteners such as the soluble saccharin salts, i.e., sodium or calcium saccharin salts, cyclamate salts and water-soluble sweeteners derived from naturally occurring water-soluble sweeteners, such as a chlorinated derivatives of ordinary sugar (sucrose), known, for example, as sucralose. In one embodiment, the sweetener is sucralose.

Flavoring agents, sweeteners and refreshing agents can be added in conventional quantities, generally up to a total amount of about 0.01% to about 10% of the weight of the film on a dry weight basis, e.g., from about 0.1% to about 7% of the weight of the film on a dry weight basis, e.g., about 0.1% to about 5% based on the weight of the film on a dry weight basis.

Other taste-masking agents include, for example polymers, oils, or waxes. In one embodiment, dexmedetomidine or a pharmaceutically acceptable salt thereof is coated with a taste-masking agent prior to formulation of the film compositions. In some embodiments, if a taste-masking agent is used to coat the active ingredient, it can be present in an amount of from about 5% to about 80% by weight of the particle or granule containing the active ingredient. In another embodiment, the taste-masking agent is present in an amount from about 25% to about 35% by weight of the particle or granule containing the active ingredient.

Antioxidants

Examples of oxygen scavengers or antioxidants that substantially improve long-term stability of the film composition against oxidative degradation include sulfite salts, such as sodium sulfite, sodium bisulfite, sodium metabisulfite and analogous salts of potassium and calcium. A suitable amount of the sulfite salt (e.g., sodium sulfite) is up to about 5%, e.g., about 0.001% to about 2% based on the weight of the film composition on a dry weight basis.

pH-Adjusting Agents/pH-Neutralizing Agents

The absorption of dexmedetomidine or a pharmaceutical acceptable salt thereof through the oral mucosa may increase in an alkaline microenvironment. As an example, this can be achieved when the film compositions are maintained at a pH of above 6, from about 6 to about 9, or about 6.5 to about 8. In some embodiments, the film may include an alkaline substance that increases the pH of the film product. Non-limiting examples of pH-adjusting/pH-neutralizing agents include bicarbonates (e.g., sodium bicarbonate), citrates (e.g., potassium citrate), carbonates (e.g., calcium carbonate), lactates (e.g., sodium lactate), acetates (e.g., calcium acetate), alkaline buffer (e.g., glycine), sodium hydroxide, sodium chloride or the like. An alkaline buffer, such as glycine, is one example of a pH-neutralizing agent. A suitable amount of pH-adjusting/pH-neutralizing agent present in the film composition includes, for example, up to about 10%, e.g., about 1% to about 5% based on the weight of the film composition on a dry weight basis Permeation Enhancer Agents Certain effective penetration enhancers that promote absorption of dexmedetomidine or a pharmaceutically acceptable salt thereof across the oral mucosa include alcohols. An alcohol penetration enhancer, such as butanol, can conveniently be added to the film composition in an amount of up to about 10%, e.g., about 0.1% to about 5%, e.g., about 1% to about 3% based on the weight of the film composition on a dry weight basis.

Mucoadhesive Agents

Examples of mucoadhesive agents that can be added to the film composition include, but are not limited to, sodium alginate, sodium carboxymethyl cellulose, guar gum, polyethylene oxide, hydroxyethyl cellulose, hydroxypropyl cellulose, hydroxypropylmethyl cellulose, karaya gum, methylcellulose, retene, tragacanth and the like. One mucoadhesive agent is polyethylene oxide, which may conveniently be added to the film composition in an amount of from about 20% to about 90%, e.g., about 40% to about 70% based on the total weight of the film composition on a dry weight basis.

Plasticizers

Plasticizers that can be effectively employed herein include polyethylene glycol, propylene glycol, tributyl citrate, triethyl citrate and glycerol. Depending on the selected film-forming polymer(s) and other components of the film formulation, a suitable amount of plasticizer included in the film composition may typically be up to about 10%, e.g., about 0.1% to about 5%, e.g., about 0.5% to about 5% based on the weight of the film on a dry weight basis. For certain applications, higher molecular weight polyethylene glycols can be utilized, including polyethylene oxide Fillers Suitable fillers that can be added to a film composition of include starch, calcium salts, such as calcium carbonate, and sugars, such as lactose, glucose, sucrose, mannose, sorbitol, mannitol, galactitol, sucralose, trehalose and combinations thereof. The amount of filler that can conveniently be added to the film formulation is typically up to about 25%, e.g., about 0.5% to about 20%, e.g., about 1% to about 15%, e.g., about 2% to about 10%, based on the weight of the film composition on a dry weight basis.

Surfactants Non-Ionic Solubilizers

The film typically incorporates at least one surfactant/non-ionic solubilizer including, for example, but are not limited to, a poloxamer, polyoxyl hydrogenated castor oil, glyceryl polyethylene glycol oxystearates, fatty acid glyceryl polyglyceryl esters, polyglyceryl esters, and combinations thereof. The amount of surfactant(s) that can be added to the film composition is typically up to about 5%, e.g., about 0.5% to about 3%, e.g., about 1% to about 3% based on the weight of the film composition on a dry weight basis.

Anti-Foaming Components

Simethicone is an example of a useful anti-foaming and/or de-foaming agent, although other anti-foaming and/or de-foaming agents may suitable be used. An anti-foaming and/or de-foaming agent such as simethicone can be added to the film composition in an amount from about 0.01% to about 5.0%, more desirably from about 0.05% to about 2.5%, and most desirably from about 0.1% to about 1.0% based on the weight of the film composition on a dry weight basis.

Colorants

Color additives that can be included in a film composition include food, drug and cosmetic colors (FD&C), drug and cosmetic colors (D&C), or external drug and cosmetic colors (Ext. D&C). These colors are dyes, their corresponding lakes, and certain natural and derived colorants. Certain examples of color additives are inorganic pigments, such as oxides of iron or titanium, added in concentrations ranging from about 0.001% to about 10%, e.g., about 0.01% to about 3%, based on the weight of the film composition on a dry weigh basis. In one embodiment, the color used for the dexmedetomidine composition (i.e. the deposit composition) is different from the color used for the film substrate (e.g., the placebo film). One color of the monolithic film and the film substrate of the micro-deposited film is emerald green, and available as Fast Emerald Green Shade (06507). One color of the dexmedetomidine composition (i.e. the deposit composition) is a different color from the color of the film substrate, e.g., blue (available as FD&C Blue No. 1). In some embodiments of the film embodiments of the present invention, for example, as described in aspects and embodiments hereinabove, is a film comprising about 180 µg or about 120 µg of dexmedetomidine or a pharmaceutically acceptable salt thereof containing two blue color microdeposited spots of dexmedetomidine hydrochloride on the green color film substrate.

In one embodiment, the oromucosal formulation is a self-supporting, dissolvable, film, comprising:
 (i) about 180 µg of dexmedetomidine or a pharmaceutically acceptable salt thereof (e.g., the hydrochloride salt);
 (ii) one or more water-soluble polymers;
 (iii) a polyethylene oxide and, optionally,
 (iv) one or more pharmaceutically acceptable carriers.

In another embodiment, the oromucosal formulation is a self-supporting, dissolvable, film, comprising:

(i) about 120 μg of dexmedetomidine or a pharmaceutically acceptable salt thereof (e.g., the hydrochloride salt);
(ii) one or more water-soluble polymers;
(iii) a polyethylene oxide and, optionally,
(iv) one or more pharmaceutically acceptable carriers.

In a particular embodiment, the just-mentioned one or more water-soluble polymers (ii) comprises a low molecular weight, water-soluble polymer and two high molecular weight, water-soluble polymers, for example wherein the low molecular weight, water-soluble polymer has a molecular weight from about 5,000 daltons to about 49,000 daltons (e.g., about 40,000 daltons), and each high molecular weight, water-soluble polymer has a molecular weight of greater than about 60,000 daltons (e.g., where one of the two high molecular weight, water-soluble polymers has a molecular weight of about 140,000 daltons, and the other high molecular weight, water-soluble polymer has a molecular weight of about 370,000 daltons). Each water-soluble polymer is, in some embodiments, hydroxypropyl cellulose. The polyethylene oxide, in some embodiments, has a molecular weight of about 600,000 daltons.

In certain embodiments, there is provided a pharmaceutical film composition comprising or consisting essentially of therapeutically effective amount of dexmedetomidine or pharmaceutically acceptable salt thereof and one or more excipients selected from polyethylene oxide, hydroxypropyl cellulose, sucralose, peppermint oil, Emerald green colorant, and FD&C blue colorant.

In another embodiment, the oromucosal formulation is a self-supporting, dissolvable, film, comprising:
(i) about 180 μg of dexmedetomidine or a pharmaceutically acceptable salt thereof (e.g., the hydrochloride salt);
(ii) a low molecular weight, water-soluble polymer having a molecular weight of about 40,000 daltons;
(iii) a high molecular weight, water-soluble polymer having a molecular weight from about 140,000 daltons;
(iv) a high molecular weight, water-soluble polymer having a molecular weight from about 370,000 daltons; and
(v) a water-soluble polyethylene oxide having a molecular weight of about 600,000 daltons.

In another embodiment, the oromucosal formulation is a self-supporting, dissolvable, film, comprising:
(i) about 120 μg of dexmedetomidine or a pharmaceutically acceptable salt thereof (e.g., the hydrochloride salt);
(ii) a low molecular weight, water-soluble polymer having a molecular weight of about 40,000 daltons;
(iii) a high molecular weight, water-soluble polymer having a molecular weight from about 140,000 daltons;
(iv) a high molecular weight, water-soluble polymer having a molecular weight from about 370,000 daltons; and
(v) a water-soluble polyethylene oxide having a molecular weight of about 600,000 daltons.

In a particular embodiment of the just-mentioned films, the film components excluding dexmedetomidine or a pharmaceutically acceptable salt thereof form a single layer film substrate, and dexmedetomidine or a pharmaceutically acceptable salt thereof is present on the surface of the film substrate (e.g., within a composition comprising dexmedetomidine or a pharmaceutically acceptable salt thereof, a low molecular weight, water-soluble polymer having a molecular weight of about 40,000 daltons, and a high molecular weight, water-soluble polymer having a molecular weight of about 140,000 daltons). Each water-soluble polymer is, in some embodiments, hydroxypropyl cellulose.

In another embodiment, the oromucosal formulation is a self-supporting, dissolvable, film, comprising:
(a) a composition consisting essentially of:
  (i) about 180 μg of dexmedetomidine hydrochloride;
  (ii) hydroxypropyl cellulose (40,000 MW); and
  (iii) hydroxypropyl cellulose (140,000 MW); and
(b) a film substrate consisting essentially of:
  (i) hydroxypropyl cellulose (40,000 MW);
  (ii) hydroxypropyl cellulose (140,000 MW);
  (iii) hydroxypropyl cellulose (370,000 MW); and
  (iv) polyethylene oxide (600,000 MW);
wherein the composition of part (a) is present on the surface of the film substrate (b).

In another embodiment, the oromucosal formulation is a self-supporting, dissolvable, film, comprising:
(a) a composition consisting essentially of:
  (i) about 120 μg of dexmedetomidine hydrochloride;
  (ii) hydroxypropyl cellulose (40,000 MW); and
  (iii) hydroxypropyl cellulose (140,000 MW); and
(b) a film substrate consisting essentially of:
  (i) hydroxypropyl cellulose (40,000 MW);
  (ii) hydroxypropyl cellulose (140,000 MW);
  (iii) hydroxypropyl cellulose (370,000 MW); and
  (iv) polyethylene oxide (600,000 MW);
wherein the composition of part (a) is present on the surface of the film substrate (b).

In a particular embodiment of the just-mentioned films, dexmedetomidine hydrochloride is present at about 0.1% to about 2% w/w of the total film weight, hydroxypropyl cellulose (40,000 MW) is present at about 4% to about 8% w/w of the total film weight, hydroxypropyl cellulose (140,000 MW) is present at about 4% to about 8% w/w of the total film weight, hydroxypropyl cellulose (370,000 MW) is present at about 25% to about 30% w/w of the total film weight, and polyethylene oxide (600,000 MW) is present at about 50% to about 60% w/w of the total film weight.

In some embodiments, the present disclosure provides pharmaceutical buccal film compositions comprising or consisting essentially of therapeutically effective amount of dexmedetomidine or pharmaceutically acceptable salt thereof, one or more mucoadhesive polymers and optional excipients selected from one or more of plasticizers, penetration enhancers, coloring agents, sweetening agents, flavoring agents, taste-making agents or salivary stimulants. Mucoadhesive polymers can be selected from hydrophilic polymers and hydrogels. Examples of hydrophilic polymers include polyvinyl alcohol (PVA), sodium carboxy methylcellulose (NaCMC), hydroxyl propyl methyl cellulose (HPMC), hydroxyl ethyl cellulose and hydroxypropyl cellulose (HPC). Examples of hydrogels include anionic polymers like carbopol, polyacrylates, cationic polymers like chitosan and non-ionic polymers like Eudragit analogues.

Sprays, Drops or Gels

In some embodiments, the present disclosure provides pharmaceutical spray compositions or drop compositions suitable for sublingual or buccal administration comprising or consisting essentially of a therapeutically effective amount of dexmedetomidine or pharmaceutically acceptable salt thereof and one or more pharmaceutically acceptable liquids (from about 1% to about 99.995% by weight). Such liquids can be solvents, co-solvents, or non-solvents for dexmedetomidine or a pharmaceutically acceptable salt thereof. Examples of pharmaceutically acceptable liquids include water, ethanol, dimethyl sulfoxide, propylene glycol, polyethylene glycol, propylene carbonate, glycerine, N-methylpyrrolidone, pharmaceutically acceptable oils (e.g., soybean, sunflower, peanut, etc.) or the like. The pharmaceutically acceptable liquid is selected either to dissolve dexmedetomidine or pharmaceutically acceptable salt thereof, to produce a stable, homogenous suspension of it, or to form any combination of a suspension or solution. In addition to these ingredients, spray or drop formulations of dexmedetomidine or pharmaceutically acceptable salt thereof may include one or more excipients such as viscosity modulating materials (e.g., polymers, sugars, sugar alcohols, gums, clays, silicas, and the like, such as polyvinylpyrrolidone (PVP)); preservatives (e.g., ethanol, benzyl alcohol, propylparaben and methylparaben); flavoring agents (e.g., peppermint oil), sweeteners (e.g., sugars such as sucrose, glucose, dextrose, maltose, fructose, etc.), artificial sweeteners (e.g., saccharin, aspartame, acesulfame, sucralose), or sugar alcohols (e.g., mannitol, xylitol, lactitol, maltitol syrup); buffers and pH-adjusting agent (e.g., sodium hydroxide, citrate, and citric acid); coloring agents; fragrances, chelating agents (e.g., EDTA); UV absorbers and antifoam agents (e.g., low molecular weight alcohols, dimethicone). In addition to one or more of the aforementioned ingredients suitable for sublingual or buccal sprays or drops, gel formulations of dexmedetomidine or pharmaceutically acceptable salt thereof may include one or more excipients such as viscosity modulating materials (e.g., water soluble or water swellable polymers such as carbopol, hydroxypropyl cellulose, hydroxypropyl methyl cellulose, carboxymethyl cellulose).

Sprays, drops, and gels can be made by mixing appropriate quantities of the foregoing ingredients in accordance with standard good manufacturing practices. Such excipients can be included in the formulation to improve patient or subject acceptance or taste, to improve bioavailability, to increase shelf-life, to reduce manufacturing and packaging costs, to comply with requirements of governmental regulatory agencies, and for other purposes. The relative amounts of each ingredient should not interfere with the desirable pharmacological and pharmacokinetic properties of the resulting formulation.

In some embodiments, there is provided an oromucosal spray composition comprising or consisting essentially of therapeutically effective amount of dexmedetomidine or pharmaceutically acceptable salt thereof and one or more pharmaceutically acceptable carrier or excipients.

A patient may, in one embodiment, be treated by administering sublingually or buccally 1 to 2 actuations from a spray pump. An advantage of spray delivery is the ability to easily titrate patients by 1 or 2 doses as required by a single actuation.

Pump action sprays are characterized in requiring the application of external pressure for actuation, for example, external manual, mechanical or electrically initiated pressure. This is in contrast to pressurized systems, e.g., propellant-driven aerosol sprays, where actuation is typically achieved by controlled release of pressure e.g., by controlled opening of a valve.

Various sublingual spray formulations comprising dexmedetomidine hydrochloride at doses of 20 µg, 30 µg, 60 µg, 90 µg, 120 µg, and 180 µg and excipients as described in Table 1.

TABLE 1

Sublingual spray formulation embodiments according to the disclosure

| Ingredients | Sublingual Spray Formulation Embodiment No. | | | |
|---|---|---|---|---|
| | 1 | 2 | 3 | 4 |
| N-methylpyrrolidone | ✓ | | | |
| Propylene Glycol | | ✓ | | |
| Polyethylene Glycol | | | ✓ | |
| Glycerine | | | | ✓ |
| Ethanol | ✓ | ✓ | ✓ | ✓ |
| Sucralose | ✓ | ✓ | ✓ | ✓ |
| Peppermint Oil | ✓ | ✓ | ✓ | ✓ |
| Purified water | ✓ | ✓ | ✓ | ✓ |
| Optionally other pharmaceutically acceptable excipients | ✓ | ✓ | ✓ | ✓ |

Various sublingual drop compositions comprising dexmedetomidine hydrochloride at doses of 20 µg, 30 µg, 60 µg, 90 µg, 120 µg, and 180 µg and excipients as described in Table 2.

TABLE 2

Sublingual drop formulation embodiments.

| Ingredients | Sublingual Drop Formulation Embodiment No. | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Povidone | ✓ | ✓ | ✓ | ✓ | ✓ | | | | | | ✓ | | | |
| N-methylpyrrolidone | ✓ | | | | | ✓ | | | | ✓ | | | | |
| Hydroxypropyl methylcellulose | | | | | | ✓ | ✓ | ✓ | ✓ | | | | | |
| Carbopol | | | | | | | | | | ✓ | ✓ | ✓ | ✓ | ✓ |
| Polyethylene glycol | | | ✓ | | | | | | | | | ✓ | | |
| Propylene glycol | | ✓ | | | | | ✓ | | | | ✓ | | | |
| Glycerine | | | | ✓ | | | | ✓ | | | | | ✓ | |
| Ethanol | | | | | ✓ | | | | ✓ | | | | | ✓ |
| Sucralose | ✓ | ✓ | ✓ | ✓ | ✓ | ✓ | ✓ | ✓ | ✓ | ✓ | ✓ | ✓ | ✓ | ✓ |
| Peppermint Oil | ✓ | ✓ | ✓ | ✓ | ✓ | ✓ | ✓ | ✓ | ✓ | ✓ | ✓ | ✓ | ✓ | ✓ |
| Purified water | ✓ | ✓ | ✓ | ✓ | ✓ | ✓ | ✓ | ✓ | ✓ | ✓ | ✓ | ✓ | ✓ | ✓ |
| Optionally other pharmaceutically acceptable excipients | ✓ | ✓ | ✓ | ✓ | ✓ | ✓ | ✓ | ✓ | ✓ | ✓ | ✓ | ✓ | ✓ | ✓ |

Various sublingual gel compositions comprising dexmedetomidine hydrochloride at doses of 20 μg, 30 μg, 60 μg, 90 μg, 120 μg and 180 μg and excipients as described in Table 3.

TABLE 3

Sublingual gel formulation embodiments.

| Ingredients | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Carbopol | ✓ | | | ✓ | | ✓ | ✓ | | | | | | ✓ | | |
| Hydroxypropyl methylcellulose | | ✓ | | ✓ | | ✓ | | | ✓ | | ✓ | | | ✓ | |
| Hydroxypropyl cellulose | | | | | | | | | | | | | | | |
| Carboxymethyl cellulose | | | ✓ | | ✓ | | | | | ✓ | | ✓ | | | ✓ |
| N-Methylpyrrolidone | | | | | ✓ | ✓ | ✓ | | | | | | | | |
| Propylene glycol | | | | | | | | ✓ | ✓ | | ✓ | | | | |
| Polyethylene glycol | | | | | | | | | | ✓ | | ✓ | ✓ | | |
| Glycerine | | | | | | | | | | | | | ✓ | ✓ | ✓ |
| Ethanol | ✓ | ✓ | ✓ | | | | | | | | | | | | |
| Sucralose | ✓ | ✓ | ✓ | ✓ | ✓ | ✓ | ✓ | ✓ | ✓ | ✓ | ✓ | | ✓ | ✓ | ✓ |
| Peppermint Oil | | ✓ | ✓ | ✓ | ✓ | ✓ | ✓ | ✓ | ✓ | ✓ | ✓ | | ✓ | ✓ | ✓ |
| Purified water | ✓ | ✓ | ✓ | ✓ | ✓ | ✓ | ✓ | ✓ | ✓ | ✓ | ✓ | ✓ | ✓ | ✓ | ✓ |
| Optionally other pharmaceutically acceptable excipients | ✓ | ✓ | ✓ | ✓ | ✓ | ✓ | ✓ | ✓ | ✓ | ✓ | ✓ | ✓ | ✓ | ✓ | ✓ |

Tablets

In some embodiments, the present disclosure provides tablet formulations suitable for oromucosal administration (e.g., sublingual or buccal administration) comprising or consisting essentially of therapeutically effective amount of dexmedetomidine or pharmaceutically acceptable salt thereof and one or more pharmaceutically acceptable carrier (from about 1% to about 99.995% by weight). Such carriers can be taste masking agents, diluents, disintegrants, binders, lubricants, glidants, flavouring agents or liquid solvents. Examples of pharmaceutically acceptable liquids include water, ethanol, dimethyl sulfoxide, propylene glycol, polyethylene glycol, propylene carbonate, glycerine, N-methylpyrrolidone, pharmaceutically acceptable oils (e.g., soybean, sunflower, peanut, etc.) or the like. Taste masking agents include, for example, amberlite, Opadry® AMB TAN, polymethacrylates (especially Eudragit® L100), sodium starch glycolate (Primojel), carbopol polymers, PEG-5M, sodium acetate, ethylcellulose, betacyclodextrin. Flavouring agents can be, for example, mint powder, menthol, vanillin, aspartame, acesulfame potassium, saccharin. Disintegrants include, for example, sodium starch glycolate, low-substituted hydroxy propyl cellulose, alginic acid, carbon dioxide, carboxymethylcellulose calcium, carboxymethylcellulose sodium, croscarmellose sodium, guar gum, methylcellulose, polacrilin potassium, poloxamer, sodium alginate. Diluents can be, for example, microcrystalline cellulose, dextrates, dextrose, fructose, mannitol, sucralose, sorbitol, starch, pregelatinized starch, sucrose, xylitol, maltose, maltodextrin, maltitol. Binders can be, for example, alginic acid, carbomer, ethyl cellulose, gelatine, liquid glucose, guar gum, hydroxyethyl cellulose, methylcellulose, polydextrose, polyethylene oxide, hydroxypropyl methylcellulose, hydroxypropyl cellulose, sodium alginate. At least one lubricant may conveniently be incorporated into the formulation to prevent the powder from adhering to tablet punches during the compression procedure. Lubricants can be, for example, talc, magnesium stearate, calcium stearate, glyceryl behenate, hydrogenated castor oil, stearic acid, sodium lauryl sulphate. Glidants are used to promote powder flow by reducing interparticle friction and cohesion. These are used in combination with lubricants as they have no ability to reduce die wall friction. Glidants, can be, for example, colloidal silicon dioxide, calcium silicate, calcium phosphate tribasic.

Various buccal tablet formulations comprising dexmedetomidine hydrochloride at doses of 20 μg, 30 μg, 60 μg, 90 μg, 120 μg and 180 μg and excipients as described in Table 4.

TABLE 4

Buccal tablet formulation embodiments.

| Ingredients | 1 | 2 | 3 | 4 | 5 |
|---|---|---|---|---|---|
| Lactose monohydrate | ✓ | ✓ | ✓ | ✓ | ✓ |
| Polyethylene oxide | ✓ | | | | |
| Hydroxypropyl cellulose | | ✓ | | | |
| Hydroxypropyl methylcellulose | | | | | ✓ |
| Sodium alginate | | | | ✓ | |
| Xanthan gum | | | ✓ | | |
| Sucralose | ✓ | ✓ | ✓ | ✓ | ✓ |
| Magnesium stearate | ✓ | ✓ | ✓ | ✓ | ✓ |
| Talc | | ✓ | ✓ | ✓ | ✓ |
| Optionally other pharmaceutically acceptable excipients | ✓ | ✓ | ✓ | ✓ | ✓ |

Various sublingual tablet compositions comprising dexmedetomidine hydrochloride at doses of 20 μg, 30 μg, 60 μg, 90 μg, 120 μg, and 180 μg and excipients as described in Table 5.

TABLE 5

| Ingredients | Sublingual Tablet Formulation Embodiment No. | | | | | | | | | |
|---|---|---|---|---|---|---|---|---|---|---|
| | 1 | 2 | 3 | 4 | 5 | 6 | 7 | 8 | 9 | 10 |
| Lactose Monohydrate | ✓ | ✓ | ✓ | ✓ | ✓ | ✓ | ✓ | ✓ | ✓ | ✓ |
| Hydroxypropyl methylcellulose | ✓ | ✓ | | | | | | | | |
| Hydroxypropyl cellulose | | | ✓ | ✓ | | | | | | |
| Croscarmellose Sodium | ✓ | | ✓ | | ✓ | | ✓ | | ✓ | |
| Sodium starch glycolate | | ✓ | | ✓ | | ✓ | | ✓ | | ✓ |
| Polyethylene oxide | | | | | ✓ | ✓ | | | | |
| Xanthan gum | | | | | | | ✓ | ✓ | | |
| Sodium alginate | | | | | | | | | ✓ | ✓ |
| Sucralose | ✓ | ✓ | ✓ | ✓ | ✓ | ✓ | ✓ | ✓ | ✓ | ✓ |
| Magnesium stearate | ✓ | ✓ | ✓ | ✓ | ✓ | ✓ | ✓ | ✓ | ✓ | ✓ |
| Optionally other pharmaceutically acceptable excipients | ✓ | ✓ | ✓ | ✓ | ✓ | ✓ | ✓ | ✓ | ✓ | ✓ |

Methods and Administration

The disclosed invention is related to the discovery that dexmedetomidine clearance was decreased in human subjects with a hepatic impairment, e.g., an impairment classified as Child-Pugh Class A, B, or C. Accordingly, such subjects can be treated with a reduced dose of an oromucosal formulation comprising dexmedetomidine or a pharmaceutically acceptable salt thereof compared to a human subject with normal hepatic function.

Accordingly, the disclosed invention provides a method of using dexmedetomidine, comprising:
  administering an initial dose of dexmedetomidine or a pharmaceutically acceptable salt thereof in an oromucosal formulation to a human subject having an agitation associated with schizophrenia or bipolar I or II disorder;
  optionally administering a second dose of dexmedetomidine or the pharmaceutically acceptable salt thereof in the oromucosal formulation to the human subject at least two hours after and within 24 hours of the initial dose; and
  optionally administering a third dose of dexmedetomidine or the pharmaceutically acceptable salt thereof in the oromucosal formulation to the human subject at least two hours after the second dose and within 24 hours of the initial dose;
  wherein the administration of the dexmedetomidine does not exceed a maximum total daily dosage;
  wherein the human subject has a hepatic impairment;
  wherein the second dose and the third dose are 60 mcg of dexmedetomidine each;
  wherein the initial dose is 90 mcg of dexmedetomidine and the maximum total daily dosage is 210 mcg of dexmedetomidine if the agitation is mild or moderate, and the hepatic impairment is mild or moderate;
  wherein the initial dose is 120 mcg of dexmedetomidine and the maximum total daily dosage is 240 mcg of dexmedetomidine if the agitation is severe, and the hepatic impairment is mild or moderate;
  wherein the initial dose is 60 mcg of dexmedetomidine and the maximum total daily dosage is 180 mcg of dexmedetomidine if the agitation is mild or moderate and the hepatic impairment is severe; and
  wherein the initial dose is 90 mcg of dexmedetomidine and the maximum total daily dosage is 210 mcg of dexmedetomidine if the agitation is severe and the hepatic impairment is severe.

The Positive and Negative Syndrome Scale-Excited Component (PEC) is an investigator-rated instrument that can be used to measure the degree of agitation. The PEC score consists of 5 items: poor impulse control, tension, hostility, uncooperativeness, and excitement. Each item is scored on a scale from 1 to 7 (1=absent, 2=minimal, 3=mild, 4=moderate, 5=moderate-severe, 6=severe, 7=extremely severe). The total PEC score ranges from 5 to 35, with higher scores reflecting greater overall symptom severity.

In some embodiments of the method, agitation that is mild or moderate is defined as a PEC score of 19 or lower (e.g., a score of 5 to 19, including scores of 5, 6, 7, 8, 9, 10, 11, 12, 13, 14, 15, 16, 17, 18, or 19). In some embodiments of the method, agitation that is mild is defined as a PEC score of 13 or lower (e.g., a score of 5 to 13, including scores of 5, 6, 7, 8, 9, 10, 11, 12, or 13). In some embodiments of the method, agitation that is moderate is defined as a PEC score of 14 to 19 inclusive (e.g., 14, 15, 16, 17, 18, or 19). In some embodiments of the method, agitation that is severe is defined as a PEC score of 20 or higher (e.g., a score of 20 to 35, including 20, 21, 22, 23, 24, 25, 26, 27, 28, 29, 30, 31, 32, 33, 34, or 35).

The Child-Pugh classification for measuring the severity of hepatic impairment (e.g., liver disease) typically is measured based on the degree of ascites, the serum concentrations of bilirubin and albumin, the prothrombin time, and the degree of encephalopathy. A point is assigned based on criterion based on increasing severity.

Encephalopathy: None=1 point, Grade 1 and 2=2 points, Grade 3 and 4=3 points
  Ascites: None=1 point, slight=2 points, moderate=3 points
  Bilirubin: under 2 mg/ml=1 point, 2 to 3 mg/ml=2 points, over 3 mg/ml=3 points
  Albumin: greater than 3.5 mg/ml=1 point, 2.8 to 3.5 mg/ml=2 points, less than 2.8 mg/ml=3 points
  Prothrombin Time (sec prolonged): less than 4 sec=1 point, 4 to 6 sec=2 points, over 6 sec=3 points Frequently the international normalized ratio (INR) will be used as a substitute for prothrombin time, with INR under 1.7=1 point, INR 1.7 to 2.2=2 points, INR above 2.2=3 points.

Typically, Child-Pugh Class A is 5 to 6 points, Child-Pugh Class B is 7 to 9 points (i.e., 7, 8, or 9 points), and Child-Pugh Class C is 10 to 15 points (i.e., 10, 11, 12, 13, 14, or 15 points).

In some embodiments of the method, the hepatic impairment is mild that is defined as Child-Pugh Class A. In some embodiments of the method, the hepatic impairment is moderate that is defined as Child-Pugh Class B. In some embodiments of the method, the hepatic impairment is severe that is defined as Child-Pugh Class C.

In some embodiments of the method, only a first dose is required and second and third doses are not needed. In some embodiments of the method, only a first and second dose are required and a third dose is not needed. In other embodiments of the method, the third dose is administered at least two hours after the second dose and within 24 hours of the initial dose.

In some embodiments of the method, the agitation is mild or moderate and the hepatic impairment is mild or moderate, and wherein the initial dose is 90 mcg of dexmedetomidine and the maximum total daily dosage is 210 mcg of dexmedetomidine. In some embodiments of the method, the second dose is administered at least two hours after the initial dose and within 24 hours of the initial dose. In some embodiments of the method, the third dose is administered at least two hours after the second dose and within 24 hours of the initial dose.

In some embodiments of the method, the agitation is severe and the hepatic impairment is mild or moderate, and wherein the initial dose is 120 mcg of dexmedetomidine and the maximum total daily dosage is 240 mcg of dexmedetomidine. In some embodiments of the method, the second dose is administered at least two hours after the initial dose and within 24 hours of the initial dose. In some embodiments of the method, the third dose is administered at least two hours after the second dose and within 24 hours of the initial dose.

In some embodiments of the method, the agitation is mild or moderate and the hepatic impairment is severe, and wherein the initial dose is 60 mcg of dexmedetomidine and the maximum total daily dosage is 180 mcg of dexmedetomidine. In some embodiments of the method, the second dose is administered at least two hours after the initial dose and within 24 hours of the initial dose. In some embodiments of the method, the third dose is administered at least two hours after the second dose and within 24 hours of the initial dose.

In some embodiments of the method, the agitation is severe and the hepatic impairment is severe, and wherein the initial dose is 90 mcg of dexmedetomidine and the maximum total daily dosage is 210 mcg of dexmedetomidine. In some embodiments of the method, the second dose is administered at least two hours after the initial dose and within 24 hours of the initial dose. In some embodiments of the method, the third dose is administered at least two hours after the second dose and within 24 hours of the initial dose.

The disclosed invention further provides a method of using an oromucosal formulation of dexmedetomidine for an acute treatment of an agitation associated with schizophrenia or bipolar I or II disorder in a human subject, wherein the human subject does not have a hepatic impairment, the method comprising:
administering an initial dose of dexmedetomidine or a pharmaceutically acceptable salt thereof in the oromucosal formulation to the human subject;
optionally administering a second dose of dexmedetomidine or the pharmaceutically acceptable salt thereof in the oromucosal formulation to the human subject at least two hours after and within 24 hours of the initial dose; and
optionally administering a third dose of dexmedetomidine or the pharmaceutically acceptable salt thereof in the oromucosal formulation to the human subject at least two hours after the second dose and within 24 hours of the initial dose;
wherein the administration of the dexmedetomidine does not exceed a maximum total daily dosage;
wherein the initial dose, the second dose, the third dose, and the maximum total daily dosage are 120 mcg, 60 mcg, 60 mcg, and 240 mcg of dexmedetomidine, respectively, if the human subject is younger than 65 years of age and if the agitation is mild or moderate;
wherein the initial dose, the second dose, the third dose, and the maximum total daily dosage are 180 mcg, 90 mcg, 90 mcg, and 360 mcg of dexmedetomidine, respectively, if the human subject is younger than 65 years of age and if the agitation is severe; and
wherein the initial dose, the second dose, the third dose, and the maximum total daily dosage are 120 mcg, 60 mcg, 60 mcg, and 240 mcg of dexmedetomidine, respectively, if the human subject is 65 years of age or older and if the agitation is mild, moderate, or severe.

In some embodiments of the method, only a first dose is required and second and third doses are not needed. In some embodiments of the method, only a first and second dose are required and a third dose is not needed. In other embodiments of the method, the third dose is administered at least two hours after the second dose and within 24 hours of the initial dose.

In some embodiments of this method, the human subject is younger than 65 years of age and the agitation is mild or moderate, and wherein the initial dose, the second dose, the third dose, and the maximum total daily dosage are 120 mcg, 60 mcg, 60 mcg, and 240 mcg of dexmedetomidine, respectively. In some embodiments of the method, the second dose is administered at least two hours after the initial dose and within 24 hours of the initial dose. In some embodiments of the method, the third dose is administered at least two hours after the second dose and within 24 hours of the initial dose.

In some embodiments of this method, the human subject is younger than 65 years of age and the agitation is severe, and wherein the initial dose, the second dose, the third dose, and the maximum total daily dosage are 180 mcg, 90 mcg, 90 mcg, and 360 mcg of dexmedetomidine, respectively. In some embodiments of the method, the second dose is administered at least two hours after the initial dose and within 24 hours of the initial dose. In some embodiments of the method, the third dose is administered at least two hours after the second dose and within 24 hours of the initial dose.

In some embodiments of this method, the human subject is 65 years of age or older and the agitation is mild, moderate, or severe, and wherein the initial dose, the second dose, the third dose, and the maximum total daily dosage are 120 mcg, 60 mcg, 60 mcg, and 240 mcg of dexmedetomidine, respectively. In some embodiments of the method, the second dose is administered at least two hours after the initial dose and within 24 hours of the initial dose. In some embodiments of the method, the third dose is administered at least two hours after the second dose and within 24 hours of the initial dose.

The disclosed invention further provides a method of using an oromucosal formulation of dexmedetomidine for an acute treatment of an agitation associated with schizophrenia or bipolar I or II disorder in a human subject, the method comprising:
administering an initial dose of dexmedetomidine or a pharmaceutically acceptable salt thereof in the oromucosal formulation to the human subject;
optionally administering a second dose of dexmedetomidine or the pharmaceutically acceptable salt thereof in the oromucosal formulation to the human subject at least two hours after and within 24 hours of the initial dose; and optionally administering a third dose of dexmedetomidine or the pharmaceutically acceptable salt thereof in the oromucosal formulation to the human subject at least two hours after the second dose and within 24 hours of the initial dose;
wherein the administration of the dexmedetomidine does not exceed a maximum total daily dosage;
wherein the initial dose, the second dose, the third dose, and the maximum total daily dosage are 120 mcg, 60 mcg, 60 mcg, and 240 mcg of dexmedetomidine, respectively, if the human subject is younger than 65 years of age and if the agitation is mild or moderate;
wherein the initial dose, the second dose, the third dose, and the maximum total daily dosage are 180 mcg, 90 mcg, 90 mcg, and 360 mcg of dexmedetomidine, respectively, if the human subject is younger than 65 years of age and if the agitation is severe; and
wherein the initial dose, the second dose, the third dose, and the maximum total daily dosage are 120 mcg, 60 mcg, 60 mcg, and 240 mcg of dexmedetomidine, respectively, if the human subject is 65 years of age or older and if the agitation is mild, moderate, or severe.

In some embodiments of the method, only a first dose is required and second and third doses are not needed. In some embodiments of the method, only a first and second dose are required and a third dose is not needed. In other embodiments of the method, the third dose is administered at least two hours after the second dose and within 24 hours of the initial dose.

In some embodiments of this method, the human subject is younger than 65 years of age and the agitation is mild or moderate, and wherein the initial dose, the second dose, the third dose, and the maximum total daily dosage are 120 mcg, 60 mcg, 60 mcg, and 240 mcg of dexmedetomidine, respectively. In some embodiments of the method, the second dose is administered at least two hours after the initial dose and within 24 hours of the initial dose. In some embodiments of the method, the third dose is administered at least two hours after the second dose and within 24 hours of the initial dose.

In some embodiments of this method, the human subject is younger than 65 years of age and the agitation is severe, and wherein the initial dose, the second dose, the third dose, and the maximum total daily dosage are 180 mcg, 90 mcg, 90 mcg, and 360 mcg of dexmedetomidine, respectively. In some embodiments of the method, the second dose is administered at least two hours after the initial dose and within 24 hours of the initial dose. In some embodiments of the method, the third dose is administered at least two hours after the second dose and within 24 hours of the initial dose.

In some embodiments of this method, the human subject is 65 years of age or older and the agitation is mild, moderate, or severe, and wherein the initial dose, the second dose, the third dose, and the maximum total daily dosage are 120 mcg, 60 mcg, 60 mcg, and 240 mcg of dexmedetomidine, respectively. In some embodiments of the method, the second dose is administered at least two hours after the initial dose and within 24 hours of the initial dose. In some embodiments of the method, the third dose is administered at least two hours after the second dose and within 24 hours of the initial dose.

In any embodiments of the method, the oromucosal formulation further comprises at least one water-soluble polymer. In some embodiments, the at least one water-soluble polymer is selected from the group consisting of hydroxypropyl cellulose, hydroxypropyl methylcellulose, hydroxyethyl cellulose, carboxy methylcellulose, methylcellulose, polyethylene oxide (PEO), and mixtures thereof. In some embodiments, the at least one water-soluble polymer is hydroxypropyl cellulose.

In some embodiments, the treatment is effective without causing significant sedation. In some embodiments, the condition is agitation or signs of agitation. In some embodiments, the agitation or signs of agitation are associated with schizophrenia. In some embodiments, the agitation or signs of agitation are associated with a bipolar illness such as bipolar I disorder or bipolar II disorder.

In some embodiments, the treatment is effective without causing clinically significant cardiovascular effects. In some embodiments, agitation or signs of agitation is treated without the subject's diastolic blood pressure falling below about 60 mmHg and/or without the subject's heart rate falling below about 50 beats per minute. In some embodiments, agitation or signs of agitation is treated without the subject's systolic blood pressure falling below about 80 mmHg and or/without the subject's diastolic blood pressure falling below about 60 mmHg and/or without the subject's heart rate falling below about 50 beats per minute.

In some embodiments, the present disclosure provides a method of treating acute agitation associated with schizophrenia and bipolar disorder (e.g., bipolar I disorder or bipolar II disorder) in a human subject, comprising oromucosally administering a film composition comprising dexmedetomidine or a pharmaceutically acceptable salt thereof (e.g., hydrochloride salt) as a single dose of 120 μg or 180 μg. In some embodiments, an additional dose (e.g., 90 μg or 60 μg) can be taken after a suitable period of time (e.g., after about 2 hours) in the event of persistent or recurrent agitation (e.g., by cutting a 180 μg or 120 μg film in half).

In some embodiments, dexmedetomidine or a pharmaceutically acceptable salt thereof is administered by the sublingual or buccal route. In some embodiments, dexmedetomidine or a pharmaceutically acceptable salt thereof is administered sublingually in the form of a tablet, film, spray, gel or drops, particularly a film. In some embodiments, the film is placed under the tongue, close to the base of the tongue, on the left or right side. In some embodiments, dexmedetomidine or a pharmaceutically acceptable salt thereof is administered buccally in the form of a film, patch or tablet, particularly a film. In some embodiments, the film is placed against the inner lip or check, close to the jaw line.

In some embodiments, the oromucosal formulation is a self-supporting, dissolvable, film comprising:
(a) a composition comprising or consisting essentially of:
(i) about 180 μg of dexmedetomidine hydrochloride;
(ii) hydroxypropyl cellulose (40,000 MW); and
(iii) hydroxypropyl cellulose (140,000 MW); and
(b) a film substrate comprising or consisting essentially of:
(i) hydroxypropyl cellulose (40,000 MW);
(ii) hydroxypropyl cellulose (140,000 MW);
(iii) hydroxypropyl cellulose (370,000 MW); and
(iv) polyethylene oxide (600,000 MW);
wherein the composition of part (a) is present on the surface of the film substrate (b).

In some embodiments, the oromucosal formulation is a self-supporting, dissolvable, film comprising:
(a) a composition comprising or consisting essentially of:
(i) about 120 μg of dexmedetomidine hydrochloride;
(ii) hydroxypropyl cellulose (40,000 MW); and
(iii) hydroxypropyl cellulose (140,000 MW); and
(b) a film substrate comprising or consisting essentially of:
(i) hydroxypropyl cellulose (40,000 MW);
(ii) hydroxypropyl cellulose (140,000 MW);
(iii) hydroxypropyl cellulose (370,000 MW); and
(iv) polyethylene oxide (600,000 MW);
wherein the composition of part (a) is present on the surface of the film substrate (b).

In some embodiments, agitation or signs of agitation are significantly reduced within 60 minutes in a patient with schizophrenia or bipolar disorder following administration of the initial dose, optional second dose, and optional third dose of dexmedetomidine or a pharmaceutically acceptable salt thereof (e.g., dexmedetomidine hydrochloride), as measured by the relative PEC scores just prior to and 60 minutes after administering dexmedetomidine or a pharmaceutically acceptable salt thereof.

In some embodiments, the relative PEC scores are different by at least six points. In another embodiment, the relative PEC scores are different by at least eight points. In yet another embodiment, the difference in relative PEC scores is maintained for at least six hours. In a particular embodiment, a difference of at least eight points is maintained for up to about 24 hours when administering the initial dose, optional second dose, and optional third dose of dexmedetomidine or a pharmaceutically acceptable salt thereof (e.g., dexmedetomidine hydrochloride).

In some embodiments, dexmedetomidine or a pharmaceutically acceptable salt thereof is administered immediately prior to or immediately following the appearance of agitation or signs of agitation in the human subject.

In some embodiments, the patient has schizophrenia, in some embodiments, the patient has bipolar disorder (e.g., bipolar I disorder or bipolar II disorder), and in some embodiments, the patient has both schizophrenia and bipolar disorder (e.g., bipolar I disorder or bipolar II disorder).

In some embodiments, dexmedetomidine or a pharmaceutically acceptable salt thereof is administered within 10 minutes following the appearance of agitation or signs of agitation in the human subject. In some embodiments, an additional dose of 60 μg and an optional third dose can be taken after a suitable period of time (e.g., two hours or more within a 24 hour time period starting from the initial dose) of prior dose. For example, the period of time can be about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, or about 23 hours. In some embodiments, the second dose is administered after a period of about 2 hours.

In accordance with some embodiments of the methods of treating agitation comprising administering the oromucosal formulation to a patient in the fasted state. In some embodiments, the oromucosoal formulation can be administered in the fed state.

In some embodiments of the methods, agitation is significantly reduced within about 2 hours of administering the composition, as measured by a mean change in Positive and Negative Syndrome Scale Excited Component (PEC) scores relative to baseline. In some embodiments, the agitation is significantly reduced within about 45 minutes to about 1 hour. In some embodiments, the agitation is significantly reduced in less than 45 minutes (e.g., about 15 minutes, about 20 minutes, about 25 minutes, about 30 minutes). In some embodiments, the patient experiences ≥40% decrease from baseline in PEC score. For example, the human subject may experience greater than or equal to about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, or about 150% from baseline. Treatment efficacy may also be compared by comparing PEC score to placebo. In some embodiments, the PEC score is ≥30% lower than placebo (e.g., the placebo group has mean change from baseline in PEC total score of −3 and the dexmedetomidine-containing composition has a score of −3.9). For example, compared to placebo, the patient's PEC score can be lower by greater than or equal to about 30,%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, or about 200%. In some embodiments, the patient experiences a mean change in PEC score of greater than about −4 (i.e. a decrease of 4 or more points) relative to baseline within 2 hours of administering the composition. For example, at the 2 hour time point, the patient may experience a mean change in PEC score of greater than about −4, about −5, about −6, about −7, about −8, about −9, about −10, about −11, or about −12. In some embodiments, the decrease in PEC score (e.g., of greater than about −4) is maintained for at least six hours following administration of the composition. For example, if a patient experiences a mean change from baseline in PEC total score of e.g., −6 at 2 hours, then at 6 hours patient's mean change in PEC score will be about −6 or lower (e.g., −7, −8, etc.). In some embodiments, the decrease in PEC score (e.g., of greater than about −4) is substantially maintained for at least six hours following administration of the composition. For example, if a patient experiences a mean change from baseline in PEC total score of e.g., −6 at 2 hours, then at 6 hours patient's mean change in PEC score will be about −4, about −5, or about −6 or lower (e.g., −7, −8, etc.). In some embodiments, the mean change in PEC score is greater than or equal to −8 and is maintained from 2 hours post administration up to at least about 6 hours following administration of the composition.

In some embodiments, the composition is administered twice daily. In some embodiments, the composition comprises a dose range of dexmedetomidine or a pharmaceutically acceptable salt thereof of between about 30 μg and about 240 μg. For example, the composition comprises a unit dose of about 30 μg, about 60 μg, about 90 μg, about 120 μg, or 180 μg of dexmedetomidine or a pharmaceutically acceptable salt thereof. In some embodiments, a single dose of a composition comprising about 60 μg, about 90 μg, or about 120 μg dexmedetomidine or a pharmaceutically acceptable salt thereof is effective for up to at least about 24 hours. In some embodiments, the composition is administered twice daily for 7 days.

In some embodiments, the present disclosure provides methods of reducing agitation to a 1 (very much improved) or 2 (much improved) within 2 hours of administering a composition comprising dexmedetomidine or a pharmaceutically acceptable salt thereof (e.g., dexmedetomidine hydrochloride), as measured by the Clinical Global Impression—Improvement Scale. In some embodiments, the agitation is reduced within about 30 minutes to about 1 hour. In some embodiments, the reduction in agitation is maintained for greater than about 2 hours. For example, the reduction in agitation is maintained for about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23, or about 24 hours. In some embodiments, the composition comprises about 120 μg of dexmedetomidine. In some embodiments, the composition comprises about 180 μg of dexmedetomidine. In some embodiments, the patient has schizophrenia. In some embodiments, the patient has bipolar disorder.

In some embodiments, the present disclosure provides methods of reducing agitation to a 3 (mild agitation) or 4 (normal behavior) within 2 hours of administering a composition comprising dexmedetomidine or a pharmaceutically acceptable salt thereof, as measured by the Agitation-Calmness Evaluation Scale (ACES). In some embodiments, the agitation is reduced within about 30 minutes to about 1 hour. In some embodiments, the reduction in agitation is reduced to a 4 (normal behavior). In some embodiments, the reduction in agitation is maintained for greater than about 2 hours. For example, the reduction in agitation is maintained for about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the composition comprises about 120 µg of dexmedetomidine. In some embodiments, the composition comprises about 180 µg of dexmedetomidine. In some embodiments, the patient has schizophrenia. In some embodiments, the patient has bipolar disorder.

In some embodiments, the present disclosure provides methods of achieving a ≥40% reduction in agitation, within 2 hours of administering a composition comprising dexmedetomidine or a pharmaceutically acceptable salt thereof, as measured by the PEC scale. In some embodiments, the agitation is reduced within about 30 minutes to about 1 hour. In some embodiments, the reduction in agitation ≥40%, ≥50%, ≥60%, ≥70%, ≥80%, ≥90%, or ≥100%. In some embodiments, the reduction in agitation is maintained for greater than about 2 hours. For example, the reduction in agitation is maintained for about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the composition comprises about 60 µg, about 90 µg, or about 120 µg of dexmedetomidine. In some embodiments, the patient has schizophrenia. In some embodiments, the patient has bipolar I or II disorder. In some embodiments, the patient has both schizophrenia and either bipolar I or II disorder.

In some embodiments, the present disclosure provides a method of achieving a PEC score reduction in agitation for a sustained period of time in a subject with bipolar or schizophrenic subject comprising administering to the subject a pharmaceutical composition comprising dexmedetomidine or a pharmaceutically acceptable salt thereof at a dose of about 60 µg, about 90 µg, or about 120 µm, wherein the PEC score reduction is about −8 to about −10 and wherein the sustained period is about 2 hours to about 6 hours. In some embodiments, the composition comprises dexmedetomidine hydrochloride. In some embodiments, the sustained period is about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the PEC score reduction is about −8, about −9, or about −10.

In some embodiments, the present disclosure provides a method of achieving an ACES score improvement for a sustained period of time in a subject with bipolar or schizophrenic subject comprising administering to the subject a pharmaceutical composition comprising dexmedetomidine or a pharmaceutically acceptable salt thereof at a dose of about 60 µg, about 90 µg, or about 120 µg, wherein the ACES score is improved to about 3 to about 4 and wherein the sustained period is about 2 hours to about 6 hours. In some embodiments, the composition comprises dexmedetomidine hydrochloride in an amount equivalent to provide about 60 µg, about 90 µg, or about 120 µg of dexmedetomidine. In some embodiments, the sustained period is about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the ACES score is about 4.

In some embodiments, the present disclosure provides a method of achieving an CGI-I score improvement for a sustained period of time in a subject with bipolar or schizophrenic subject comprising administering to the subject a pharmaceutical composition comprising dexmedetomidine or a pharmaceutically acceptable salt thereof at a dose of about 60 µg, about 90 µg, or about 120 µg, wherein the CGI-I score is improved to about a 1 (very much improved) or about a 2 (much improved) and wherein the sustained period is about 2 hours to about 6 hours. In some embodiments, the oromucosal formulation comprises dexmedetomidine hydrochloride in an amount equivalent to provide about 60 µg, about 90 µg, or about 120 µg of dexmedetomidine. In some embodiments, the sustained period is about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the CGI-I score is about 1.

EXAMPLES

The example presented below is provided for the purpose of illustration only and the embodiments described herein should in no way be construed as being limited to this example. Rather, the embodiments should be construed to encompass any and all variations which become evident as a result of the teaching provided herein.

Example 1: Dexmedetomidine Sublingual Film Formulation

TABLE 6

Dexmedetomidine deposited on the surface of a polymer matrix film composition

| Ingredients | Concentration g/100 g (10 µg film) | Concentration g/100 g (20 µg film) | Function |
| --- | --- | --- | --- |
| Drug-containing composition | | | |
| Dexmedetomidine hydrochloride | 0.136 | 0.267 | Active agent |
| Hydroxypropyl cellulose, HPC-SSL (MW = 40,000) | 0.301 | 0.593 | Film former |
| Hydroxypropyl cellulose (MW = 140,000) | 0.301 | 0.593 | Film former |
| FD&C Blue #1 Granular | 0.002 | 0.004 | Color |
| Ethyl Alcohol as a solvent | qs | qs | Solvent |
| Polymer matrix composition | | | |
| Hydroxypropyl cellulose (MW = 140,000) | 4.803 | 4.768 | Film former |
| Hydroxypropyl cellulose, HPC-SSL (MW = 40,000) | 4.803 | 4.768 | Film former |

TABLE 6-continued

Dexmedetomidine deposited on the surface of a polymer matrix film composition

| Ingredients | Concentration g/100 g (10 μg film) | Concentration g/100 g (20 μg film) | Function |
|---|---|---|---|
| Hydroxypropyl cellulose (MW = 370,000) | 28.809 | 28.601 | Film former |
| Fast Emerald Green Shade (NO. 06507) | 0.129 | 0.128 | Color |
| Sucralose, USP-NF Grade | 0.993 | 0.985 | Sweetener |
| Peppermint Oil, NF | 2.104 | 2.089 | Flavor |
| Polyethylene oxide (Sentry Polyox WSR 205 LEO NF) (MW = 600,000) | 57.618 | 57.202 | Film former & Mucoadhesive |
| Water as a solvent | qs | qs | Solvent |

(A) Process for the Preparation of Polymer Matrix:

Polymer mixture: Polyethylene oxide and fast emerald green shade were mixed in water for at least 180 minutes at about 1400 rpm to about 2000 rpm. Sucralose, hydroxypropyl cellulose (molecular weight 140K), hydroxypropyl cellulose, HPC-SSL (molecular weight 40K) and hydroxypropyl cellulose (molecular weight 370K) were added and mixed for at least 120 minutes at about 1600 rpm to 2000 rpm. Peppermint Oil was added to water and the resultant dispersion was then added to the polymer mixture and mixed for at least 30 minutes. The resultant mixture was further mixed under vacuum (248 torr) for at least for 30 minutes at a speed of 350 rpm and at temperature of 22.9° C.

Coating station: A roll was placed on an unwind stand and the leading edge was thread through guide bars and coating bars. The silicone-coated side of the liner was placed faced up. A gap of 40 millimeters was maintained between the coating bars. The oven set point was adjusted to 70° C. and the final drying temperature was adjusted to 85° C.

Coating/drying process: The polymer mixture was poured onto the liner between the guide bars and the coating bars. The liner was pulled slowly through the coating bar at a constant speed by hand until no liquid was remained on the coating bars. The liner was cut to approximately 12-inch length hand sheets using a safety knife. Each hand sheet was placed on a drying board and was tapped on the corners to prevent curl during drying. The hand sheets were dried in the oven until the moisture content was less than 5% (approximately 30 minutes) and then removed from the drying board. The coating weights were checked against the acceptance criteria, and if met, the hand sheets were then stacked and placed in a 34 inch×40 inch foil bag that was lined with PET release liner.

(B) Process for the Preparation of Deposition Solution:

FDC blue was dissolved in ethyl alcohol for at least 180 minutes. Dexmedetomidine hydrochloride was added to the ethyl alcohol solution with continuous stirring for 10 minutes at about 400 rpm to about 800 rpm. Hydroxypropyl cellulose (40K) and hydroxypropyl cellulose (140K) were added to the mixture, and stirred for at least 30 minutes until all the materials were dissolved.

(C) Process for the Preparation of Micro-Deposited Matrix:

The deposition solution obtained in Step (B) above was filled into a pipette to the required volume (determined according to the specific drug product strength of the final product). An appropriate amount (1.5 microliters=approximately 5 μg) of the deposition solution were deposited (e.g., as droplets) onto the polymer matrix obtained in Step (A), and repeated to a total of 10 times (i.e. 10 deposits/droplets) with space between each deposit to prevent merging of the deposits/droplets and allow subsequent cutting of the film into individual drug-containing units. The film was initially die cut in individual units with dimensions of 22 mm×8.8 mm containing a single deposit of the drug-containing composition. The die cut micro-deposited matrixes were then dried in an oven for 70° C. for 10 minutes and further die cut into 10 units with each unit containing a single deposit of the drug-containing composition.

(D) Packaging:

Each defect-free unit was sealed individually into a foil pouch, which was then heat sealed. If the heat seal was acceptable the package was considered as an acceptable unit for commercial use.

Other unit strengths (e.g., 40 μg and 60 μg films) were similarly prepared by varying the concentrations of drug, polymers and colorant within the drug-containing composition. For example, the 40 μg and 60 μg, films were prepared from drug-containing compositions containing, respectively, approximately 2× and 3×, the amounts of drug, polymers and colorant that appear in the 20 μg drug-containing composition described in table 6 above.

Example 2

TABLE 7

Dexmedetomidine deposited on the surface of a polymer matrix film composition

| Ingredients | Concentration mg/unit (80 μg film) | Concentration mg/unit (120 μg film) | Concentration mg/unit (180 μg film) | Function |
|---|---|---|---|---|
| Drug-containing composition | | | | |
| Dexmedetomidine hydrochloride | 0.0945 | 0.142 | 0.213 | Active agent |
| Hydroxypropyl cellulose, HPC-SSL (MW = 40,000) | 0.0812 | 0.122 | 0.183 | Film former |
| Hydroxypropyl cellulose (MW = 140,000) | 0.0812 | 0.122 | 0.183 | Film former |
| FD&C Blue #1 Granular | 0.0008 | 0.001 | 0.002 | Color |
| Ethyl Alcohol as a solvent | q.s | q.s. | q.s. | Solvent |

TABLE 7-continued

Dexmedetomidine deposited on the surface of a polymer matrix film composition

| Ingredients | Concentration mg/unit (80 μg film) | Concentration mg/unit (120 μg film) | Concentration mg/unit (180 μg film) | Function |
|---|---|---|---|---|
| Polymer matrix composition | | | | |
| Hydroxypropyl cellulose (MW =140,000) | 0.627 | 0.627 | 0.627 | Film former |
| Hydroxypropyl cellulose, HPC-SSL (MW = 40,000) | 0.627 | 0.627 | 0.627 | Film former |
| Hydroxypropyl cellulose (MW = 370,000) | 3.763 | 3.763 | 3.763 | Film former |
| Fast Emerald Green Shade (NO. 06507) | 0.017 | 0.017 | 0.017 | Color |
| Sucralose, USP-NF Grade | 0.130 | 0.130 | 0.130 | Sweetener |
| Peppermint Oil, NF | 0.275 | 0.275 | 0.275 | Flavor |
| Polyethylene oxide (Sentry Polyox WSR 205 LEO NF) (MW = 600,000) | 7.526 | 7.526 | 7.526 | Film former & Mucoadhesive |
| Water as a solvent | qs | qs | qs | Solvent |

The formulations (80 μg, 120 μg and 180 μg) in Table 7 were prepared using the same manufacturing process as described above in Example 1.

Example 3: A Phase Ib Multicenter, Randomized, Double-Blind, Placebo-Controlled, Multiple Ascending Dose Study to Determine Efficacy, Pharmacokinetics and Safety of Dexmedetomidine Hydrochloride Sublingual Film in Treating Agitation Associated with Schizophrenia Primary Objective:

To determine the doses of dexmedetomidine hydrochloride sublingual film needed to effectively reduce symptoms of acute agitation associated with schizophrenia, schizoaffective disorder or schizophreniform disorder assessed using the Positive and Negative Syndrome Scale-Excited Component (PEC) change from baseline after drug treatment.

Secondary Objective:

Determine PK, safety and tolerability of the various film strengths of dexmedetomidine hydrochloride sublingual film in patients with acute agitation associated with schizophrenia, schizoaffective disorder or schizophreniform disorder.
1. Describe overall clinical improvement after drug administration by Clinical Global Impression-Improvement scale (CGI-I).
2. Describe the duration of calming effect as measured by PEC and ACES.
3. Determine the safety profile of dexmedetomidine hydrochloride sublingual film as measured by vital signs and reports of adverse events.
4. Describe the overall tolerability in terms of adverse event reports and local site (oral/sublingual) tolerability of the sublingual film.
5. Describe the pharmacokinetics of dexmedetomidine hydrochloride sublingual film in the patient population.
6. Visual Analog Scales (VAS) to capture subject's opinion on taste and acceptability as well as questions regarding likability of study medication.

Methodology: This was a two-stage adaptive Phase Ib trial design. It was a randomized, double-blind, placebo-controlled, multiple ascending dose study assessing efficacy, pharmacokinetics, safety and tolerability of dexmedetomidine hydrochloride sublingual film dosing in adult (18-65 years old) males and females with acute agitation associated with schizophrenia, schizoaffective disorder, or schizophreniform disorder.

The first stage was designed to characterize a safe and tolerable dose range which produced a calming effect as measured using the PEC total score. The second stage was designed to enroll a total of 40 subjects per dose group in a three-arm placebo-controlled design to better characterize the broader range of safety and tolerability as well as better estimate variability (effect size).

Adaptive evaluation of escalating dose regimens of 20 μg, 60 μg and 120 μg were performed for the first stage, with an option to test a different dose should a safety or tolerability signal be observed. Male and female adults with acute agitation associated with schizophrenia, schizoaffective disorder, or schizophreniform disorder were enrolled in each cohort. Investigators were permitted to repeat dosing 1 hour after administration if there was a lack of significant efficacy (PEC change from baseline ≤40%) (maximum number of doses per subject was 2) and in the absence of safety concerns.

Blinded periodic safety data reviews were undertaken after completion of dosing each cohort to review all safety data as it became available. Dose escalation was allowed unless a safety or tolerability issue became evident upon periodic regular safety reviews. Based upon blinded analyses of the safety and tolerability of all subject cohorts, additional doses were selected.

Eligible subjects (acutely agitated subjects with schizophrenia, schizoaffective, or schizophreniform disorder) were identified in outpatient clinics, mental health, psychiatric or medical emergency services including medical/psychiatric observation units, or as newly admitted to a hospital setting for acute agitation or already in hospital for chronic underlying conditions. Subjects were domiciled in a clinical research setting or hospitalized to remain under medical supervision while undergoing screening procedures to assess eligibility.

Upon confirmation of eligibility, subjects were randomized to dexmedetomidine hydrochloride sublingual film or placebo film. At the beginning of each study session, a single dose of dexmedetomidine hydrochloride sublingual film was self-administered sublingually, after training with a placebo film and under the supervision of an unblinded staff who did not participate in evaluation of safety or efficacy. The drug film was retained in the sublingual (SL) cavity until dissolved. Participants were also evaluated for local irritation around the area where the film was placed. Efficacy and safety assessments were conducted periodically before and after dosing. If reduction in PEC was less than or equal to 40% one hour after the first administration, the investigator could administer a second dose of dexmedetomidine hydrochloride sublingual film (of the same randomized dose) with an additional PEC assessment completed at 1.5 hr post-dose. All efforts were made to have the patient perform all assessments as per protocol. However, should the patient's situation warrant it, standard of care treatment was initiated, e.g., after the 4 hr assessments were completed. In Stage 1 each cohort included 27 subjects randomized 2:1 to dexmedetomidine hydrochloride sublingual film or placebo film (i.e., 18 received dexmedetomidine hydrochloride sublingual film and 9 received placebo film). Three doses were initially planned (total of 81 subjects). Per protocol, different or additional doses could be tested based on ongoing safety reviews, and two additional dose levels were tested: 80 μg and 180 μg (Table 8).

Efficacy Assessments:

The efficacy of dexmedetomidine hydrochloride sublingual film on reducing acute agitation was assessed using the Positive and Negative Syndrome Scale-Excited Component (PEC) scale which was performed at screening, baseline (i.e., also referred to as pre-dose) and at 10, 20, 30, 45 min; 1, 1.5, 2, 4, 6, and 24 hours post the first dose.

Overall agitation and sedation were evaluated with the Agitation-Calmness Evaluation Scale (ACES), which was performed at baseline (pre-dose) and at 2 and 4 hours post-first dose.

The change in agitation in response to treatment was also measured by the Clinical Global Impressions—Improvement (CGI-I), performed at 1, 2 and 4 hours post the first dose.

Safety and Tolerability Assessments:

AEs, clinical laboratory tests, electrocardiogram (ECG) with rhythm strip, and vital signs were monitored for tolerability assessment. All observed and volunteered AEs were recorded. The relationship of AEs to the study drugs was graded as not related, unlikely/remotely related, possibly related, probably related or definitely related by the investigators.

Resting vital signs including systolic blood pressure (SBP), diastolic blood pressure (DBP), and heart rate, as well as ECG were measured at prior to the PK assessments. Resting vital signs (SBP, DBP and HR) were taken at screening, baseline (pre-dose) and at 30 min, 1, 2, 4 and 8 hours post-first dose. Orthostatic measurements which included (SBP, DBP, HR, respiratory rate and temperature) were taken at screening, pre-dose, 2, 4 and 24 hours post-first dose. ECGs were conducted at screening, baseline (pre-dose), 2 and 24 hours post-first dose. The application site of the SL preparation (buccal mucosa) were also inspected for any signs of local irritation.

Safety and tolerability assessments were continued until the morning of Day 3 (day of discharge) and were repeated on Day 7 (+2). AEs evaluation were conducted at screening, baseline (pre-dose), 2 hours, Day 3 and Day 7 (+2) post-the first dose. Safety Labs including chemistry, hematology, urinalysis, UDS, alcohol breathalyzer, and urine pregnancy were performed at screening, Day 3 and Day 7 (+2).

Any abnormal vital sign measurement, clinical laboratory test, physical examination finding, or ECG parameter deemed clinically significant by the investigator was repeated, including test results obtained on the final study day or upon early termination. For any test abnormality deemed clinically significant, repeat analysis was performed during the follow-up period and until the value returned to baseline (or within normal limits) or the investigator deemed the abnormality to be stable and no longer of clinical concern.

Three analysis populations were defined for the study:
Safety Population: All subjects who receive study drug
Intent to treat (ITT) Population: All subjects in the Safety Population who have a PEC Score
Per Protocol (PP) Population: All subjects in the ITT Population with no major protocol deviations Subjects were on a range of typically prescribed antipsychotics.

TABLE 8

Arms and Interventions

| Arms | Intervention |
| --- | --- |
| Placebo Comparator: Placebo Sublingual Film with no active drug; single administration | Drug: Placebo film<br>Placebo film for dexmedetomidine hydrochloride |
| Experimental: 20 μg Sublingual Film containing 20 μg dexmedetomidine; single administration with repeat dose after 1 hour | Drug: Sublingual film containing dexmedetomidine hydrochloride<br>Administration: Sublingual film containing dexmedetomidine for the treatment of agitation associated with Schizophrenia |
| Experimental: 60 μg Sublingual Film containing 60 μg dexmedetomidine; single administration | Drug: Sublingual film containing dexmedetomidine hydrochloride.<br>Administration: Sublingual film containing dexmedetomidine for the treatment of agitation associated with Schizophrenia |
| Experimental: 80 μg Sublingual Film containing 80 μg dexmedetomidine; single administration | Drug: Sublingual film containing dexmedetomidine hydrochloride.<br>Administration: Sublingual film containing dexmedetomidine for the treatment of agitation associated with Schizophrenia |
| Experimental: 120 μg 2 Sublingual Films, each containing 60 μg dexmedetomidine; single administration of 2 films | Drug: Sublingual film containing dexmedetomidine hydrochloride.<br>Administration: Sublingual film containing dexmedetomidine for the treatment of agitation associated with Schizophrenia |

TABLE 8-continued

Arms and Interventions

| Arms | Intervention |
| --- | --- |
| Experimental: 180 µg 3 Sublingual Films, each containing 60 µg dexmedetomidine; single administration of 3 films | Drug: Sublingual film containing dexmedetomidine hydrochloride. Administration: Sublingual film containing dexmedetomidine for the treatment of agitation associated with Schizophrenia |

Number of Subjects (Planned and Analyzed):

An estimated 81 subjects in Stage 1 were planned in 3 cohorts (27 per cohort), however including the 2 additional cohorts (80 µg and 180 µg dexmedetomidine hydrochloride sublingual films), a total of 135 subjects were enrolled in 5 cohorts and analyzed.

Diagnosis and Main Criteria for Eligibility:

Inclusion Criteria:
1. Male and female patients between the ages of 18 to 65 years, inclusive.
2. Patients who had met Diagnostic and Statistical Manual of Mental Disorders, Fifth Edition (DSM-5) criteria for schizophrenia, schizoaffective, or schizophreniform disorder.
3. Patients who were judged to be clinically agitated at screening and baseline (pre-dose with a total score of ≥14 on the 5 items (poor impulse control, tension, hostility, uncooperativeness, and excitement) comprising the PANSS Excited Component (PEC).
4. Patients who have a score of ≥4 on at least 1 of the 5 items on the PEC at baseline (pre-dose).
5. Patients who read, understood and provide written informed consent.
6. Patients who were in good general health prior to study participation as determined by a detailed medical history, physical examination, 12-lead ECG with rhythm strip, blood chemistry profile, hematology, urinalysis and in the opinion of the Principal Investigator.
7. Female participants, if of child-bearing potential and sexually active, and male participants, if sexually active with a partner of child-bearing potential, who agreed to use a medically acceptable and effective birth control method throughout the study and for one week following the end of the study. Medically acceptable methods of contraception that could be used by the participant and/or his/her partner include abstinence, birth control pills or patches, diaphragm with spermicide, intrauterine device (IUD), condom with foam or spermicide, vaginal spermicidal suppository, surgical sterilization and progestin implant or injection. Prohibited methods include: the rhythm method, withdrawal, condoms alone, or diaphragm alone.

Exclusion Criteria:
1. Patients with agitation caused by acute intoxication, including positive identification of alcohol by breathalyzer or drugs of abuse or non-prescription drugs (with the exception of tetrahydrocannabinol (THC)) during urine screening.
2. Patients treated within 4 hours prior to study drug administration with benzodiazepines, other hypnotics or oral or short-acting intramuscular antipsychotics.
3. Treatment with alpha-1 noradrenergic blockers (terazosin, doxazosin, tamsulosin, and alfuzosin, and prazocin) or other prohibited medications.
4. Patients with significant risk of suicide or homicide per the investigator's assessment, or any suicidal behaviour in last 6 months prior to screening.
5. Female patients who had a positive pregnancy test at screening or were breastfeeding.
6. Patients who had hydrocephalus, seizure disorder, or history of significant head trauma, stroke, transient ischemic attack, subarachnoid bleeding, brain tumor, encephalopathy, meningitis, Parkinson's disease or focal neurological findings.
7. History of syncope or other syncopal attacks, current evidence of hypovolemia, orthostatic hypotension, a screening heart rate of <55 beats per minutes (bpm) or systolic blood pressure (SBP)<110 mmHg or diastolic blood pressure (DBP)<70 mmHg.
8. Patients with laboratory or ECG abnormalities considered clinically significant by the investigator or qualified designee [Advanced heart block (second-degree or above atrioventricular block without pacemaker), diagnosis of Sick sinus syndrome] that would have clinical implications for the patient's participation in the study.
9. Patients with serious or unstable medical illnesses. These include current hepatic (moderate severe hepatic impairment), renal, gastroenterologic, respiratory, cardiovascular (including ischemic heart disease, congestive heart failure), endocrinologic, or hematologic disease.
10. Patients who had received an investigational drug within 30 days prior to the current agitation episode.
11. Patients who were unable to use the sublingual film or considered by the investigator, for any reason, to be an unsuitable candidate for receiving dexmedetomidine; e.g., patients with a history of allergic reactions to dexmedetomidine.

Test Product, Dose and Mode of Administration:

Dexmedetomidine sublingual film (formulation of Examples 1 and 2 above) was tested in a small, solid-dose film formulations with dimensions of approximately 193.6 mm$^2$ in area and 0.7 mm thick designed to completely dissolve in the SL space within 2-3 minutes. Reference therapy, Dose and Mode of Administration:

Matching placebo films to be taken sublingually as described above.

Duration of Treatment: 1 Day

Criteria for Evaluation: The primary endpoints in this study pertained to the efficacy, pharmacokinetics, safety, and tolerability of each dose level.

Efficacy: The efficacy of dexmedetomidine hydrochloride sublingual film on acute agitation was assessed using the Positive and Negative Syndrome Scale-Excited Component (PEC) scale. PEC comprised 5 items associated with agitation: poor impulse control, tension, hostility, uncooperativeness, and excitement; each scored 1 (minimum) to 7 (maximum). The PEC, the sum of these 5 subscales, thus ranging from 5 to 35.

Overall agitation and sedation were evaluated with the Agitation-Calmness Evaluation Scale (ACES), where 1 indicates marked agitation; 2—moderate agitation; 3—mild agitation; 4—normal behavior; 5—mild calmness; 6—moderate calmness; 7—marked calmness; 8—deep sleep; and 9—unarousable.

The change in agitation in response to treatment was also measured by the Clinical Global Impressions-Improvement (CGI-I). CGI-I scores range from 1 to 7:0=not assessed (missing), 1=very much improved, 2=much improved, 3=minimally improved, 4=no change, 5=minimally worse, 6=much worse, 7=very much worse.

Pharmacokinetics:

Pharmacokinetic analysis was performed using dexmedetomidine plasma concentrations after administration of dexmedetomidine hydrochloride sublingual films. A dose proportionality analysis was conducted.

Safety and tolerability: AEs, clinical laboratory tests, ECG with rhythm strip, vital signs and signs of local irritation (buccal) were monitored for safety and tolerability.

Additional Assessments:
  Demographic Data
  Medical History
  Prior and Concomitant Medication
  Physical Examination and
  Pregnancy testing Statistical Analysis:

Efficacy Analyses: The primary efficacy endpoint of the study was the absolute change from baseline in PEC score at 120 mins (2 hours). The intent to treat population (ITT) was analyzed and consisted of all patients who took any study medication and who had both baseline and at least 1 efficacy assessment after dosing. Analyses were conducted using a restricted maximum likelihood repeated measures mixed model on change from baseline values with baseline as a covariate and timepoint, and its interaction with treatment groups as repeated measures using an unstructured covariance structure. Responder comparisons were made via Fisher's exact test.

Pharmacokinetic Analyses:

Pharmacokinetic analysis was conducted using a validated install of Phoenix® WinNonlin® version 8.1. Non-compartmental analysis was also conducted on the final audited data which consisted of a total of 135 participants in 5 cohorts receiving 20, 60, 80 (1×20 µg films and 1×60 µg films), 120 (2×60 µg films) and 180 µg (3×60 µg films) of dexmedetomidine sublingual films. All areas under the concentration-time curve (AUCs) were calculated using the linear trapezoidal method. Dose proportionality was assessed using a power model for PK parameters. Mean and individual concentration (sorted by dose level) versus time plots were generated.

Safety and Tolerability Analyses:

Safety data analysis was conducted on all subjects receiving at least 1 dose of study drug. The number and percentage of subjects experiencing 1 or more AEs were summarized by treatment, relationship to study drug, and severity. AEs were coded using Medical Dictionary for Regulatory Activities (Med DRA) terminology. Listings of subjects who experience withdrawal due to an AE, serious AEs and/or death were presented. Laboratory parameters were summarized by treatment using descriptive statistics and data listings of clinically significant abnormalities. Vital signs and ECG data were summarized by changes from baseline values at each dose level using descriptive statistics.

Sample Size Determination: The sample size is based on clinical experience and judgment relative to the study design and objectives in Stage 1. A sample size of at least 18 subjects on active drug in each dosing cohort should provide adequate clinical information to meet the objectives of the study.

All efficacy, safety, and tolerability measurements were conducted at regularly scheduled intervals as described in table 9.

TABLE 9

Schedule of Events

| | | | | | | | | | | | | | | | |
|---|---|---|---|---|---|---|---|---|---|---|---|---|---|---|---|
| | | | Treatment Evaluation Day 1 | | | | | | | | | | Day 2 | | |
| | Screening | Pre-Dose[1] | Post Dose Time[1] | | | | | | | | | | Follow-Up (+1) | Day 3 Discharge | Day 7 (+2) |
| | | | Time point | | | | | | | | | | | | |
| | Pre-treatment | −1 hr to time 0 | 10 min | 20 min | 30 min | 45 min | 1 hr | 1.5 hr | 2 hr | 4 hr | 6 hr | 8 hr | 24 hr (−9/+12 hr) | | End of Study |
| Informed Consent | X | | | | | | | | | | | | | | |
| Medical History | X | | | | | | | | | | | | | | |
| Demographics | X | | | | | | | | | | | | | | |
| Weight | X | | | | | | | | | | | | X | | |
| Height | X | | | | | | | | | | | | | | |
| BMI | X | | | | | | | | | | | | | | |
| MINI | X | | | | | | | | | | | | | | |
| PANSS[10] | | X | | | | | | | | | | X | X | | |
| Physical Exam | X | | | | | | | | | | | | X | | |
| Safety Labs[5] | X | | | | | | | | | | | | | X | X |
| ECG with rhythm strip [9] | X | X | | | | | | | X | | | | X | | |
| Resting vital signs[2] | X | X | | X | | X | X | X | X | X | X | X | | | |
| Orthostatic vital signs[2] | X | X | | | | | | X | X | | X | X | | | |
| Admit to Unit | X | | | | | | | | | | | | | | |
| Training/Review of study drug administration | | X | | | | | | | | | | | | | |

TABLE 9-continued

Schedule of Events

| | | | Treatment Evaluation Day 1 | | | | | | | | | | | Day 2 | Day 3 | Day 7 |
|---|---|---|---|---|---|---|---|---|---|---|---|---|---|---|---|---|
| | Screening | Pre-Dose[1] | Post Dose Time[1] Time point | | | | | | | | | | | Follow-Up (+1) | Discharge | (+2) |
| | Pre-treatment | −1 hr to time 0 | 10 min | 20 min | 30 min | 45 min | 1 hr | 1.5 hr | 2 hr | 4 hr | 6 hr | 8 hr | | 24 hr (−9/+12 hr) | | End of Study |
| Inclusion/Exclusion criteria | X | X | | | | | | | | | | | | | | |
| Randomization | | X | | | | | | | | | | | | | | |
| Study drug administration[8] | | X | | | | | | | | | | | | | | |
| PCRS[11] | X | X | | | | | | | X | | | | | X | | |
| PEC[3] | X | X | X | X | X | X | X | X | X | X | X | | | X | | |
| ACES | | X | | | | | | | | X | X | | | | | |
| CGI-Severity[4] | X | X | | | | | | | | | | | | | | |
| CGI-Improvement[4] | | | | | | | X | | X | X | | | | | | |
| C-SSRS | X | | | | | | | | | | | | | X | | |
| Buccal (SL) assessment for local irritation[7] | | | | | X | | | | X | X | | | | X | | |
| Visual Analog Scales | | | X | | | | | | | | | | | | | |
| Likability Question | | | X | | | | | | | | | | | | | |
| PK Sampling[6] | | X | | | | | X | X | X* | X | X | X | | X | | |
| Concomitant Medications | X | X | | | | | | | | | | | | X | X | X |
| Adverse Events | X | X | X | X | X | X | X | X | X | X | X | X | | X | X | X |

Abbreviations:
ACES = Agitation-Calmness Evaluation Scale;
BMI = body mass index;
CLIA = Clinical Laboratory Improvement Amendments;
CGI-I = Clinical Global Impression-Improvement;
CGI-S = Clinical Global Impression-Severity;
C-SSRS = Columbia-Suicide Severity Rating Scale;
DBP = diastolic blood pressure;
ECG = electrocardiogram;
MINI = Mini International Neuropsychiatric Interview;
PANSS = Positive and Negative Syndrome Scale;
PCRS = Placebo Control Reminder Script;
PEC = Positive and Negative Syndrome Scale-Excited Component;
PK = pharmacokinetic;
SBP = systolic blood pressure;
SL = sublingual;
UDS = urine drug screen Notes to the Schedule of Events:

[1] Pre-dose assessments had a window of 60 minutes prior to first dose. Timing of all subsequent assessments was relative to the first dose. All post-dose assessment had a window of ±3 minutes until 2 hours and ±10 minutes until 8 hours.

[2] Resting vital signs (SBP, DBP and HR) will be taken at Screening, Pre-dose and at 30 min, 1, 2, 4 and 8 hours post first dose. Triplicate measurements were performed in case of Systolic BP < 90 mmHg, Diastolic BP < 60 mmHg or Pulse < 60 bpm. Orthostatic measurements (SBP, DBP, HR, respiratory rate and temperature) were taken at Screening, Pre-dose, 2, 4 and 24 hours post first dose. Vital signs were done prior to each PK sample.

[3] PEC was performed at Screening, Pre-dose and at 10, 20, 30, 45 min; 1, 1.5, 2, 4, 6 and 24 hours post first dose.

[4] CGI-Severity was performed at Screening and pre-dose. CGI-Improvement was performed at 1, 2 and 4 hours post first dose. The PEC (preceded by the Placebo Control Reminder Script [PCRS], when required) was done prior to any other assessments.

[5] Safety Labs included chemistry, hematology, urinalysis, UDS (local lab)(only conducted at screening), alcohol breathalyzer (only conducted at screening), and urine pregnancy (only conducted at screening). Screening/enrollment labs: local labs drawn within 7 days prior to screening may suffice with the exception of urine drug screen. If results not available on the same day, a 'desktop' or non-CLIA test might be performed; to confirmed, results from a CLIA-certified laboratory should be recorded once available.

[6] PK blood samples were collected Predose (up to 15 min prior to first dose), 1, 1.5, 2, 4, 6, 8-10 hrs (collect one sample between 8 and 10 hours) and 24 hr after first dose. A sample may not be collected if the Physician indicates in source documents that the patients is in a mental state that was not conducive to PK sample collection. Non-compliance or refusal of all or any PK draw were exclusionary nor result in ET. All PK collections had a window of ±3 minutes with the exception of the 24 hour post-dose collection which had a window of ±1 hour.

*For re-dosed subjects only: PK blood sample was collected at 2.5 hrs post first dose in addition to the other times.

[7] Buccal exam (at 30 min ± 15, and other times ± 30 min) for local irritation performed by blinded staff.

Day 2 follow up with ±1 day window.

[8] In the investigator's clinical judgement the same randomized dose might be repeated at 1 hr if there was no clinical effect (PEC change from baseline ≤ 40%) and in the absence of safety concerns.

[9] ECG for pre-dose was not repeated if screening ECG was conducted on the day of dosing. ECGs collected following treatment were performed prior to PK assessments.

[10] PANSS had administered at any time on the day of dosing prior to dosing and post-dose. Full PANSS was to be conducted in addition to stand alone PEC.

[11] PCRS was performed immediately prior to the PEC

Results Summary:
1. Data Sets Analyzed

The number of subjects in each dataset were the same for all 3 populations (ie, Safety, ITT and PP) (Table 10). Additionally, the number of subjects in each dataset were the same for the pharmacokinetic population, as all subjects provided blood samples for analysis.

TABLE 10

Summary of Datasets Analyzed

| Dataset | Placebo (N = 45) | Dexmedetomidine sublingual film | | | | | Overall (N = 135) |
| --- | --- | --- | --- | --- | --- | --- | --- |
| | | 20 μg (N = 18) | 60 μg (N = 18) | 80 μg (N = 18) | 120 μg (N = 18) | 180 μg (N = 18) | |
| Safety Population | 45 (100.0) | 18 (100.0) | 18 (100.0) | 18 (100.0) | 18 (100.0) | 18 (100.0) | 135 (100.0) |
| Intent-to-Treat Population | 45 (100.0) | 18 (100.0) | 18 (100.0) | 18 (100.0) | 18 (100.0) | 18 (100.0) | 135 (100.0) |
| Per-Protocol Population | 45 (100.0) | 18 (100.0) | 18 (100.0) | 18 (100.0) | 18 (100.0) | 18 (100.0) | 135 (100.0) |

Disposition:

A total of 135 subjects were enrolled and received study drug and comprised the Safety Population. Of the 135 subjects, all subjects completed the inpatient study drug treatment period; 127 subjects completed the end of the study period (i.e. study Day 7). Of the 8 subjects who did not complete the study, 7 subjects were lost to follow-up after discharge from the inpatient facility on study Day 3 and 1 subject withdrew from the study on study Day 3.

2. Demographics and Baseline Characteristics:

For subjects in the Safety Population (N=135), mean age was 47.6 years, the majority of subjects were male (65.9% [89/135]), and mean BMI was 30.58 kg/m2. Subjects were predominantly Black or African American (74.8% [101/135]) and not Hispanic or Latino (90.4% [122/135]). The majority of subjects in all treatment groups had a diagnosis of schizophrenia (assessed by the Mini-International Neuropsychiatric Interview [MINI-Plus] instrument). The proportion of subjects with schizophrenia ranged from 72.2% to 83.3% in the Dexmedetomidine sublingual film treatment groups. Based on MINI-Plus results, all subjects in the study met the inclusion criteria of having a diagnosis of schizophrenia, schizoaffective, or schizophreniform disorder (Table 11).

TABLE 11

Demographics and Baseline Characteristics

| Variable | Placebo (N = 45) | Dexmedetomidine sublingual film | | | | | Overall (N = 135) |
| --- | --- | --- | --- | --- | --- | --- | --- |
| | | 20 μg (N = 18) | 60 μg (N = 18) | 80 μg (N = 18) | 120 μg (N = 18) | 180 μg (N = 18) | |
| Age (years) | | | | | | | |
| Mean (SD) | 48.4 (10.88) | 50.1 (7.37) | 45.8 (10.87) | 50.2 (9.72) | 40.5 (8.40) | 49.1 (10.61) | 47.6 (10.26) |
| Median | 52.0 | 50.0 | 47.0 | 52.0 | 40.0 | 48.0 | 50.0 |
| Min-Max | 21, 63 | 29, 59 | 26, 63 | 26, 63 | 25, 54 | 26, 64 | 21, 64 |
| Gender, n % | | | | | | | |
| Male | 27 (60.0) | 9 (50.0) | 15 (83.3) | 13 (72.2) | 13 (72.2) | 12 (66.7) | 89 (65.9) |
| Female | 18 (40.0) | 9 (50.0) | 3 (16.7) | 5 (27.8) | 5 (27.8) | 6 (33.3) | 46 (34.1) |
| Race, n % | | | | | | | |
| Black or African American | 37 (82.2) | 13 (72.2) | 11 (61.1) | 12 (66.7) | 15 (83.3) | 13 (72.2) | 101 (74.8) |
| White | 7 (15.6) | 5 (57.8) | 7 (38.9) | 6 (33.3) | 2 (11.1) | 4 (22.2) | 31 (23.0) |
| Asian | 0 | 0 | 0 | 0 | 0 | 1 (5.6) | 1 (0.7) |
| Multiple | 1 (2.2) | 0 | 0 | 0 | 0 | 0 | 1 (0.7) |
| Unknown | 0 | 0 | 0 | 0 | 1 (5.6) | 0 | 1 (0.7) |
| Ethnicity, n % | | | | | | | |
| Not Hispanic or Latino | 44 (97.8) | 16 (88.9) | 15 (83.3) | 15 (83.3) | 16 (88.9) | 16 (88.9) | 122 (90.4) |
| Hispanic or Latino | 1 (2.2) | 2 (11.1) | 3 (16.7) | 3 (16.7) | 2 (11.1) | 2 (11.1) | 13 (9.6) |
| Height (cm) | | | | | | | |
| Mean (SD) | 171.15 (10.25) | 169.29 (10.63) | 174.08 (11.12) | 174.90 (10.66) | 175.33 (13.81) | 174.87 (8.95) | 172.85 (10.87) |
| Median | 169.00 | 170.30 | 174.05 | 175.90 | 175.70 | 175.25 | 173.00 |
| Min-Max | 149.9, 198.1 | 149.9, 188.0 | 150.5, 195.0 | 157.0, 198.1 | 137.0, 205.0 | 160.0, 188.4 | 137.0, 205.0 |
| Weight (kg) | | | | | | | |
| Mean (SD) | 86.86 (16.62) | 86.92 (18.83) | 94.89 (15.53) | 92.84 (19.77) | 90.54 (18.04) | 100.53 (19.10) | 91.05 (18.06) |
| Median | 84.10 | 82.50 | 97.10 | 91.95 | 90.80 | 100.45 | 91.00 |
| Min-Max | 56.8, 121.2 | 58.9, 119.6 | 64.9, 127.7 | 65.3, 133.6 | 57.2, 135.4 | 68.4, 143.2 | 56.8, 143.2 |

TABLE 11-continued

Demographics and Baseline Characteristics

| | | Dexmedetomidine sublingual film | | | | | |
|---|---|---|---|---|---|---|---|
| Variable | Placebo (N = 45) | 20 μg (N = 18) | 60 μg (N = 18) | 80 μg (N = 18) | 120 μg (N = 18) | 180 μg (N = 18) | Overall (N = 135) |
| | | | Body Mass Index (kg/m$^2$) | | | | |
| Mean (SD) | 29.74 (5.61) | 30.23 (5.37) | 31.45 (5.47) | 30.56 (7.02) | 29.81 (6.96) | 32.97 (6.47) | 30.58 (6.06) |
| Median | 29.27 | 29.58 | 31.09 | 30.03 | 29.08 | 32.56 | 29.40 |
| Min-Max | 17.9, 41.5 | 20.9, 40.3 | 22.5, 42.8 | 20.9, 44.5 | 18.3, 45.4 | 24.8, 45.4 | 17.9, 45.4 |

Abbreviations:
cm = centimeter;
kg = kilogram;
max = maximum;
min = minimum;
SD = standard deviation;
Percentages are based on the number of Safety Population subjects in each treatment arm.

3. Efficacy

Dexmedetomidine sublingual film significantly improved the severity of agitation from baseline as measured by PEC, ACES scales and CGI-I scores. Key efficacy findings at 2 hours post-dose are presented below.

(a) Primary Efficacy Endpoint (PEC reduction): a reduction in the PEC score (PANSS or the Positive and Negative Syndrome Scale, Excitatory Component) for agitation was observed with rapid calming without excessive sedation at the clinical regulatory endpoint and at earlier time-points. The primary efficacy endpoint was the mean change from baseline in PEC total score at 2 hours (120 minutes) compared to placebo. There were 5 dose cohorts (20 μg, 60 μg, 80 μg, 120 μg and 180 μg) with 18 active patients (total of 90 patients) and 9 placebo patients (total of 45 patients) in each cohort. Active patients in each of the 5 dose cohorts were compared to placebo patients from all 5 cohorts (pooled placebo group). The change from baseline in PEC at 2 hours for patients treated with dexmedetomidine sublingual film was compared with placebo using a mixed model repeated measures (MMRM) analysis, with baseline PEC, treatment group, time, the interaction between treatment groups and time, and the interaction between baseline PEC and time as covariates.

Figure 1:
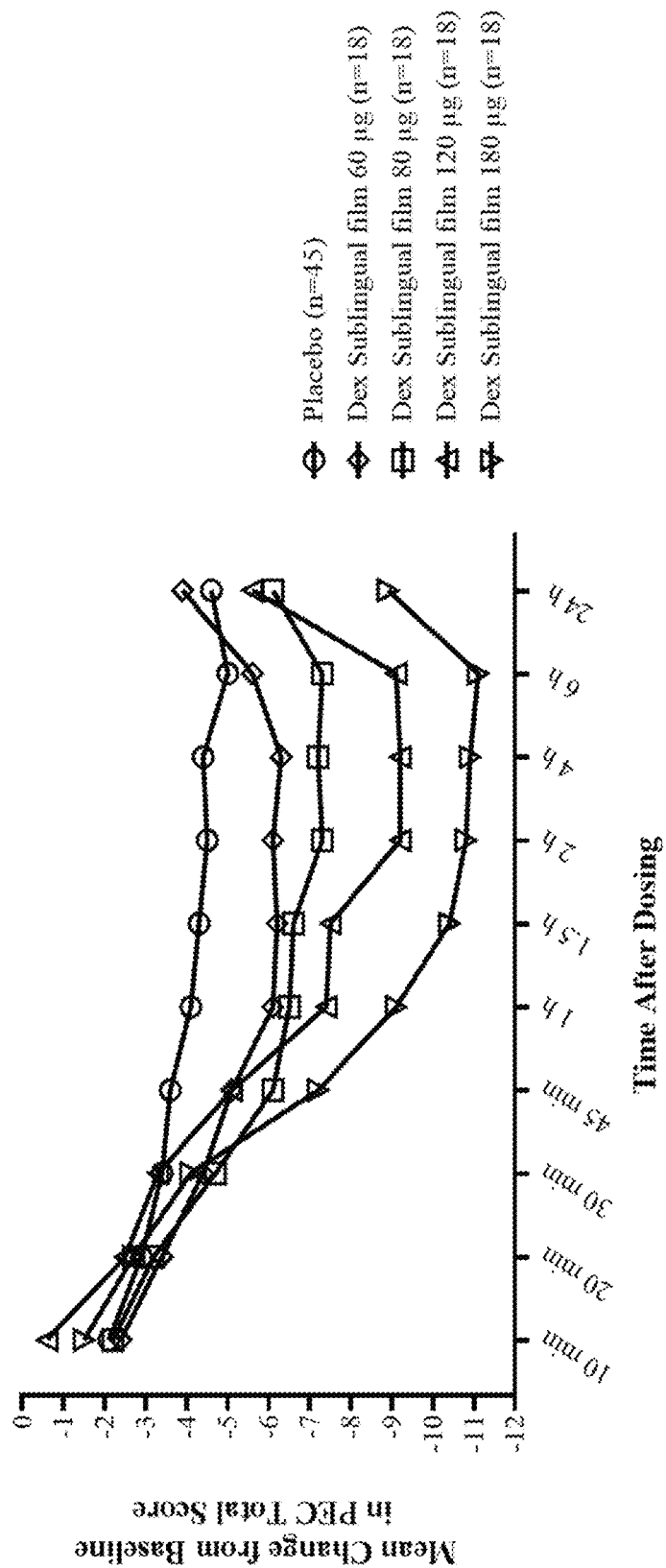
FIG. 1 depicts the mean change from baseline in PEC total score in schizophrenic patients (Intent to treat Population) treated with a sublingual film containing dexmedetomidine hydrochloride (60 µg, 80 µg, 120 µg and 180 µg) versus a placebo group. The preparation of dexmedetomidine hydrochloride sublingual film (60 µg) is exemplified in Example 1 and dexmedetomidine hydrochloride sublingual films (80 µg, 120 µg and 180 µg) are exemplified in Example 2.

The efficacy of dexmedetomidine hydrochloride sublingual film as measured by PEC reduction is dose-responsive and robust. The decrease from baseline in PEC score in the 180 μg dose group showed significant response with a −10.8 mean change from baseline (CFB) total PEC score at 2 hours post dosing compared to placebo (Table 12 and FIG. 1). Mean changes from baseline were −9.2 and −7.3 points, respectively for the 120 μg and 80 μg treatment groups, compared to placebo (−4.5 Mean change). LSM mean differences from placebo were −2.9 (P=0.0210), −4.6 (P=0.0003), and −6.3 (P<0.0001) for the 80 μg, 120 μg, and 180 μg treatment groups (table 11) Mean changes from baseline at 2 hours post dosing in the 20 μg and 60 μg groups were not significantly different than placebo. Additionally, as early onset of action is an important attribute for therapy in reducing agitation, the 180 μg group showed a statistically significant separation from placebo as early as 45 minutes post dosing (LS mean difference of −3.5 [P<0.0049]).

TABLE 12

Summary of Change from Baseline at all Timepoints in PANSS-PEC
Total Score by Treatment Group (Intent to treat population)

| | | Dexmedetomidine Sublingual film | | | | |
|---|---|---|---|---|---|---|
| Time Point Statistics | Placebo (N = 45) | 20 μg (N = 18) | 60 μg (N = 18) | 80 μg (N = 18) | 120 μg (N = 18) | 180 μg (N = 18) |
| | | Baseline, n | | | | |
| Mean (SD) | 18.1 (2.37) | 17.5 (2.33) | 17.5 (2.07) | 17.4 (1.42) | 18.3 (1.64) | 18.3 (2.95) |
| | | 10 minutes post-dose | | | | |
| Mean (SD) | 16.0 (4.33) | 16.2 (2.86) | 15.1 (3.92) | 15.2 (3.26) | 17.8 (3.19) | 16.8 (4.26) |
| Change from baseline, mean (SD) | −2.1 (3.60) | −1.3 (1.67) | −2.4 (3.45) | −2.2 (3.01) | −0.6 (2.31) | −1.5 (2.68) |
| Change from baseline, LS mean (SE) | −2.1 (0.5) | −1.4 (0.7) | −2.5 (0.7) | −2.3 (0.7) | −0.5 (0.7) | −1.4 (0.7) |
| LSM difference (SE)$^a$ | | 0.7 (0.9) | −0.4 (0.9) | −0.2 (0.9) | 1.6 (0.9) | 0.7 (0.9) |
| | | 20 minutes post-dose | | | | |
| Mean (SD) | 15.2 (4.41) | 15.1 (2.88) | 14.1 (4.64) | 14.2 (3.81) | 15.8 (3.47) | 15.6 (4.12) |
| Change from baseline, mean (SD) | −2.9 (3.60) | −2.4 (2.33) | −3.4 (4.29) | −3.2 (3.89) | −2.5 (3.03) | −2.7 (2.72) |
| Change from baseline, LS mean (SE) | −2.9 (0.5) | −2.5 (0.8) | −3.5 (0.8) | −3.3 (0.8) | −2.4 (0.8) | −2.6 (0.8) |
| LSM difference (SE)$^a$ | | 0.4 (1.0) | −0.6 (1.0) | −0.4 (1.0) | 0.5 (1.0) | 0.2 (1.0) |
| | | 30 minutes post-dose | | | | |
| Mean (SD) | 14.8 (4.94) | 14.2 (2.79) | 13.1 (4.97) | 12.7 (3.82) | 15.0 (3.74) | 14.2 (4.48) |
| Change from baseline, mean (SD) | −3.3 (4.46) | −3.3 (3.07) | −4.4 (4.67) | −4.7 (3.82) | −3.3 (3.56) | −4.1 (3.26) |
| Change from baseline, LS mean (SE) | −3.2 (0.6) | −3.4 (0.9) | −4.5 (0.9) | −4.8 (0.9) | −3.2 (0.9) | −4.0 (0.9) |
| LSM difference (SE)$^a$ | | −0.2 (1.1) | −1.2 (1.1) | −1.5 (1.1) | 0.0 (1.1) | −0.7 (1.1) |

TABLE 12-continued

Summary of Change from Baseline at all Timepoints in PANSS-PEC Total Score by Treatment Group (Intent to treat population)

| Time Point Statistics | Placebo (N = 45) | Dexmedetomidine Sublingual film | | | | |
|---|---|---|---|---|---|---|
| | | 20 µg (N = 18) | 60 µg (N = 18) | 80 µg (N = 18) | 120 µg (N = 18) | 180 µg (N = 18) |
| *45 minutes post-dose* | | | | | | |
| Mean (SD) | 14.5 (4.88) | 13.8 (3.15) | 12.4 (5.41) | 11.3 (4.80) | 13.3 (4.66) | 11.1 (5.08) |
| Change from baseline, mean (SD) | −3.6 (4.14) | −3.7 (2.83) | −5.1 (5.11) | −6.1 (5.13) | −5.1 (4.92) | −7.2 (4.73) |
| Change from baseline, LS mean (SE) | −3.6 (0.7) | −3.8 (1.0) | −5.2 (1.0) | −6.2 (1.0) | −5.0 (1.0) | −7.1 (1.0) |
| LSM difference (SE)[a] | | −0.2 (1.2) | −1.6 (1.2) | −2.6 (1.2) | −1.4 (1.2) | −3.5 (1.2) |
| *1 hour post-dose* | | | | | | |
| Mean (SD) | 14.0 (4.65) | 13.0 (4.33) | 11.4 (5.40) | 10.9 (5.03) | 10.9 (5.29) | 9.2 (4.08) |
| Change from baseline, mean (SD) | −4.1 (4.29) | −4.5 (3.67) | −6.1 (5.49) | −6.5 (5.28) | −7.4 (5.48) | −9.1 (4.58) |
| Change from baseline, LS mean (SE) | −4.0, 0.7 | −4.6 (1.1) | −6.2 (1.1) | −6.6 (1.1) | −7.3 (1.1) | −9.0 (1.1) |
| LSM difference (SE)[a] | | −0.6 (1.3) | −2.2 (1.3) | −2.6 (1.3) | −3.3 (1.3) | −5.0 (1.3) |
| P-value[b] | | 0.6647 | 0.0968 | 0.0488 | 0.0130 | 0.0002 |
| *1.5 hours post-dose* | | | | | | |
| Mean (SD) | 13.8 (4.62) | 12.1 (4.13) | 11.3 (5.26) | 10.8 (5.81) | 10.8 (5.52) | 7.8 (3.05) |
| Change from baseline, mean (SD) | −4.3 (4.43) | −5.4 (3.96) | −6.2 (5.24) | −6.6 (6.05) | −7.5 (5.57) | −10.4 (4.38) |
| Change from baseline, LS mean (SE) | −4.3 (0.7) | −5.5 (1.1) | −6.3 (1.1) | −6.7 (1.1) | −7.4 (1.1) | −10.4 (1.1) |
| LSM difference (SE)[a] | | −1.2 (1.3) | −2.0 (1.3) | −2.4 (1.3) | −3.1 (1.3) | −6.1 (1.3) |
| P-value[b] | | 0.3661 | 0.1279 | 0.0743 | 0.0199 | <0.0001 |
| *2 hours post-dose* | | | | | | |
| Mean (SD) | 13.6 (4.56) | 11.0 (3.87) | 11.4 (5.07) | 10.1 (5.45) | 9.1 (4.20) | 7.4 (2.68) |
| Change from baseline, mean (SD) | 4.5 (4.58) | −6.5 (3.91) | −6.1 (5.09) | −7.3 (5.70) | −9.2 (4.47) | −10.8 (3.15) |
| Change from baseline, LS mean (SE) | −4.5 (0.7) | −6.6 (1.0) | −6.1 (1.0) | −7.4 (1.0) | −9.1 (1.0) | −10.8 (1.0) |
| LSM difference (SE)[a] | | −2.1 (1.2) | −1.7 (1.2) | −2.9 (1.2) | −4.6 (1.2) | −6.3 (1.2) |
| P-value[b] | | 0.0933 | 0.1850 | 0.0210 | 0.0003 | <0.0001 |
| *4 hours post-dose* | | | | | | |
| Mean (SD) | 13.7 (4.13) | 9.4 (3.90) | 11.2 (5.11) | 10.2 (5.12) | 9.1 (3.69) | 7.3 (2.54) |
| Change from baseline, mean (SD) | −4.4 (4.44) | −8.1 (4.32) | −6.3 (5.22) | −7.2 (5.48) | −9.2 (4.02) | −10.9 (3.61) |
| Change from baseline, LS mean (SE) | −4.3 (0.7) | −8.1 (1.0) | −6.4 (1.0) | −7.3 (1.0) | −9.1 (1.0) | −10.9 (1.0) |
| LSM difference (SE)[a] | | −3.8 (1.2) | −2.1 (1.2) | −2.9 (1.2) | −4.8 (1.2) | −6.5 (1.2) |
| P-value[b] | | 0.0022 | 0.0895 | 0.0172 | 0.0001 | <0.0001 |
| *6 hours post-dose* | | | | | | |
| Mean (SD) | 13.1 (4.22) | 10.0 (4.00) | 11.9 (5.21) | 10.1 (4.90) | 9.3 (4.23) | 7.2 (2.51) |
| Change from baseline, mean (SD) | −5.0 (4.79) | −7.5 (4.03) | −5.6 (5.19) | −7.3 (5.30) | −9.1 (5.00) | −11.1 (3.47) |
| Change from baseline, LS mean (SE) | −4.9 (0.7) | −7.6 (1.1) | −5.6 (1.1) | −7.4 (1.1) | −9.0 (1.1) | −11.0 (1.1) |
| LSM difference (SE)[a] | | −2.7 (1.3) | −0.7 (1.3) | −2.5 (1.3) | −4.0 (1.3) | −6.0 (1.3) |
| P-value[b] | | 0.0375 | 0.5752 | 0.0490 | 0.0018 | <0.0001 |
| *24 hours post-dose* | | | | | | |
| Mean (SD) | 13.5 (3.91) | 11.4 (3.58) | 13.6 (4.10) | 11.3 (4.18) | 12.8 (3.59) | 9.4 (4.82) |
| Change from baseline, mean (SD) | −4.6 (4.03) | −6.1 (4.23) | −3.9 (4.34) | −6.1 (4.50) | −5.6 (3.29) | −8.9 (3.53) |
| Change from baseline, LS mean (SE) | −4.6 (0.6) | −6.2 (0.9) | −4.0 (0.9) | −6.2 (0.9) | −5.5 (0.9) | −8.8 (0.9) |
| LSM difference (SE)[a] | | −1.6 (1.1) | 0.6 (1.1) | −1.6 (1.1) | −0.9 (1.1) | −4.2 (1.1) |
| P-value[b] | | 0.1464 | 0.5697 | 0.1407 | 0.4310 | 0.0002 |

Figure 2:
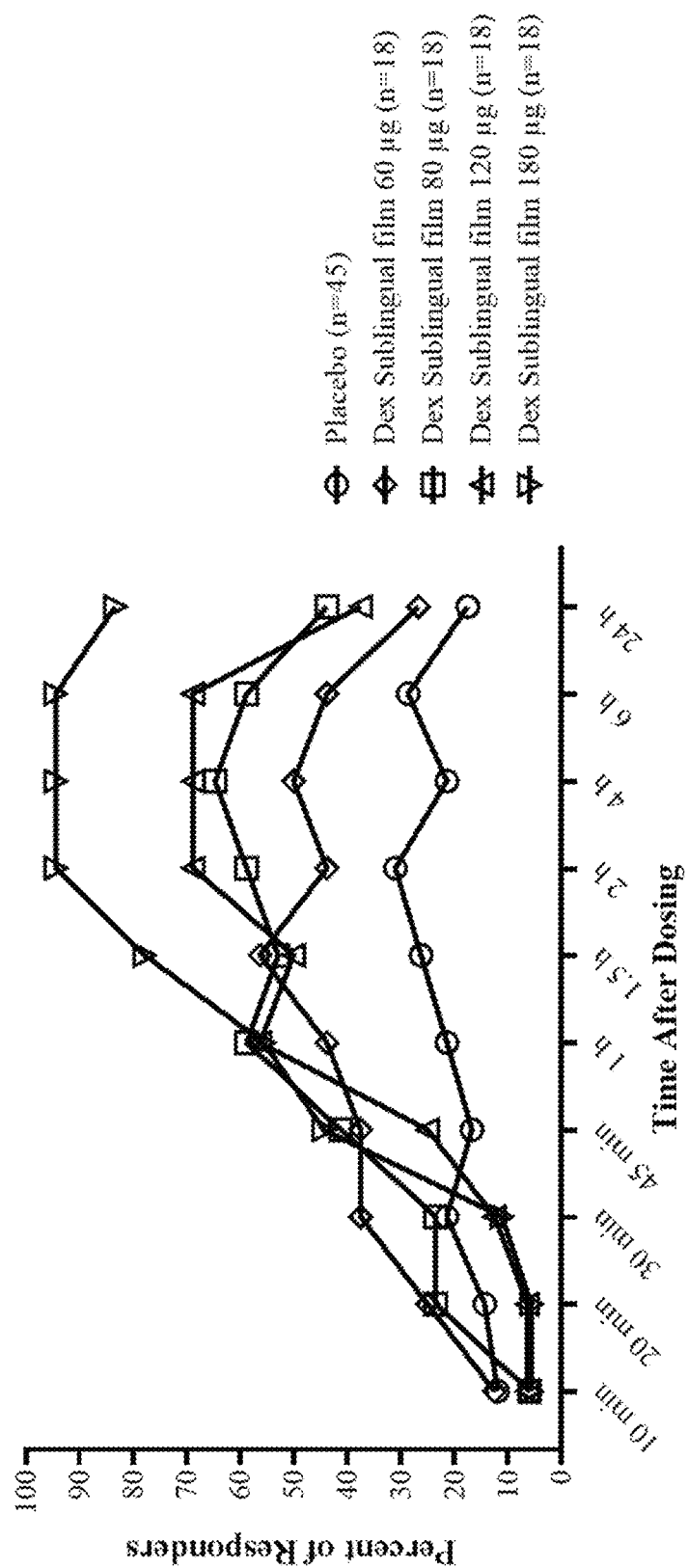
FIG. 2 depicts the percent of responders in PEC total score over time in schizophrenic patients (Intent to treat Population) treated with a sublingual film containing dexmedetomidine hydrochloride (60 µg, 80 µg, 120 µg and 180 µg) versus a placebo group. The preparation of dexmedetomidine hydrochloride sublingual film (60 µg) is exemplified in Example 1 and dexmedetomidine hydrochloride sublingual films (80 µg, 120 µg and 180 µg) are exemplified in Example 2.

Note:
subjects counts for all timepoints were 18 subjects for each dexmedetomidine sublingual film treatment group and 45 subjects for the placebo group
[a]Treatment effect between dexmedetomidine sublingual film and placebo
[b]p value comparing dexmedetomidine sublingual film and placebo PEC Responder Analyses: The proportion of treatment responders, defined as those with a 40% decrease from baseline in PEC total score at 2 hours post dose, was greatest in the 180 µg group (94.4% [P<0.0001] for 180 µg, 68.8% [P=0.0158] for 120 µg, 58.8% for 80 µg [P=0.0759]) and significantly greater than placebo (31% responders) (Table 13 and FIG. 2). Response rates with 180 µg were significantly higher than placebo starting at 45 minutes post dose (44.4% versus 16.7%, respectively), continued to increase after 2 hours (to 94.4% at 4 and 6 hours) and sustained until at least 24 hours post-dose (83.3% versus 17.5%, respectively). Finally, the durability of calming effects of the 180 µg dose was remarkably prolonged with a sustained statistically significant reduction in PEC evident after 24 hrs. After a single dose in the 180 µg group, 83.3% of subjects maintained response after 24 hours with a mean PEC decrease of −8.9 (Mean CFB) compared to 37.5% in the 120 µg group (−5.6 Mean CFB) and 43.8% in the 80 µg group (−6.1 Mean CFB. Response rates over time for the 80 µg and 120 µg groups were high and similar between the 2 µgroups (Table 13 and FIG. 2).

TABLE 13

Percent of Responders in the PEC Score (Intent to treat Population)

| Time Point Statistics | Placebo (N = 45) | Dexmedetomidine Sublingual Film | | | | |
|---|---|---|---|---|---|---|
| | | 20 µg (N = 18) | 60 µg (N = 18) | 80 µg (N = 18) | 120 µg (N = 18) | 180 µg (N = 18) |
| 10 minutes post-dose | | | | | | |
| Percent responders | 11.9% | 0% | 12.5% | 5.9% | 6.3% | 5.6% |
| 20 minutes post-dose | | | | | | |
| Percent responders | 14.3% | 0% | 25.0% | 23.5% | 6.3% | 5.6% |
| 30 minutes post-dose | | | | | | |
| Percent responders | 21.4% | 11.8% | 37.5% | 23.5% | 12.5% | 11.1% |
| 45 minutes post-dose | | | | | | |
| Percent responders | 16.7% | 17.6% | 37.5% | 41.2% | 25.0% | 44.4% |
| 1 hour post-dose | | | | | | |
| Percent responders | 21.4% | 29.4% | 43.8% | 58.8% | 56.3% | 55.6% |
| P-value[a] | | 0.5178 | 0.1091 | 0.0120 | 0.0236 | 0.0150 |
| 1.5 hours post-dose | | | | | | |
| Percent responders | 26.2% | 41.2% | 56.3% | 52.9% | 50.0% | 77.8% |
| P-value[a] | | 0.3505 | 0.0612 | 0.0699 | 0.1190 | 0.0004 |
| 2 hours post-dose | | | | | | |
| Percent responders | 31.0% | 58.8% | 43.8% | 58.8% | 68.8% | 94.4% |
| P-value[a] | | 0.0759 | 0.3735 | 0.0759 | 0.0158 | <0.0001 |
| 4 hours post-dose | | | | | | |
| Percent responders | 21.4% | 64.7% | 50.0% | 64.7% | 68.8% | 94.4% |
| P-value[a] | | 0.0024 | 0.0519 | 0.0024 | 0.0015 | <0.0001 |
| 6 hours post-dose | | | | | | |
| Percent responders | 28.6% | 64.7% | 43.8% | 58.8% | 68.8% | 94.4% |
| P-value[a] | | 0.0173 | 0.3510 | 0.0399 | 0.0075 | <0.0001 |
| 24 hours post-dose | | | | | | |
| Percent responders | 17.5% | 43.8% | 26.7% | 43.8% | 37.5% | 83.3% |
| P-value[a] | | 0.0838 | 0.4676 | 0.0838 | 0.1610 | <0.0001 |

A responder is defined as a subject who achieved a ≥40% decrease from baseline in PEC score after dosing.
The number of subjects with non-missing data in the dexmedetomidine sublingual film treatment groups were: 18 (180 µg), 17 (20 µg and 80 µg), and 16 (60 µg and 120 µg); 42 subjects in the placebo group had non-missing data.
[a] P-value based on a comparison of dexmedetomidine sublingual film versus placebo via a Fisher's exact test PANSS-EC (5 Items Subscale Scores): The PEC 5 subscale scores associated with agitation (ie, poor impulse control, tension, hostility, uncooperativeness, and excitement) were summarized in table 14, at 2 hours post dosing, significant improvements (ie, decreases) from baseline in all 5 PEC subscale scores were observed in the 80 µg, 120 µg and 180 µg groups compared to placebo; with the exception of "excitement" in the 80 µg group.

TABLE 14

Change from Baseline in PANSS-PEC subscale scores at 2 hours post dosing in schizophrenia patients (Intent to treat Population)

| PANNS-EC Subscale Statistics | Placebo (N = 45) | Dexmedetomidine Sublingual Film | | | | |
|---|---|---|---|---|---|---|
| | | 20 µg (N = 18) | 60 µg (N = 18) | 80 µg (N = 18) | 120 µg (N = 18) | 180 µg (N = 18) |
| Poor Impulse Control | | | | | | |
| Baseline, Mean (SD) | 3.5 (0.63) | 3.5 (0.62) | 3.5 (0.62) | 3.3 (0.49) | 3.4 (0.50) | 3.4 (0.70) |
| 2 hours post-dose | | | | | | |
| Mean (SD) | 2.7 (0.87) | 2.1 (1.13) | 2.2 (1.11) | 1.9 (1.06) | 1.7 (0.75) | 1.4 (0.70) |
| Change from baseline, mean (SD) | −0.8 (0.89) | −1.4 (1.14) | −1.3 (1.13) | −1.4 (1.04) | −1.7 (1.03) | −2.0 (0.91) |
| Change from baseline, LS mean (SE) | −0.8 (0.1) | −1.4 (0.2) | −1.3 (0.2) | −1.4 (0.2) | −1.7 (0.2) | −2.0 (0.2) |
| LSM difference (SE)[a] | | −0.6 (0.3) | −0.5 (0.3) | −0.6 (0.3) | −0.9 (0.3) | −1.2 (0.3) |
| p value | | 0.0307 | 0.0810 | 0.0178 | 0.0009 | <0.0001 |

TABLE 14-continued

Change from Baseline in PANSS-PEC subscale scores at 2 hours post dosing in schizophrenia patients (Intent to treat Population)

| PANNS-EC Subscale Statistics | Placebo (N = 45) | Dexmedetomidine Sublingual Film | | | | |
|---|---|---|---|---|---|---|
| | | 20 µg (N = 18) | 60 µg (N = 18) | 80 µg (N = 18) | 120 µg (N = 18) | 180 µg (N = 18) |
| Tension | | | | | | |
| Baseline, Mean (SD) | 4.0 (0.64) | 3.8 (0.65) | 3.6 (0.92) | 3.8 (0.71) | 4.1 (0.47) | 4.1 (0.87) |
| 2 hours post-dose | | | | | | |
| Mean (SD) | 3.0 (1.13) | 2.4 (1.15) | 2.3 (1.32) | 2.1 (1.23) | 1.9 (1.06) | 1.5 (0.71) |
| Change from baseline, mean (SD) | −1.0 (1.24) | −1.3 (1.14) | −1.3 (1.19) | −1.7 (1.45) | −2.2 (0.92) | −2.6 (1.04) |
| Change from baseline, LS mean (SE) | −0.9 (0.2) | −0.5 (0.3) | −0.5 (0.3) | −0.8 (0.3) | −1.2 (0.3) | −1.6 (0.3) |
| LSM difference (SE)a | | −0.5 (0.3) | −0.5 (0.3) | −0.8 (0.3) | −1.2 (0.3) | −1.6 (0.3) |
| p value | | 0.1397 | 0.0947 | 0.0085 | 0.0002 | <0.0001 |
| Hostility | | | | | | |
| Baseline, Mean (SD) | 3.5 (0.73) | 3.5 (0.62) | 3.6 (0.70) | 3.3 (0.77) | 3.6 (0.62) | 3.6 (0.61) |
| 2 hours post-dose | | | | | | |
| Mean (SD) | 2.6 (1.12) | 2.2 (0.71) | 2.4 (1.04) | 1.9 (1.11) | 1.8 (0.79) | 1.4 (0.51) |
| Change from baseline, mean (SD) | −0.9 (1.11) | −1.3 (0.84) | −1.2 (1.15) | −1.4 (1.14) | −1.7 (1.18) | −2.2 (0.71) |
| Change from baseline, LS mean (SE) | −0.9 (0.1) | −1.3 (0.2) | −1.1 (0.2) | −1.5 (0.2) | −1.7 (0.2) | −2.1 (0.2) |
| LSM difference (SE)a | | −0.4 (0.3) | −0.2 (0.3) | −0.6 (0.3) | −0.8 (0.3) | −1.2 (0.3) |
| p value | | 0.0973 | 0.3609 | 0.0272 | 0.0029 | <0.0001 |
| Uncooperativeness | | | | | | |
| Baseline, Mean (SD) | 3.3 (0.72) | 3.2 (0.81) | 3.3 (0.83) | 3.4 (0.92) | 3.4 (0.70) | 3.2 (0.81) |
| 2 hours post-dose | | | | | | |
| Mean (SD) | 2.5 (0.97) | 2.0 (0.84) | 2.2 (0.94) | 2.0 (1.24) | 1.7 (0.91) | 1.4 (0.62) |
| Change from baseline, mean (SD) | −0.8 (0.98) | −1.2 (1.06) | −1.1 (1.11) | −1.4 (1.33) | −1.8 (1.06) | −1.8 (0.81) |
| Change from baseline, LS mean (SE) | −0.8 (0.1) | −1.3 (0.2) | −1.1 (0.2) | −1.4 (0.2) | −1.7 (0.2) | −1.8 (0.2) |
| LSM difference (SE)a | | −0.5 (0.3) | −0.3 (0.3) | −0.6 (0.3) | −1.0 (0.3) | −1.0 (0.3) |
| p value | | 0.0669 | 0.2607 | 0.0268 | 0.0004 | 0.0001 |
| Excitement | | | | | | |
| Baseline, Mean (SD) | 3.8 (0.64) | 3.5 (0.62) | 3.6 (0.70) | 3.5 (0.62) | 3.8 (0.71) | 3.9 (0.64) |
| 2 hours post-dose | | | | | | |
| Mean (SD) | 2.7 (1.07) | 2.3 (0.83) | 2.3 (1.24) | 2.1 (1.37) | 1.9 (1.06) | 1.6 (0.70) |
| Change from baseline, mean (SD) | −1.1 (1.11) | −1.2 (0.88) | −1.2 (1.22) | −1.4 (1.46) | −1.9 (1.02) | −2.3 (0.77) |
| Change from baseline, LS mean (SE) | −1.1 (0.2) | −1.3 (0.2) | −1.3 (0.2) | −1.5 (0.2) | −1.8 (0.2) | −2.2 (0.2) |
| LSM difference (SE)a | | −0.2 (0.3) | −0.2 (0.3) | −0.4 (0.3) | −0.8 (0.3) | −1.2 (0.3) |
| p value | | 0.3967 | 0.4394 | 0.1577 | 0.0081 | <0.0001 |

Secondary Efficacy Endpoints:

Changes in secondary efficacy measures (i.e., ACES and CGI-J scores) at 2 hours post-dose were consistent with the results for PEC total scores and were indicative of improvement in symptoms of agitation after treatment with dexmedetomidine sublingual film.

Figure 3:
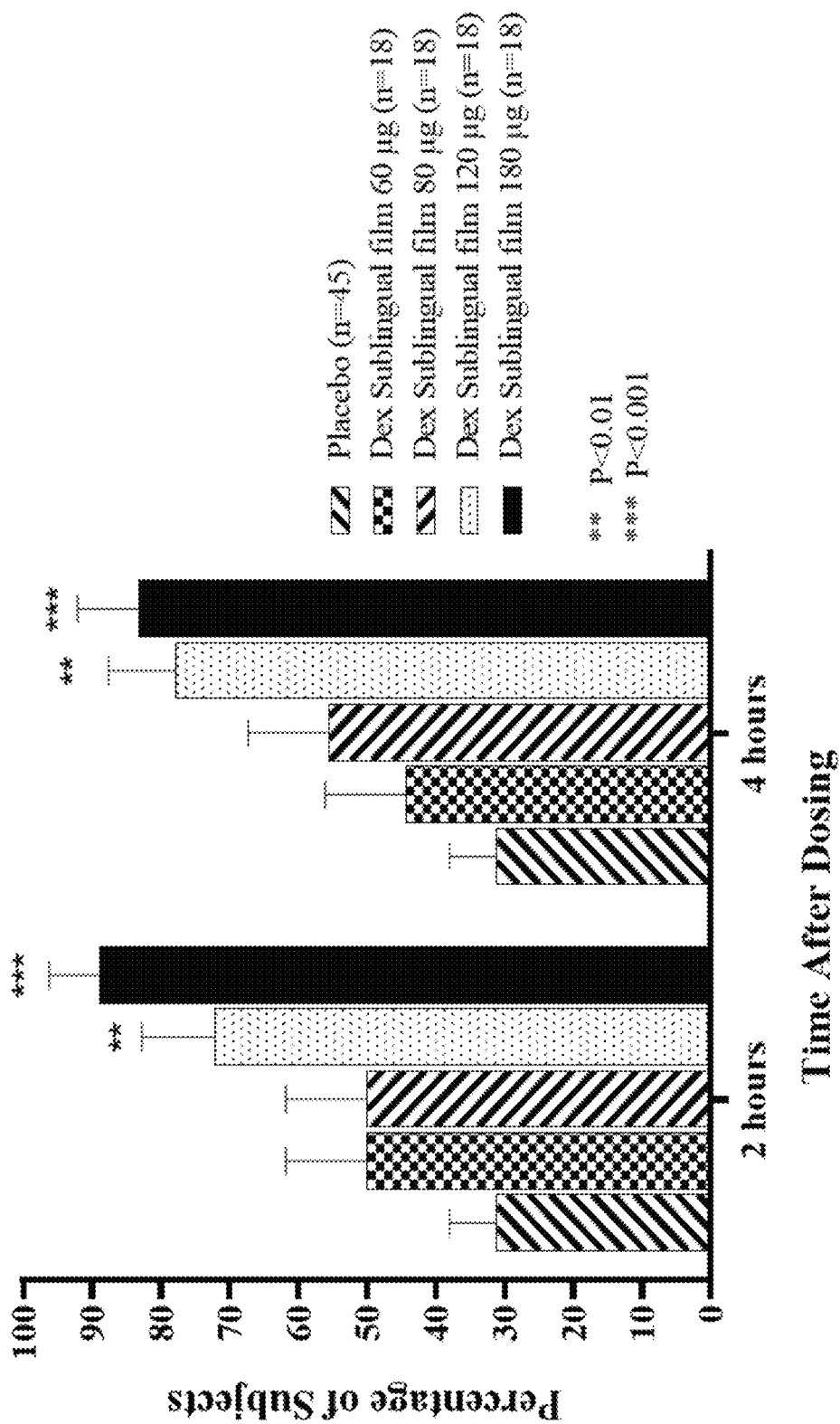
FIG. 3 depicts resolution of agitation as measured by achieving an ACES Score of at least 4 over time in schizophrenic patients (Intent to treat Population) treated with a sublingual film containing dexmedetomidine hydrochloride (60 µg, 80 µg, 120 µg and 180 µg) versus a placebo group. The error bars in the figure represent "standard error." The preparation of dexmedetomidine hydrochloride sublingual films (60 µg) is exemplified in Example 1 and dexmedetomidine hydrochloride sublingual films (80 µg, 120 µg and 180 µg) are exemplified in Example 2.

ACES scores: A secondary objective for this study was to evaluate the duration of calming effect of dexmedetomidine sublingual thin film drug utilizing the Agitation-Calmness Evaluation Scale (ACES) collected at pre-dose, 2 hr, and 4 hr after first dose. The ACES assessment was consistent with the analysis of the primary endpoint, and met statistically significance for calming as measured by ACES at two hours compared to placebo in the three highest doses evaluated (80 µg; p=0.0150), (120 µg; p=0.0003) and (180 µg; p<0.0001). At 2 hours after dosing, subjects in the 80 µg, 120 µg, and 180 µg treatment groups showed significantly greater improvements relative to placebo in ACES scores (+2.3 [P=0.0150], +3.1 [P=0.0003], and +4.2 [P=<0.0001], respectively, compared to placebo of +1.2). The improvements at 4 hours post-dose were similar (+2.1 [P=0.0252], +3.2 [P=<0.0001], and +4.1 [P=<0.0001], placebo was +1.1). (Table 15 and FIG. 3). In terms of calming effect (as measured by ACES scores), mean scores in 120 µg and 180 µg groups increased from a baseline of approximately 2 "moderate agitation" to 5.1 "mild calmness" and 6.2 "moderate calmness," respectively at 2 hours post-dose, compared with a score of 3.4 "mild agitation" in the placebo group. The improvements in calmness in the groups were statistically significant with P values of 0.0003 and <0.0001, respectively, compared with placebo (Table 15).

Time to resolution of agitation: The percentage of subjects achieving an ACES score of at least 4 (normal)) at 2 and 4 hours post dosing is displayed in FIG. 3. At 2 and 4 hours after dosing, the percentage of subjects who achieved a ACES score of at least 4, which indicated resolution of agitation, was significantly greater in the 120 µg group (72.2% [P=0.0045] and 77.8% [P=0.0016], respectively) and the 180 µg group (88.9% [P<0.0001] and 83.3% [P=0.0002], respectively) compared with the placebo group (31.1% at both 2 and 4 hours post-dose). In terms of sedation (as measured by ACES scores) the results indicated that a total of 9 subjects in the treatment groups had scores of 8 "deep sleep" at 2 hours and/or 4 hours post-dose, however, no subject in any of the treatment groups had a score of 9 "unarousable." (Table 16). Calming effect was durable lasting at least 6 hours as evidenced by separation from placebo for 80 µg, 120 µg and 180 µg dose groups.

TABLE 15

Change from Baseline in ACES Score at 2 and 4 hours post dosing (Intent to treat population)

|  | Placebo (N = 45) | Dexmedetomidine Sublingual Film | | | | |
|---|---|---|---|---|---|---|
| Time Post dose | | 20 μg (N = 18) | 60 μg (N = 18) | 80 μg (N = 18) | 120 μg (N = 18) | 180 μg (N = 18) |
| Baseline, n | | | | | | |
| Mean (SD) | 2.1 (0.55) | 2.3 (0.49) | 2.2 (0.55) | 2.2 (0.55) | 2.0 (0.34) | 1.9 (0.54) |
| 2 hours post-dose | | | | | | |
| Mean (SD) | 3.4 (1.55) | 3.8 (1.11) | 4.2 (1.70) | 4.6 (2.25) | 5.1 (2.05) | 6.2 (1.58) |
| Change from baseline, mean (SD)[a] | 1.2 (1.46) | 1.4 (1.29) | 2.0 (1.71) | 2.3 (2.43) | 3.1 (2.03) | 4.2 (1.83) |
| Change from baseline, LS mean (SE)[b] | 1.2 (0.3) | 1.6 (0.4) | 2.1 (0.4) | 2.4 (0.4) | 3.0 (0.4) | 4.1 (0.4) |
| LSM difference (SE)[c] | | 0.4 (0.5) | 0.8 (0.5) | 1.2 (0.5) | 1.8 (0.5) | 2.9 (0.5) |
| P-value[d] | | 0.4371 | 0.0795 | 0.0150 | 0.0003 | <0.0001 |
| 4 hours post-dose | | | | | | |
| Mean (SD) | 3.2 (1.42) | 4.4 (1.54) | 3.9 (1.76) | 4.3 (2.22) | 5.2 (1.72) | 6.0 (1.75) |
| Change from baseline, mean (SD)[a] | 1.1 (1.40) | 2.1 (1.53) | 1.7 (1.81) | 2.1 (2.19) | 3.2 (1.69) | 4.1 (2.04) |
| Change from baseline, LS mean (SE)[b] | 1.1 (0.3) | 2.3 (0.4) | 1.8 (0.4) | 2.2 (0.4) | 3.1 (0.4) | 3.9 (0.4) |
| LSM difference (SE)[c] | | 1.2 (0.5) | 0.7 (0.5) | 1.1 (0.5) | 2.0 (0.5) | 2.8 (0.5) |
| P-value[d] | | 0.0164 | 0.1524 | 0.0252 | <0.0001 | <0.0001 |

[a] Change from baseline (pre-dose) ACES score, with positive values in favor of improvement.
[b] Least square mean and standard error per treatment group.
[c] Treatment Effect: Least square mean difference, standard error, and 95% confidence intervals between Dexmedetomidine sublingual film and Placebo.
[d] p value comparing Dexmedetomidine sublingual film and Placebo

TABLE 16

Subjects Rates with an ACES Scores of 8 (Deep Sleep) or 9 (Unarousable Sleep) for all dose groups

| ACES Score | Dose Group | Number of Subjects at Baseline | Number of Subjects at 2 hr | Number of Subjects at 4 hr |
|---|---|---|---|---|
| Deep Sleep ACES Score = 8 | Placebo | 0 | 0 | 0 |
| | 20 μg | 0 | 0 | 1 |
| | 60 μg | 0 | 0 | 0 |
| | 80 μg | 0 | 1 | 1 |
| | 120 μg | 0 | 2 | 0 |
| | 180 μg | 0 | 2 | 3 |
| Unarousable Sleep ACES Score = 9 | Placebo | 0 | 0 | 0 |
| | 20 μg | 0 | 0 | 0 |
| | 60 μg | 0 | 0 | 0 |
| | 80 μg | 0 | 0 | 0 |
| | 120 μg | 0 | 0 | 0 |
| | 180 μg | 0 | 0 | 0 |

CGI-I scores: Mean baseline CGI-S scores were comparable across all treatment groups (range: 3.9 to 4.3). The CGI-S scores indicated that the subjects were clinically agitated (ie, moderately ill) prior to dosing (Table 17).

Figure 4:
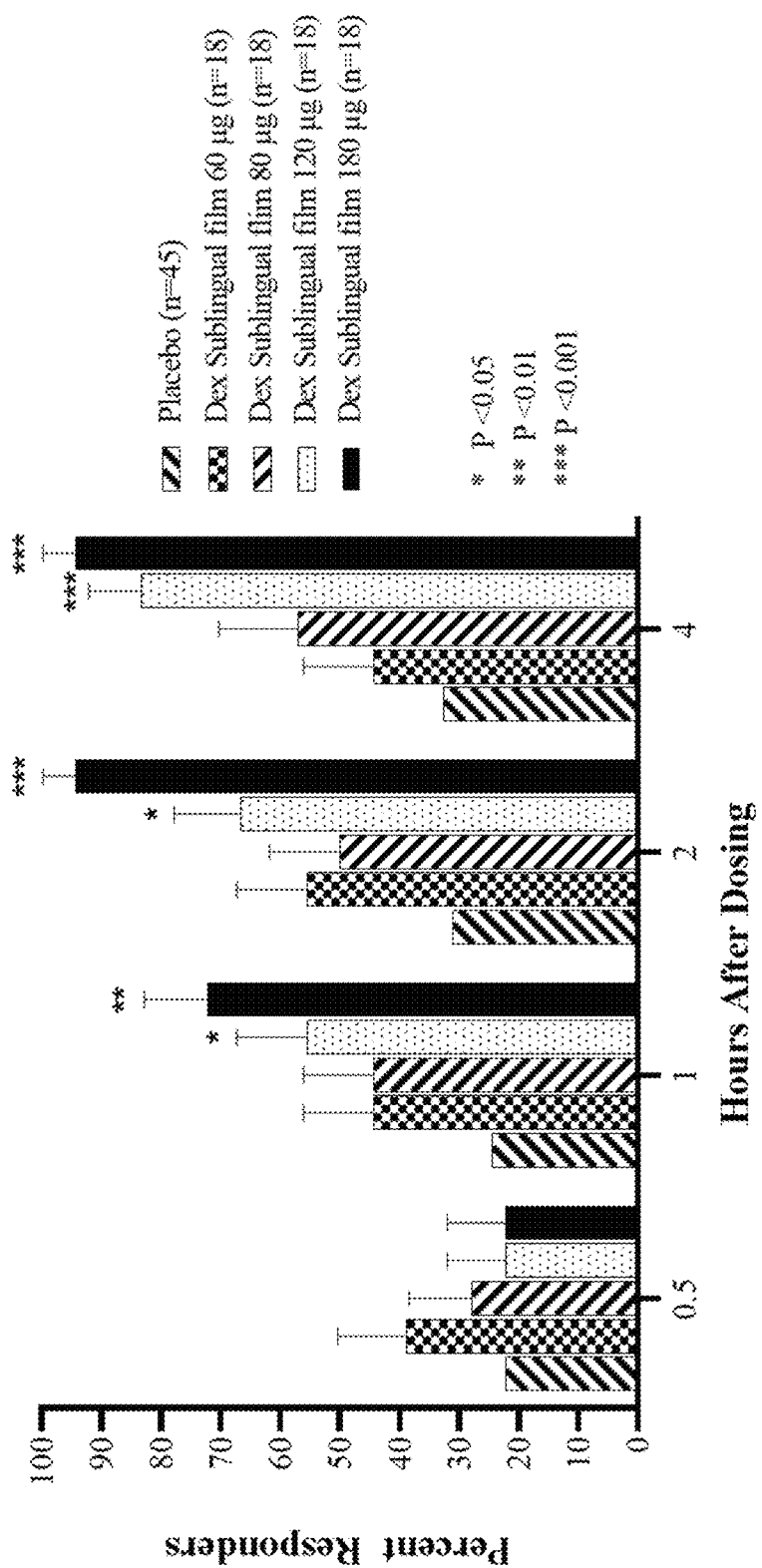
FIG. 4 depicts percent of responders in CGI-I Score over time in schizophrenic patients (Intent to treat Population)

Significant improvements in agitation (ie, lower CGI-I scores) from baseline were observed at 1 hour after dosing in the dexmedetomidine sublingual film 120 μg and 180 μg groups. Mean (SD) scores were 2.3 (1.13) and 2.1 (0.87), respectively, compared with 3.0 (0.98) in the placebo group (Table 18). LSM differences from placebo were −0.7 (P=0.0167) and −0.9 (P=0.0019) in the 120 μg and 180 μg groups, respectively. Significant improvements in agitation (i.e. lower mean CGI-I scores) from baseline were observed at 2 hours post-dose in the 120 μg group (1.9 [P=0.0007]) and in the 180 μg group (1.4 [P<0.0001]), compared with a mean score of 3 in the placebo group (Table 18). LSM differences from placebo were −1.1 (P=0.0007) and −1.6 (P3.0001). Significant improvements were also observed at 4 hours post-dose in the dexmedetomidine sublingual film 120 μg and 180 bggroups The percentage of subjects achieving CGI-I scores of 1 or 2 ('very much improved' or 'much improved') at 2 hours post-dose was significantly higher in the 120 μg group (66.78 [P=0.0125]) and in the 180 μg dose group (94.4% [P<0.0001]), compared with placebo (31.0%). Significant improvements were also observed at 1 hour and at 4 hours after dosing for both treatment groups (Table 19 and FIG. 4).

TABLE 17

CGI-S Mean Scores at Baseline (Intent to treat Population)

| Time Point Statistics | Placebo (N = 45) | Dexmedetomidine Sublingual Film | | | | |
|---|---|---|---|---|---|---|
| | | 20 μg (N = 18) | 60 μg (N = 18) | 80 μg (N = 18) | 120 μg (N = 18) | 180 μg (N = 18) |
| Number of subjects | 45 | 18 | 18 | 18 | 18 | 18 |
| Baseline (pre-dose) | | | | | | |
| Mean (SD) | 4.2 (0.44) | 3.9 (0.47) | 4.1 (0.68) | 4.1 (0.32) | 4.3 (0.57) | 4.3 (0.46) |
| Minimum-Maximum | 3.0-5.0 | 3.0-5.0 | 3.0-5.0 | 4.0-5.0 | 3.0-5.0 | 4.0-5.0 |

TABLE 18

Summary of Change from Baseline for CGI-I Score (Intent to treat Population)

|  | | Dexmedetomidine Sublingual Film | | | | |
|---|---|---|---|---|---|---|
| Time Point Statistics | Placebo (N = 45) | 20 μg (N = 18) | 60 μg (N = 18) | 80 μg (N = 18) | 120 μg (N = 18) | 180 μg (N = 18) |
| Number of subjects | 45 | 18 | 18 | 18 | 18 | 18 |
| | | | 30 minutes post-dose | | | |
| Mean (SD) | 3.1 (1.04) | 3.1 (0.76) | 2.8 (1.15) | 3.2 (1.15) | 3.1 (0.76) | 3.1 (0.76) |
| LS mean (SE)a | 3.2 (0.1) | 3.1 (0.2) | 2.8 (0.2) | 3.2 (0.2) | 3.1 (0.2) | 3.1 (0.2) |
| LSM difference (SE)[b] | | −0.1 (0.3) | −0.4 (0.3) | −0.0 (0.3) | −0.1 (0.3) | −0.1 (0.3) |
| P-value[c] | | 0.7431 | 0.1778 | 0.9022 | 0.7431 | 0.7431 |
| | | | 1 hour post-dose | | | |
| Mean (SD) | 3.0 (0.98) | 2.9 (0.83) | 2.4 (1.20) | 2.8 (1.42) | 2.3 (1.13) | 2.1 (0.87) |
| LS mean (SE)[a] | 3.0 (0.2) | 2.9 (0.3) | 2.4 (0.3) | 2.8 (0.3) | 2.3 (0.3) | 2.1 (0.3) |
| LSM difference (SE)[b] | | −0.1 (0.3) | −0.6 (0.3) | −0.2 (0.3) | −0.7 (0.3) | −0.9 (0.3) |
| P-value[c] | | 0.7098 | 0.0645 | 0.5769 | 0.0167 | 0.0019 |
| | | | 2 hours post-dose | | | |
| Mean (SD) | 3.0 (1.09) | 2.4 (0.98) | 2.3 (1.13) | 2.6 (1.54) | 1.9 (1.00) | 1.4 (0.61) |
| LS mean (SE)[a] | 3.0 (0.2) | 2.4 (0.3) | 2.3 (0.3) | 2.6 (0.3) | 1.9 (0.3) | 1.4 (0.3) |
| LSM difference (SE)[b] | | −0.6 (0.3) | −0.7 (0.3) | −0.4 (0.3) | −1.1 (0.3) | −1.6 (0.3) |
| P-value[c] | | 0.0701 | 0.0190 | 0.2034 | 0.0007 | <0.0001 |
| | | | 4 hours post-dose | | | |
| Mean (SD) | 3.0 (1.08) | 2.4 (0.92) | 2.8 (1.22) | 2.6 (1.60) | 1.8 (0.73) | 1.4 (0.62) |
| LS mean (SE)[a] | 3.0 (0.2) | 2.4 (0.3) | 2.8 (0.3) | 2.7 (0.3) | 1.8 (0.3) | 1.4 (0.3) |
| LSM difference (SE)[b] | | −0.6 (0.3) | −0.2 (0.3) | −0.3 (0.3) | −1.2 (0.3) | −1.5 (0.3) |
| P-value[c] | | 0.0516 | 0.5071 | 0.4139 | 0.0001 | <0.0001 |

Clinical Global Impression-Improvement scores range from 1 (Very much improved) to 7 (Very much worse). Test statistics and estimates are from a restricted maximum likelihood repeated measures mixed model on observed values with timepoint and its interaction with treatment group as repeated measures using an unstructured covariance structure.
[a]Least square mean and standard error per treatment group. The corresponding estimates for the placebo group are not included as they vary with the dexmedetomidine sublingual film dosing group being compared.
[b]Treatment Effect: Least square mean difference, standard error, and 95% confidence intervals between dexmedetomidine sublingual film and Placebo
[c]P value comparing dexmedetomidine sublingual film and Placebo

TABLE 19

Percent of Responders in the CGI-I Scale over Time (Intent-to-Treat Population)

|  | | Dexmedetomidine sublingual film | | | | |
|---|---|---|---|---|---|---|
| Time Point Statistics | Placebo (N = 45) | 20 μg (N = 18) | 60 μg (N = 18) | 80 μg (N = 18) | 120 μg (N = 18) | 180 μg (N = 18) |
| | | | 30 minutes post-dose | | | |
| Percent responders | 22.2% | 22.2% | 38.9% | 27.8% | 22.2% | 22.2% |
| P-value[a] | | 1.000 | 0.2158 | 0.7457 | 1.000 | 1.000 |
| | | | 1 hour post-dose | | | |
| Percent responders | 24.4% | 38.9% | 44.4% | 44.4% | 55.6% | 72.2% |
| P-value[a] | | 0.3549 | 0.1383 | 0.1383 | 0.0361 | 0.0011 |
| | | | 2 hours post-dose | | | |
| Percent responders | 31.1% | 55.6% | 55.6% | 50.0% | 66.7% | 94.4% |
| P-value[a] | | 0.0896 | 0.0896 | 0.2462 | 0.0125 | <0.0001 |
| | | | 4 hours post-dose | | | |
| Percent responders | 32.6% | 55.6% | 44.4% | 57.1% | 83.3% | 94.4% |
| P-value[a] | | 0.1499 | 0.3968 | 0.1231 | 0.0005 | <0.0001 |

[a]P-value based on a comparison of dexmedetomidine sublingual film versus placebo via a Fisher's exact test Pharmacokinetic Results:

Pharmacokinetic analysis was conducted using a validated install of Phoenix® WinNonlin® version 8.1. Non-compartmental analysis was also conducted on the final audited data which consisted of a total of 135 participants in 5 cohorts receiving 20, 60, 80 (1×20 μg films and 1×60 μg films), 120 (2×60 μg films) and 180 μg (3×60 kg films) of dexmedetomidine sublingual film. Measurable concentrations of dexmedetomidine were observed at the first collected post dose plasma sample (1 hr) for all dose levels and tabulated in table 20. There were no measurable concentrations at pre-dose (0 hr) at any dose level. Measurable concentrations of dexmedetomidine were observable until 8 hr for all dose levels with measurable concentrations at 24 hr in some subjects at each dose level (Table 20; FIGS. 5A and 5B). Dexmedetomidine sublingual film is absorbed rapidly with maximum concentration achieved on average within about 2.5 hours after administration. The median Tmax ranged from 1.50-2.31 hr while the median t½ ranged from 2.36-3.06 hr across the 5 dose levels. The exposure (Cmax and AUC) increased in an approximately dose proportional manner within the dose range (20 μg-180 μg) studied after single administration. The median Cmax ranged from about 40 ng/L to about 500 ng/L. After absorption, it was eliminated with about a 3-hour half-life which was consistent across dose groups. In 20 μg dose group, 8 of 18 subjects were given a second dose of dexmedetomidine sublingual film, the exposure (Cmax and AUC) was about 2-fold higher than in the group which was not redosed Observed exposures following a single dose of 180 μg (Mean Cmax: 379 ng/L; Mean AUC 2881 ng/L) (Table 20) are significantly below the mean exposures (IV PRECEDEX® at approved dose is estimated): Cmax: 1339 ng/L; AUC: 31713 ng·h/L (PKPD18-1054) with the highest approved dose of dexmedetomidine.

TABLE 20

Individual and summary statistics of PK parameter estimates of dexmedetomidine in plasma after administration of dexmedetomidine sublingual film in schizophrenia patients.

| Cohort | Dose (ug) | Redose | Subject ID | Cmax (ng/L) | Tmax (hr) | AUClast (hr*ng/L) | AUCinf_obs (hr*ng/L) | t1/2 (hr) |
|---|---|---|---|---|---|---|---|---|
| 1 | 20 | No | 01-001 | 35.54 | 1.50 | 224.01 | NC | NC |
| | | | 01-002 | 38.55 | 1.50 | 186.08 | NC | 3.79 |
| | | | 01-010 | 59.82 | 1.00 | 104.40 | NC | 2.12 |
| | | | 01-026 | 14.07 | 4.02 | 57.43 | NC | NC |
| | | | 07-015 | 33.41 | 1.53 | 177.60 | NC | 5.36 |
| | | | 07-030 | 34.31 | 2.00 | 176.11 | 203.81 | 2.29 |
| | | | 10-027 | 35.38 | 2.00 | 184.37 | NC | 3.64 |
| | | | 23-016 | 69.05 | 1.48 | 264.45 | NC | 2.95 |
| | | | 23-018 | 40.37 | 1.97 | 154.62 | 186.40 | 3.17 |
| | | | 23-020 | 38.49 | 1.95 | 190.81 | 226.26 | 2.51 |
| | | | N | 10 | 10 | 10 | 3 | 8 |
| | | | Mean | 39.90 | 1.89 | 171.99 | 205.49 | 3.23 |
| | | | SD | 15.02 | 0.81 | 57.74 | 19.98 | 1.05 |
| | | | CV % | 37.64 | 42.89 | 33.57 | 9.72 | 32.61 |
| | | | Min | 14.07 | 1.00 | 57.43 | 186.40 | 2.12 |
| | | | Median | 37.02 | 1.74 | 180.99 | 203.81 | 3.06 |
| | | | Max | 69.05 | 4.02 | 264.45 | 226.26 | 5.36 |
| | | | Geometric Mean | 37.16 | 1.78 | 160.36 | 204.85 | 3.09 |
| | | | Geometric CV % | 43.89 | 36.99 | 45.49 | 9.72 | 31.23 |
| 1 | 20 | Yes | 01-009 | 130.44 | 2.00 | 662.46 | NC | 3.94 |
| | | | 01-013 | 122.23 | 2.00 | 486.82 | 563.33 | 2.73 |
| | | | 05-007 | 49.87 | 2.50 | 230.06 | NC | 4.02 |
| | | | 05-008 | 66.64 | 2.12 | 272.47 | 304.52 | 2.00 |
| | | | 05-021 | 86.86 | 2.50 | 410.74 | NC | 3.10 |
| | | | 05-023 | 52.29 | 2.50 | 236.04 | NC | NC |
| | | | 05-024* | 138.69 | 8.03 | 1912.52 | NC | NC |
| | | | 07-028 | 125.70 | 2.00 | 476.62 | 519.25 | 1.81 |
| | | | N | 8 | 8 | 8 | 3 | 6 |
| | | | Mean | 96.59 | 2.96 | 585.96 | 462.37 | 2.93 |
| | | | SD | 36.95 | 2.06 | 556.20 | 138.47 | 0.94 |
| | | | CV % | 38.26 | 69.85 | 94.92 | 29.95 | 31.98 |
| | | | Min | 49.87 | 2.00 | 230.06 | 304.52 | 1.81 |
| | | | Median | 104.54 | 2.31 | 443.68 | 519.25 | 2.91 |
| | | | Max | 138.69 | 8.03 | 1912.52 | 563.33 | 4.02 |
| | | | Geometric Mean | 89.71 | 2.61 | 453.42 | 446.60 | 2.80 |
| | | | Geometric CV % | 44.50 | 49.35 | 78.77 | 34.37 | 34.49 |
| 2 | 60 | No | 01-044 | 93.67 | 1.00 | 442.23 | NC | 3.10 |
| | | | 01-047 | 73.42 | 1.00 | 265.85 | 293.67 | 2.23 |
| | | | 01-055 | 113.35 | 1.50 | 474.46 | 562.60 | 2.87 |
| | | | 01-056 | 154.79 | 1.50 | 413.53 | 428.64 | 1.48 |
| | | | 03-036 | 83.52 | 1.55 | 347.11 | 369.07 | 1.62 |
| | | | 05-050 | 121.52 | 1.00 | 355.87 | 381.27 | 1.84 |
| | | | 05-052 | 105.84 | 1.50 | 330.30 | 369.14 | 2.36 |
| | | | 06-033 | 253.14 | 1.45 | 737.87 | 834.44 | 2.27 |
| | | | 06-034 | 206.42 | 1.53 | 887.27 | 1007.71 | 2.35 |
| | | | 06-041 | 144.27 | 2.07 | 1714.29 | 1882.10 | 6.98 |
| | | | 06-043 | 186.40 | 1.02 | 748.96 | 877.63 | 2.53 |
| | | | 07-048 | 201.12 | 0.98 | 874.85 | 1030.25 | 2.81 |
| | | | 08-046* | 93.22 | 2.00 | 346.61 | NC | NC |
| | | | 09-042 | 146.17 | 3.95 | 2072.02 | 2195.38 | 5.43 |
| | | | 10-032 | 136.25 | 1.50 | 650.22 | NC | NC |
| | | | 10-035 | 127.27 | 1.50 | 519.54 | 616.68 | 2.78 |
| | | | 10-039 | 144.93 | 1.00 | 603.55 | 691.00 | 2.27 |
| | | | 10-045 | 127.30 | 1.50 | 495.69 | 548.50 | 2.30 |
| | | | N | 18 | 18 | 18 | 15 | 16 |
| | | | Mean | 139.59 | 1.53 | 680.71 | 805.85 | 2.83 |
| | | | SD | 47.22 | 0.69 | 481.66 | 555.95 | 1.42 |

TABLE 20-continued

Individual and summary statistics of PK parameter estimates of dexmedetomidine in plasma after administration of dexmedetomidine sublingual film in schizophrenia patients.

| Cohort | Dose (ug) | Re-dose | Subject ID | Cmax (ng/L) | Tmax (hr) | AUClast (hr*ng/L) | AUCinf_obs (hr*ng/L) | t1/2 (hr) |
|---|---|---|---|---|---|---|---|---|
| | | | CV % | 33.83 | 45.0 | 70.76 | 68.89 | 50.15 |
| | | | Min | 73.42 | 0.98 | 265.85 | 293.67 | 1.48 |
| | | | Median | 131.78 | 1.50 | 507.61 | 616.68 | 2.36 |
| | | | Max | 253.14 | 3.95 | 2072.02 | 2195.38 | 6.98 |
| | | | Geometric Mean | 132.56 | 1.43 | 575.95 | 674.14 | 2.60 |
| | | | Geometric CV % | 33.88 | 36.02 | 59.93 | 65.01 | 40.94 |
| 3 | 120 | No | 01-059 | 128.89 | 2.00 | 1143.72 | 1192.51 | 5.28 |
| | | | 01-062 | 380.78 | 2.00 | 2927.15 | 2958.80 | 3.64 |
| | | | 01-065 | 393.58 | 4.00 | 3935.47 | 4063.95 | 4.62 |
| | | | 01-080 | 316.57 | 1.00 | 1536.77 | 1538.84 | 2.60 |
| | | | 01-082 | 315.51 | 4.00 | 4156.65 | 4371.55 | 5.32 |
| | | | 01-086 | 201.58 | 1.00 | 915.85 | 918.48 | 2.56 |
| | | | 03-068 | 308.19 | 1.02 | 1039.39 | 1039.79 | 2.02 |
| | | | 06-077 | 108.84 | 3.82 | 585.94 | 586.93 | 2.59 |
| | | | 06-078 | 228.53 | 1.47 | NC | NC | NC |
| | | | 06-083 | 154.65 | 1.47 | 592.96 | 593.28 | 2.01 |
| | | | 06-084 | 160.33 | 1.47 | 682.91 | 683.47 | 2.59 |
| | | | 07-066 | 366.09 | 2.00 | 3920.86 | 4012.15 | 4.35 |
| | | | 10-063 | 184.22 | 2.00 | NC | NC | 3.50 |
| | | | 10-076 | 149.11 | 2.00 | 990.19 | 989.76 | 2.81 |
| | | | 23-069 | 286.88 | 2.00 | 1230.19 | 1230.90 | 1.98 |
| | | | 23-070 | 243.63 | 1.52 | NC | NC | 3.21 |
| | | | 23-073* | 125.62 | 4.00 | NC | NC | NC |
| | | | 23-074 | 233.12 | 1.55 | 1162.59 | 1166.09 | 2.83 |
| | | | N | 18 | 18 | 18 | 14 | 16 |
| | | | Mean | 238.12 | 2.13 | 1513.91 | 1810.47 | 3.25 |
| | | | SD | 92.98 | 1.06 | 1264.13 | 1395.65 | 1.1 |
| | | | CV % | 39.05 | 50.03 | 83.50 | 77.09 | 34.27 |
| | | | Min | 108.84 | 1.00 | 499.50 | 586.93 | 1.98 |
| | | | Median | 230.83 | 2.00 | 970.38 | 1179.30 | 2.82 |
| | | | Max | 393.58 | 4.00 | 4158.05 | 4371.55 | 5.32 |
| | | | Geometric Mean | 220.53 | 1.91 | 1169.33 | 1411.79 | 3.08 |
| | | | Geometric CV % | 42.89 | 49.10 | 78.73 | 81.15 | 33.71 |
| 4 | 180 | No | 01-089 | 490.60 | 1.00 | 5498.99 | 5592.92 | 3.92 |
| | | | 01-097 | 636.45 | 1.50 | 2508.31 | 2676.44 | 1.76 |
| | | | 01-105 | 685.45 | 1.00 | 2628.09 | 3126.77 | 2.73 |
| | | | 01-111* | 88.10 | 8.00 | 1311.33 | NC | NC |
| | | | 05-088 | 127.77 | 1.02 | 520.53 | 569.19 | 2.03 |
| | | | 05-098 | 563.94 | 1.47 | 2435.38 | 2644.08 | 1.86 |
| | | | 05-100 | 487.88 | 1.47 | 4630.43 | 4705.04 | 3.90 |
| | | | 06-091 | 592.99 | 3.98 | 6835.79 | 7310.47 | 5.92 |
| | | | 06-093 | 406.57 | 2.07 | 2173.00 | NC | 3.22 |
| | | | 07-095* | 443.70 | 2.00 | 1911.81 | NC | NC |
| | | | 10-090 | 546.65 | 2.00 | 3808.10 | NC | 5.19 |
| | | | 10-123 | 797.37 | 1.50 | 8928.20 | 9468.70 | 5.80 |
| | | | 10-127 | 640.01 | 2.00 | 2444.45 | 2746.20 | 2.30 |
| | | | 10-129 | 483.07 | 2.00 | 3578.09 | 4340.66 | 9.65 |
| | | | 23-103 | 225.12 | 1.98 | 1034.07 | 1140.28 | 1.90 |
| | | | 23-104 | 227.51 | 1.97 | 1086.53 | NC | 2.94 |
| | | | 23-125 | 237.95 | 1.98 | 943.23 | 1049.33 | 2.10 |
| | | | 23-126 | 224.88 | 1.98 | 1243.11 | NC | 2.84 |
| | | | N | 18 | 18 | 18 | 12 | 16 |
| | | | Mean | 439.22 | 2.16 | 2973.31 | 3780.85 | 3.63 |
| | | | SD | 206.41 | 1.60 | 2255.10 | 2663.22 | 2.12 |
| | | | CV % | 46.99 | 73.99 | 75.84 | 70.44 | 58.29 |
| | | | Min | 88.10 | 1.00 | 520.53 | 569.19 | 1.76 |
| | | | Median | 485.48 | 1.98 | 2439.91 | 2936.49 | 2.89 |
| | | | Max | 797.37 | 8.00 | 8928.20 | 9468.70 | 9.65 |
| | | | Geometric Mean | 379.13 | 1.87 | 2294.38 | 2881.18 | 3.20 |
| | | | Geometric CV % | 68.19 | 52.19 | 87.67 | 100.34 | 53.08 |
| 5 | 80 | No | 01-144 | 160.18 | 2.00 | 784.24 | 917.99 | 2.49 |
| | | | 02-133 | 142.99 | 2.03 | 747.42 | 886.35 | 2.41 |
| | | | 02-142 | 222.79 | 2.00 | 2480.66 | 2594.62 | 5.37 |
| | | | 03-112 | 68.41 | 1.55 | 416.50 | NC | NC |
| | | | 03-114 | 70.46 | 1.03 | 244.38 | NC | NC |
| | | | 03-120 | 107.00 | 1.53 | 450.79 | 531.82 | 2.67 |
| | | | 03-134 | 135.30 | 1.55 | 759.89 | 894.79 | 2.57 |
| | | | 08-092 | 167.57 | 1.88 | 938.26 | NC | NC |

TABLE 20-continued

Individual and summary statistics of PK parameter estimates of dexmedetomidine in plasma after administration of dexmedetomidine sublingual film in schizophrenia patients.

| Cohort | Dose (ug) | Re-dose | Subject ID | Cmax (ng/L) | Tmax (hr) | AUClast (hr*ng/L) | AUCinf_obs (hr*ng/L) | t1/2 (hr) |
|---|---|---|---|---|---|---|---|---|
| | | | 08-094 | 199.63 | 1.45 | 684.60 | 737.33 | 1.88 |
| | | | 08-109 | 102.29 | 1.50 | 561.56 | NC | 3.12 |
| | | | 09-137 | 151.89 | 2.25 | 635.19 | 767.51 | 3.07 |
| | | | 20-115 | 224.70 | 1.22 | 1114.91 | 1366.03 | 2.72 |
| | | | 20-138 | 175.94 | 4.32 | 2218.17 | 2334.99 | 5.33 |
| | | | 20-140 | 182.32 | 1.58 | 659.20 | 702.28 | 1.78 |
| | | | 20-141 | 253.29 | 1.20 | 888.38 | NC | 4.75 |
| | | | 22-131 | 184.62 | 2.12 | 1020.28 | NC | 2.96 |
| | | | 24-116 | 315.11 | 1.53 | 1145.23 | 1305.66 | 2.53 |
| | | | 24-130 | 139.94 | 4.03 | 1325.85 | 1375.38 | 4.93 |
| | | | N | 18 | 18 | 18 | 12 | 15 |
| | | | Mean | 166.91 | 1.93 | 948.64 | 1201.23 | 3.24 |
| | | | SD | 62.75 | 0.88 | 579.45 | 651.50 | 1.22 |
| | | | CV % | 37.59 | 45.71 | 61.08 | 54.24 | 37.76 |
| | | | Min | 68.41 | 1.03 | 244.38 | 531.82 | 1.78 |
| | | | Median | 163.88 | 1.57 | 772.07 | 906.39 | 2.72 |
| | | | Max | 315.11 | 4.32 | 2480.66 | 2594.62 | 5.37 |
| | | | Geometric Mean | 155.27 | 1.79 | 816.58 | 1071.37 | 3.05 |
| | | | Geometric CV % | 42.27 | 38.50 | 60.56 | 51.21 | 36.76 |

3. Safety and Tolerability:

Dexmedetomidine sublingual film (formulations of Example 1 and 2) was well tolerated and had a favourable safety profile in the treatment of subjects with agitation. An overview of subjects who experienced at least 1 treatment emergent adverse event (TEAE) by treatment group for the safety population is given in Tables 21 and 22. Overall, a total of 55 subjects (40.7% [55/135]) experienced a least 1 TEAE. The proportion of subjects who experienced TEAEs was similar in the 80 µg, 120 µg, and 180 µg dose groups (55.6%, 66.7%, and 66.7%, respectively). In comparison, the proportion of subjects with TEAEs was lower in the 20 µg and 60 µg dose groups (27.8% and 33.3%, respectively) and the placebo group (22.2%). Most (81.1%) of the TEAEs in all treatment groups were mild in severity. Almost all (90.9%) of the TEAEs were considered to be related to study drug in all treatment groups. None of the subjects experienced a TEAE that was considered to be severe in intensity. There were no deaths, SAEs, or discontinuations due to an AE reported in this study (Tables 21 and 22).

The TEAEs reported in this study were consistent with known common side effects of dexmedetomidine, namely, dry mouth, bradycardia, hypotension, and somnolence (Table 21).

The most frequently reported TEAE was somnolence with 26 subjects experiencing the event of which 20 events were mild in severity and 4 events were moderate in severity. Incidences for somnolence in the groups were 16.7% (20 µg and 60 µg), 22.2% (120 µg), 33.3% (80 µg), and 44.4% (180 µg); incidence in the placebo group was 4.4%. The second most frequently reported TEAE was dry mouth which was reported by 5.6%, 16.7%, 16.7%, and 11.1% of subjects in the 20 µg, 80 µg, 120 µg, and 180 µg groups, respectively, compared with 13.3% of subjects in the placebo group. No subject in the 60 µg dose group reported an event of dry mouth. All cases of dry mouth were mild in severity.

In the dexmedetomidine hydrochloride treatment groups, TEAEs associated with vital signs were: hypotension in 6 subjects (n=2 [120 µg], n=4 [180 µg]), orthostatic hypotension (n=1 [80 µg], n=1 [120 µg], and n=1 [180 µg]), and bradycardia (n=1 [20 µg]). All subjects recovered from the events.

Three laboratory related adverse events (3× upper limit of normal for T Bili, 3+ Glucose in urine, and 4+ Protein in urine) were being followed-up at each respective clinical site and remained unresolved at this time. Otherwise there were no clinically significant changes in laboratory parameters and ECG assessments. No physical examination finding was considered clinically significant by the investigators. None of the subjects had a negative reaction (i.e. local irritation) to study drug as determined by buccal examination.

Also, the dose dependent decreases in SBP and DBP were observed with maximum changes at 2 hours post-dose:
- SBP: −4.6 (9.63), −5.6 (10.85), −8.2 (11.50), −12.1 (20.50), and −14.7 (12.09) mmHg in the 20 µg, 60 µg, 80 µg, 120 µg, and 180 µg groups, respectively, and +1.2 (9.23) mmHg in the placebo group.
- DBP: 0.3 (10.39), −5.3 (7.86), −6.4 (8.05), −7.8 (9.40), and −6.6 (6.41) mmHg in the 20 µg, 60 µg, 80 µg, 120 µg, and 180 µg groups, respectively, and +0.2 (7.82) mmHg in the placebo group.
- HR: −0.1 (6.24), −3.9 (9.13), −0.8 (8.39), −2.2 (13.03), and −10.7 (12.97) bpm in the 20 µg, 60 µg, 80 µg, 120 µg, and 180 µg groups, respectively, and −0.8 (8.29) bpm in the placebo group.

Further, the orthostatic measurements of SBP, DBP, and HR were performed after the subject had been standing for a total of 5 minutes.

Mean changes from baseline at hours 2 postdosing for standing SBP, DBP, and HR are provided below (FIGS. 7A, 7B and 7C). These changes are similar to the changes from baseline values for resting measurements for SBP, DP, and HR (FIGS. 6A, 6B and 6C). Total of 3 subjects (1 in each dose groups 80 µg, 120 µg, and 180 µg) experienced TEAEs of orthostatic hypotension.

Mean (±SD) changes from baseline at 2 hours postdosing for standing SBP, DBP, and HR were:
- SBP: −3.1 (8.34), −4.6 (9.04), −12.6 (12.83), −11.9 (16.43) and −15.0 (11.3) mmHg in the 20 µg, 60 µg, 80 µg, 120 µg, and 180 µg dose groups, respectively, and +0.5 (8.35) mmHg in the placebo group.
- DBP: −1.4 (6.97), −4.2 (4.78), −6.7 (8.49), −6.9 (7.86), and −7.1 (8.51) mmHg in the 20 µg, 60 µg, 80 µg, 120

μg, and 180 μg dose groups, respectively, and −1.3 (7.36) mmHg in the placebo group.

HR: 0.6 (7.92), −4.3 (11.87), −1.1 (10.47), −1.7 (13.98), and −10.4 (10.08) bpm in the 20 μg, 60 μg, 80 μg, 120 μg, and 180 μg dose groups, respectively, and −0.3 (9.88) bpm in the placebo group.

line as measured by PEC, CGI-I, and ACES scales in schizophrenia patients. The primary efficacy endpoint was met in 80 μg, 120 μg, and 180 μg treatment groups as there was significant improvements in PEC total scores from baseline at 2 hours post-dose with mean changes of −7.3, −9.2, and −10.8 points, respectively, versus −4.5 for placebo.

TABLE 21

Treatment Emergent Adverse Events by System Organ Class and Preferred Term During the Treatment Period (Safety Population)

| System Organ Class Preferred Term | Placebo (N = 45) | Dexmedetomidine sublingual film | | | | |
|---|---|---|---|---|---|---|
| | | 20 μg (N = 18) | 60 μg (N = 18) | 80 μg (N = 18) | 120 μg (N = 18) | 180 μg (N = 18) |
| Any AEs | 10 (22.2) | 5 (27.8) | 6 (33.3) | 10 (55.6) | 12 (66.7) | 12 (66.7) |
| Nervous system disorders | 6 (13.3) | 4 (22.2) | 4 (22.2) | 8 (44.4) | 9 (50.0) | 9 (50.0) |
| Somnolence | 2 (4.4) | 3 (16.7) | 3 (16.7) | 6 (33.3) | 4 (22.2) | 8 (44.4) |
| Headache | 2 (4.4) | 1 (5.6) | 0 | 1 (5.6) | 3 (16.7) | 0 |
| Dizziness | 2 (4.4) | 0 | 2 (11.1) | 1 (5.6) | 1 (5.6) | 0 |
| Paraesthesia | 0 | 0 | 0 | 1 (5.6) | 1 (5.6) | 0 |
| Hypoaesthesia | 0 | 0 | 1 (5.6) | 0 | 0 | 0 |
| Sedation | 0 | 0 | 0 | 0 | 0 | 1 (5.6) |
| Gastrointestinal disorders | 7 (15.6) | 2 (11.1) | 1 (5.6) | 4 (22.2) | 4 (22.2) | 2 (11.1) |
| Dry mouth | 6 (13.3) | 1 (5.6) | 0 | 3 (16.7) | 3 (16.7) | 2 (11.1) |
| Constipation | 0 | 0 | 1 (5.6) | 1 (5.6) | 0 | 0 |
| Diarrhoea | 0 | 0 | 0 | 0 | 1 (5.6) | 0 |
| Dyspepsia | 0 | 1 (5.6) | 0 | 0 | 0 | 0 |
| Nausea | 1 (2.2) | 0 | 0 | 0 | 0 | 0 |
| Toothache | 1 (2.2) | 0 | 0 | 0 | 0 | 0 |
| Vascular disorders | 0 | 0 | 0 | 1 (5.6) | 3 (16.7) | 5 (27.8) |
| Hypotension | 0 | 0 | 0 | 0 | 2 (11.1) | 4 (22.2) |
| Orthostatic hypotension | 0 | 0 | 0 | 1 (5.6) | 1 (5.6) | 1 (5.6) |
| Investigations | 3 (6.7) | 0 | 1 (5.6) | 0 | 1 (5.6) | 1 (5.6) |
| Alanine aminotransferase increased | 1 (2.2) | 0 | 0 | 0 | 0 | 0 |
| Aspartate aminotransferase increased | 1 (2.2) | 0 | 0 | 0 | 0 | 0 |
| Blood bilirubin increased | 0 | 0 | 1 (5.6) | 0 | 0 | 0 |
| Glucose urine present | 0 | 0 | 0 | 0 | 1 (5.6) | 0 |
| Heart rate increased | 1 (2.2) | 0 | 0 | 0 | 0 | 0 |
| Liver function test increased | 1 (2.2) | 0 | 0 | 0 | 0 | 0 |
| Protein urine present | 0 | 0 | 0 | 0 | 0 | 1 (5.6) |
| Infections and infestations | 1 (2.2) | 0 | 1 (5.6) | 0 | 1 (5.6) | 0 |
| Cellulitis | 0 | 0 | 0 | 0 | 1 (5.6) | 0 |
| Nasopharyngitis | 1 (2.2) | 0 | 0 | 0 | 0 | 0 |
| Urinary tract infection | 0 | 0 | 1 (5.6) | 0 | 0 | 0 |
| Cardiac disorders | 0 | 0 | 0 | 0 | 1 (5.6) | 0 |
| Bradycardia | 0 | 0 | 0 | 0 | 1 (5.6) | 0 |
| Musculoskeletal and connective tissue disorders | 0 | 0 | 0 | 1 (5.6) | 0 | 0 |
| Pain in extremity | 0 | 0 | 0 | 1 (5.6) | 0 | 0 |

TABLE 22

Summary of Adverse Events (Safety Population)

| Category, n (%) | Dose groups | | | | | |
|---|---|---|---|---|---|---|
| | Placebo (N = 45) | 20 μg (N = 18) | 60 μg (N = 18) | 80 μg (N = 18) | 120 μg (N = 18) | 180 μg (N = 18) |
| Any TEAE | 10 (22.2) | 5 (27.8) | 6 (33.3) | 10 (55.6) | 12 (66.7) | 12 (66.7) |
| Any treatment related TEAE | 10 (22.2) | 4 (22.2) | 5 (27.8) | 10 (55.6) | 10 (55.6) | 11 (61.1) |
| TEAE severity | | | | | | |
| Mild | 8 (17.8) | 5 (27.8) | 5 (27.8) | 9 (50.0) | 11 (61.1) | 7 (38.9) |
| Moderate | 2 (4.4) | 0 | 1 (5.6) | 1 (5.6) | 1 (5.6) | 5 (27.8) |
| Severe | 0 | 0 | 0 | 0 | 0 | 0 |
| Any SAE | 0 | 0 | 0 | 0 | 0 | 0 |
| Any AE leading to discontinuation | 0 | 0 | 0 | 0 | 0 | 0 |

Abbreviations: AE = adverse events; TEAE = treatment-emergent adverse event; SAE = serious adverse event
Percentages are based on the number of Safety Population subjects in each treatment arm.
If a subject experienced more than one adverse event in a category, the subject is counted only once in that category.

Conclusion: Dexmedetomidine sublingual film treatment significantly improved the severity of agitation from baseline LSM differences from placebo were −2.9 (P=0.0210), −4.6 (P=0.0003), and −6.3 (P<0.0001) for the 80 μg, 120 μg, and 180 µg groups, compared with placebo The proportion of responders (ie, a ≥40% decrease in PEC total score) at 2 hours post-dose was significantly higher in the 120 µg and 180 µg dose groups (68.8% [P=0.0158]) and 94.4% [P<0.0001], respectively) compared with placebo (31.0%). Further, changes in secondary efficacy measures (ie, CGI-I and ACES scores) at 2 hours post-dose were consistent with the results for PEC total scores and were indicative of improvement in symptoms of agitation after treatment with Dexmedetomidine sublingual film.

Example 4: Phase 1, Randomized, Single-Blind, Placebo-Controlled, Single Ascending Dose Study of the Pharmacokinetics, Safety & Tolerability of Dexmedetomidine Sublingual Film (Example 1 Formulation) in Healthy Adult Volunteers This was a randomized, single-blind, placebo-controlled, single ascending dose pharmacokinetics, safety and tolerability study with 4 dosing groups in healthy adult (18-65 years-old) males and females. The study protocol was reviewed and approved by an institutional review board of site(s). This study was conducted in accordance with the Declaration of Helsinki and ICH— Good Clinical Practices (GCP).

Primary Objective: Determine the PK, safety and tolerability of the various film strengths of dexmedetomidine sublingual film for identification of appropriate film dosage strengths to be carried forward into subsequent clinical trials.

Secondary Objectives:
1. Determine the PD effects of the various film strengths of dexmedetomidine sublingual film.
2. Determine the relationship between PD effects and plasma concentrations of the dexmedetomidine.
3. Determine the time to onset of drowsiness after dexmedetomidine sublingual film administration.
4. Determine the length of sedative effect after dexmedetomidine sublingual film administration.
5. Determine the approximate dissolution time of dexmedetomidine sublingual films in the SL space.
6. Determine local irritation that may be caused by dexmedetomidine sublingual film.

Endpoints
Primary
Pharmacokinetics
1. Area under the curve (AUC0-12, AUC0-24, AUC0-inf) for 0 to 12 hours and 0 to 24 hours post dosing for dexmedetomidine plasma concentration.
2. Determine peak plasma dexmedetomidine concentration (Cmax).
3. Determine time corresponding to peak dexmedetomidine concentration level (Tmax).
4. Determine terminal half-life (t½) of dexmedetomidine from the central compartment.
5. Determine the volume of distribution (Vz) of dexmedetomidine.
6. Determine the clearance of dexmedetomidine (CL) from the central compartment.

Safety and Tolerability
1. Determine electrocardiogram (ECG) and vital sign abnormalities including adverse effects on blood pressure (BP), heart rate, or respirations with various film strengths of dexmedetomidine sublingual film.
2. Determine abnormal laboratory values following administration of dexmedetomidine sublingual film.
3. Determine changes in physical examination following administration of dexmedetomidine sublingual film
4. Number of subjects experiencing an AE up to Day 14 following dexmedetomidine sublingual film administration.
5. Number of subjects who discontinued study treatment or removed SL films due to an AE or other reason.
6. The degree to which AEs can be tolerated by assessing the number of subjects requiring:
   Hemodynamic interventions for maintaining BP;
   Cardiac interventions for maintaining heart rate;
   Respiratory interventions for maintaining oxygen saturation.

Secondary
1. The sedative effect assessed by RASS and Visual analogue scales/sedation (VAS/S) on day of dexmedetomidine sublingual film dosing.
2. Time in minutes and seconds from administration of dexmedetomidine sublingual film until RASS of −1 on day of dexmedetomidine sublingual film dosing.
3. Time in minutes and seconds from RASS of −1 till resolution of drowsiness on day of dexmedetomidine sublingual film dosing.
4. Time in minutes and seconds from SL administration of dexmedetomidine sublingual film till its complete dissolution or up to 30 minutes.

Study design: It was a randomized, single-blind, placebo controlled, single ascending dose PK, safety and tolerability study conducted in healthy adult (18-65-year-old) males and females. The study evaluated increasing doses of dexmedetomidine sublingual film in 4 cohorts of healthy adult participants.

Four (4) doses were evaluated derived from three film strengths of 10 µg, 40 µg, and 60 µg: 10 µg, 20 µg (2×10 µg film), 40 µg, and 60 µg in Cohort 1, 2, 3 and 4 respectively. During the review of the safety and tolerability data from Cohort 3 dosing (40 µg), it was observed that 6 symptomatic subjects had reported dizziness upon standing, four of whom had concomitant intermittent hypotension or bradycardia (SBP/DBP/heart rate with >30 mmHg decrease from baseline, SBP <90 or DBP <60 or heart rate <50). While the results remained blinded, it was decided to decrease the planned dose for Cohort 4 to 40 µg. The actual doses administered to subjects in this study included 10 µg (cohort 1), 20 µg (cohort 2) and 40 µg (cohorts 3 and 4).

All eligible participants, who have been previously screened, arrived at the clinical research unit (CRU) a day before for admission and baseline assessment. They were domiciled in the CRU for 4 days (Day −1, 1, 2 and 3) and discharged on Day 4, and were under medical supervision during this time. The pre-dose evaluation of all the participants was done approximately between 07:00 and 09:00 hours, after an overnight fast of at least 8 hours. The participants were given free access to drinking water until at least one hour before dosing. A venous catheter was inserted for allowing sampling for PK. At the beginning of each study session, a single dose of dexmedetomidine sublingual film (Example 1) was administered sublingually by an unblinded staff. The dexmedetomidine sublingual film was retained in the sublingual cavity until dissolved. Evaluations were done every 5 minutes for the first 15 minutes and then every 15 minutes to determine the time to dissolution of the film. Subjects were also evaluated for local irritation around the area where the film was placed. The subjects were not allowed to sit or stand up during the first 2 hours after dexmedetomidine sublingual film dosing, except when performing standing BP measurements. After 2 hours, the subjects were allowed to sit in their beds, however, during sampling, they had to rest in supine or semi-recumbent position. The ECG, BP and oxygen saturation were monitored as per the schedule (Table 23). Subjects were allowed water as desired at least 1 hour after drug administration. Standard meals were offered at approximately 4, 8, and 12 hours after dexmedetomidine sublingual film dosing. However, no food or drinks were permitted until an investigator confirms that each subject was capable of oral intake, based on the degree of sedation and ability to control urination. Lavatory visits were also allowed, but along with an attendant. Day 2 and 3 had no dietary restriction, but there was complete restriction on smoking and alcohol intake during the length of CRU stay. After plasma sampling for 24 hours following dosing of dexmedetomidine sublingual film, the safety and tolerability assessments were continued until the morning of Day 4 (day of discharge), and were repeated on Day 5, Day 7±1 and Day 14±2.

Number of Subjects:

The study evaluated increasing doses of dexmedetomidine sublingual film (example 1-formulation) in 4 cohorts of healthy adult subjects. In the first two cohorts (Cohort 1 and Cohort 2), twelve (12) new subjects were enrolled per cohort, randomized in a ratio of 2:1, i.e. 8 receiving dexmedetomidine sublingual film and 4 receiving Placebo film.

Subjects receiving active drug in Cohort 1/Cohort 2 were to be escalated to receive high dose of active drug in Cohort 3/Cohort 4 and subjects receiving Placebo in Cohort 1/Cohort 2 were to receive Placebo in Cohort 3/Cohort 4 respectively. Six new subjects were to be randomized to receive the active drug in Cohort 3/Cohort 4. Dose-proportionality and dose-exposure response were to be evaluated in the subjects that crossed over to Cohort 3/Cohort 4. The effect of dexmedetomidine sublingual film on BP, heart rate, RASS score, other AEs and PK parameters were to be evaluated in new subjects who were not previously exposed to dexmedetomidine sublingual films. In case of placebo dropouts, while escalating from Cohort 1 to Cohort 3 or Cohort 2 to Cohort 4, additional new subjects were to be randomized to make up the total subjects to 4 subjects in Placebo arm of Cohort 3 and Cohort 4.

TABLE 23

Schedule of Assessments

| Activity | Screen | Day -1 Admission; Visit 1) | Day 1 (Study drug dosing) [1] | Day 2 & 3 (Observation in CRU) | Day 4 (At time of discharge) | Day 5 (Visit 2)[4] | Day 7 ± 1 (Visit 3)[4] | Day 14 ± 2 (Visit 4, EOS)[4] |
|---|---|---|---|---|---|---|---|---|
| Informed Consent Form | X | | | | | | | |
| Demographics | X | | | | | | | |
| Medical History | X | X | | | | | | |
| Weight/Body Mass Index | X | X | | | X | X | X | X |
| Height | X | | | | | | | |
| Inclusion/Exclusion criteria | X | X | X | | | | | |
| Randomization | | X | | | | | | |
| Safety Labs (Chemistry, hematology, U/A, UDS[2] were done by the unit's local lab) | X | X | | | X | | | |
| Pregnancy test (Blood HCG) | X | | | | | | | |
| Pregnancy test (Urine HCG) | | X | | | | | | |
| Coagulation (PT/INR) | X | | | | | | | |
| Physical Exam | X | X | | X | X | X | X | X |
| Complete Neurological Exam | X | | | | | | X | |
| Brief Neurological Exam | | X | X (at resolution of drowsiness after drug administration) | | | | | |
| Vital signs (systolic and diastolic blood pressure, pulse rate, respiration and oxygen saturation) | X | X | 0 (predose), 10, 20 and 30 min, then every 15 min till 6 hours. Thereafter prior to PK samples (if any) (±15 min) or hourly until time of sleep and again with last sample at 24-hour (±15 min). | X | X | X | X | X |
| Standing blood pressue | | X (at night) | X (-2 hours predose, 2, 4, 6 hours postdose) | X | X | | | |
| ECG | X | X | Every 3 hours (from 0 until 6 hours postdose (±15 min). | X | X | X | X | X |
| Admit to Unit | | X | | | | | | |
| Study Drug Prepartion (unblinded pharmacist) | | | X | | | | | |
| Venous Catheter Placement | | | X | | | | | |
| Study drug Sublingually | | | X | | | | | |
| Film buccal dissolution | | | X | | | | | |
| Buccal/Sublingual Exam for local irritation | X | X | X (at every hour starting from predose until time of sleep and again with last sample at 24-hour (±15 min) | X | X | X | X | X |

TABLE 23-continued

Schedule of Assessments

| Activity | Screen | Day −1 Admission; Visit 1) | Day 1 (Study drug dosing)[1] | Day 2 & 3 (Observation in CRU) | Day 4 (At time of discharge) | Day 5 (Visit 2)[4] | Day 7 ± 1 (Visit 3)[4] | Day 14 ± 2 (Visit 4, EOS)[4] |
|---|---|---|---|---|---|---|---|---|
| RASS[3] | | | X 0 min, every 5 min until drowsiness is achieved (RASS of −1); then every 15 min until resolution of drowsiness Prior to PK sample collection, till resolution of drowsiness | | | | | |
| VAS/S | | | 0 min, every 30 min until resolution of drowsiness Prior to PK sample collection (±5 min) | | | | | |
| Training | | X | | | | | | |
| PK Sampling | | | As per sampling schedule | | | | | |
| Discharge | | | | | X | | | |
| Concomitant Meds | X | X | X | X | X | X | X | X |
| Adverse Events | X | X | X | X | X | X | X | X |

ECG: electrocardiogram; HCG: human chorionic gonadotropin; PK: pharmacokinetic; PT/INR: prothrombin time/international normalized ratio; RASS: Richmond Agitation Sedation Scale; U/A: Urine Analysis; UDS: Urinary Drug Screen; VAS/S: visual analogue scales/sedation
[1]Predose assessments had a window of 60 min prior to drug administration.
[2]UDS was not done at the discharge day
[3]If a subject did not achieve drowsiness (RASS of −1) on or before the 90 minute postdose timepoint, the procedure was to be performed at 5 minute increments until 90 minutes postdose, then at 15-minute increments until 120 minutes postdose. Rass had a 3 minute window period.
[4]Any abnormal vital sign measurement, clinical laboratory test, physical examination finding, or ECG parameter deemed clinically significant by the investigator was to be repeated, including test results obtained on the final single-blind study day or upon early termination. For any test abnormality deemed clinically significant, repeat analysis was to be performed during the follow-up period and until the value returned to baseline (or within normal limits) or the investigator deemed the abnormality to be of no clinical significance.

Inclusion Criteria:
1. Healthy males and non-pregnant/non-breast-feeding females between 18 and 65 years of age, both inclusive.
2. Subjects who were capable of giving written informed consent for the study
3. Subjects that had body weight ≥50 kg with body mass index (BMI) in the range of 19-30 kg/m2, both inclusive
4. Subjects having physical examination and vital signs judged to be within normal limits by the PI or designee.
5. Subjects whose clinical laboratory tests (complete blood count, blood chemistry, and urinalysis) were within normal limits or are clinically acceptable to the PI or designee.
6. Subjects who were sufficiently physically healthy to receive a SL dose strength of dexmedetomidine sublingual film, and tolerate drowsiness, in the opinion of the PI or designee.
7. Subjects who were fluent in English and have ability to understand written and verbal protocol-related requirements in English.
8. Subjects who were willing and able to be confined to the CRU for approximately 4-5 days per dosing cohort and comply with the study schedule and study requirements.
9. Subjects that had reliable intravascular access from which to draw blood samples.
10. Male subjects, if non-vasectomized, must agree to use a condom with spermicide or abstain from sexual intercourse, during the trial and for 3 months after stopping the medication.
11. Male subject must not donate sperm starting at screening and throughout the study period, and for 90 days after the final study drug administration.
12. For female subjects of child-bearing potential, the subject must be willing to practice a clinically accepted method of birth control from at least 30 days prior to the first administration of the study medication, during the study, and for at least 30 days after the last dose of the study medication.
13. For female of non-childbearing potential, the subject was surgically sterile (i.e. has undergone hysterectomy, bilateral oophorectomy, or tubal ligation) or in a menopausal state (at least 1 year without menses), as confirmed by Follicle stimulating hormone (FSH) levels.

Exclusion Criteria:
1. The subjects with a history of allergic reaction or intolerance to the study drug or related compounds and additives.
2. The subjects with a history of major surgery within 4 weeks of screening.
3. The subjects with a history of significant traumatic brain injury.
4. The subjects with a history of alcohol or drug dependence by Diagnostic and Statistical Manual of Mental Disorders IV criteria during the 6-month period prior to study entry.
5. The subjects with a history of or presence of clinically significant psychiatric illnesses mental retardation, borderline personality disorder, anxiety disorder, or organic brain syndrome.
6. The subjects with a history of orthostatic hypotension (i.e., a sustained reduction of systolic BP (SBP) of at least 20 mmHg or diastolic BP (DBP) of 10 mmHg, or both, within 3 min of standing or head-up tilt to at least 600 on a tilt table) and high vagal tone.
7. The subjects who regularly consume large amounts of xanthine-containing substances (i.e., more than 5 cups of coffee or equivalent amounts of xanthine-containing substances per day).
8. The subjects who were on maintenance medications that could inhibit or induce the CYP2A6 enzyme.
9. The subjects who had received dexmedetomidine or other alpha-2-agonists within 1 week of the study date.

10. The subjects who had clinically significant sleep apnea or chronic obstructive pulmonary disease or history of asthma.
11. The subjects with suicidal tendency in the judgement of the PI or designee.
12. The subjects with clinical laboratory abnormalities (including positivity for Hep B, Hep C, HIV) unless treated to remission status.
13. The subjects with abnormal vital signs measurement in the judgement of the PI or designee, unless treated to remission status.
14. The subjects those were enrolled in another clinical study (e.g., laboratory or clinical evaluation) or have received an investigational drug in the past 30 days (or within 5 half-lives of the investigational drug, if >30 days).
15. The subjects that had a resting heart rate of <65 beats per minute or SBP <110 mmHg or >140 mmHg or DBP <70 mmHg or >100 mmHg at screening and pre-dosing. Have evidence of a clinically significant 12 lead ECG abnormality. Subjects that previously failed eligibility criteria at the Screening visit or Day 1 predose due to Exclusion 15 for a resting heart rate <70 beats per minute but not <65 beats per minute may be rescreened.
16. The subjects with an aberrant oral/buccal anatomy, inflammation or pathology which in the opinion of the PI, may affect SL drug administration and absorption.
17. The subjects with hepatic impairment or who have hepatic dysfunction defined as a history of hepatic dysfunction and an Alanine Aminotransferase (ALT) and Aspartate Aminotransferase (AST) values greater than 2 times normal in the past 6 months prior to study drug administration.
18. The subjects who had donated blood within 30 days prior to screening or plasma donation within 7 days prior to screening.
19. The subject who was part of the study staff personnel or family members of the study staff personnel.

Study duration: 39-42 days.

Treatments Administered

The following treatments were administered on Day 1:
Active: Dexmedetomidine hydrochloride SL film at dose levels of 10 μg (1×10 μg film), 20 μg (2×10 μg films) and 40 μg (1×40 μg film)
Placebo: Placebo SL film
Cohort 1 and Cohort 2 were given 10 μg and 20 μg (2×10 μg films), respectively, Cohort 3 and Cohort 4 received 40 μg of dexmedetomidine sublingual film. All Cohorts were given accompanying Placebo. Except for the first dose cohort (10 μg dose), each subsequent dose level was authorized after safety review of the previous dosing cohort. Dexmedetomidine hydrochloride sublingual film (having dot) was different from Placebo in appearance.

Results:

Data Sets Analyzed

Safety Population

The safety population includes all randomized subjects who received at least 1 dose of single-blind study drug (n=42).

Pharmacokinetic Population

The PK population includes 28 subjects receiving dexmedetomidine sublingual film. Fourteen subjects who received placebo were not included in the PK analysis. For the subjects receiving placebo only visual analogue scale/sedation (VAS/S), Richmond Agitation-Sedation Scale (RASS), and vital signs (diastolic blood pressure, systolic blood pressure, pulse rate, respiratory rate, and oxygen saturation) versus time plots were provided.

Pharmacodynamic Population

The PD population includes all randomized subjects who received at least 1 dose of single-blind study drug and had post-baseline PD assessments performed (n=42).

Demographic and Other Baseline Characteristics

Overall, the majority of healthy subjects participating in the study (59.5%) were white (non-Hispanic or Latino), a smaller proportion (31.8%) were black (African American). There was 1 (2.4%) Hispanic or Latino subject and 1 (2.4%) Asian subject in the study.

Overall, the number of male and female subjects in the study was comparable: 22 (52.4%) of all subjects were male and 20 (47.6%) were female. The mean age was 44.8 years; the subjects ranged in age from 20 to 65 years; 22 (52.4%) subjects were between 20 and 49 years and 20 (47.6%) subjects were between >49 and 65 years.

The majority of the subjects in the Placebo group were male (64.3%). Among the subjects administered dexmedetomidine sublingual film, the proportion of male (46.4%) and female (53.6%) subjects was comparable.

The physical measurements in the placebo and dexmedetomidine sublingual film group were comparable as well: a mean body mass index (BMI) was 25.50 kg/m² in the subjects administered dexmedetomidine sublingual film and 25.83 kg/m² in the Placebo group.

Pharmacokinetic results: Dexmedetomidine was rapidly absorbed with measurable concentrations observed at 10 minutes for all dose levels and until 8 hours postdose for the 10 μg dose levels and until 10 and 12 hours postdose for 20 μg and 40 μg dose levels, respectively, with a short mean $t_{1/2}$ that ranged between 1.82-2.16 h. Mean±SD DEX plasma concentrations-time profiles at each dose (semi-log scale) plotted against sampling time until 8 hrs postdose are presented in FIG. 8. Dose proportionality assessment indicated that Cmax and AUCs increased in a dose-proportional manner with mean $C_{max}$ ranged between 29.21 and 122.84 ng/L and mean $AUC_{0-inf}$ ranged between 130.62 and 561.57 hr·ng/L. Similar trends were seen with $AUC_{last}$ and $AUC_{0-24}$ (Tables 30 to 32; FIGS. 9A to 9C)).

TABLE 24 summarizes pharmacokinetics parameters of 10 micrograms dexmedetomidine sublingual film in healthy volunteers
10 μg dexmedetomidine sublingual film

| Subject ID | $C_{max}$ (ng/L) | $T_{max}$ (hr) | $t_{1/2}$ (hr) | $AUC_{last}$ (hr*ng/L) | $AUC_{0-INF}$ (hr*ng/L) |
|---|---|---|---|---|---|
| 1001 | 37.94 | 1.5 | 2.06 | 179.19 | 201.32 |
| 1002 | 18.27 | 1.00 | 1.17 | 49.45 | 58.27 |
| 1005 | 33.28 | 2.00 | 1.86 | 116.63 | 140.07 |
| 1007 | 35.74 | 2.00 | 2.95 | 142.22 | 168.59 |
| 1009 | 24.15 | 3.02 | 2.70 | 102.76 | |
| 1011 | 30.87 | 1.00 | 2.75 | 114.35 | 138.82 |
| 1012 | 24.53 | 1.50 | 2.58 | 98.28 | |
| 1016 | 35.19 | 2.00 | 1.24 | 119.28 | 129.17 |
| N | 8 | 8 | 8 | 8 | 6 |
| Mean | 30 | 1.752 | 2.163 | 115.271 | 139.37 |
| SD | 6.930 | 0.66 | 0.693 | 37.05 | 47.69 |
| CV % | 23.1 | 37.62 | 32.0 | 32.1 | 34.22 |
| Min | 18.27 | 1.00 | 1.17 | 49.45 | 58.27 |
| Median | 32.08 | 1.75 | 2.32 | 115.49 | 139.45 |
| Max | 37.94 | 3.02 | 2.95 | 179.19 | 201.32 |
| Geometric Mean | 29.214 | 1.65 | 2.051 | 109.22 | 130.62 |
| Geometric CV % | 25.79 | 39.08 | 37.61 | 38.59 | 44.75 |

TABLE 25 summarizes pharmacokinetics parameters of 20 micrograms
dexmedetomidine sublingual film in healthy volunteers
20 µg dexmedetomidine sublingual film

| Subject ID | $C_{max}$ (ng/L) | $T_{max}$ (hr) | $t_{1/2}$ (hr) | $AUC_{last}$ (hr*ng/L) | $AUC_{0\text{-}INF}$ (hr*ng/L) |
|---|---|---|---|---|---|
| 2001 | 0.00 | | | 0.00 | 0.00 |
| 2003 | 83.08 | 1.00 | 2.2 | 359.59 | 389.48 |
| 2004 | 65.17 | 2.00 | 1.72 | 259.50 | 279.49 |
| 2007 | 84.90 | 1.50 | 1.60 | 401.79 | 416.92 |
| 2011 | 70.76 | 2.00 | 1.85 | 309.75 | 337.01 |
| 2013 | 85.92 | 1.00 | 1.85 | 307.97 | 330.48 |
| 2016 | 42.34 | 3.00 | 1.97 | 198.79 | 225.81 |
| 2106 | 66.75 | 1.50 | 1.57 | 283.34 | 301.60 |
| N | 8 | 7 | 7 | 8 | 8 |
| Mean | 62.37 | 1.71 | 1.824 | 265.092 | 285.10 |
| SD | 28.982 | 0.70 | 0.221 | 123.337 | 129.91 |
| CV % | 46.47 | 40.75 | 12.1 | 46.5 | 45.57 |
| Min | 0.00 | 1.00 | 1.57 | 0.00 | 0.00 |
| Median | 68.76 | 1.50 | 1.85 | 295.66 | 316.04 |
| Max | 85.92 | 3.00 | 2.20 | 401.79 | 416.92 |
| Geometric Mean | — | 1.601 | 1.813 | — | — |
| Geometric CV % | — | 41.30 | 11.95 | — | — |

TABLE 26 summarizes pharmacokinetics parameters of 40 µg
dexmedetomidine sublingual film in healthy volunteers
40 µg dexmedetomidine sublingual film

| Subject ID | $C_{max}$ (ng/L) | $T_{max}$ (hr) | $t_{1/2}$ (hr) | $AUC_{last}$ (hr*ng/L) | $AUC_{0\text{-}INF}$ (hr*ng/L) |
|---|---|---|---|---|---|
| 3011 | 140.25 | 1.00 | 1.78 | 685.15 | 709.61 |
| 3012 | 78.69 | 2.00 | 2.00 | 427.97 | 461.18 |
| 3013 | 97.01 | 1.07 | 1.76 | 292.84 | 310.29 |
| 3023 | 126.60 | 1.00 | 1.86 | 493.89 | 508.98 |
| 3026 | 135.02 | 1.50 | 1.38 | 482.44 | 499.41 |
| 3032 | 78.06 | 2.00 | | 378.67 | |
| 3114 | 167.99 | 1.00 | 2.05 | 777.66 | 806.08 |
| 3131 | 123.52 | 2.02 | 2.42 | 600.88 | 627.60 |
| 4001 | 109.62 | 1.00 | 1.82 | 419.51 | 446.40 |
| 4022 | 204.03 | 1.00 | 1.82 | 664.47 | 704.50 |
| 4026 | 123.68 | 2.00 | 1.83 | 507.83 | 534.00 |
| 4130 | 143.95 | 2.00 | 1.97 | 772.97 | 798.78 |
| N | 12 | 12 | 11 | 12 | 11 |
| Mean | 127.37 | 1.47 | 1.88 | 542.02 | 582.24 |
| SD | 35.79 | 0.49 | 0.25 | 157.144 | 158.70 |
| CV % | 28.10 | 33.75 | 13.44 | 28.99 | 27.25 |
| Min | 78.06 | 1.00 | 1.38 | 292.84 | 310.29 |
| Median | 125.14 | 1.28 | 1.83 | 500.86 | 534.00 |
| Max | 204.03 | 2.02 | 2.42 | 777.66 | 806.08 |
| Geometric Mean | 122.84 | 1.39 | 1.87 | 520.58 | 561.57 |
| Geometric CV % | 28.87 | 35.22 | 13.7 | 30.84 | 29.65 |

Pharmacodynamic Results:

The sedative effect of dexmedetomidine sublingual film was assessed by RASS and Visual analogue scales/sedation (VAS/S) on day of dexmedetomidine sublingual film dosing. The assessment included:

Time in minutes and seconds from administration of dexmedetomidine sublingual film until RASS of −1;

Time in minutes and seconds from RASS of −1 till resolution of drowsiness;

Time in minutes and seconds from SL administration of dexmedetomidine sublingual film till its complete dissolution or 30 minutes.

Richmond Agitation Sedation Scale

All RASS scores assessed during the study ranged between −2 (Light Sedation) and 0 (Alert and Calm). The baseline score for all subjects was 0 (Alert and Calm). Overall, a total of 14 subjects achieved drowsiness (RASS of −1) across all treatments. Of these, 2 received 10 µg dose group, 4 received 20 µg dose group, 5 received 40 µg dose group, and 3 received Placebo. Two subjects also achieved light sedation (RASS of −2), 1 received 10 µg dose group and the other one received Placebo.

The mean times to achieve drowsiness from baseline for subjects administered dexmedetomidine sublingual film and placebo is summarized in Table 33. Overall, the time to achieve drowsiness was variable across all treatment groups and ranged from 19 minutes to 85 minutes in dexmedetomidine sublingual film groups and from 19 minutes 17 seconds to 107 minutes 29 seconds in placebo group. No statistically significant between-group differences were observed for either 10 µg or 40 µg treatment groups.

The duration from onset of drowsiness (RASS of −1) until resolution for subjects administered dexmedetomidine sublingual film and Placebo is summarized in Table 34. Overall, the duration from onset of drowsiness (RASS of −1) until resolution was variable across all treatment groups and ranged from 05 minutes 05 seconds to 91 minutes. Mean duration in subjects administered dexmedetomidine sublingual film was 48 minutes 24 seconds, and subjects administered placebo presented a mean duration of 37 minutes 25 seconds.

TABLE 27

Achievement of Drowsiness (in minutes:seconds) from Baseline Assessed by RASS of −1

| | Dexmedetomidine sublingual film | | | | | | | |
|---|---|---|---|---|---|---|---|---|
| | Cohort 1 (10 µg) | | Cohort 2 (20 µg) | Cohort 3 (40 µg) | | Cohort 4 (40 µg) | Cohort 3 + 4 (40 µg) | |
| Statistics | Active (N = 8) | Placebo (N = 4) | Active (N = 8) | Active (N = 8) | Placebo (N = 4) | Active (N = 4) | Active (N = 12) | Placebo (N = 6) |
| n | 2 | 2 | 4 | 3 | 1 | 2 | 5 | 1 |
| Mean (SD) | 31:30 (3:32) | 65:47 (58:58) | 59:16 (18:16) | 47:30 (10:27) | 19:17 | 24:00 (7:40) | 38:60 (15:15) | 19:17 |
| Median | 31:30 | 65:47 | 54:20 | 44:20 | 19:17 | 24:00 | 39:00 | 19:17 |
| Min, Max | 29:00, 34:00 | 24:50, 107:29 | 44:00, 85:00 | 39:00, 59:10 | 19:17, 19:17 | 19:00, 29:00 | 19:00, 59:10 | 19:17, 19:17 |

TABLE 27-continued

Achievement of Drowsiness (in minutes:seconds) from Baseline Assessed by RASS of −1

| | Dexmedetomidine sublingual film | | | | | | | |
|---|---|---|---|---|---|---|---|---|
| | Cohort 1 (10 µg) | | Cohort 2 (20 µg) | Cohort 3 (40 µg) | | Cohort 4 (40 µg) | Cohort 3 + 4 (40 µg) | |
| Statistics | Active (N = 8) | Placebo (N = 4) | Active (N = 8) | Active (N = 8) | Placebo (N = 4) | Active (N = 4) | Active (N = 12) | Placebo (N = 6) |
| P-value vs Placebo<sup>a</sup> | 1.000 | | | 0.5000 | | | 0.6667 | |

<sup>a</sup>P-value is based on a non-parametric two-sided (exact) Wilcoxon test.
n-number of subjects who have reached at least RASS of −1 at any time in the first 2 hours

TABLE 28

Duration from RASS of −1 till Resolution of Drowsiness (in minutes:seconds)

| | Dexmedetomidine sublingual film | | | | | | | |
|---|---|---|---|---|---|---|---|---|
| Statistics | Cohort 1 10 µg (N = 8) | Cohort 2 20 µg (N = 8) | Cohort 3 40 µg (N = 8) | Cohort 4 40 µg (N = 4) | Cohort 3 and 4 40 µg (N = 12) | Overall Active<sup>a</sup> (N = 28) | Pooled Placebo<sup>a</sup> (N = 14) | Overall<sup>a</sup> (N = 42) |
| n | 2 | 4 | 3 | 2 | 5 | 11 | 2 | 13 |
| Mean | 84:30 | 53:49 | 28:00 | 32:03 | 29:37 | 48:24 | 37:25 | 46:43 |
| (SD) | (9:12) | (10:56) | (30:29) | (38:07) | (28:52) | (28:45) | (10:38) | (26:44) |
| Median | 84:30 | 52:39 | 15:01 | 32:03 | 15:01 | 59:00 | 37:25 | 45:12 |
| Min, Max | 78:00, 91:00 | 44:00, 66:00 | 6:10, 62:50 | 5:05, 59:00 | 5:05, 62:50 | 5:05, 91:00 | 29:54, 44:56 | 5:05, 91:00 |

<sup>a</sup>Overall Active, Pooled Placebo and Overall columns include assessment counts not subject level counts.
n-number of subjects who have reached at least RASS of −1 at any time in the first 2 hours Visual Analogue Scales/Sedation:

The subjective sedative effect of dexmedetomidine was assessed by means of VAS. Subjects were asked to score their feeling on a 100-mm horizontal scale, with 0 indicating very sleepy and 100 indicating very alert. Overall, VAS scores were variable with the lowest scores being generally observed at the 1.0 and 1.5-hour timepoints for subjects dosed with dexmedetomidine sublingual film. Mean scores observed at pre-dose 0.5, 1, 1.5- and 2-hours following treatment with dexmedetomidine sublingual film or placebo and P-values are presented in Table 29 and FIG. 10. There were no statistically significant between-group differences (Active vs. Placebo) observed in Cohorts 1 (10 µg), Cohort 2 (20 µg) and Cohorts 3 and 4 combined (40 g dose). Statistically significant differences were only seen in Cohort 3 (40 µg). However, the statistical significance in this cohort was also reported for the pre-dose assessment (P<0.05; Table 29) indicating that the study environments and score variability may have affected the outcome.

Dexmedetomidine Sublingual Film Dissolution Time:

A single dose of dexmedetomidine sublingual film was administered sublingually. For 20 g dose cohort, two (2) 10 µg films were administered simultaneously. The drug film was retained in the sublingual cavity until it had dissolved. There was an evaluation every 5 minutes for the first 15 minutes, and then every 15 minutes to determine the time to dissolution of the film. Mean, median, and min and max dissolution time for each treatment group in minutes:seconds are presented in Table 30. Overall, duration from the SL administration of dexmedetomidine sublingual film or Placebo film until its complete dissolution was variable and ranged from 3 minutes to 44 minutes 11 second. Mean (SD) and median dissolution times were similar for dexmedetomidine sublingual film (14:09 (11:33); 11:11, minutes: seconds) and Placebo (13:32 (12:49); 8:28, minutes: seconds) films. No subject presented aberrant oral/buccal anatomy or inflammation during the buccal mucosal irritation examination.

Safety Evaluation:

Based on the results in this study, the following safety conclusions can be made:

There were no deaths or serious TEAEs reported in the study. One subject administered dexmedetomidine sublingual film 10-µg had a decrease in heart rate >30 beats per minute (withdrawal criterion) therefore had become ineligible to participate in Cohort 3. An overall summary of AEs is provided in Table 31. A total of 52 TEAEs were reported by 25 of the 28 subjects (89%) administered dexmedetomidine sublingual film and 20 TEAEs were reported by 10 of the 14 subjects (71%) administered placebo. All TEAEs were recovered by the end of the study.

Subjects administered dexmedetomidine sublingual film reported TEAEs with an incidence of 75% for 10 µg dose group, 88% for 20 µg dose group and 100% for 40 µg dose group. Drug-related TEAEs were reported with an incidence of 75% following administration of 10 µg dose group, 88% following administration of 20 µg dose group, 92% following administration of g dose group and 64% following administration of placebo.

The most experienced TEAE during the study was somnolence, which was reported with a slightly higher frequency at doses of 20 µg and 40 µg (75% each) compared to the 10 µg dose and placebo (50% each) (Table 32). The majority of TEAEs were mild in severity in all treatment groups with only few moderate TEAEs reported. Moderate TEAEs were experienced following administration of 10 µg dose (¹/₁₂; 8%), 40 µg dose (²/₃₀; 7%) and administration of placebo (⁴/₂₀; 20%). No severe TEAEs were reported in this study.

No subject dosed in this study required hemodynamic/medical interventions for maintaining BP, cardiac interventions for maintaining heart rate or respiratory interventions for maintaining oxygen saturation. No subject was withdrawn due to a TEAE. The data is further depicted in FIGS. 11 to 15.

Two subjects presented symptomatic changes in vital signs that were considered clinically significant and reported as vital signs related TEAEs. One subject administered placebo had a decrease in DBP and SBP that were recorded as drug-related TEAEs of moderate and mild intensity, respectively and 1 subject administered 40 µg dose group had decreases in heart rate that were recorded as 2 drug-related TEAEs of mild intensity. All TEAEs were resolved within 1 day from onset.

There were no clinically significant changes in laboratory parameters and ECG assessments. No physical examination finding was considered clinically significant by the investigator. All neurological examinations performed during the study were normal and no subject presented aberrant oral/buccal anatomy or inflammation during the buccal mucosal irritation examination.

TABLE 29

Summary of Visual Analogue Scales/Sedation

| Timepoint | Statistics | Cohort 1 (10 µg) | | Cohort 2 (20 µg) | | Cohort 3 (40 µg) | | Cohort 4 (40 µg) | | Cohort 3 + 4 (40 µg) | | Overall (N = 42) |
|---|---|---|---|---|---|---|---|---|---|---|---|---|
| | | Active (N = 8) | Placebo (N = 4) | Active (N = 8) | Placebo (N = 4) | Active (N = 8) | Placebo (N = 4) | Active (N = 4) | Placebo (N = 2) | Active (N = 12) | Placebo (N = 6) | |
| Pre-dose | n | 8 | 4 | 8 | 4 | 8 | 4 | 4 | 2 | 12 | 6 | 60 |
| | Mean | 95.5 | 97.8 | 97.4 | 86.5 | 74.8 | 100 | 86.8 | 70.5 | 78.8 | 90.2 | 87.5 |
| | (SD) | (12.73) | (4.50) | (6.25) | (21.30) | (35.29) | (0.00) | (25.84) | (41.72) | (31.78) | (24.09) | (24.18) |
| | P-value | 1 | | 0.2384 | | 0.0485* | | 0.8 | | 0.139 | | |
| 0.5 Hour | n | 8 | 4 | 8 | 4 | 8 | 4 | 4 | 2 | 12 | 6 | 60 |
| | Mean | 78.8 | 90.0 | 74.4 | 55.8 | 73.0 | 93.0 | 75.0 | 64.5 | 73.7 | 83.5 | 76.3 |
| | (SD) | (23.50) | (11.52) | (20.87) | (35.61) | (25.72) | (12.68) | (22.67) | (48.79) | (23.71) | (28.09) | (24.24) |
| | P-value | 0.4788 | | 0.2788 | | 0.0465* | | 0.8 | | 0.2203 | | |
| 1.0 Hour | n | 5 | 4 | 8 | 4 | 8 | 4 | 4 | 2 | 12 | 6 | 57 |
| | Mean | 67.6 | 93.8 | 43.0 | 48.5 | 42.8 | 94.3 | 71.5 | 64.0 | 52.3 | 84.2 | 61.7 |
| | (SD) | (33.30) | (6.65) | (38.26) | (48.50) | (32.98) | (10.18) | (22.61) | (49.50) | (32.13) | (28.22) | (34.97) |
| | P-value | 0.3175 | | 0.9737 | | 0.0121* | | 0.8 | | 0.0691 | | |
| 1.5 Hour | n | 8 | 4 | 8 | 4 | 7 | 3 | 4 | 2 | 11 | 5 | 56 |
| | Mean | 63.0 | 80.3 | 43.8 | 53.5 | 53.0 | 99.7 | 78.8 | 70.0 | 62.4 | 87.8 | 65.0 |
| | (SD) | (29.69) | (30.18) | (40.02) | (48.64) | (41.68) | (0.58) | (25.59) | (42.43) | (37.52) | (26.72) | (36.06) |
| | P-value | 0.4586 | | 0.4869 | | 0.0167* | | 0.9333 | | 0.0627 | | |
| 2.0 Hour | n | 8 | 4 | 8 | 4 | 7 | 3 | 3 | 2 | 10 | 5 | 54 |
| | Mean | 81.8 | 74.5 | 54.9 | 59.0 | 50.9 | 99.7 | 73.0 | 72.5 | 57.5 | 88.8 | 67.9 |
| | (SD) | (25.97) | (42.19) | (38.92) | (47.79) | (36.22) | (0.58) | (24.88) | (37.48) | (33.56) | (23.93) | (34.28) |
| | P-value | 0.9253 | | 0.8848 | | 0.0167* | | 0.8 | | 0.0513 | | |

P-values are calculated for Active vs Placebo for each cohort.
P-value based on non-parametric two-sided (exact) Wilcoxon test.
*Statistically significant between-group difference (Active vs Placebo)

TABLE 30

Duration from SL Administration (in minutes:seconds) of Dexmedetomidine sublingual film till its Complete Dissolution (PD Population)

| | Dexmedetomidine sublingual film | | | | | | | |
|---|---|---|---|---|---|---|---|---|
| Statistics | Cohort 1 10 µg (N = 8) | Cohort 2 20 µg (N = 8) | Cohort 3 40 µg (N = 8) | Cohort 4 40 µg (N = 4) | Cohort 3 and Cohort 4 40 µg (N = 12) | Overall Active* (N = 28) | Pooled Placebo* (N = 14) | Overall* (N = 42) |
| n | 8 | 8 | 8 | 4 | 12 | 28 | 13 | 41 |
| Mean (SD) | 9:03 (7:52) | 23:49 (12:36) | 14:26 (10:04) | 4:26 (2:24) | 11:06 (9:30) | 14:09 (11:33) | 13:32 (12:49) | 13:58 (11:49) |
| median | 5:11 | 29:01 | 14:05 | 3:23 | 8:09 | 11:11 | 8:28 | 8:28 |
| Min, Max | 3:00, 24:30 | 8:00, 44:01 | 3:18, 29:01 | 3:00, 8:00 | 3:00, 29:01 | 3:00, 44:01 | 3:00, 44:11 | 3:00, 44:11 |

*Overall Active, Pooled Placebo and Overall columns include assessment counts not subject level counts.

TABLE 31

Summary of Adverse Events

| | Dexmedetomidine sublingual film | | | | | | | |
|---|---|---|---|---|---|---|---|---|
| | Cohort 1 10 μg (n = 8) n (%) | Cohort 2 20 μg (n = 8) n (%) | Cohort 3 40 μg (N = 8) n (%) | Cohort 4 40 μg (N = 4) n (%) | Cohort 3 and Cohort 4 40 μg (N = 12) n (%) | Overall (N = 28) n (%) | Placebo (N = 14) n (%) | Overall (N = 42) n (%) |
| AEs reported | | | | | | | | 75 |
| TEAEs reported | 12 | 10 | 24 | 6 | 30 | 52 | 20 | 72 |
| Subjects with at least one TEAE[a] | 6 (75.0) | 7 (87.5) | 8 (100.0) | 4 (100.0) | 12 (100.0) | 25 (89.3) | 10 (71.4) | 35 (83.3) |
| Subjects with at least one drug-related TEAE[a] | 6 (75.0) | 7 (87.5) | 8 (100.0) | 3 (75.0) | 11 (91.7) | 24 (85.7) | 9 (64.3) | 33 (78.6) |
| TEAEs relationship[b] | | | | | | | | |
| Possibly related | 4 (33.3) | 2 (20.0) | 5 (20.8) | 0 | 5 (16.7) | 11 (21.2) | 4 (20.0) | 15 (20.8) |
| Probably related | 2 (16.7) | 0 | 7 (29.2) | 1 (16.7) | 8 (26.7) | 10 (19.2) | 3 (15.0) | 13 (18.1) |
| Definitely related | 3 (25.0) | 8 (80.0) | 12 (50.0) | 3 (50.0) | 15 (50.0) | 26 (50.0) | 10 (50.0) | 36 (50.0) |
| Related | 0 | 0 | 0 | 0 | 0 | 0 | 1 (5.0) | 1 (1.4) |
| Unrelated/unlikely | 3 (25.0) | 0 | 0 | 2 (33.3) | 2 (6.7) | 5 (9.6) | 2 (10.0) | 7 (9.7) |
| TEAEs severity[b] | | | | | | | | |
| Mild | 11 (91.7) | 10 (100.0) | 22 (91.7) | 6 (100.0) | 28 (93.3) | 49 (94.2) | 16 (80.0) | 65 (90.3) |
| Moderate | 1 (8.3) | 0 | 2 (8.3) | 0 | 2 (6.7) | 3 (5.8) | 4 (20.0) | 7 (9.7) |
| Severe | 0 | 0 | 0 | 0 | 0 | 0 | 0 | 0 |
| STEAEs reported[b] | 0 | 0 | 0 | 0 | 0 | 0 | 0 | 0 |
| Subjects with at least one STEAE[a] | 0 | 0 | 0 | 0 | 0 | 0 | 0 | 0 |
| Subjects with at least one study drug-related STEAE[a] | 0 | 0 | 0 | 0 | 0 | 0 | 0 | 0 |
| Subjects with at least one TEAE leading to study discontinuation[a] | 0 | 0 | 0 | 0 | 0 | 0 | 0 | 0 |
| Deaths[a] | 0 | 0 | 0 | 0 | 0 | 0 | 0 | 0 |

AE: adverse event; N: number of subjects; n (%): number and percent of subjects included; SAE: serious adverse event; STEAE: serious treatment-emergent adverse event; TEAE: treatment-emergent adverse event
Notes:
Overall Active, Pooled Placebo and Overall columns include assessment counts not subject level counts.
Possibly Related, Probably Related, Related, or Definitely Related categories are counted under Drug-Related.
[a]Percentages are based on the number of subjects in the Safety popluation in each treatment group.
[b]Percentages are based on the total number of treatment-emergent adverse events reported in each treatment group

TABLE 32

Treatment-Emergent Adverse Events Reported in Two or More Subjects Overall

| | Dexmedetomidine sublingual film | | | | | | | |
|---|---|---|---|---|---|---|---|---|
| System Organ Class Preferred Term | Cohort 1 10 μg (N = 8) n (%) | Cohort 2 20 μg (N = 8) n (%) | Cohort 3 40 μg (N = 8) n (%) | Cohort 4 40 μg (N = 4) n (%) | Cohort 3 and Cohort 4 40 μg (N = 12) n (%) | Overall (N = 28) n (%) | Placebo (N = 14) n (%) | Overall (N = 42) n (%) |
| Subjects with at least one TEAE | 6 (75.0) | 7 (87.5) | 8 (100.0) | 4 (100.0) | 12 (100.0) | 25 (89.3) | 10 (71.4) | 35 (83.3) |
| Nervous system disorders | 5 (62.5) | 7 (87.5) | 7 (87.5) | 2 (50.0) | 9 (75.0) | 21 (75.0) | 8 (57.1) | 29 (69.0) |
| Somnolence | 4 (50.0) | 6 (75.0) | 7 (87.5) | 2 (50.0) | 9 (75.0) | 19 (67.9) | 7 (50.0) | 26 (61.9) |
| Dizziness | 1 (12.5) | 1 (12.5) | 6 (75.0) | 0 | 6 (50.0) | 8 (28.6) | 2 (14.3) | 10 (23.8) |
| Headache | 1 (12.5) | 1 (12.5) | 0 | 0 | 0 | 2 (7.1) | 3 (21.4) | 5 (11.9) |
| Gastrointestinal disorders | 2 (25.0) | 1 (12.5) | 3 (37.5) | 1 (25.0) | 5 (33.3) | 7 (25.0) | 2 (14.3) | 9 (21.4) |
| Nausea | 1 (12.5) | 0 | 2 (25.0) | 0 | 2 (16.7) | 3 (10.7) | 0 | 3 (7.1) |
| Dry Mouth | 0 | 0 | 1 (12.5) | 1 (25.0) | 2 (16.7) | 2 (7.1) | 1 (7.1) | 3 (7.1) |
| Vomiting | 0 | 0 | 1 (12.5) | 0 | 1 (8.3) | 2 (7.1) | 1 (7.1) | 3 (7.1) |

TABLE 32-continued

Treatment-Emergent Adverse Events Reported in Two or More Subjects Overall

| | Dexmedetomidine sublingual film | | | | | | | |
|---|---|---|---|---|---|---|---|---|
| System Organ Class Preferred Term | Cohort 1 10 µg (N = 8) n (%) | Cohort 2 20 µg (N = 8) n (%) | Cohort 3 40 µg (N = 8) n (%) | Cohort 4 40 µg (N = 4) n (%) | Cohort 3 and Cohort 4 40 µg (N = 12) n (%) | Overall (N = 28) n (%) | Placebo (N = 14) n (%) | Overall (N = 42) n (%) |
| General disorders and administration site conditions | 1 (12.5) | 0 | 2 (25.0) | 1 (25.0) | 3 (25.0) | 4 (14.3) | 1 (7.1) | 5 (11.9) |
| Fatigue | 1 (12.5) | 0 | 2 (25.0) | 0 | 2 (16.7) | 3 (10.7) | 0 | 3 (7.1) |

Conclusion: Overall, PK, PD and safety results presented in this study support further development of dexmedetomidine sublingual film for the acute treatment of agitation associated with dementia, schizophrenia, and bipolar disorders as a minimally invasive rapid-delivery dosage form of dexmedetomidine.

Example 5: Clinical Study of the Efficacy (Sedation and Anti-Agitation), Pharmacokinetics and Safety of Dexmedetomidine Infused Intravenously in Subjects Suffering from Schizophrenia A key objective of the study was to determine the optimal intravenous (IV) dose of dexmedetomidine hydrochloride in the target population in terms of efficacy and safety to achieve arousable sedation (RASS of −1) which can be reversed by verbal stimulation. When this goal was achieved in each participant, the IV infusion of dexmedetomidine hydrochloride ceased. Another Key Objective of the study was to determine the reduction in the level of agitation, as determined by their PEC score, at the doses to achieve a RASS of −1.

In addition, the following Secondary Objectives were:
1. Determine how rapidly the drug can be administered up to the total dose needed to achieve RASS−1.
2. Determine how long the calming effect persists after discontinuation of study drug administration.
3. Determine whether any adverse effects on blood pressure, heart rate, or respiratory drive occurs before or coincident with the achievement of Primary Objective. Stopping rules for blood pressure and heart rate, indicating a clinically significant event, are:
   drop in systolic BP<90 mm of Hg.
   drop in diastolic BP<60 mm of Hg
   drop below 50 beats per minute Participants were provided written informed consent before any study related procedures were performed. All participants were screened for inclusion and exclusion criteria. The participants were admitted to the site at screening (Day −1), the day before the infusion. Baseline assessments were performed on Day −1, as well as on the day of infusion (Day 1). The participants were on Day 1 prepared for the infusion, infused for up to 3 hours and monitored for resolution of sedation and any decreases in blood pressure or heart rate which met stopping criteria. The participants were not discharged from the research unit until three hours after resolution of any reduction in the level of arousal (e.g., RASS−1) and/or resolution of any decrease in blood pressure or heart rate meeting stopping criteria. The Principal Investigator had discretion to keep the participant overnight at the site the evening of Day 1 for extended monitoring and then discharge home the participant on Day 2 if the Principal Investigator or designee determined that the participant has returned to their baseline state.

The study population included 14 participants, 10 active and 4 placebo. Patients 5, 7, 8 and 9 received placebo. Patients 1, 2, 3, 4, 11, 12, 14, 16, 17, 18 were infused with intravenous dexmedetomidine hydrochloride, starting at a rate of 0.2 mcg/kg/hr, and rising by 0.1 mcg/kg/hr every 30 minutes until stopping criteria were reached up or to a maximum duration of 3 hours (Table 33). Participants randomized to placebo received a matching intravenous infusion of placebo solution.

TABLE 33

Study Treatments

| Treatment | Formulation | Frequency |
|---|---|---|
| Dexmedetomidine hydrochloride | PRECEDEX® | Continuous infusion, increment every 30 minutes |
| Placebo | Normal Saline | Continuous infusion |

Once the participant was drowsy (RASS−1), the infusion was stopped. The maximum total dose administered was 1.6 mcg/kg/hr, when either the desired level of sedation was achieved or the maximum allowable decrease in either systolic or diastolic blood pressure or heart rate occurred.

The participants were continuously monitored during the study by the site personnel, including monitoring blood pressure and heart rate. Intermittent electrocardiograms were taken from the start of the infusion through resolution of the sedation and/or any adverse effects on blood pressure or heart rate.

Whenever the above stopping criteria was met, the site stopped the infusion and the site continued to monitor the participant's vital signs every 15 minutes until the participant has reached their baseline parameters or in the judgment of the principal investigator the participant has reached a stable and acceptable level of blood pressure and heart rate. Return to baseline parameters is defined as BP falling within 15 mm of Hg of baseline reading prior to drug administration or HR falling within 10 beats per minute of baseline reading prior to drug administration.

In the event the investigator deemed the fall in blood pressure or heart rate to be clinically significant, suitable remedial drugs could be administered in addition to termination of the dexmedetomidine hydrochloride infusion, based on investigator's judgement.

Adverse events (AEs), including serious adverse events (SAEs), were assessed, recorded, and reported in accordance with FDA guidance. Should any SAE occur, the study would be stopped until a cause for the SAE was determined.

Efficacy Assessment:

(1) Richmond Agitation Sedation Scale (RASS): The desired endpoint was how rapidly drowsiness (RASS-1) could be achieved without causing changes in heart rate or blood pressure greater than that specified by the protocol. The study also monitored how long the participant remained at that level of sedation; sedation was considered resolved when the participant was awake and spontaneously responding.

(2) PANSS: Change from baseline for mildly agitated patients (3) Clinical Global Impression of Improvement (CGI-I) (National Institute of Mental Health 1976) ranging from 1 (very much improved) to 7 (very much worse) compared with baseline. Each participant was rated, based on the severity of agitation, at 15 and 30 minutes for every dose infusion, at the endpoint, and at the time the participant returned to baseline (in terms of level of arousal). CGI-I focused on the severity of agitation rather than the severity of the illness.

(4) After the infusion was stopped, the participants were judged for the suitability for discharge by the principal investigator or designee as witnessed by a return to their baseline level of alertness and awareness with no impairment in balance, gait, and reaction time as determined by the principal investigator or designee.

Results (A) Efficacy Study

RASS (Richmond Agitation-Sedation Scale)

9 out of 10 patients in the treatment arm (subjects 1-3, 11, 12, 14, and 16-18) achieved a RASS score of at least −1, while no patients in the placebo arm (subjects 5, and 7-9) experienced meaningful sedation (see FIG. 16 and Table 34).

TABLE 34

Depicts the RASS score of Schizophrenia patients receiving infusion of dexmedetomidine hydrochloride and normal saline

| Infusion (minutes) | RASS values after infusion start Patient No. | | | | | | | | | | | | | |
|---|---|---|---|---|---|---|---|---|---|---|---|---|---|---|
| | 1 | 2 | 3 | 4 | 5 | 7 | 8 | 9 | 11 | 12 | 14 | 16 | 17 | 18 |
| | T | T | T | T | P | P | P | P | T | T | T | T | T | T |
| 0 | 1 | 3 | 1 | 1 | 1 | 1 | 1 | 1 | 1 | 1 | 1 | 1 | 1 | 0 |
| 15 | −2 | | | | | | | | | | | | | −1 |
| 30 | | 0 | 0 | 0 | 1 | 1 | 1 | 1 | 0 | 0 | 0 | 0 | 0 | |
| 45 | | 0 | | | | | | | | | | | −1 | |
| 60 | | 0 | −1 | 0 | 1 | 1 | 0 | 1 | 0 | 0 | 0 | 0 | | |
| 75 | −1 | | | | | | | | −1 | | −1 | −1 | | |
| 90 | | | | 0 | 1 | 0 | 0 | 1 | | 0 | | | | |
| 105 | | | | | | | | | | | | | | |
| 120 | | | | 0 | 0 | 0 | 0 | 1 | | −1 | | | | |
| 135 | | 0 | | | | | | | | | | | | |
| 150 | | | | | 0 | 0 | 0 | 1 | | | | | | |
| 165 | | | | | | | | | | | | | | |
| 180 | | | | | 0 | 0 | 0 | 1 | | | | | | |

T-treatment arm; P-placebo arm

PEC (PANSS Excitement Component)

9 out of 10 patients in the treatment arm (subjects 1-4, 11, 12, 14, 16 and 17) had agitation reduced to a minimum (as measured by a PEC score of 7 or below) (see Table 35 and FIG. 17).

TABLE 35

Depicts the PEC data of schizophrenia patients receiving infusion of dexmedetomidine and normal saline

| Time (Mins) | PEC values after infusion start Patient No. | | | | | | | | | | | | | |
|---|---|---|---|---|---|---|---|---|---|---|---|---|---|---|
| | 1 | 2 | 3 | 4 | 5 | 7 | 8 | 9 | 11 | 12 | 14 | 16 | 17 | 18 |
| | T | T | T | T | P | P | P | P | T | T | T | T | T | T |
| 0 | 9 | 16 | 12 | 9 | 11 | 12 | 9 | 13 | 13 | 13 | 10 | 10 | 10 | |
| 15 | 5 | 13 | 12 | 9 | 10 | 12 | 9 | 13 | 13 | 13 | 9 | 9 | 8 | |
| 30 | | 12 | 10 | 8 | 9 | 9 | 8 | 12 | 11 | 13 | 6 | 6 | 7 | |
| 45 | | 11 | 7 | 8 | 9 | 8 | 8 | 12 | 9 | 10 | 6 | 6 | 5 | |
| 60 | | 9 | 6 | 7 | 8 | 8 | 8 | 13 | 9 | 10 | 5 | 7 | | |
| 75 | | 7 | | 7 | 8 | 8 | 7 | 11 | 7 | 8 | 5 | 5 | | |
| 90 | | | | 7 | 7 | 9 | 7 | 11 | | 6 | | | | |
| 105 | | | | 7 | 8 | 8 | 7 | 10 | | 5 | | | | |
| 120 | | | | 7 | 8 | 8 | 7 | 10 | | | | | | |
| 135 | | | | 7 | 8 | 7 | 7 | 9 | | | | | | |
| 150 | | | | | 8 | 7 | 7 | 9 | | | | | | |
| 165 | | | | | 8 | 8 | 7 | 9 | | | | | | |
| 180 | | | | | 8 | 8 | 7 | 10 | | | | | | |

T-treatment arm; P-placebo arm (B) Pharmacokinetic Study: (PK Study)

The level of dexmedetomidine in the plasma of patients was also measured over the time of infusion. The results are tabulated in Table 36. The maximum dexmedetomidine concentrations in schizophrenic patients ($C_{max}$) ranged from about 22.45 µg/mL to about 406.3 µg/mL. Time to reach $C_{max}$ ranged from about 15 minutes to about 105 minutes. Mean infusion rate is 0.36 mcg/kg/hr with the maximum rate ranging from about 0.2 mcg/kg/hr to about 0.6 mcg/kg/hr (see FIGS. 18 to 20).

TABLE 36 depicts the plasma concentrations (pg/mL) of schizophrenia patients at different timepoints during the infusion of dexmedetomidine hydrochloride and normal saline

| Time (Mins) | 1 T | 2 T | 3 T | 4 T | 5 P | 7 P | 8 P | 9 P | 11 T | 12 T | 14 T | 16 T | 17 T | 18 T |
|---|---|---|---|---|---|---|---|---|---|---|---|---|---|---|
| 0 | BLQ | BLQ |  | BLQ | BLQ | BLQ | BLQ | BLQ | BLQ | BLQ | BLQ | BLQ | BLQ | BLQ |
| 15 | 22.45 |  |  | BLQ | BLQ | BLQ | BLQ | BLQ | 41.01 | BLQ | BLQ | 2.56 | 15.87 | 48.36 |
| 30 | 14.72 | BLQ | BLQ | BLQ | BLQ | BLQ | BLQ | BLQ | 62.91 | 44.87 | 52.66 | 15.59 | BLQ | 54.53 |
| 45 |  |  | BLQ | BLQ | BLQ | BLQ | BLQ | BLQ | 124.07 | 50.51 | 46.53 | 41.17 | 39.93 |  |
| 60 |  |  |  | BLQ | BLQ | BLQ | BLQ | BLQ | 150.47 | 108.6 | 406.3 | 67.88 |  |  |
| 75 |  | BLQ |  | BLQ | BLQ | BLQ | BLQ | BLQ |  | 158.54 | 72.26 |  |  |  |
| 90 |  |  |  | 44.3 | BLQ | BLQ | BLQ | BLQ |  | 237.83 |  |  |  |  |
| 105 |  |  |  | BLQ | BLQ | BLQ | BLQ | BLQ |  | 267.3 |  |  |  |  |
| 120 |  |  |  | BLQ | BLQ | BLQ | BLQ | BLQ |  |  |  |  |  |  |
| 135 |  |  |  |  | BLQ | BLQ | BLQ | BLQ |  |  |  |  |  |  |
| 150 |  |  |  |  | BLQ | BLQ | BLQ | BLQ |  |  |  |  |  |  |
| 165 |  |  |  |  | BLQ | BLQ | BLQ | BLQ |  |  |  |  |  |  |
| 180 |  |  |  |  | BLQ | BLQ | BLQ | BLQ |  |  |  |  |  |  |
| Total duration of infusion (Mins) | 19 | 75 | 60 | 149 | 180 | 180 | 180 | 179 | 68 | 103 | 64 | 66 | 36 | 30 |

*BLQ-below limit of quantification
T-Treatment; P-Placebo

Discussion: The administration of dexmedetomidine hydrochloride by the IV route produced a >=50% reduction in PEC score in a total of 7 of 10 subjects, with one subject (Patient 1) responding at a Cmax of 22 µg/mL. 5 of 10 subjects (Patients 1, 2, 3, 16 and 17) exhibited a 40% reduction in PEC score at a Cmax of =<72 µg/mL. The good response rates at these plasma exposure levels indicated that sublingual dexmedetomidine hydrochloride administration at similar or higher $C_{max}$ exposure levels achieved good anti-agitation effects. As demonstrated in Example 7 above, sublingual dexmedetomidine hydrochloride administered to healthy volunteers produced good plasma exposure levels at doses of 10, 20 and 40 micrograms, indicating that such doses were suitable for obtaining good anti-agitation effects (e.g., as measured by a reduction in PEC score) in agitated subjects, including subjects with schizophrenia, without also producing clinically meaningful detrimental effects on blood pressure and/or heart rate.

Example 6: A Phase III Multicenter, Randomized, Double-Blind, Placebo-Controlled Study to Determine Efficacy and Safety of Dexmedetomidine Sublingual Film in Agitation Associated with Schizophrenia Objectives:

Primary Objective

To determine if a single dose of Dexmedetomidine sublingual film effectively reduced symptoms of acute agitation associated with schizophrenia, schizoaffective disorder or schizophreniform disorder assessed using the Positive and Negative Syndrome Scale-Excited Component (PEC) change from baseline as compared to placebo.

Key Secondary Objective:

To determine the earliest time where an effect on agitation was apparent as measured by the change from baseline in PEC total score in contrast with placebo.

Other Exploratory Objectives:
1. Overall clinical improvement after drug administration as measured by the Clinical Global Impression-Improvement Scale (CGI-I) score.
2. Agitation-Calmness Evaluation Scale (ACES) scores at 2, 4 and 8 hrs after dose administration.
3. Change from baseline in total PEC score over time measured from 10 min through 24 hrs after dosing.
4. PEC Responders and CGI-I Responders at 2 hours following dose of Dexmedetomidine sublingual film, compared with placebo:
   a. PEC responders were defined as those who achieve at least a 40% reduction in PEC total score from baseline at or before 2 hours post-dose.
   b. CGI-I responders were defined as subjects with a score of 1 or 2 on the CGI-I scale (the CGI-I non-responders were defined as subjects with scores from 3 to 7 at 2 hours).
5. Time to rescue medication during the entire 24 hrs Post-treatment Evaluation Period for subjects who received Dexmedetomidine sublingual film compared to placebo.
6. Proportion of subjects per treatment group who received rescue medication by 4 hrs and within 24 hrs after dosing.
7. Duration of calming effect as described by the change from baseline in PEC total score, and ACES score at 2, 4 and 8 hrs after dosing.
8. Describe effect on overall psychotic symptoms and subscales (PANSS total, positive, negative, and general psychopathology subscales)

9. Determine the safety profile of Dexmedetomidine sublingual film as measured by vital signs and treatment-emergent adverse event reports and vital signs.
10. Describe the overall tolerability in terms of adverse event reports and local site (oral/sublingual) tolerability of oral film.
11. Descriptive pharmacokinetics of Dexmedetomidine sublingual film in the patient population.
12. Determine patient acceptability, taste and likability of study medication using likert scales to capture subject's acceptability, opinion on taste and questions regarding likability.

Study Design: This was a randomized, double-blind, placebo-controlled Phase III study assessing efficacy, safety and tolerability of dexmedetomidine sublingual film dosing in adult (18-75 years old) males and females with acute agitation associated with schizophrenia, schizoaffective disorder, or schizophreniform disorder. This in-clinic study randomized subjects 1:1:1 to receive Dexmedetomidine sublingual film (180 µg or 120 µg dose of DEX) or matching placebo film. The randomization was be stratified by age; age <65 and age ≥65.

Eligible subjects (acutely agitated subjects with schizophrenia, schizoaffective, or schizophreniform disorder) might be identified in outpatient clinics, mental health, psychiatric or medical emergency services including medical/psychiatric observation units, or as newly admitted to a hospital setting for acute agitation or already hospitalized for chronic underlying conditions. Subjects were domiciled in a clinical research setting or hospitalized to remain under medical supervision while undergoing screening procedures to assess eligibility.

Upon confirmation of eligibility, subjects were randomized to receive either 180 µg or 120 µg Dexmedetomidine sublingual film or matching placebo. At the time of dosing, patients were instructed on how to take the investigational product sublingually, and that they should retain the investigational product in the sublingual cavity until dissolved. The patient was self-administered under the supervision of a trained staff member. If the patient was unable to self-administer, the event was recorded, and the subject's participation was concluded. In the event of persistent or recurrent agitation, investigators might chose to repeat dose at 90 µg or 60 µg (half of 180 µg or 120 µg film) after the 2-hour time point as measured by a PEC change from baseline <40% but in the absence of safety concerns. Patients could only be re-dosed if they were hemodynamically stable, not hypotensive (must be greater than 90/60 diastolic/systolic) and not bradycardic (must be greater than 60 bpm). Patients also could not be re-dosed if they were orthostatic (a drop of 20 points in either SBP or DBP) or if they were experiencing an AE that when assessed by the PI precludes redosing. The maximum number of repeat doses per subject was 2, during the 12 hours post first dose. Doses might not be administered sooner than 2 hours after a previous dose. If the PEC change from baseline was >40% repeat dosing was not allowed.

Participants were also be evaluated for local irritation around the area where the film was placed. Efficacy and safety assessments were conducted periodically before and after dosing. All efforts should be made to have the patient perform all assessments as per protocol. Vital Signs, pulse oximetry, and ECG with rhythm strip were measured as per schedule of assessments (Table 33), prior to any PK assessments. Participants were allowed water as desired 15 minutes after completion of dosing. Safety and tolerability assessments were conducted at various timepoints.

Any abnormal vital sign measurement, clinical laboratory test, physical examination finding, or ECG parameter deemed clinically significant by the investigator repeated, including test results obtained on the final study day or upon early termination. For any test abnormality deemed clinically significant, repeat analysis was performed during the follow-up period and until the value returns to baseline (or within normal limits) or the investigator deems the abnormality to be stable and no longer of clinical concern.

Approximately 4 mL of venous blood (to obtain a minimum of 1.2 mL plasma) was taken into K2-EDTA tubes at set time intervals for the determination of plasma concentrations of study drug (or Placebo). The PK plasma samples were collected within 10 min of the scheduled sampling time on Day 1.

Number of subjects (planned): Approximately 375 subjects were enrolled at up to 30 study sites in the United States.

Diagnosis and Main Criteria for Eligibility:
Inclusion Criteria:
(1) Male and female patients between the ages of 18 to 75 years, inclusive.
(2) Patients who had met DSM-5 criteria for schizophrenia, schizoaffective, or schizophreniform disorder.
(3) Patients who were judged to be clinically agitated at Baseline with a total score of ≥14 on the 5 items (poor impulse control, tension, hostility, uncooperativeness, and excitement) comprising the PANSS Excited Component (PEC).
(4) Patients who had a score of ≥4 on at least 1 of the 5 items on the PEC or PEC score at baseline
(5) Patients who read, understood and provided written informed consent.
(6) Patients who were in good general health prior to study participation as determined by a detailed medical history, physical examination, 12-lead ECG with rhythm strip, blood chemistry profile, hematology, urinalysis and in the opinion of the Principal Investigator.
(7) Female participants, if of child-bearing potential and sexually active, and male participants, if sexually active with a partner of child-bearing potential, who agreed to use a medically acceptable and effective birth control method throughout the study and for one week following the end of the study. Medically acceptable methods of contraception that might be used by the participant and/or his/her partner included abstinence, birth control pills or patches, diaphragm with spermicide, intrauterine device (IUD), condom with foam or spermicide, vaginal spermicidal suppository, surgical sterilization and progestin implant or injection. Prohibited methods included: the rhythm method, withdrawal, condoms alone, or diaphragm alone.

Exclusion Criteria:
(1) Patients with agitation caused by acute intoxication, including positive identification of alcohol by breathalyzer or drugs of abuse (with the exception of THC) during urine screening.
(2) Patients treated within 4 hours prior to study drug administration with benzodiazepines, other hypnotics or oral or short-acting intramuscular antipsychotics.
(3) Treatment with alpha-1 noradrenergic blockers (terazosin, doxazosin, tamsulosin, alfuzosin, or prazocin) or other prohibited medications.
(4) Patients with significant risk of suicide or homicide per the investigator's assessment, or any patient with an answer of "yes" to item 4 or 5 on the CSSRS.

(5) Female patients who had a positive pregnancy test at screening or are breastfeeding.
(6) Patients who had hydrocephalus, seizure disorder, or history of significant head trauma, stroke, transient ischemic attack, subarachnoid bleeding, brain tumor, encephalopathy, meningitis, Parkinson's disease or focal neurological findings.
(7) History of syncope or other syncopal attacks, current evidence of hypovolemia, orthostatic hypotension (average of 1, 3 and 5 min measurements), a screening and baseline heart rate of <55 beats per minutes or systolic blood pressure <110 mmHg or diastolic BP<70 mmHg.
(8) Patients with laboratory or ECG abnormalities considered clinically significant by the investigator or qualified designee [Advanced heart block (second-degree or above atrioventricular block without pacemaker), diagnosis of Sick sinus syndrome] that would had clinical implications for the patient's participation in the study.
(9) Patients with serious or unstable medical illnesses. These include current hepatic (moderate severe hepatic impairment), renal, gastroenterologic, respiratory, cardiovascular (including ischemic heart disease, congestive heart failure), endocrinologic, or hematologic disease.
(10) Patients who had received an investigational drug within 30 days prior to the current agitation episode.
(11) Patients who were considered by the investigator, for any reason, to be an unsuitable candidate for receiving dexmedetomidine; e.g., patients with a history of allergic reactions to dexmedetomidine.

Study Treatments

Test Product, Dose, and Mode of Administration:

Dexmedetomidine hydrochloride was a thin film formulation of DEX for sublingual (SL) administration. Dosing delivers 180 μg or 120 μg of DEX sublingually. The product is a small, solid-dose film formulation, approximately 193.6 mm$^2$ in area and 0.7 mm thick, designed to completely dissolve in the SL space within 1-3 minutes.

Reference Therapy, Dosage and Mode of Administration:

Matching placebo films was taken sublingually as described above.

Duration of Treatment: 1 day

Study Procedures

Subjects provided written informed consent before any study-related procedures were initiated, including the cessation of prohibited concomitant therapy.

The schedule of events performed during the study were provided in Table 37.

TABLE 37

Schedule of Events

| | | Treatment Evaluation Day 1 | | | | | | | | | | | | | |
|---|---|---|---|---|---|---|---|---|---|---|---|---|---|---|---|
| | | Pre-Dose[1] −1 hr to | Post Dose Time[1] | | | | | | | | | | Day 2 Follow-Up (+1) | | Day 7 (+2) End |
| Activity time point | Screening Pre-treatment | time 0 | 10 min | 20 min | 30 min | 45 min | 1 hr | 1.5 hr | 2 hr | 4 hr | 6 hr | 8 hr | 24 hr (−9/+12 hr) | Day 3 Discharge | of Study |
| Informed Consent | X | | | | | | | | | | | | | | |
| Medical History | X | | | | | | | | | | | | | | |
| Demographics | X | | | | | | | | | | | | | | |
| Weight | X | | | | | | | | | | | | X | | |
| Height | X | | | | | | | | | | | | | | |
| BMI | X | | | | | | | | | | | | | | |
| Alcohol breathalyzer | X | | | | | | | | | | | | | | |
| MINI | X | | | | | | | | | | | | | | |
| Physical Exam | X | | | | | | | | | | | | X | | |
| Safety Labs[2] | X | | | | | | | | | | | | | X | X |
| ECG with rhythm strip[3] | X | X | | | | | | | X | | | | X | | |
| Pulse oximetry | | X | | | X | | X | | X | X | | X | | | |
| Resting vital signs[4] | X | X | | | X | | X | | X | X | X | X | X | X | X |
| Orthostatic vital signs[4] | X | X | | | | | | | X | X | | X | X | X | X |
| Admit to Unit | X | | | | | | | | | | | | | | |
| Inclusion/Exclusion criteria | X | X | | | | | | | | | | | | | |
| Randomization | | X | | | | | | | | | | | | | |
| Study drug administration[10] | | X | | | | | | | | | | | | | |
| PANSS[9] | | X | | | | | | | | | X | | X | | |
| PCRS[5] | X | X | | | | | | | X | | | | X | | |
| PEC[5] | X | X | X | X | X | X | X | X | X | X | X | X | X | | |
| ACES[5] | | X | | | | | | | | X | X | | X | | |
| CGI-Severity[6] | X | X | | | | | | | | | | | | | |
| CGI-Improvement[6] | | | | | | X | | X | | X | X | | | | |
| C-SSRS | X | | | | | | | | | | | | X | | |
| Buccal (SL) assessment for local irritation[7] | | | | | X | | | | | X | X | | X | | |
| Likert scales | | | | | X | | | | | | | | | | |
| Likability Question | | | | | X | | | | | | | | | | |
| PK Sampling[8] | | | | | | | X | | | X | | X | | | |

TABLE 37-continued

Schedule of Events

| Activity time point | Screening Pre-treatment | Pre-Dose[1] -1 hr to time 0 | Post Dose Time[1] | | | | | | | | | | Day 2 Follow-Up (+1) 24 hr (-9/+12 hr) | Day 3 Discharge | Day 7 (+2) End of Study |
|---|---|---|---|---|---|---|---|---|---|---|---|---|---|---|---|
| | | | 10 min | 20 min | 30 min | 45 min | 1 hr | 1.5 hr | 2 hr | 4 hr | 6 hr | 8 hr | | | |
| Concomitant Medications | X | X | | | | X | | | | | | | X | X | X |
| Adverse Events | X | X | | | | X | | | | | | | X | X | X |

Notes to the Schedule of Events:

[1]Pre-dose assessments had a window of 60 minutes prior to dose with the exception of PEC and ACES which were performed within 15 minutes of dosing (15 to 0 min). All post-dose assessments had a window of −5/+15 minutes through the 1.5 hour assessments, −5/+25 minutes for the 2 hour assessments (with the exception of the PEC which will have a +/−5 minute window) and ±30 minutes for the 4, 6 and 8 hour assessments.

[2]Safety Labs were chemistry, hematology, urinalysis, UDS (local lab, only conducted at screening), alcohol breathalyzer (only conducted at screening), and urine pregnancy (only conducted at screening). Screening/enrollment labs: local labs drawn within 7 days prior to screening might suffice with the exception of urine drug screen. If results not available on the same day, a 'desktop' or non-CLIA test might be performed: to confirm results from a CLIA-certified laboratory was recorded once available. Central Labs was performed on Screening, Day 3 and Day 7.

[3] ECG for pre-dose did not need to be repeated if screening ECG was conducted on the day of dosing. ECGs collected following treatment were to be performed prior to PK assessments.

4Resting (recumbent) vital signs (SBP, DBP, and HR) were taken upon having the subject recumbent for 5 min at Screening, Pre-dose and at 30 min, 1, 2, 4, 6, 8 and 24 hours post dose, was well as Day 3 and Day 7. Triplicate measurments performed in case of Systolic BP <90 mmHg, Diastolic BP <60 mmHg or Pulse <60 bpm. Orthostatic measurements (SBP, DBP and HR, respiratory rate and temperature) was taken upon having the subject stand, with measurements taken after 1, 3 and 5 minutes at Screening, Pre-dose, 2, 4, 8 and 24 hours post first dose, as well as Day 3 and Day 7.

[5]PEC was performed at Screening, Pre-dose (withing 15 min prior to dose) and at 10, 20, 30, 45 min; 1, 1.5, 2, 4, 6, 8 and 24 hours post dose. The PCRS must be performed prior to PEC rating, when required. At 6 and 24 hrs the PEC rating must be performed before the PANSS interview. ACES was performed at Pre-dose (within 15 min of dose), 2, 4, and 8 hrs post dose.

[6]CGI-Severity was performed at Screening and pre-dose. CGI-Improvement was performed at 30 minutes, 1, 2 and 4 hours post dose.

[7]Buccal exam at 30 min, 2, 4 and 24 hr post-dose for local irritation.

[8]PK blood samples were collected 1, 4, and 8 hr (while awake) after dose. A sample might not be collected if the Physician indicated in source documents that the patient was in a mental state that was not conducive to PK sample collection. Non-compliance or refusal of all or any PK draw was not exclusionary nor result in ET. Vital signs were to be done prior to PK sample draws, when performed at the same timepoints.

[9]Pre-Dose PANSS might be administered at any time prior to dosing on the day of dosing and 6 and 24 hrs (−1/+2 hr) post-dose. At 6 and 24 hrs PANSS interview must be performed after PEC rating. The 6 hour and 24 hr PANSS was conducted with reference to the predose PANSS.

[10]The investigator might choose to re-dose the patient with half of a film after the 2 hour post-dose assessments are performed if the PEC change from baseline is <40%. Patients could be re-dosed up to 2 times during 12 hours post first dose. All assessments listed in this Schedule of Events at the 2 hour post first dose timepoint repeated at 2 hours post every re-dose.

Criteria for Evaluation:

Efficacy assessment: Assessment of Drug Effects on acute agitation was done by the Positive and Negative Syndrome Scale-Excited Component (PEC). The PEC comprises 5 items associated with agitation: poor impulse control, tension, hostility, uncooperativeness, and excitement; each scored 1 (minimum) to 7 (maximum). The PEC, the sum of these 5 subscales, thus ranges from 5 to 35.

Overall agitation and sedation were evaluated with the Agitation-Calmness Evaluation Scale (ACES), where 1 indicates marked agitation; 2—moderate agitation; 3—mild agitation; 4—normal behavior; 5—mild calmness; 6—moderate calmness; 7—marked calmness; 8—deep sleep; and 9—unarousable.

The overall clinical improvement in agitation in response to treatment was also be measured by the Clinical Global Impressions-Improvement (CGI-I). CGI-I scores range from 1 to 7: 0=not assessed (missing), 1=very much improved, 2=much improved, 3=minimally improved, 4=no change, 5=minimally worse, 6=much worse, 7=very much worse.

Safety and tolerability assessments: AEs, clinical laboratory tests, ECG with rhythm strip, pulse oximetry, and vital signs were monitored for tolerability assessment. All observed and volunteered AEs were recorded. The relationship of AEs to the study drug were graded as not related, unlikely/remotely related, possibly related, probably related or definitely related by the investigators. Vital signs including systolic blood pressure (SBP), diastolic blood pressure (DBP), and heart rate were monitored. The application site of the SL preparation (buccal mucosa) was inspected for any signs of local irritation Additional Assessments:

Demographics, Medical and Psychiatric History, psychotic symptoms (PANSS), Smoking history, Prior and Concomitant Medication, Physical Examination, Pregnancy Pharmacokinetics: A sparse PK sampling of plasma concentrations at specified timepoints were reported. A population PK/PD analysis of plasma concentration vs. clinical response was reported using a separate SAP and report. A graphical assessment of PK vs. vital signs and other potential PD parameters were included.

Statistical Analysis:

Efficacy Analyses

The primary efficacy endpoint of the study was the absolute change from baseline in the PEC total score at 120 min. The intent to treat population was analyzed and consist of all patients who took any study medication and who had both baseline and at least 1 efficacy assessment after dosing. The key secondary endpoints were: change from baseline in the PEC score at 90 min, 60 min, 45 min, 30 min, 20 min and 10 min. Other exploratory endpoints were same as listed under exploratory objectives.

Safety Analyses: Safety data analysis was conducted on all subjects receiving at least 1 dose of study drug. The number and percentage of subjects experiencing 1 or more AEs were summarized by treatment, relationship to study drug, and severity. AEs were coded using the Medical Dictionary for Regulatory Activities (Med DRA) terminology. Listings of subjects who experienced withdrawal due to an AE, serious AEs and/or death will be presented. Laboratory parameters were summarized by treatment using descriptive statistics and data listings of clinically significant abnormalities. Vital signs and ECG data were summarized by changes from baseline values using descriptive statistics.

Pharmacokinetic Analyses

Plasma concentrations and concentration-time data for dexmedetomidine were used to calculate PK parameters; these data and results were reported separately. All pharmacokinetic parameters were calculated using non-compartmental analysis using WinNonlin Version 5.2 or higher. Actual sampling times were used in all pharmacokinetic analyses. Per protocol times were used to calculate mean plasma concentrations for graphical displays. Other PK analyses were performed as appropriate.

Results Summary:

Demographics

The demographics and baseline characteristics is shown below in Table 38.

TABLE 38

Demographics

| | Dexmedetomidine Sublingual film | | | |
|---|---|---|---|---|
| | 180 ug (N = 126) | 120 ug (N = 129) | Placebo (N = 126) | Overall (N = 381) |
| Mean age (years) | 46.0 (11.91) | 45.7 (11.32) | 45.1 (11.13) | 45.6 (11.43) |
| Female N (%) | 44 (34.9) | 52 (40.3) | 44 (34.9) | 140 (36.7) |
| Race (% white/ % non-white) | 16.7/83.3 | 25.6/74.4 | 16.7/83.3 | 19.7/80.3 |
| BMI | 32.53 (7.8) | 31.24 (7.6) | 32.56 (7.4) | 32.10 (7.6) |
| Diagnosis Schizophrenia | 85.70% | 87.60% | 80.20% | 84.50% |
| Schizophrenia | 14.30% | 12.40% | 19.80% | 15.50% |
| Baseline PEC means | 17.6 | 17.5 | 17.6 | NA |

Efficacy

Dexmedetomidine sublingual film significantly improved the severity of agitation from baseline as measured by PEC, ACES scales and CGI-I scores. Key efficacy findings at 2 hours post-dose are presented below.

(a) Primary Efficacy Endpoint (PEC reduction): a reduction in the PEC score (PANSS or the Positive and Negative Syndrome Scale, Excitatory Component) for agitation was observed with rapid calming without excessive sedation at the clinical regulatory endpoint and at earlier time-points. The primary efficacy endpoint was the mean change from baseline in PEC total score at 2 hours (120 minutes) compared to placebo. There were 2 dose cohorts (120 µg (N=129) and 180 µg (N=126)) and 126 placebo patients. Active patients in each of the 2 dose cohorts were compared to placebo patients. The change from baseline in PEC at 2 hours for patients treated with dexmedetomidine sublingual film was compared with placebo using a mixed model repeated measures (MMRM) analysis, with baseline PEC, treatment group, time, the interaction between treatment groups and time, and the interaction between baseline PEC and time as covariates.

The efficacy of dexmedetomidine hydrochloride sublingual film as measured by PEC reduction is dose-responsive and robust. The decrease from baseline in PEC score in the 180 µg dose group showed significant response with a −10.3 mean change from baseline (CFB) total PEC score at 2 hours post dosing compared to placebo (Table 39 and FIGS. 21A and 21B). Mean changes from baseline were −8.5 points for the 120 µg treatment groups, compared to placebo (−4.8 Mean change). Additionally, as early onset of action is an important attribute for therapy in reducing agitation, the 180 µg group showed a statistically significant separation from placebo as early as 20 minutes post dosing (FIG. 21A and FIG. 21B). Further, the decrease from baseline in PEC score in the 180 µg and 120 µg dose groups showed significant responses at 6 hours post dosing compared to placebo (FIG. 21B).

PEC Responder Analyses: The proportion of treatment responders, defined as those with a 40% decrease from baseline in PEC total score at 2 hours post dose, was greatest in the 180 µg group (87% for 180 µg, 67% for 120 µg) as compared to placebo (34%) (Table 39). The durability of calming effects of the 180 µg dose was remarkably prolonged with a sustained statistically significant reduction in PEC evident after 24 hrs.

TABLE 39

Summary of Change from Baseline at 2 hours in PANSS-PEC Total Score and Percent of Responders at 2 hours in the PEC Score by Treatment Group

| | | | Dexmedetomidine Sublingual film | |
|---|---|---|---|---|
| Endpoint (120 min) PEC Total score | N | Placebo | 120 µg (N = 126) | 180 µg (N = 126) |
| Change from Baseline (LSM) | N = 126 (180 µg) N = 129 (120 µg) | −4.8 | −8.5 *** | −10.3 *** |
| Response ° | 126 | 34% | 67% | 87% |

° Proportion achieving ≥ 40% PEC reduction;
* p < 0.025;
*** p < 0.0001

Secondary Efficacy Endpoints:

Changes in secondary efficacy measures (i.e., ACES and CGI-I scores) at 2 hours post-dose were consistent with the results for PEC total scores and were indicative of improvement in symptoms of agitation after treatment with dexmedetomidine sublingual film.

ACES scores: A secondary objective for this study was to evaluate the duration of calming effect of dexmedetomidine sublingual thin film drug utilizing the Agitation-Calmness Evaluation Scale (ACES) collected at pre-dose, 2 hr, and 4 hr after first dose. The ACES assessment was consistent with the analysis of the primary endpoint, and met statistically significance for calming as measured by ACES at two hours compared to placebo in 120 µg and 180 µg (120 µg; p=0.0001) and (180 µg; p<0.0001). At 2 hours after dosing, subjects in the 120 µg and 180 µg treatment groups showed significantly greater improvements relative to placebo in ACES scores (+about 2.8 [P<0.0001] for 120 µg; +about 3.75 [P<0.0001] for 180 µg, compared to placebo of +about 1.0). The improvements at 4 hours post-dose were similar (+about 2.8 [P<0.0001] for 120 µg; +about 3.2 [P<0.0001] for 180 µg, compared to placebo of +about 1.0). (FIG. 22).

CGI-scores: The percentage of subjects achieving CGI-I scores of 1 or 2 ('very much improved' or 'much improved') at 2 hours post-dose was significantly higher in the 120 µg group (about 65% [p<0.0001]) and in the 180 µg dose group (about 90% [p<0.0001]), compared with placebo (about 35%). Significant improvements were also observed at 30 minutes, 1 hour, and 4 hours after dosing for both treatment groups [in the 180 µg dose group (p<0.0001) and in the 120 µg dose group (p<0.0075)] (FIG. 23).

Conclusion: Dexmedetomidine sublingual film treatment significantly improved the severity of agitation from baseline as measured by PEC, CGI-I, and ACES scales in schizophrenia patients. The primary efficacy endpoint was met in 120 µg, and 180 µg treatment groups as there was significant improvements in PEC total scores from baseline at 2 hours post-dose with mean changes of −8.5 and −10.3 points, respectively, versus −4.8 for placebo. Reduction in agitation was observed as early as 20 minutes compared to placebo. Further, changes in secondary efficacy measures (ie, CGI-I and ACES scores) at 2 hours post-dose were consistent with the results for PEC total scores and were indicative of improvement in symptoms of agitation after treatment with Dexmedetomidine sublingual film.

Example 7: A Phase III Multicenter, Randomized, Double-Blind, Placebo-Controlled Study to Determine the Efficacy and Safety of Dexmedetomidine Hydrochloride Sublingual Film in Subjects with Agitation Associated with Bipolar Disorder (SERENITY II)

Objectives:
Primary Endpoint

The primary efficacy endpoint of the study was the absolute change from baseline in the PEC total score at 2 hours. The intent to treat population was analyzed and consists of all patients who took any study medication and who had both baseline and at least 1 efficacy assessment after dosing. Observations recorded after use of rescue medication were censored.

Key Secondary Endpoint Included:

The key secondary efficacy endpoint was the earliest time where an effect on agitation was apparent as measured by change from baseline PEC total score in contrast with placebo.

Exploratory Endpoints Included:
1. Overall clinical improvement after drug administration as measured by the Clinical Global Impression-Improvement Scale (CGI-I) score.
2. Agitation-Calmness Evaluation Scale (ACES) scores at 2, 4 and 8 hrs after dose administration.
3. Change from baseline in total PEC score over time measured from 10 min through 24 hrs. after dosing.
4. PEC Responders and CGI-I Responders at 2 hours following dose of dexmedetomidine hydrochloride, compared with placebo:
    a. PEC responders were defined as those who achieved at least a 40% reduction in PEC total score from baseline at or before 2 hours post-dose.
    b. CGI-I responders were defined as subjects with a score of 1 or 2 on the CGI-I scale (the CGI-I non-responders were defined as subjects with scores from 3 to 7 at 2 hours).
5. Time to rescue medication during the entire 24 hrs Post-treatment Evaluation Period for subjects receiving dexmedetomidine hydrochloride compared to placebo.
6. Proportion of subjects per treatment group who received rescue medication by 4 hrs and within 24 hrs after dosing.
7. Duration of calming effect as described by the change from baseline in PEC total score, and ACES score at 2, 4 and 8 hrs. after dosing.
8. Determined the safety profile of dexmedetomidine hydrochloride as measured by vital signs and treatment-emergent adverse event reports.
9. Described the overall tolerability in terms of adverse event reports and local site (oral/sublingual) tolerability of oral film.
10. Descriptive pharmacokinetics of dexmedetomidine hydrochloride in the patient population.
11. Determined patient acceptability, taste and likability of study medication using Likert scales to capture subject's acceptability, opinion on taste and questions regarding likability.
12. Characterized the patient population utilizing the Young Mania Rating Scale (YMRS).

Study Design:

The study enrolled approximately 381 subjects randomized 1:1:1 to dose regimens of 180 µg, 120 µg dexmedetomidine hydrochloride, or placebo stratified by age <65 and age ≥65. The doses were selected based on the results of the prior Phase Ib clinical trial.

Male and female adults with acute agitation associated with bipolar I or II disorder were enrolled.

Eligible subjects (acutely agitated subjects with bipolar I or II disorder, generally hypomanic, manic or mixed episodes) can be identified in outpatient clinics, mental health, psychiatric or medical emergency services, including medical/psychiatric observation units, or as newly admitted to a hospital setting for acute agitation or already in hospital for chronic underlying conditions. Subjects were domiciled in a clinical research setting or hospitalized to remain under medical supervision while undergoing screening procedures to assessed eligibility.

Upon confirmation of eligibility, subjects were randomized to 180 µg dexmedetomidine hydrochloride sublingual film or 120 µg dexmedetomidine hydrochloride sublingual film or matching placebo. Efficacy and safety assessments were conducted periodically before and after dosing.

Vital signs, pulse oximetry and ECG with rhythm strip were measured as per schedule of assessments, prior to any PK assessments. Participants were allowed water as desired 15 minutes after completion of dosing. Safety and tolerability assessments were conducted at various timepoints. Please refer to the Table 40 for Schedule of events.

Any abnormal vital sign measurement, clinical laboratory test, physical examination finding, or ECG parameter deemed clinically significant by the investigator were repeated, including test results obtained on the final study day or upon early termination. For any test abnormality deemed clinically significant, repeat analysis performed during the follow-up period and until the value returns to baseline (or within normal limits) or the investigator deemed the abnormality to be stable and no longer of clinical concern.

Approximately 4 mL of venous blood (to obtain a minimum of 1.2 mL plasma) was taken into K2-EDTA tubes at set time intervals for the determination of plasma concentrations of study drug (or placebo). The PK plasma samples were collected within 10 min of the scheduled sampling time on Day 1. Blood samples were collected per Table 40 Schedule of Events.

Discussion of Study Design

This was a definitive study to support the safety and efficacy evaluation of dexmedetomidine hydrochloride sublingual film for the acute treatment of agitation in bipolar disorder. The study was designed to characterize the efficacy, safety and tolerability of dexmedetomidine hydrochloride sublingual film in agitation associated with bipolar disorder. A dose of dexmedetomidine hydrochloride was chosen based on results that showed rapid efficacy in a large proportion of subjects was well tolerated and had an acceptable safety profile. In the event of persistent or recurrent agitation, investigators might chose to administer an additional reduced dose of 90 µg or 60 µg (half of 180 µg or 120 µg film) after the 2-hour time point as measured by a PEC change from baseline ≤40%, but in the absence of safety concerns. Patients could only be re-dosed if they were hemodynamically stable, not hypotensive (must be greater than 90/60 systolic/diastolic) and not bradycardic (must be greater than 60 bpm). Patients also could not be re-dosed if they were orthostatic (a drop of >20 mm Hg systolic, or 10 mm Hg diastolic) or if they were experiencing an Adverse Event (AE) that in the assessment of the PI precludes re-dosing. The maximum number of repeat doses per subject is 2, during the 12 hours post-first dose. Doses might not be administered sooner than 2 hours after a previous dose. If the PEC change from baseline is >40%, repeat dosing was not allowed.

Placebo was chosen as a comparator to more accurately assess efficacy as well as safety and tolerability. The randomized, double-blind parallel-group design ensures the sponsor, all subjects, and study staff involved were shielded from treatment assignment and outcomes and therefore minimized any potential bias. The randomization ratio provided an additional element that ensured blinding by decreasing the odds of guessing treatment arms.

Diagnosis and Main Criteria for Eligibility:
Inclusion Criteria
1. Male and female patients between the ages of 18 to 75 years, inclusive.
2. Patients who had met DSM-5 criteria for bipolar I or II disorder, generally hypomanic, manic or mixed episodes.
3. Patients who were judged to be clinically agitated at Screening and Baseline with a total score of ≥14 on the 5 items (poor impulse control, tension, hostility, uncooperativeness, and excitement) comprising the PANSS Excited Component (PEC).
4. Patients who had a score of ≥4 on at least 1 of the 5 items on the PEC at Baseline.
5. Patients who read, understand and provided written informed consent.
6. Patients who were in good general health prior to study participation as determined by a detailed medical history, physical examination, 12-lead ECG with rhythm strip, blood chemistry profile, hematology, urinalysis, and in the opinion of the Principal Investigator.
7. Female participants, if of child-bearing potential and sexually active, and male participants, if sexually active with a partner of child-bearing potential, who agreed to use a medically acceptable and effective birth control method throughout the study and for one week following the end of the study. Medically acceptable methods of contraception that might be used by the participant and/or his/her partner include abstinence, birth control pills or patches, diaphragm with spermicide, intrauterine device (IUD), condom with foam or spermicide, vaginal spermicidal suppository, surgical sterilization, and progestin implant or injection. Prohibited methods include: the rhythm method, withdrawal, condoms alone, or diaphragm alone.

Exclusion Criteria
1. Patients with agitation caused by acute intoxication, including positive identification of alcohol by breathalyzer or drugs of abuse (with the exception of THC) during urine screening.
2. Use of benzodiazepines or other hypnotics or antipsychotic drugs in the 4 hours before study treatment.
3. Treatment with alpha-1 noradrenergic blockers (terazosin, doxazosin, tamsulosin, alfuzosin, or prazosin) or other prohibited medications.
4. Patients judged to be at serious risk of suicide must be excluded.
5. Female patients who had a positive pregnancy test at screening or are breastfeeding.
6. Patients who had hydrocephalus, seizure disorder, or history of significant head trauma, stroke, transient ischemic attack, subarachnoid bleeding, brain tumor, encephalopathy, meningitis, Parkinson's disease or focal neurological findings.
7. History of syncope or other syncopal attacks, current evidence of hypovolemia, orthostatic hypotension (average of 1, 3 and 5 min measurements), a screening and baseline heart rate of <55 beats per minutes or systolic blood pressure <110 mmHg or diastolic BP <70 mmHg.
8. Patients with laboratory or ECG abnormalities considered clinically significant by the investigator or qualified designee [Advanced heart block (second-degree or above atrioventricular block without pacemaker), diagnosis of Sick sinus syndrome] that would had clinical implications for the patient's participation in the study.
9. Patients with serious or unstable medical illnesses. These include current hepatic (moderate-severe hepatic impairment), renal, gastroenterologic, respiratory, cardiovascular (including ischemic heart disease, congestive heart failure), endocrinologic, or hematologic disease.
10. Patients who had received an investigational drug within 30 days prior to the current agitation episode.
11. Patients who were considered by the investigator, for any reason, to be an unsuitable candidate for receiving dexmedetomidine hydrochloride, e.g., patients with a history of allergic reactions to dexmedetomidine hydrochloride.

Study Treatments
Method of Assigning Subjects to Treatment Groups

Upon confirmation of eligibility, subjects were randomized to 180 µg dexmedetomidine hydrochloride film or 120 µg dexmedetomidine hydrochloride film or placebo. Randomization was 1:1:1 (180 µg or 120 µg dexmedetomidine hydrochloride or placebo and stratified by age <65, age ≥65) with 125 patients assigned to each arm by a permuted block design. Study randomization was computer generated.

Test Product, Dose, and Mode of Administration:

Dexmedetomidine hydrochloride was in a film formulation for sublingual (SL) administration. Dosing delivered 180 µg or 120 µg of dexmedetomidine hydrochloride sublingually. The product was a small, solid-dose film formulation, approximately 193.6 mm$^2$ in area and 0.7 mm thick, designed to completely dissolve in the SL space within about 1-3 minutes.

Treatment Administration

At the time of dosing, patients were instructed on how to take dexmedetomidine hydrochloride film sublingually, and that they should retained the dexmedetomidine hydrochloride film in the sublingual cavity until dissolved. The patient self-administered under the supervision of a trained staff member. If the patient was unable to self-administer, the event was recorded, and the subject's participation was concluded.

In the event of persistent or recurrent agitation, investigators might choose to re-dose at 90 µg or 60 µg (dividing the 180 µg or 120 µg film in half) after the 2-hour time point as measured by a PEC change from baseline ≤40% but in the absence of safety concerns.

Study Procedures

Subjects provided written informed consent before any study-related procedures were initiated, including the cessation of concomitant therapy.

The schedule of events performed during the study was provided in Table 40.

TABLE 40

Schedule of Events

| Activity Time Point | Screening Pre-treatment | Pre-Dose[1] −1 hr to time 0 | Treatment Evaluation Day 1 Post Dose Time[1] | | | | | | | | | | Day 2 Follow-Up (+1) 24 hr (−9/+12 hr) | Day 3 Discharge | Day 7 (+2) End of Study |
|---|---|---|---|---|---|---|---|---|---|---|---|---|---|---|---|
| | | | 10 min | 20 min | 30 min | 45 min | 1 hr | 1.5 hr | 2 hr | 4 hr | 6 hr | 8 hr | | | |
| Informed Consent | X | | | | | | | | | | | | | | |
| Medical History | X | | | | | | | | | | | | | | |
| Demographics | X | | | | | | | | | | | | | | |
| Weight | X | | | | | | | | | | | | X | | |
| Height | X | | | | | | | | | | | | | | |
| BMI | X | | | | | | | | | | | | | | |
| Alcohol Breathalyzer | X | | | | | | | | | | | | | | |
| MINI | X | | | | | | | | | | | | | | |
| Physical Exam | X | | | | | | | | | | | | X | | |
| Safety Labs[2] | X | | | | | | | | | | | | | X | X |
| ECG with rhythm strip[3] | X | X | | | | | | X | | | | | | | |
| Pulse oximetry | | X | | | X | | X | | X | X | | X | | | |
| Resting vital signs[4] | X | X | | | X | | X | | X | X | X | X | X | X | X |
| Orthostatic vital signs[4] | X | X | | | | | | | X | X | | X | X | X | X |
| Admit to Unit | X | | | | | | | | | | | | | | |
| Inclusion/Exclusion criteria | X | X | | | | | | | | | | | | | |
| Randomization | | X | | | | | | | | | | | | | |
| Study drug administration[9] | | X | | | | | | | | | | | | | |
| YMRS | | X | | | | | | | | | | | X | | |
| PCRS[5] | X | X | | | | | | | X | | | | X | | |
| PEC[5] | X | X | X | X | X | X | X | X | X | X | X | X | X | | |
| ACES[5] | | X | | | | | | | | | | | | | |
| CGI-Severity[6] | X | X | | | | | | | | | | | | | |
| CGI-Improvement[6] | | | | | X | | X | | X | X | | | | | |
| C-SSRS | X | X | | | | | | | | | | | X | X | |
| Buccal (SL) assessment for local irritation[7] | | | | | X | | | | X | X | | | X | | |
| Likert scales | | | | X | | | | | | | | | | | |
| Likability Question | | | | X | | | | | | | | | | | |
| Pharmacokinetic Sampling[8] | | | | | | | X | | | X | | X | | | |
| Concomitant Meds | X | X | | | | | X | | | | | | X | X | X |
| Adverse Events | X | X | | | | | X | | | | | | X | X | X |

Notes to the Schedule of Events:

[1] Pre-dose assessments had a window of 60 minutes prior to dose with the exception of PEC and ACES which were performed within 15 minutes of dosing (15 to 0 min). All post-dose assessments had a window of −5/+15 minutes through the 1.5 hour assessments, −5/+25 minutes for the 2 hour assessements (with the exception of the PEC which had a +/−5 minute window) and ±30 minutes for the 4, 6 and 8 hour assessments and YMRS could be performed at any time.
[2] Safety Labs included chemisty, hematology, urinalysis, UDS (local lab, only conducted at screening), alcohol breathalyser (only conducted at screening), and urine pregnancy (only condcuted at screening). Screening/enrollment labs: local labs drawn within 7 days prior to screening might suffice with the exception of urine drug screen. If results not available on the same day, a 'desktop' or non-CLIA test might be performed; to confirm, results from a CLIA-certified laboratory should be recorded once available. Central Labs should be performed on Screening, Day 3 and Day 7.
[3] ECG for pre-dose does not need to be repeated if screening ECG was conducted on the day of dosing. ECGs collected following treatment were performed prior to PK assessments.
[4] Resting (recumbent) vital signs (SBP, DBP and HR) were taken upon having the subject recumbent for 5 min at Screening, Pre-dose and at 30 min, 1, 2, 4, 6, 8 and 24 hours post dose, as well as Day 3 and Day 7. Triplicate measurements were performed in case of Systolic BP <90 mmHg. Diastolic BP <60 mmHg or Pulse <60 pbm. Orthostatic measurements (SBP, DBP, HR, respiratory rate) were taken upon having the subject stand, with measurements taken after 1, 3 and 5 minutes and temperature were taken at Screening, Pre-dose, 2, 4, 8 and 24 hours post first dose, as well as Day 3 and Day 7.
[5] PEC was performed at Screening, Pre-dose (within 15 min prior to dose) and at 10, 20, 30, 45 min; 1, 1.5, 2, 4, 6, 8 and 24 hours post dose. The PCRS must be performed prior to PEC rating, when required. ACES was performed at Pre-dsoe (within 15 min of dose), 2, 4 and 8 hrs post dose.
[6] CGI-Severity was performed at Screening and pre-dose. CGI-Improvement was performed at 30 minutes, 1, 2, and 4 hours post dose.
[7] Buccal examined at 30 min, 2, 4, and 24 hr post-dose for local irriation.
[8] PK blood samples were collected 1, 4, and 8 hr (while awake) after dose. A sample might not be collected if the Physician indicated in source documents that the patient was in a mental state that was not conducive to PK sample collection. Non-compliance or refusal of all or any PK draw was not exclusionary nor result in ET. Vital signs were to be done prior to PK sample draws, when performed at the same timepoints.
[9] The investigator might chose to re-dose the patient after the 2 hours post-dose assessments are performed if the PEC change from baseline is ≤40%. Patients could re-dosed after completing the 2 hour post first dose assessements. Repeat dosing administers half of a film. Patients could redosed twice in the 12 hour period post first dose. All assessments listed in this Schedule of Events at the 2 hour post first dose timepoint should be repeated at 2 hours post every re-dose. Assessments at 4, 6, or 8 hours post first dose that occur within 1 hour of a post re-dose assessment were not required to be performed Study Assessments
Efficacy The effect of study drug was evaluated using several validated instruments as described below.
PANSS—Excitatory Component (PEC)
Agitation-Calmness Evaluation Scale (ACES)
CGI-S and CGI-I Clinical Global Impression of Severity (CGI-S) was rated based upon the severity of agitation at screening and pre-dose (immediately prior to start of dosing).

Severity of illness was assessed based on following scale:
0=Not assessed
1=Not at all ill
2=Borderline mentally ill
3=Mildly ill
4=Moderately ill
5=Markedly ill
6=Severely ill
7=Among the most extremely ill subjects Drug response on agitation was evaluated by the Clinical Global Impressions-Improvement (CGI-I). It was performed at 30 minutes, 1, 2 and 4 hrs post dose. The CGI-I scores range from 1 to 7:
0=not assessed (missing),
1=very much improved,
2=much improved, 3=minimally improved,
4=no change,
5=minimally worse,
6=much worse,
7=very much worse Both CGI-I and CGI-S were focused on the severity of agitation rather than the severity of the overall illness of bipolar disorder.

Young Mania Rating Scale (YMRS)

The YMRS was an 11-item scale evaluating mania symptoms based on the patient's subjective report of their clinical condition. It was used to characterize the patient population enrolled in the study.

Placebo-Control Reminder Script (PCRS)

The Placebo-Control Reminder Script (PCRS) © Hassman and Cohen, 2019, Version 5.0 educates clinical trial participants of key causes of the placebo and nocebo effects, namely the tempering of participant study expectations, reminding subjects what a placebo is and how that relates to their reporting of symptoms and potential side effects, and explaining how interactions with research site staff differ from their experience with previous providers. To do this, the PCRS informs subjects that they were to be honest about their symptoms, site staff had no expectations of symptom improvement or worsening and was not disappointed if they feel better, worse or the same, and asked participants to explain in their own words its content to ensure comprehension. The PEC Rater was read the PCRS study source before administering the PEC to each subject at each visit (time point) listed on the study specific PCRS, typically taking about 2 minutes to read.

Likert Scales

After dosing with the study drug, subjects assessed their preference of the study medication by answering the statements "I like the taste of the medication" and "The medication is acceptable" using a five-level Likert scale as below:

Strongly disagree
Disagree
Neither agree nor disagree
Agree
Strongly agree

Drug Likability

Subjects responded to open ended questions regarding their experience. Additional comments about aftertaste, smell, dissolve time, etc. were asked as Yes/No questions with Yes responses prompting an explanation field.

Safety

Safety was assessed during the study by the monitoring and recording of AEs, clinical laboratory test results (hematology, biochemistry, and urinalysis), vital sign measurements (systolic and diastolic blood pressures, heart rate measured as pulse, respiratory rate, and temperature), ECG, and physical examination findings. Should a known safety issue be identified (e.g., a high incidence of severe hypotension or bradycardia in the active 180 µg dose arm or the 120 µg arm), the DSMB notified the sponsor. Should this occur, sponsor notified FDA, and sponsor might chose to continue dosing the patients at a lower dose.

Pharmacokinetics

Blood samples (4 ml) were collected per Table 40—Schedule of Events. For each subject, up to 3 blood samples (12 mL of blood) were collected during the study for PK analysis. In addition, approximately 30 mL of blood was collected at screening, approximately 15 mL of blood was collected at Day 3 Discharge, and approximately 15 mL of blood was collected at Day 7 (+2) for clinical laboratory testing. The total volume of blood collected during the study was expected to be approximately 72 mL. For each subject, up to 3 blood samples (12 mL of blood) were collected during the study for PK analysis. In addition, approximately 30 mL of blood was collected at screening, approximately 15 mL of blood was collected at Day 3 Discharge, and approximately 15 mL of blood was collected at Day 7 (+2) for clinical laboratory testing. The total volume of blood collected during the study was expected to be approximately 72 mL.

Statistical Analyses

Pharmacokinetic Analyses

Plasma concentrations and concentration-time data for dexmedetomidine were used to calculate PK parameters; these data and results were reported separately. Details regarding the analyses of PK data were described in a separate PK SAP. The separate SAP for the PK analyses was prepared and finalized prior to database lock.

Safety Analyses

All safety analyses were performed using the Safety Population. All subjects who received at least one dose of study drug were included in the population for safety analysis. Adverse events (AEs) were characterized by type, severity, seriousness, and relationship to treatment. Adverse events were coded by preferred term and system organ class using MedDRA version 20.0.

Efficacy Analyses

The primary efficacy endpoint of the study was the absolute change from baseline in the PEC total score at 120 min. The intent to treat population was analyzed and consist of all patients who took any study medication and who had both baseline and at least 1 efficacy assessment after dosing.

Results Summary:

Demographics

The demographics and baseline characteristics is shown below in Table 41.

TABLE 41

| | Demographics | | | |
|---|---|---|---|---|
| | Dexmedetomidine sublingual film | | | |
| | 180 µg (N = 126) | 120 µg (N = 129) | Placebo (N = 126) | Overall (N = 381) |
| Mean age (years) | 46.0 (11.91) | 45.7 (11.32) | 45.1 (11.13) | 45.6 (11.43) |
| Female N (%) | 44 (34.9) | 52 (40.3) | 44 (34.9) | 140 (36.7) |
| Race (% white/% non-white) | 38.9/61.1 | 44.4/55.6 | 39.7/60.3 | 41.0/59 |
| BMI | 32.53 (7.8) | 31.24 (7.6) | 32.56 (7.4) | 32.10 (7.6) |
| Diagnosis: Depressed | 22% | 16% | 21% | 20% |
| Diagnosis: Hypomania | 4% | 11% | 8% | 8% |
| Diagnosis: Mania | 47% | 46% | 50% | 47% |
| Diagnosis: Mixed Episodes | 24% | 21% | 17% | 21% |
| Diagnosis: Unspecified | 3% | 6% | 4% | 4% |
| Baseline PEC means | 18 | 18 | 17.9 | NA |

3. Efficacy

Dexmedetomidine sublingual film significantly improved the severity of agitation from baseline as measured by PEC, ACES scales and CGI-I scores. Key efficacy findings at 2 hours post-dose are presented below.

(a) Primary Efficacy Endpoint (PEC reduction): a reduction in the PEC score (PANSS or the Positive and Negative Syndrome Scale, Excitatory Component) for agitation was observed with rapid calming without excessive sedation at the clinical regulatory endpoint and at earlier time-points. The primary efficacy endpoint was the mean change from baseline in PEC total score at 2 hours (120 minutes) compared to placebo. There were 2 dose cohorts (120 µg (N=129) and 180 µg (N=126)) and 126 placebo patients. Active patients in each of the 2 dose cohorts were compared to placebo patients. The change from baseline in PEC at 2 hours for patients treated with dexmedetomidine sublingual film was compared with placebo using a mixed model repeated measures (MMRM) analysis, with baseline PEC, treatment group, time, the interaction between treatment groups and time, and the interaction between baseline PEC and time as covariates.

The efficacy of dexmedetomidine hydrochloride sublingual film as measured by PEC reduction is dose-responsive and robust. The decrease from baseline in PEC score in the 180 µg dose group showed significant response with a −10.4 mean change from baseline (CFB) total PEC score at 2 hours post dosing compared to placebo (Table 42 and FIG. 24A and FIG. 24.B). Mean changes from baseline were −9.1 points for the 120 µg treatment groups, compared to placebo (−5 Mean change). Additionally, as early onset of action is an important attribute for therapy in reducing agitation, the 180 µg group showed a statistically significant separation from placebo as early as 20 minutes post dosing (FIG. 24A and FIG. 24.B). Further, the decrease from baseline in PEC score in the 180 µg and 120 µg dose groups showed significant responses at 6 hours post dosing compared to placebo (FIG. 24B).

TABLE 42

Summary of Change from Baseline at 2 hours in PANSS-PEC Total Score and Percent of Responders at 2 hours in the PEC Score by Treatment Group

| Endpoint | | | Dexmedetomidine sublingual film | |
|---|---|---|---|---|
| (120 min) | N | Placebo | 120 µg | 180 µg |
| PEC Total score Change from Baseline (LSM) | 126 (180 µg) 129 (120 µg) | −5.0 | −9.1 *** | −10.4 *** |
| Response ° | 126 | 37% | 69% | 85% |

° Proportion achieving ≥ 40% PEC reduction;
* p < 0.025;
*** p < 0.0001

PEC Responder Analyses: The proportion of treatment responders, defined as those with a 40% decrease from baseline in PEC total score at 2 hours post dose, was greatest in the 180 µg group (85% for 180 µg, 69% for 120 µg)) as compared to placebo (37%) (Table 42). The durability of calming effects of the 180 µg dose was remarkably prolonged with a sustained statistically significant reduction in PEC evident after 24 hrs.

Secondary Efficacy Endpoints:

Changes in secondary efficacy measures (i.e., ACES and CGI-I scores) at 2 hours post-dose were consistent with the results for PEC total scores and were indicative of improvement in symptoms of agitation after treatment with dexmedetomidine sublingual film.

ACES scores: A secondary objective for this study was to evaluate the duration of calming effect of dexmedetomidine sublingual thin film drug utilizing the Agitation-Calmness Evaluation Scale (ACES) collected at pre-dose, 2 hr, and 4 hr after first dose. The ACES assessment was consistent with the analysis of the primary endpoint, and met statistically significance for calming as measured by ACES at two hours compared to placebo in 120 µg and 180 µg (120 µg; p<0.0001) and (180 µg; p<0.0001). At 2 hours after dosing, subjects in the 120 µg and 180 µg treatment groups showed significantly greater improvements relative to placebo in ACES scores (+about 3.0 [p<0.0001] for 120 µg; +about 3.7 [p<0.0001] for 180 µg, compared to placebo of +about 1.0. The improvements at 4 hours post-dose were similar (+about 2.8 [p<0.0001] for 120 µg; +about 3.2 [p<0.0001] for 180 µg, compared to placebo of +about 1.0) (FIG. 25).

CGI scores: The percentage of subjects achieving CGI-I scores of 1 or 2 ('very much improved' or 'much improved') at 2 hours post-dose was significantly higher in the 120 µg group (about 70% [p<0.0001]) and in the 180 µg dose group (about 90% [p<0.0001]), compared with placebo (about 38%). Significant improvements were also observed at 30 minutes, 1 hour, and 4 hours after dosing for both treatment groups (FIG. 26).

Safety and Tolerability:

Dexmedetomidine sublingual film (formulations of Example 2) was well tolerated in schizophrenia and bipolar I disorder patients and had a favourable safety profile in the treatment of subjects with agitation. An overview of subjects who experienced at least 1 treatment emergent adverse event (TEAE) by treatment group for the safety population is given in Table 43.

TABLE 43

Summary of adverse events in Phase III trial (schizophrenia and bipolar disorder patient)

| Event | | Dexmedetomidine sublingual film | | Placebo (N = 252) |
|---|---|---|---|---|
| | | 180 µg (N = 252) | 120 µg (N = 255) | |
| Somnolence | Mild | 40 (15.9) | 43 (16.9) | 15 (6.0) |
| | Moderate | 16 (6.3) | 11 (4.3) | 1 (0.4) |
| Dizziness | Mild | 13 (5.2) | 7 (2.7) | 2 (0.8) |
| | Moderate | 2 (0.8) | 3 (1.2) | 0 |
| Hypotension | Mild | 10 (4.0) | 10 (3.9) | 0 |
| | Moderate | 3 (1.2) | 4 (1.6) | 0 |
| Orthostatic | Mild | 9 (3.6) | 7 (2.7) | 1 (0.4) |
| hypotension | Moderate | 4 (1.6) | 0 | 0 |
| Hypoaesthesia oral | | 12 (4.8) | 7 (2.7) | 1 (0.4) |
| Dry mouth | | 11 (4.4) | 19 (7.5) | 3 (1.2) |
| Nausea | | 7 (2.8) | 6 (2.4) | 4 (1.6) |
| Headache | | 6 (2.4) | 12 (4.7) | 12 (4.8) |
| Paraesthesia oral | | 6 (2.4) | 7 (2.7) | 1 (0.4) |

Conclusion: Dexmedetomidine sublingual film treatment significantly improved the severity of agitation from baseline as measured by PEC, CGI-I , and ACES scales in schizophrenia patients. The primary efficacy endpoint was met in 120 µg, and 180 µg treatment groups as there was significant improvements in PEC total scores from baseline at 2 hours post-dose with mean changes of −9.1 and −10.4 points, respectively, versus −5.0 for placebo. Reduction in agitation was observed as early as 20 minutes compared to placebo. Further, changes in secondary efficacy measures (i.e., CGI-I and ACES scores) at 2 hours post-dose were consistent with the results for PEC total scores and were indicative of improvement in symptoms of agitation after treatment with Dexmedetomidine sublingual film Example 8: Exemplary Oromucosal Formulations

TABLE 44

Composition for a tablet formulation used for oromucosal delivery (with muco-adhesive properties)

| Ingredient(s) | Amount | % w/v |
|---|---|---|
| Dexmedetomidine hydrochloride | 180 μg (equivalent to dexmedetomidine) | 0.36% |
| Lactose Monohydrate | 44.27 mg | 88.54% |
| Hypromellose (or) Hydroxy propyl cellulose (or) Polyethylene oxide (or) Xanthan gum (or) Sodium alginate | 2.5 mg | 5.0% |
| Croscarmellose Sodium (or) sodium starch glycollate | 2.5 mg | 5.0% |
| Sucralose | 0.05 mg | 0.1% |
| Magnesium Stearate | 0.5 mg | 1.0% |
| Tablet weight | 50.0 mg | 100% |

Manufacturing Process:
1. Dexmedetomidine, binder (hypromellose (or) hydroxy propyl cellulose (or) polyethylene oxide (or) xanthan gum (or) sodium alginate) and sucralose are dissolved or dispersed in water to prepare a solution or dispersion.
2. Remaining ingredients except magnesium stearate are blended in a suitable mixer and sifted with the help of an appropriate sieve.
3. The blend obtained in step 2 is granulated using a suitable granulator.
4. Granules are dried in a suitable fluid bed dryer or any other suitable dryer and size appropriately in quadro-co-mill or multimill.
5. Granules are loaded into a suitable blender such as V-blender and lubricate with magnesium stearate.
6. The lubricated blend obtained in step 5 is compressed into tablets of specific dimensions using appropriate tooling.

TABLE 45

Composition for a tablet formulation used for buccal delivery (with muco-adhesive nature)

| Ingredient(s) | Amount | % w/v |
|---|---|---|
| Dexmedetomidine hydrochloride | 180 μg (equivalent to dexmedetomidine) | 0.36% |
| Lactose monohydrate | 43.77 mg | 87.54% |
| Hypromellose (or) Hydroxy propyl cellulose (or) Polyethylene oxide (or) Xanthan gum (or) Sodium alginate | 5.0 mg | 10.0% |
| Sucralose | 0.05 mg | 0.1% |
| Magnesium Stearate | 0.5 mg | 1.0% |
| Talc | 0.5 mg | 1.0% |
| Tablet weight | 50.0 mg | 100% |

Manufacturing Process:
1. Dexmedetomidine hydrochloride, binder (hypromellose (or) hydroxy propyl cellulose (or) polyethylene oxide (or) xanthan gum (or) sodium alginate) and sucralose are dissolved or dispersed in water to prepare a solution or dispersion.
2. Remaining ingredients except magnesium stearate and talc are blended in a suitable mixer and sifted with the help of an appropriate sieve.
3. The blend obtained in step 2 is granulated using a suitable granulator.
4. Granules are dried in a suitable fluid bed dryer or other dryer and size appropriately in quadro-co-mill or multimill.
5. Granules are loaded into a suitable blender such as V-blender and lubricated with magnesium stearate and talc.
6. The lubricated blend obtained in step 5 is compressed into tablets of specific dimensions using appropriate tooling.

TABLE 46

Composition for Dexmedetomidine hydrochloride spray formulation for sublingual delivery

| Ingredients | Amount | % w/v |
|---|---|---|
| Dexmedetomidine hydrochloride | 180 μg (equivalent to dexmedetomidine) | 0.18% |
| N-Methylpyrrolidone (or) Propylene Glycol (or) Polyethylene glycol (or) Glycerine | 10 μL | 10% |
| Ethanol | 5 μL | 5% |
| Sucralose | 0.1 mg | 0.1% |
| Peppermint Oil | 1 μL | 1.0% |
| Purified water | q.s. 100 μL | q.s. 100% |

Manufacturing Process:
1. The polymer (N-methylpyrrolidone (or) propylene glycol (or) polyethylene glycol) or glycerine is dissolved or dispersed in a part of the total water quantity.
2. Dexmedetomidine hydrochloride is mixed with rest of the excipients and the solution or dispersion obtained in step 1.
3. The final volume is made with water in a suitable vessel.
4. The resultant solution is filled into appropriate spray canisters using appropriate tooling such as metered nozzles.

TABLE 47

Composition for Dexmedetomidine hydrochloride drops formulation for sublingual delivery

| Ingredient(s) | Amount | % w/v |
|---|---|---|
| Dexmedetomidine hydrochloride | 180 μg (equivalent to dexmedetomidine) | 0.18% |
| Povidone or Hypromellose or Carbopol | 5 mg | 5.0% |
| N-Methylpyrrolidone (or) propylene glycol (or) polyethylene glycol (or) glycerine (or) ethanol | 10 μL | 10.0% |
| Sucralose | 0.1 mg | 0.1% |
| Peppermint oil | 1 μL | 1.0% |
| Purified water | q.s. 100 μL | q.s. 100% |

Manufacturing Process: Simple Mixing Process
1. The polymer (N-methylpyrrolidone (or) propylene glycol (or) polyethylene glycol) or Glycerine is dissolved or dispersed in a part of the total water quantity.
2. Dexmedetomidine hydrochloride is mixed with rest of the excipients and the solution or dispersion obtained in step 1.
3. The final volume is made with water in a suitable vessel.
4. The resultant solution is filled into appropriate pack or bottles.

TABLE 48

Composition for Dexmedetomidine hydrochloride gel formulation for sublingual delivery

| Ingredient(s) | Amount | % w/v |
|---|---|---|
| Dexmedetomidine | 180 μg | 0.18% |
| Carbopol or Hypromellose or HPC or CMC | 10 mg | 10.0% |
| N-Methylpyrrolidone (or) Propylene Glycol (or) Polyethylene glyol (or) Glycerine (or) Ethanol | 10 μL | 10.0% |
| Sucralose | 0.1 mg | 0.1% |
| Peppermint Oil | 1 μL | 1.0% |
| Purified water | q.s. 100 μL | q.s. 100% |

Manufacturing Process:
1. The polymer (N-methylpyrrolidone (or) propylene glycol (or) polyethylene glycol) or glycerine) is dissolved or dispersed in a part of the total water quantity.
2. Remaining ingredients are dissolved or dispersed in other part of the water.
3. Resultant solutions or dispersions of Step 1 and step 2 are mixed and final volume is made.
4. The resultant mixture of step 3 is packed into appropriate pack or containers Example 9. Some aspects of the disclosed invention are directed to two phase III Multicenter, Randomized, Double-blind, Placebo-controlled Studies to determine Efficacy and Safety of Dexmedetomidine sublingual film in agitation associated with schizophrenia and in bipolar disorder as reported in Examples 6 and 7 and in US approved label of IGALMI™ (dexmedetomidine) that is incorporated herein in its entirety.

The following is a draft of prescribing information or approved label in US:

IGALMI™ (dexmedetomidine) sublingual film, for sublingual or buccal use:

Indications and Usage

IGALMI™ is indicated for the acute treatment of agitation associated with schizophrenia or bipolar I or II disorder in adults.

Limitations of Use:

The safety and effectiveness of IGALMI™ have not been established beyond 24 hours from the first dose.

Dosage and Administration

Important Recommendations Prior to Initiating IGALMI™ and During Therapy

IGALMI™ should be administered under the supervision of a healthcare provider. A healthcare provider should monitor vital signs and alertness after IGALMI™ administration to prevent falls and syncope IGALMI™ is for sublingual or buccal administration. Do not chew or swallow IGALMI™ Do not eat or drink for at least 15 minutes after sublingual administration, or at least one hour after buccal administration.

Recommended Dosage

Table 49 includes dosage recommendations for IGALMI™ based on agitation severity for adults, patients with hepatic impairment, and geriatric patients. Lower dosages are recommended for patients with hepatic impairment and geriatric patients.

If agitation persists after the initial dose, up to two additional doses may be administered at least two hours apart. The dosage recommendations for additional doses vary depending upon the patient population and agitation severity (see Table 49). Assess vital signs including orthostatic measurements prior to the administration of any subsequent doses.

Due to risk of hypotension, additional half-doses are not recommended in patients with systolic blood pressure (SBP) less than 90 mmHg, diastolic blood pressure (DBP) less than 60 mmHg, heart rate (HR) less than 60 beats per minute, or postural decrease in SBP ≥20 mmHg or in DBP ≥10 mmHg.

TABLE 49

Dosage Recommendations for IGALMI™ in Adults, Adult Patients with Hepatic Impairment, and Geriatric Patients with Agitation Associated with Schizophrenia or Bipolar I or II Disorder

| Patient Population | Agitation Severity | Initial Dose* | Optional $2^{nd}/3^{rd}$ Doses* | Maximum Recommended Total Daily Dosage |
|---|---|---|---|---|
| Adults | Mild or Moderate | 120 mcg | 60 mcg | 240 mcg |
| | Severe | 180 mcg | 90 mcg | 360 mcg |
| Patients with Mild or Moderate Hepatic Impairment† | Mild or Moderate | 90 mcg | 60 mcg | 210 mcg |
| | Severe | 120 mcg | 60 mcg | 240 mcg |
| Patients with Severe Hepatic Impairment† | Mild or Moderate | 60 mcg | 60 mcg | 180 mcg |
| | Severe | 90 mcg | 60 mcg | 210 mcg |
| Geriatric Patients (≥65 years old) | Mild, Moderate, or Severe | 120 mcg | 60 mcg | 240 mcg |

*IGALMI™ 120 mcg and 180 mcg dosage strengths may be cut in half to obtain the 60 mcg and 90 mcg doses, respectively
†Hepatic impairment: Mild (Child-Pugh Class A); Moderate (Child-Pugh Class B); Severe (Child-Pugh Class C)

Preparation and Administration Instructions

Keep IGALMI™ in the foil pouch until ready to administer. IGALMI™ should be immediately administered once the pouch is opened and the dose prepared.

Prepare and administer IGALMI™ under the supervision of a healthcare provider as follows:
1. Open the sealed foil pouch by tearing straight across at the notch.
    (i) Perform Steps 2a, 2b, 2c and 2d only if a 60 mcg or 90 mcg dose (half of a film) is needed, then proceed to Step 3.
    (ii) If administering a full dose (1 film), proceed directly to Step 3.
2a. Remove the film from the pouch with clean dry hands.
2b. Cut the film in half between the dots with clean, dry scissors.
2c. Discard unused half in waste container.
2d. Place the half film for administration to the patient back into the pouch.
3. Immediately give the pouch to the patient.
4. Instruct patient to remove the film from the pouch with clean dry hands.
5. For sublingual administration: Instruct patient to place film under the tongue. The film will stick in place. Note: Patient may not eat or drink for 15 minutes after sublingual administration.
6. For buccal administration: Instruct patient to place film behind lower lip. The film will stick in place. Note: Patient may not eat or drink for one hour after buccal administration.
7. Instruct patient to:
    (a) Close their mouth.
    (b) Allow the film to dissolve.
    (c) Do not chew or swallow the film.

Dosage Forms and Strengths

IGALMI™ is a blue rectangular sublingual film containing on its surface two darker blue spots in dose strengths of 120 mcg and 180 mcg.

Contraindications: None.

Warnings and Precautions

Hypotension, Orthostatic Hypotension, and Bradycardia

IGALMI™ causes dose-dependent hypotension, orthostatic hypotension, and bradycardia. In clinical studies, 18%, 16%, and 9% of patients treated with 180 mcg of IGALMI™, 120 mcg of IGALMI™, and placebo, respectively, experienced orthostatic hypotension (defined as SBP decrease ≥20 mmHg or DBP decrease ≥10 mmHg after 1, 3, or 5 minutes of standing) at 2 hours post-dose. In those studies, 7%, 6%, and 1% of patients treated with 180 mcg of IGALMI, 120 mcg of IGALMI™, and placebo, respectively, experienced HR ≤50 beats per minute within 2 hours of dosing. In clinical studies with IGALMI™, patients were excluded if they had treatment with alpha-1 noradrenergic blockers, benzodiazepines, other hypnotics or antipsychotic drugs four hours prior to study drug administration; had a history of syncope or syncopal attacks; SBP <110 mmHg; DBP <70 mmHg; HR<55 beats per minute; or had evidence of hypovolemia or orthostatic hypotension.

Reports of hypotension and bradycardia, including some resulting in fatalities, have been associated with the use of another dexmedetomidine product given intravenously (IGALMI™ is for sublingual or buccal use and is not approved for intravenous use). Clinically significant episodes of bradycardia and sinus arrest have been reported after administration of this other dexmedetomidine product to young, healthy adult volunteers with high vagal tone and when this product was given by rapid intravenous or bolus administration.

Because IGALMI™ decreases sympathetic nervous system activity, hypotension and/or bradycardia may be more pronounced in patients with hypovolemia, diabetes mellitus, or chronic hypertension, and in geriatric patients.

Avoid use of IGALMI™ in patients with hypotension, orthostatic hypotension, advanced heart block, severe ventricular dysfunction, or history of syncope. After IGALMI™ administration, patients should be adequately hydrated and should sit or lie down until vital signs are within normal range. If a patient is unable to remain seated or lying down, precautions should be taken to reduce the risk of falls. Ensure that a patient is alert and not experiencing orthostatic hypotension or symptomatic hypotension prior to allowing them to resume ambulation.

QT Interval Prolongation

IGALMI prolongs the QT interval. Avoid use of IGALMI™ in patients at risk of torsades de pointes or sudden death including those with known QT prolongation, a history of other arrhythmias, symptomatic bradycardia, hypokalemia or hypomagnesemia, and in patients receiving other drugs known to prolong the QT interval.

Somnolence

IGALMI™ can cause somnolence. In placebo-controlled clinical studies in adults with agitation associated with schizophrenia or bipolar I or II disorder, somnolence (including fatigue and sluggishness) was reported in 23% and 22% of patients treated with IGALMI™ 180 mcg and 120 mcg, respectively, compared to 6% of placebo-treated patients. Patients should not perform activities requiring mental alertness, such as operating a motor vehicle or operating hazardous machinery, for at least eight hours after taking IGALMI™

Risk of Withdrawal Reactions

Symptoms of withdrawal have been observed after procedural sedation with another dexmedetomidine product administered intravenously. In this study, 12 (5%) adult patients who received intravenous dexmedetomidine up to 7 days (regardless of dose) experienced at least 1 event related to withdrawal within the first 24 hours after discontinuing dexmedetomidine and 7 (3%) adult patients who received intravenous dexmedetomidine experienced at least 1 event related with withdrawal 24 to 48 hours after discontinuing dexmedetomidine. The most common withdrawal reactions were nausea, vomiting, and agitation. In these subjects, tachycardia and hypertension requiring intervention occurred at a frequency of <5% in the 48 hours following intravenous dexmedetomidine discontinuation.

IGALMI™ was not studied for longer than 24 hours after the first dose. There may be a risk of physical dependence and a withdrawal syndrome if IGALMI™ is used in a manner other than indicated.

Tolerance and Tachyphylaxis

Use of another dexmedetomidine product administered intravenously beyond 24 hours has been associated with tolerance and tachyphylaxis and a dose-related increase in adverse reactions.

IGALMI™ was not studied for longer than 24 hours after the first dose. There may be a risk of tolerance and tachyphylaxis if IGALMI™ is used in a manner other than indicated).

Adverse Reactions

The following adverse reactions are discussed in detail in other sections of the labeling:

Hypotension, Orthostatic Hypotension, and Bradycardia, QT Interval Prolongation, Somnolence, Risk of Withdrawal Reactions and Tolerance and Tachyphylaxis Clinical Studies Experience Because clinical trials are conducted under widely varying conditions, adverse reactions rates observed in the clinical trials of a drug cannot be directly compared to rates in clinical trials of another drug and may not reflect the rates observed in practice.

The safety of IGALMI™ was evaluated in 507 adult patients with agitation associated with schizophrenia (N=255) or bipolar I or II disorder (N=252) in two randomized, placebo-controlled studies (Studies 1 and 2) In both studies, patients were admitted to a clinical research unit or a hospital and remained under medical supervision for at least 24 hours following treatment. Patients were 18 to 71 years of age (mean age was 46 years old); 45% were female and 55% were male; 66% were Black, 31% were White, 2% were multiracial, and 1% were other.

In these studies, patients received an initial dose of IGALMI™ 180 mcg (N=252), IGALMI™ 120 mcg (N=255), or placebo (N=252). Patients who were hemodynamically stable (i.e., those with systolic blood pressure (SBP) >90 mmHg, diastolic blood pressure (DBP) >60 mmHg, and heart rate (HR) >60 beats per minute) and without orthostatic hypotension (i.e., reduction in SBP <20 mmHg or DBP <10 mmHg upon standing) were eligible for an additional dose after 2 hours. An additional half dose (90 mcg, 60 mcg, or placebo) was given to 7.1% ($^{18}/_{252}$), 22.7% ($^{58}/_{255}$) and 44.0% ($^{111}/_{252}$) of patients in the IGALMI™ 180 mcg, IGALMI™ 120 mcg or placebo arms, respectively. After at least an additional 2 hours, an additional second half dose (total IGALMI™ dose of 360 mcg, total IGALMI™ dose of 240 mcg, or placebo, respectively) was given to 3.2% (8/252), 9.4% (24/255), and 21.0% (53/252) of patients in the IGALMI™ 180 mcg, IGALMI™ 120 mcg or placebo arms, respectively.

In these studies, one patient discontinued treatment due to an adverse reaction of oropharyngeal pain.

The most common adverse reactions (incidence ≥5% and at least twice the rate of placebo) were: somnolence, oral paresthesia or oral hypoesthesia, dizziness, dry mouth, hypotension, and orthostatic hypotension.

Table 50 presents the adverse reactions that occurred in IGALMI™-treated patients at a rate of at least 2% and at a higher rate than in placebo-treated patients in Studies 1 and 2.

TABLE 50

Adverse Reactions Reported in ≥2% of IGALMI ™-Treated Patients and Greater than Placebo in Two Placebo-Controlled Studies of Agitated Adult Patients with Schizophrenia or Bipolar I or II Disorder (Studies 1 and 2)

| Adverse Reaction | IGALMI ™ 180 mcg (N = 252) % | IGALMI ™ 120 mcg (N = 255) % | Placebo N = 252 % |
|---|---|---|---|
| Somnolence* | 23 | 22 | 6 |
| Paresthesia oral or hypoesthesia oral | 7 | 6 | 1 |
| Dizziness | 6 | 4 | 1 |
| Hypotension | 5 | 5 | 0 |
| Orthostatic hypotension | 5 | 3 | <1 |
| Dry mouth | 4 | 7 | 1 |
| Nausea | 3 | 2 | 2 |
| Bradycardia | 2 | 2 | 0 |
| Abdominal discomfort† | 2 | 0 | 1 |

*Somnolence includes the terms fatigue and sluggishness
†Abdominal discomfort includes dyspepsia, gastroesophageal reflux disease Hypotension, Orthostatic Hypotension, and Bradycardia in Two Placebo-Controlled Studies In clinical studies, patients were excluded if they were treated with alpha-1 noradrenergic blockers, benzodiazepines, antipsychotic drugs, or other hypnotics four hours prior to study drug administration; had a history of syncope or syncopal attacks; their SBP was less than 110 mmHg; their DBP was less than 70 mmHg; their HR was less than 55 beats per minute; or they had evidence of hypovolemia or orthostatic hypotension. In these studies, vital signs were monitored (at 30 minutes, 1-, 2-, 4-, 6-, and 8-hours post-dose), including orthostatic vital signs at 2-, 4-, and 8-hours post-dose. Maximum positional decreases in SBP and DBP after standing were observed at two hours post-dose. Maximal reductions on BP and HR were observed two hours post-dose. Table 51 presents the mean BP and HR decrease across all patients from both studies at 2 hours post dose.

TABLE 51

Mean Blood Pressure and Heart Rate Decrease at 2 Hours Post-Dose

|  | IGALMI ™ 180 mcg (N = 252) | IGALMI ™ 120 mcg (N = 255) | Placebo (N = 252) |
|---|---|---|---|
| Mean SBP Decrease (mmHg) | 15 | 13 | 1 |
| Mean DBP Decrease (mmHg) | 8 | 7 | <1 |
| Mean Heart Rate Decrease (bpm) | 9 | 7 | 3 |

In the clinical studies:

(a) 13%, 8%, and <1% of patients in the single dose 180 mcg IGALMI™, 120 mcg IGALMI™, and placebo groups, respectively, experienced SBP <90 mmHg and a decrease ≥20 mmHg of SBP within 24 hours of dosing.

(b) 19%, 17%, and 2% of the patients in the 180 mcg IGALMI™, 120 mcg IGALMI™, and placebo groups, respectively, had a DBP ≤60 mmHg and a DBP decrease ≥10 mmHg within 24 hours of dosing.

(c) 4%, 3%, and 0% of patients in the 180 mcg IGALMI™, 120 mcg IGALMI™, and placebo groups, respectively, had a HR≤50 beats per minute and a HR decrease ≥20 beats per minute within 24 hours of dosing.

At 8 hours post-dose, 2% of patients in the IGALMI™ 180 mcg group experienced a SBP ≤90 mmHg and decrease ≥20 mmHg compared with one patient (<1%) in the IGALMI™ 120 mcg group and none in the placebo group. At 24 hours, none of the patients in the IGALMI™ 180 mcg group experienced a SBP ≤90 mmHg and decrease ≥20 mmHg compared with one patient (<1%) in the IGALMI™ 120 mcg group and none in the placebo group. At 8 hours post-dose, none of the patients in the IGALMI™ 180 mcg group had a HR ≤50 beats per minute and a HR decrease ≥20 beats per minute compared with one patient in the 120 mcg group (<1%) and none in the placebo group.

Postmarketing Experience

The following adverse reactions have been identified during post approval use of another dexmedetomidine product given intravenously (IGALMI™ is not approved for intravenous use). Because these reactions are reported voluntarily from a population of uncertain size, it is not always possible to reliably estimate their frequency or establish a causal relationship to drug exposure.

Blood and Lymphatic System Disorders: Anemia

Cardiac Disorders: Arrhythmia, atrial fibrillation, atrioventricular block, bradycardia, cardiac arrest, cardiac disorder, extrasystoles, myocardial infarction, supraventricular tachycardia, tachycardia, ventricular arrhythmia, ventricular tachycardia Eye Disorders: Photopsia, visual impairment Gastrointestinal Disorders: Abdominal pain, diarrhea, nausea, vomiting General Disorders and Administration Site Conditions: Chills, hyperpyrexia, pain, pyrexia, thirst Hepatobiliary Disorders: Hepatic function abnormal, hyperbilirubinemia Investigations: Alanine aminotransferase increased, aspartate aminotransferase increased, blood alkaline phosphatase increased, blood urea increased, electrocardiogram T wave inversion, gammaglutamyltransferase increased, electrocardiogram QT prolonged Metabolism and Nutrition Disorders: Acidosis, hyperkalemia, hypoglycemia, hypovolemia, hypernatremia Nervous System Disorders: Convulsion, dizziness, headache, neuralgia, neuritis, speech disorder Psychiatric Disorders: Agitation, confusional state, delirium, hallucination, illusion Renal and Urinary Disorders: Oliguria, polyuria Respiratory, Thoracic and Mediastinal Disorders: Apnea, bronchospasm, dyspnea, hypercapnia, hypoventilation, hypoxia, pulmonary congestion, respiratory acidosis Skin and Subcutaneous Tissue Disorders: Hyperhidrosis, pruritus, rash, urticaria Surgical and Medical Procedures: Light anesthesia Vascular Disorders: Blood pressure fluctuation, hemorrhage, hypertension, hypotension Drug Interactions Drugs that Prolong the QT Interval Concomitant use of drugs that prolong the QT interval may add to the QT-prolonging effects of IGALMI™ and increase the risk of cardiac arrhythmia. Avoid the use of IGALMI™ in combination with other drugs known to prolong the QT interval.

Anesthetics, Sedatives, Hypnotics, and Opioids

Concomitant use of IGALMI™ with anesthetics, sedatives, hypnotics, or opioids is likely to lead to enhanced CNS depressant effects. Specific studies with another dexmedetomidine product given intravenously have confirmed these effects with sevoflurane, isoflurane, propofol, alfentanil, and midazolam. Due to possible enhanced CNS effects when given concomitantly with IGALMI, consider a reduction in dosage of IGALMI™ or the concomitant anesthetic, sedative, hypnotic, or opioid.

Use in Specific Populations

Pregnancy

Risk Summary

There are no available data on IGALMI™ use in pregnant women to evaluate for a drug-associated risk of major birth defects, miscarriage or other adverse maternal or fetal effects. Available data from published randomized controlled trials and case reports over several decades of use with intravenously administered dexmedetomidine during pregnancy have not identified a drug-associated risk of major birth defects or miscarriage; however, the reported exposures occurred after the first trimester. Most of the available data are based on studies with exposures that occurred at the time of cesarean-section delivery, and these studies have not identified an adverse effect on maternal outcomes or infant Apgar scores. Available data indicate that dexmedetomidine crosses the placenta.

In animal reproductive studies fetal toxicity occurred in the presence of maternal toxicity with subcutaneous administration of dexmedetomidine to pregnant rats during organogenesis at doses 5 times the maximum recommended human dose [MRHD] of 360 mcg/day based on mg/m2 body surface area. Adverse developmental effects, including early implantation loss and decreased viability of second generation offspring, occurred when pregnant rats were subcutaneously administered doses less than or equal to the MRHD based on mg/m2 from late pregnancy through lactation and weaning.

The estimated background risk of major birth defects and miscarriage for the indicated population is unknown. All pregnancies have a background risk of birth defect, loss, or other adverse outcomes. In the U.S. general population, the estimated background risk of major birth defects and miscarriage in clinically recognized pregnancies is 2 to 4% and 15 to 20%, respectively.

Data

Animal Data

Increased post-implantation losses and reduced live pups in the presence of maternal toxicity (decreased body weight) occurred in a rat embryo-fetal development study in which pregnant dams were administered subcutaneous doses of dexmedetomidine of 200 mcg/kg/day (equivalent to 5 times the MRHD of 360 mcg/day based on mg/m2) during the period of organogenesis (Gestation Day (GD) 5 to 16). No embryo-fetal toxicity was observed at 20 mcg/kg/day (less than the MRHD of 360 mcg/day based on mg/m2). No malformations were reported at any dose level.

No malformation or embryo-fetal toxicity were observed in a rabbit embryo-fetal developmental study in which pregnant dams were administered dexmedetomidine intravenously at doses up to 96 mcg/kg/day (equivalent to 5 times the MRHD of 360 mcg/day based on mg/m2) during the period of organogenesis (GD 6 to 18).

Reduced pup and adult offspring weights and grip strength were reported in a rat developmental toxicology study in which pregnant females were administered dexmedetomidine subcutaneously at 8 mcg/kg/day (less than the MRHD of 360 mcg/day based on mg/m2) during late pregnancy through lactation and weaning (GD 16 to postnatal day [PND] 25). Decreased viability of second generation offspring and an increase in early implantation loss along with delayed motor development occurred at 32 mcg/kg/day (equivalent to the MRHD of 360 mcg/day based on mg/m2) when first generation offspring were mated. This study limited dosing to hard palate closure (GD 15-18) through weaning instead of standard dosing from implantation (GD 6-7) to weaning (PND 21).

Lactation

Risk Summary

Available published literature report the presence of dexmedetomidine in human milk following intravenous administration. There is no information regarding the effects of dexmedetomidine on the breastfed child or the effects on milk production. Advise women to monitor the breastfed infant for irritability. The developmental and health benefits of breastfeeding should be considered along with the mother's clinical need for IGALMI™ and any potential adverse effects on the breastfed child from IGALMI™ or from the underlying maternal condition.

Pediatric Use

The safety and effectiveness of IGALMI™ have not been established in pediatric patients.

Geriatric Use

Fifteen geriatric patients (≥65 years of age) were enrolled (no patients were 75 years of age and older) in the clinical studies for acute treatment of agitation associated with schizophrenia or bipolar I or II disorder. Of the total number of IGALMI™-treated patients in these clinical studies, 11/507 (2.2%) were 65 years of age and older.

Dosage reduction of IGALMI™ is recommended in geriatric patients. A higher incidence of bradycardia and hypotension was observed in geriatric patients compared to younger adult patients after intravenous administration of another dexmedetomidine product. The pharmacokinetic profile of intravenous dexmedetomidine was not altered in geriatric subjects.

Hepatic Impairment

Dexmedetomidine clearance was decreased in patients with hepatic impairment (Child-Pugh Class A, B, or C). Thus, a dosage reduction of IGALMI™ is recommended in patients with hepatic impairment compared to patients with normal hepatic function.

Drug Abuse and Dependence

Controlled Substance

IGALMI™ contains dexmedetomidine, which is not a controlled substance.

Dependence

Physical Dependence

Physical dependence is a state that develops as a result of physiological adaptation in response to repeated drug use, manifested by withdrawal signs and symptoms after abrupt discontinuation or a significant dose reduction of a drug. The dependence potential of dexmedetomidine has not been studied in humans. However, because studies in rodents and primates have demonstrated that intravenous dexmedetomidine exhibits pharmacologic actions similar to those of clonidine, it is possible that dexmedetomidine may produce a clonidine-like withdrawal syndrome upon abrupt discontinuation.

IGALMI™ was not studied for longer than 24 hours after the first dose. There may be risk of physical dependence and a withdrawal syndrome if IGALMI™ is used in a manner other than indicated.

Tolerance

Tolerance is a physiological state characterized by a reduced response to a drug after repeated administration (i.e., a higher dose of a drug is required to produce the same effect that was once obtained at a lower dose).

IGALMI™ has not been studied for longer than 24 hours after the first dose. There may be a risk for tolerance if IGALMI™ is administered in a manner other than indicated.

Overdosage

In a tolerability study of intravenous dexmedetomidine in which healthy adult subjects were administered doses at and above the recommended dose of 0.2 to 0.7 mcg/kg/hour, the maximum blood concentration was approximately 13 times the upper boundary of the therapeutic range for the intravenous dexmedetomidine (IGALMI™ is not approved for intravenous use). The most notable effects observed in two subjects who achieved the highest doses were first degree atrioventricular block and second-degree heart block.

Five adult patients received an overdose of intravenous dexmedetomidine in intensive care unit sedation studies. Two patients who received a 2 mcg/kg loading dose (twice the recommended loading dose) over 10 minutes, experienced bradycardia and/or hypotension.

One patient who received a loading intravenous bolus dose of undiluted dexmedetomidine (19.4 mcg/kg), had cardiac arrest from which he was successfully resuscitated.

Description

IGALMI™ contains dexmedetomidine, an alpha-2 adrenergic receptor agonist, present as dexmedetomidine hydrochloride, the S-enantiomer of medetomidine chemically described as 4-[(1S)-1-(2, 3-dimethylphenyl) ethyl]-1H-imidazole hydrochloride. The empirical formula is $C_{13}H_{16}N_2 \cdot HCl$ with a molecular weight of 236.7 µg/mol. The structural formula of dexmedetomidine hydrochloride is:

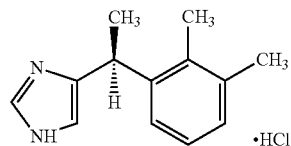

Dexmedetomidine hydrochloride is a white or almost white powder that is freely soluble in water and has a pKa of 7.1. Its partition coefficient in octanol/water at pH 7.4 is 2.89.

IGALMI™ is for sublingual or buccal use. Each IGALMI™ sublingual film contains 120 mcg or 180 mcg of dexmedetomidine equivalent to 141.8 mcg and 212.7 mcg of dexmedetomidine hydrochloride, respectively.

IGALMI™ contains the following inactive ingredients: FD&C Blue #1 colorant, hydroxypropyl cellulose, peppermint oil, polyethylene oxide, and sucralose.

Clinical Pharmacology

Mechanism of Action

Dexmedetomidine is an alpha-2 adrenergic receptor agonist. The mechanism of action of IGALMI in the acute treatment of agitation associated with schizophrenia or bipolar I or II disorder is thought to be due to activation of presynaptic alpha-2 adrenergic receptors.

Pharmacodynamics

Dexmedetomidine acts as an agonist at alpha-2 adrenergic receptors with binding affinities (Ki values) of 4 to 6 nM at the alpha-2 adrenergic receptor subtypes.

Cardiac Electrophysiology

IGALMI™ exhibits a concentration dependent QT prolongation. Table 52 shows the mean (upper 90% confidence interval) QTcF increase from baseline for respective dosing regimens.

TABLE 52

QTcF Increase from Baseline by Dosage of IGALMI™

| IGALMI™ Dosage | Mean QTcF Increase from Baseline (upper 90% confidence interval) |
| --- | --- |
| 120 mcg single use | 6 (7) msec |
| 120 mcg + 2 additional doses of 60 mcg 2 hours apart (total 3 doses) | 8 (9) msec |
| 180 mcg single use | 8 (11) msec |
| 180 mcg + 2 additional doses of 90 mcg 2 hours apart (total 3 doses) | 11 (14) msec |

Pharmacokinetics

Dexmedetomidine exposure ($C_{max}$ and AUC) increased in a dose proportional manner in the dose range of 20 mcg (0.17 times the lowest recommended initial dose of 120 mcg) to 180 mcg after single sublingual administration of IGALMI™.

The mean time for film to dissolve in the mouth was about 6 to 8 minutes and 18 minutes following sublingual and buccal administration, respectively. Dexmedetomidine was quantifiable in plasma generally after 5 to 20 minutes post dosing.

Absorption

The absolute bioavailability of dexmedetomidine was about 72% and 82% following sublingual and buccal administration of IGALMI™, respectively. When water was taken at two hours post dose, comparable exposures of dexmedetomidine were observed when IGALMI™ was administered by both routes.

Mean maximal plasma concentrations of dexmedetomidine were reached approximately two hours after sublingual or buccal administration of IGALMI™. Following sublingual administration of 40 mcg of IGALMI™ (0.33 times the lowest recommended initial dose) with water drinking at two hours post dose and 20 mcg dexmedetomidine intravenous infusion for 90 minutes in healthy volunteers. The mean peak plasma concentration (Cmax) of dexmedetomidine was 143 ng/L and 144 ng/L, respectively. The mean area under concentration curve (AUC) of dexmedetomidine was 851 hour*ng/L and 584 hour*ng/L, respectively.

Effect of Drinking Water on Absorption

Compared to drinking water at two hours post sublingual administration of IGALMI, early water intake (as early as 15 minutes post dose) had minimal effects on the rate or extent of absorption of dexmedetomidine.

Effects of early water intake (i.e., before two hours post dose) on the absorption of dexmedetomidine has not been evaluated following buccal administration.

Distribution

The steady-state volume of distribution (Vss) of dexmedetomidine following intravenous administration was approximately 118 liters. Dexmedetomidine protein binding was assessed in the plasma of healthy male and female subjects. The average protein binding was 94% and was constant across the different plasma concentrations tested. Protein binding was similar in males and females. The fraction of dexmedetomidine that was bound to plasma proteins was significantly decreased in subjects with hepatic impairment compared to healthy subjects.

The potential for protein binding displacement of dexmedetomidine by fentanyl, ketorolac, theophylline, digoxin and lidocaine was explored in vitro, and negligible changes in the plasma protein binding of dexmedetomidine IV were observed. The potential for protein binding displacement of phenytoin, warfarin, ibuprofen, propranolol, theophylline and digoxin by dexmedetomidine hydrochloride injection was explored in vitro and none of these compounds appeared to be significantly displaced by intravenous dexmedetomidine.

Elimination
Metabolism

Dexmedetomidine undergoes almost complete biotransformation with very little unchanged dexmedetomidine excreted in urine and feces. Biotransformation involves both direct glucuronidation as well as cytochrome P450 mediated metabolism. The major metabolic pathways of dexmedetomidine are: direct N-glucuronidation to inactive metabolites; aliphatic hydroxylation (mediated primarily by CYP2A6 with a minor role of CYP1A2, CYP2E1, CYP2D6 and CYP2C19) of dexmedetomidine to generate 3-hydroxy-dexmedetomidine, the glucuronide of 3-hydroxy-dexmedetomidine, and 3-carboxy-dexmedetomidine; and N-methylation of dexmedetomidine to generate 3-hydroxy N-methyl-dexmedetomidine, 3-carboxy N-methyl-dexmedetomidine, and dexmedetomidine-N-methyl O-glucuronide.

Excretion

The mean terminal elimination half-life ($t_{1/2}$) of dexmedetomidine is approximately 2.8 hours following sublingual or buccal administration of IGALMI™. Clearance is estimated to be approximately 39 L/h following intravenous administration.

A mass balance study demonstrated that after nine days, an average of 95% of the radioactivity, following intravenous administration of radiolabeled dexmedetomidine, was recovered in the urine and 4% in the feces. No unchanged dexmedetomidine was detected in the urine. Approximately 85% of the radioactivity recovered in the urine was excreted within 24 hours after the infusion. Fractionation of the radioactivity excreted in urine demonstrated that products of N-glucuronidation accounted for approximately 34% of the cumulative urinary excretion. In addition, aliphatic hydroxylation of parent drug to form 3-hydroxy-dexmedetomidine, the glucuronide of 3-hydroxy-dexmedetomidine, and 3-carboxylic acid-dexmedetomidine together represented approximately 14% of the dose in urine. N-methylation of dexmedetomidine to form 3-hydroxy N-methyl dexmedetomidine, 3-carboxy N-methyl dexmedetomidine, and N-methyl O-glucuronide dexmedetomidine accounted for approximately 18% of the dose in urine. The N-methyl metabolite itself was a minor circulating component and was undetected in urine. Approximately 28% of the urinary metabolites have not been identified.

Specific Populations
Male and Female Patients

There was no observed difference in the pharmacokinetics of intravenous dexmedetomidine due to sex.

Geriatric Patients

The pharmacokinetic profile of intravenous dexmedetomidine was not altered by age. There were no differences in the pharmacokinetics of intravenous dexmedetomidine in young (18-40 years), middle age (41-65 years), and geriatric (>65 years) subjects.

Patients with Hepatic Impairment

In subjects with varying degrees of hepatic impairment (Child-Pugh Class A, B, or C), clearance values for intravenous dexmedetomidine were lower than in subjects with normal hepatic function [see Dosage and Administration (2.2)]. After an intravenous infusion of 0.6 mcg/kg of this dexmedetomidine product over 10 minutes the mean clearance values for subjects with mild, moderate, and severe hepatic impairment were 74%, 64% and 53% of those observed in subjects with normal hepatic function, respectively. Mean clearances for free drug were 59%, 51% and 32% of those observed in subjects with normal hepatic function, respectively.

Patients with Renal Impairment

Dexmedetomidine pharmacokinetics ($C_{max}$, Tmax, AUC, t½, CL, and V) were not significantly different in patients with creatinine clearance <30 mL/minute compared to subjects with normal renal function.

Drug Interactions Studies

In vitro studies in human liver microsomes demonstrated no evidence of cytochrome P450 mediated drug interactions that are likely to be of clinical relevance.

Nonclinical Toxicology
Carcinogenesis, Mutagenesis, Impairment of Fertility
Carcinogenesis Animal carcinogenicity studies have not been performed with dexmedetomidine.

Mutagenesis

Dexmedetomidine was not mutagenic in the in vitro Ames bacterial reverse mutation test or mammalian mouse lymphoma cell forward mutation assay. Dexmedetomidine was not clastogenic in the in vitro human lymphocyte chromosome aberration test in the absence or presence of human liver S9 metabolic activation, however, a weak clastogenic response was noted in the presence of rat liver S9 metabolic activation. Dexmedetomidine was not clastogenic in the in vivo bone marrow micronucleus test in CD-1 mice, although there was some evidence for clastogenicity in NMRI mice.

Impairment of Fertility

Fertility in male or female rats was not affected after daily subcutaneous injections of dexmedetomidine at doses up to 54 mcg/kg (1.5 times the MRHD of 360 mcg/day on a mg/m2 basis) administered from 10 weeks prior to mating in males, and 3 weeks prior to mating and during mating in females.

Animal Toxicology and/or Pharmacology

Twice daily sublingual administration of 120 to 320 mcg/day of dexmedetomidine to dogs for 28 days caused decreased heart rate and moderate sedation up to 3.5 hours post dose. A single male dog (out of 32 treated dogs) dosed 320 mcg/day (equivalent to the MRHD of 360 mcg/day) exhibited inflammation, necrosis, myofiber degeneration, and hemorrhage at the sublingual treatment site. No adverse effects were noted at 240 mcg/day (less than the MRHD of 360 mcg/day).

Clinical Studies

The effectiveness of IGALMI™ for the acute treatment of agitation associated with schizophrenia or bipolar I or II disorder in adults was established in two randomized, double-blind, placebo-controlled, fixed-dose studies (Studies 1 and 2):

Study 1 (NCT04268303) included 380 patients who met DSM-5 criteria for schizophrenia, schizoaffective or schizophreniform disorder. The population was 18 to 71 years of age (mean age was 46 years old); 37% female and 63% male; 78% Black, 20% White, 1% multiracial, and 1% Asian.

Study 2 (NCT04276883) included 378 patients who met DSM-5 criteria for bipolar I or II disorder. The population was 18 to 70 years of age (mean age was 47 years old); 55% female and 45% male; 56% Black, 41% White, 1% Asian, 1% multiracial, and 1% other.

The Positive and Negative Syndrome Scale-Excited Component (PEC) is an investigator-rated instrument consisting of 5 items: poor impulse control, tension, hostility, uncooperativeness, and excitement. Each item is scored on a scale from 1 to 7 (1=absent, 2=minimal, 3=mild, 4=moderate, 5=moderate-severe, 6=severe, 7=extremely severe). The total PEC score ranges from 5 to 35, with higher scores reflecting greater overall symptom severity. For enrollment in the studies, patients had to be judged to be clinically agitated with a total PEC score of ≥14, with at least one individual item score ≥4. In both studies, patients were admitted to a clinical research unit or a hospital and remained under medical supervision for at least 24 hours following treatment.

Patients were randomized to receive a single sublingual dose of 180 mcg of IGALMI™ 120 mcg of IGALMI™, or placebo. The primary efficacy endpoint in both studies was the change from baseline in the PEC score, assessed two hours following the initial dose. The key secondary endpoint was the time to effect onset, assessed by measuring the change from baseline in PEC score at 10, 20, 30, 45, 60, and 90 minutes after the initial dose administration.

In both studies, mean baseline PEC scores were similar in all treatment groups (Table 53). The mean change from baseline in the PEC total score at two hours after the first dose in patients treated with 180 mcg and 120 mcg of IGALMI™ was statistically greater than patients who received placebo (Table 53).

Examination of population subsets (race and sex) on the primary endpoint did not show evidence for differential responsiveness between White and Black or female and male patients. The clinical studies did not include enough patients of other races or patients ≥65 years of age to determine whether there were differences in effectiveness for those groups.

TABLE 53

Primary Efficacy Results for Change from Baseline in the PEC Score at Two Hours in Agitated Patients with Schizophrenia or Bipolar I or II Disorder (Studies 1 and 2)

| Study | Treatment Group | Number of Patients | Mean Baseline PEC Score (SD) | LS Mean Change from Baseline to 2 hour Post First Dose (SE) | LS Mean Difference (95% CI) |
|---|---|---|---|---|---|
| Study 1 | IGALMI™ 180 mcg* | 125 | 17.6 (2.7) | −10.3 (0.4) | −5.5 (−6.5, −4.4) |
| | IGALMI™ 120 mcg* | 129 | 17.5 (2.5) | −8.5 (0.4) | −3.7 (−4.8, −2.7) |
| | Placebo | 126 | 17.6 (2.3) | −4.8 (0.4) | — |
| Study 2 | IGALMI™ 180 mcg* | 126 | 18.0 (3.0) | −10.4 (0.4) | −5.4 (−6.5, −4.3) |
| | IGALMI™ 120 mcg* | 126 | 18.0 (2.7) | −9.1 (0.4) | −4.1 (−5.1, −3.0) |
| | Placebo | 126 | 17.9 (2.9) | −5.0 (0.4) | — |

SD = standard deviation;
SE = standard error;
LS Mean = least-squares mean;
CI = unadjusted confidence interval;
PEC = Positive and Negative Syndrome Scale-Excited Component
*IGALMI ™ doses that were statistically significantly superior to placebo after adjusting for multiplicity.

How Supplied/Storage and Handling
How Supplied

IGALMI (dexmedetomidine) sublingual film is supplied as a blue rectangular sublingual film, containing on its surface two darker blue spots in dose strengths of 120 mcg and 180 mcg and is packaged as individual films in heat-sealed foil pouches in 10-count and 30-count films per carton. The NDC number for each packaging configuration is: 120 mcg 10-count NDC #81092-1120-1, 120 mcg 30-count NDC #81092-1120-3, 180 mcg 10-count NDC #81092-1180-1, 180 mcg 30-count NDC #81092-1180-3

Storage and Handling

Store at controlled room temperature, 20° C. to 25° C. (68° F. to 77° F.). Excursions permitted from 15° C. to 30° C. (59° F. to 86° F.). See USP Controlled Room Temperature.

Keep IGALMI in the foil pouch until ready to administer.
Patient Counseling Information
Administration Information Advise patients to place IGALMI™ under the tongue, close to the base of the tongue, on the left or right side (sublingual) or behind the lower lip (buccal).

Advise patients not to chew or swallow IGALMI™. Also, advise patients not to eat or drink for at least 15 minutes after sublingual administration, or at least 1 hour after buccal administration.

Hypotension, Orthostatic Hypotension, and Bradycardia

Advise patients that IGALMI™ can cause dose-dependent hypotension, orthostatic hypotension, and bradycardia. Inform patients to remain sitting or lying down after receiving IGALMI™ and to inform the healthcare provider if they have any symptoms of hypotension or bradycardia.

QT Interval Prolongation

Inform patients to consult their physician immediately if they feel faint or have heart palpitations.

Somnolence

Advise patients that IGALMI™ can cause somnolence and may impair the ability to perform tasks that require complex motor and mental skills. Advise patients that they should avoid doing activities that require them to be alert, such as driving a car or operating machinery for at least eight hours after receiving IGALMI™

Lactation

Advise patients exposed to IGALMI™ to monitor breast-fed infants for irritability.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A method of treating agitation associated with schizophrenia or bipolar I or II disorder in a human subject comprising:
   administering a first dose of dexmedetomidine or a pharmaceutically acceptable salt thereof in an oromucosal formulation to the human subject;
   optionally administering a second dose of dexmedetomidine or a pharmaceutically acceptable salt thereof in an oromucosal formulation that is administered to the human subject at least two hours after and within 24 hours of the first dose and wherein the second dose is 60 mcg of dexmedetomidine;
   optionally administering a third dose of dexmedetomidine or a pharmaceutically acceptable salt thereof in an oromucosal formulation that is administered to the human subject at least two hours after the second dose and within 24 hours of the first dose and wherein the third dose is 60 mcg of dexmedetomidine;
   wherein the human subject has a severe hepatic impairment and the agitation is mild or moderate; and
   wherein the first dose is 60 mcg of dexmedetomidine or the equivalent amount of a pharmaceutically acceptable salt thereof;
   wherein the maximum daily dose is 180 mcg.

2. The method of claim 1, wherein the oromucosal formulation further comprises at least one water-soluble polymer.

3. The method of claim 2, wherein the at least one water-soluble polymer is selected from the group consisting of hydroxypropyl cellulose, hydroxypropyl methylcellulose, hydroxyethyl cellulose, carboxy methylcellulose, methylcellulose, polyethylene oxide (PEO), and mixtures thereof.

4. The method of claim 3, wherein the at least one water-soluble polymer is hydroxypropyl cellulose.

5. The method of claim 1, wherein the second dose of dexmedetomidine or a pharmaceutically acceptable salt thereof is administered and is 60 mcg of dexmedetomidine or the equivalent amount of a pharmaceutically acceptable salt thereof.

6. The method of claim 5, wherein the third dose of dexmedetomidine or a pharmaceutically acceptable salt thereof is administered and is 60 mcg of dexmedetomidine or the equivalent amount of a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 12,090,140 B2 | |
| APPLICATION NO. | : 18/526686 | |
| DATED | : September 17, 2024 | |
| INVENTOR(S) | : Vasukumar Kakumanu et al. | |

It is certified that error appears in the above-identified patent and that said Letters Patent is hereby corrected as shown below:

In the Drawings

Sheet 5, Fig. 5A, please delete the units of the y-axis "ng/mL" and insert --ng/L--.

Sheet 26, Fig. 19, please delete the "¶" on the y-axis.

In the Specification

In Column 21, Lines 40-57, please delete each instance of "μg" and replace each instance with --g--.

In Column 56, Line 34, delete "(table 11)" and insert --(Table 12).--.

In Column 82, Line 44, delete "Tables 30 to 32" and insert --Tables 24 to 26--.

Signed and Sealed this
Fourth Day of February, 2025

Coke Morgan Stewart
*Acting Director of the United States Patent and Trademark Office*